(12) United States Patent
de Leeuw et al.

(10) Patent No.: US 10,941,114 B2
(45) Date of Patent: Mar. 9, 2021

(54) SMALL MOLECULE LIPID II INHIBITORS

(71) Applicant: University Of Maryland, Baltimore, Baltimore, MD (US)

(72) Inventors: Erik de Leeuw, Baltimore, MD (US); Alexander MacKerell, Baltimore, MD (US); Steven Fletcher, Baltimore, MD (US); Jamal Chauhan, Baltimore, MD (US)

(73) Assignee: University Of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 16/724,821

(22) Filed: Dec. 23, 2019

(65) Prior Publication Data

US 2020/0216394 A1    Jul. 9, 2020

Related U.S. Application Data

(63) Continuation-in-part of application No. 16/064,276, filed as application No. PCT/US2016/067774 on Dec. 20, 2016.

(60) Provisional application No. 62/270,184, filed on Dec. 21, 2015.

(51) Int. Cl.
| | | |
|---|---|---|
| *C07D 213/20* | (2006.01) | |
| *C07D 213/26* | (2006.01) | |
| *A61P 31/04* | (2006.01) | |

(52) U.S. Cl.
CPC ............ *C07D 213/26* (2013.01); *A61P 31/04* (2018.01); *C07D 213/20* (2013.01)

(58) Field of Classification Search
CPC .................................................... C07D 213/20
See application file for complete search history.

(56) References Cited

U.S. PATENT DOCUMENTS

| | | | |
|---|---|---|---|
| 2,461,484 | A | 2/1949 | Thompson |
| 3,250,615 | A | 5/1966 | Van Allen et al. |
| 6,124,342 | A | 9/2000 | Okamoto et al. |
| 8,796,323 | B2 | 8/2014 | Leeuw et al. |
| 9,351,963 | B2 | 5/2016 | Leeuw et al. |
| 2013/0331413 | A1 | 12/2013 | De Leeuw et al. |
| 2014/0308317 | A1 | 10/2014 | Fan et al. |

FOREIGN PATENT DOCUMENTS

| | | | | |
|---|---|---|---|---|
| EP | 0024169 A2 | 2/1981 | | |
| WO | WO-2017112668 A1 | * | 6/2017 | ........... C07D 405/06 |

OTHER PUBLICATIONS

ISA/EP: Search Report, European Patent Application No. 16879970.8, dated Jun. 7, 2019, pp. 1-10.

ISA/US: International Search Report and Written Opinion, International Patent Application No. PCT/US16/067774, dated Feb. 17, 2017, pp. 1-8.

Boiko, I.I. et al., "Abstract: Styryls of the α-pyrylium series and the nature of their absorption bands," Ukrainiskii Khimicheskii Zhurnal, 1987, pp. 412-416, vol. 108, No. 7484.

Chauhan, J., et al., "Towards Development of Small Molecule Lipid II Inhibitors as Novel Antibiotics," PLOS ONE, 2016, pp. 1-19, Published in: https://doi.org/10.1371/journal.pone.0164515.

Essig A., et al., "Copsin a novel peptide-based fungal antibiotic interfering with the peptidoglycan synthesis", J Biological Chem, 2014, pp. 34953-34964, vol. 289, Issue 50.

Fletcher S., et al, "Structure-activity exploration of a small-molecule lipid II inhibitor", Drug Design Development Therapy, 2015, pp. 2383-2394, vol. 9.

Ganz T., "Defensins: antimicrobial peptides of innate immunity", Nature Reviews, 2003, pp. 710-720, vol. 3.

(Continued)

*Primary Examiner* — Emily A Bernhardt
(74) *Attorney, Agent, or Firm* — Wolter Van Dyke Davis, PLLC; Martha Cassidy

(57) ABSTRACT

Newly synthesized derivatives of BAS00127538 have been discovered to possess antibiotic activity and to combat resistant bacterial strains. Compounds and pharmaceutical compositions containing these compounds are described, and are based on a genetic scaffold structure. Synthetic methods and methods of using the compounds also are described. Preferred compounds bind to Lipid II with high affinity, have markedly reduced cytotoxicity compared to BAS00127538, and retain activity against drug-resistant strains of Enterococci. They are stable in plasma, have dramatically improved pharmacokinetic and pharmacodynamics properties, and possess in vivo efficacy in a mouse model of sepsis.

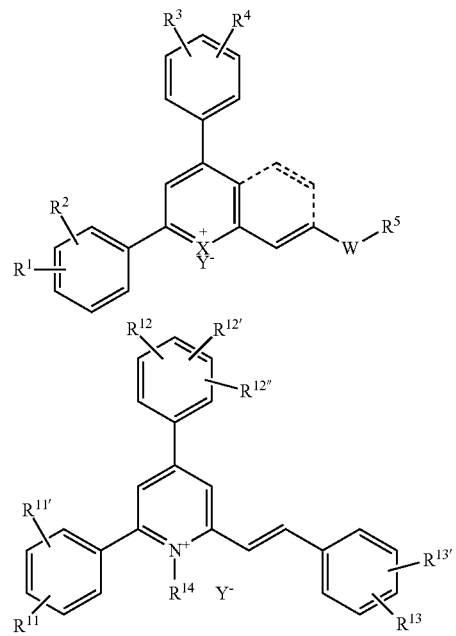

15 Claims, 25 Drawing Sheets

(56) References Cited

OTHER PUBLICATIONS

Gavrilyuk, I., et al, "Pyrylocyanines. Unsymmetrical α-pyrylo- and α-pyridocyanines", Chemistry of Heterocyclic Compounds, Jan. 1, 1985, pp. 34-38, vol. 21, No. 1, Published in: NY, USA.

Haucke, G., et al., "Absorption and Fluorescence of Pyrylium Salts", Ber. Bunsenges. Phys. Chem, Jul. 1, 1992, pp. 880-886, vol. 96, No. 7, Publisher: Verlagsgesellschaft, Published in: https://doi.org/10.1002/bbpc.19920960706.

Munch D., et al, "Identification and in vitro analysis of the GatD/MurT enzyme-complex catalyzing lipid II amidation in *staphylococcus aureus*", PLoS, 2012, pp. 1-11, vol. 8.

Oeemig J., et al., "eurocin a new fungal defensin", J Biological Chem, 2012, pp. 42361-42372, vol. 287, Issue 50.

Okamoto, et al., Abstract for EP 659407, 1995, vol. 123, No. 221957.

Oppedijk S., et al., "Hit 'em where it hurts: the growing and structurally diverse family of peptides that target lipid II" Biochem and Biophys, 2016, pp. 947-957.

Reynolds, G., et al., "The Preparation and Certain Reactions of 3-Formyl-4H-flavene", "Journal of Organic Chemistry", Feb. 1, 1971, pp. 600-602, vol. 36, No. 4, Published in: https://doi.org/10.1021/jo00803a026.

Reynolds, G., et al., "Solvent Shifts of Certain Aminoarylpyrylium Salts", "Journal of Heterocyclic Chemistry", Apr. 1, 1975, pp. 367-368, vol. 12, No. 2, Published in: https://doi.org/10.1002/jhet.5570120231.

Sass V., et al., "Human B-defensin 3 inhibits cell wall biosynthesis in staphylococci", Infection and Immunity, 2010, pp. 2793-2800, vol. 78, Issue 6.

Schmitt P., et al, "Insight into invertebrate defensin mechanism of action", J Biological Chem, 2010, pp. 29208-29216, vol. 285, Issue 38.

Schneider T., et al., "Plectasin a fungal defensin targets the bacterial cell wall precursor lipid II", Science, 2010, pp. 1168-1172, vol. 328.

Schneider T, et al, "Lipid II and other bactoprenol-bound cell wall precursors as drug targets", Curr. Op. Investigational Drugs, 2010, pp. 157-164, vol. 11.

Van Heijenoort J., "Lipid intermediates in the biosynthesis of bacterial peptidoglycan", Microbiol and molecular biol. rev., 2007, pp. 620-635, vol. 71, Issue 4.

Varney K., "Turning defense into offense: defensin mimetics as novel antibiotics targeting lipid II", PLoS, 2013, pp. 1-14, vol. 9, Issue 11.

Allen N., et al., "Inhibition of peptidoglycan biosynthesis in vancomycin-susceptible and -resistant bacteria by a semisynthetic glycopeptide antibiotic", Antimicrobial Agents and Chemotherapy, 1996, pp. 2356-2362, vol. 40, Issue 10.

Aqvist J,. et al, "A new method for predicting binding affinity in computer-aided drug design", Protein Engineering, 1994, pp. 385-391, vol. 7, Issue 3.

Breukink E., et al., "Use of the cell wall precursor lipid II by a pore-forming peptide antibiotic", Science, 1999, pp. 2361-2364, vol. 286.

Breukink E., et al., "Lipid II is an intrinsic component of the pore induced by nisin in bacterial membranes", J of Biological Chem, 2003, pp. 19898-19903, vol. 278, Issue 22.

Breukink E., et al., "Lipid II as a target for antibiotics", Nature reviews drug discovery, 2009, pp. 1-12, vol. 5, Issue 4.

De Leeuw E., et al., "Functional Interaction of human neutrophil peptide-1 with the cell wall precursor lipid II", Febs Lett, 2010, pp. 1543-1548, vol. 548, Issue 8.

De Leeuw E., "Efficacy of the small molecule inhibitor of lipid II BAS00127538 against Acinetobacter baumannii", Drug Design Development and Therapy, 2014, pp. 1061-1064, vol. 8.

Den Blaauwen T., et al, Bacterial cell division proteins as antibiotic targets, Bioorganic chem, 2014, pp. 27-38, vol. 55.

\* cited by examiner

Scheme 1: A. Synthesis of lead compound 6jc48-1(BF$_4^-$ salt) and pyridinium analogs 4.
B.-C. Procedures to introduce chemical diversity into pyridinium and hindered pyrylium analogs.

FIG. 10A

| | 6jc37 | 6jc38 | 6jc39 | 6jc41-1 | 6jc43-1 | 6jc43-2 | 6jc48-1 | 6jc48-2 | Jc-49-1 | 6jc51-1 | BAS-00127538 |
|---|---|---|---|---|---|---|---|---|---|---|---|
| S. aureus MRSA 1094 | 16 | 64 | 2 | 16 | 4 | >=64 | 32 | >=64 | 8 | 1 | 0.5 |
| S. aureus HFH-30123 (MRSA) | 16 | >=64 | 4 | 32 | 4 | >=64 | 32 | >=64 | 8 | 2 | 0.5 |
| E. faecium EF1509 (VRE) | 64 | >=64 | 4 | 22.62742 | 4 | 64 | 2.828427 | 4 | 16 | 0.5 | 2 |
| E. faecium F118 (VRE) | 64 | >=64 | 4 | 8 | 4 | >=64 | 5.656854 | 16 | 16 | 2 | 2 |
| K. pneumoniae NR-15410 (KPC) | >=64 | >=64 | 64 | >=64 | >=64 | >=64 | >=64 | >=64 | >=64 | 16 | 8 |
| K. pneumoniae NR-15411 (KPC) | >=64 | >=64 | >=64 | >=64 | >=64 | >=64 | >=64 | >=64 | >=64 | 64 | 16 |
| A. baumanii ATCC 19606 | >=64 | >=64 | 16 | >=64 | 45.25483 | >=64 | >=64 | >=64 | >=64 | 8 | 4 |
| P. aeruginosa PA01 | >=64 | >=64 | >=64 | >=64 | >=64 | >=64 | >=64 | >=64 | >=64 | 64 | 64 |
| P. aeruginosa X13273 | >=64 | >=64 | >=64 | >=64 | >=64 | >=64 | >=64 | >=64 | >=64 | 45.25483 | >=64 |
| P. aeruginosa ATCC 27853 | >=64 | >=64 | >=64 | >=64 | >=64 | >=64 | >=64 | >=64 | >=64 | 64 | 64 |
| E. cloacae ATCC 13047 | >=64 | >=64 | >=64 | >=64 | >=64 | >=64 | >=64 | >=64 | >=64 | 64 | 32 |
| E. aerogenes ATCC 13048 | >=64 | >=64 | >=64 | >=64 | >=64 | >=64 | >=64 | >=64 | >=64 | 64 | 16 |
| $CC_{50\%}$ (72 h HeLa cells) | 18.96 | >32 | 1.31 | >32 | 0.93 | >32 | >100 | 60.51 | 2.2 | <.78125 | 0.56 |
| $CC_{30\%MIC}$ (based on S. aureus) | 1.185 | NA | 0.655 | >2 | 0.2325 | NA | 3.125 | <0.945 | 0.275 | <.78125 | 1.12 |
| Lipid II binding Kd. $\mu$M | No | No | 39±4 | 34±4 | 62±6 | ND | 0.15±0.03 | 1.11±0.3 | 0.17±0.05 | 9.2±2 | 1.81±0.3 |

FIG. 10B

| | 6jc51-2 | 6jc53-2 | 6jc58 | 6jc59-1 | 6jc59-3 | 6jc60-1 | 6jc64-1 | 6jc64-2 | 6jc64-3 | 6jc65-1 | BAS-00127538 |
|---|---|---|---|---|---|---|---|---|---|---|---|
| S. aureus MRSA 1094 | 2 | 2 | 1.414214 | 2 | 4 | 8 | 4 | 8 | 5.66 | 2.83 | 0.5 |
| S. aureus HFH-30123 (MRSA) | 4 | 4 | 2 | 2 | 4 | 8 | 4 | 8 | 4 | 2 | 0.5 |
| E. faecium EF1509 (VRE) | 0.5 | 8 | 4 | 4 | 8 | 8 | 4 | 5.66 | 8 | 2 | 2 |
| E. faecium F118 (VRE) | 2 | 5.656854249 | 4 | 4 | 8 | 8 | 5.66 | 16 | 8 | 4 | 2 |
| K. pneumoniae NR-15410 (KPC) | 64 | >=64 | 45.25483 | >=64 | >=64 | >=64 | >=64 | >=64 | 64 | 64 | 8 |
| K. pneumoniae NR-15411 (KPC) | >=64 | >=64 | 64 | >=64 | >=64 | >=64 | >=64 | >=64 | 64 | >=64 | 16 |
| A. baumannii ATCC 19606 | 32 | >=64 | 8 | >=64 | >=64 | >=64 | 16 | >=64 | >=64 | 11.31 | 4 |
| P. aeruginosa PA01 | >=64 | >=64 | 64 | >=64 | >=64 | >=64 | >=64 | >=64 | >=64 | 64 | 64 |
| P. aeruginosa X13273 | >=64 | >=64 | 32 | >=64 | >=64 | >=64 | >=64 | >=64 | >=64 | 64 | >=64 |
| P. aeruginosa ATCC 27853 | >=64 | >=64 | 64 | >=64 | >=64 | >=64 | >=64 | >=64 | >=64 | 64 | >=64 |
| E. cloacae ATCC 13047 | >=64 | >=64 | 64 | >=64 | >=64 | >=64 | >=64 | >=64 | 64 | 64 | 32 |
| E. aerogenes ATCC 13048 | >=64 | >=64 | 32 | >=64 | >=64 | >=64 | >=64 | >=64 | >=64 | 32 | 16 |
| $CC_{50}$ (72 h HeLa cells) | <.78125 | 1.12 | <.78125 | <.78125 | 1.35 | <.78125 | <.78125 | <.78125 | 3.29 | <.78125 | 0.56 |
| $CC_{50}$:MIC (based on S. aureus) | <.39 | 0.56 | 0.56 | 0.39 | 0.3375 | 0.097 | 0.195 | 0.097 | 0.581 | 0.276 | 1.12 |
| Lipid II binding $K_d$ μM | 9.5±2 | 10±3 | 17±4 | 1.9±0.3 | 27.9±3 | 37.9±4 | 07.28±0.3 | 23.8±4 | 4.92±0.5 | 2.17±0.2 | 1.81±0.3 |

FIG. 10C

| | 6jc65-2 | 6jc66-1 | 6jc66-2 | 6jc66-3 | 6jc66-4 | 6jc-67A | 6jc-69-1 | 6jc-69-3 | 6jc-69-4 | 6jc-69-5 | BAS-00127538 |
|---|---|---|---|---|---|---|---|---|---|---|---|
| S. aureus MRSA 1094 | 2 | 2.83 | 4 | 8 | 2 | 1 | 2 | 4 | 8 | >=64 | 0.5 |
| S. aureus HFH-30123 (MRSA) | 2 | 4 | 4 | 8 | 2 | 1 | 2 | 4 | 8 | 64 | 0.5 |
| E. faecium EF1509 (VRE) | 2 | 4 | 4 | 4 | 2 | 2 | 2 | 2.83 | 4 | 6 | 2 |
| E. faecium F118 (VRE) | 4 | 8 | 5.66 | 11.31 | 4 | 1.41 | 2 | 4 | 5.66 | 11.31 | 2 |
| K. pneumoniae NR-15410 (KPC) | 64 | >=64 | 64 | >=64 | 64 | 16 | >=64 | >=64 | >=64 | >=64 | 8 |
| K. pneumoniae NR-15411 (KPC) | >=64 | >=64 | >=64 | >=64 | >=64 | 32 | >=64 | >=64 | >=64 | >=64 | 16 |
| A. baumanii ATCC 19606 | 32 | 45.25 | 64 | >=64 | 64 | 4 | 32 | >=64 | >=64 | >=64 | 4 |
| P. aeruginosa PA01 | >=64 | >=64 | >=64 | >=64 | >=64 | 64 | >=64 | >=64 | >=64 | >=64 | 64 |
| P. aeruginosa X13273 | >=64 | >=64 | >=64 | >=64 | >=64 | 32 | >=64 | >=64 | >=64 | >=64 | >=64 |
| P. aeruginosa ATCC 27853 | >=64 | >=64 | >=64 | >=64 | >=64 | 32 | >=64 | >=64 | >=64 | >=64 | >=64 |
| E. cloacae ATCC 13047 | 64 | >=64 | >=64 | >=64 | >=64 | 32 | >=64 | >=64 | >=64 | >=64 | 32 |
| E. aerogenes ATCC 13048 | 64 | >=64 | >=64 | >=64 | >=64 | 16 | >=64 | >=64 | >=64 | >=64 | 16 |
| $CC_{50\%}$ (72 h HeLa cells) | 0.94 | 1.36 | 1.42 | 5.68 | 0.92 | <.78125 | <.78125 | <.78125 | 3.09 | 4.43 | 0.56 |
| $CC_{50\%MIC}$ (based on S. aureus) | 0.47 | 0.48 | 0.355 | 0.71 | 0.46 | 0.78 | 0.39 | 0.195 | 0.38 | 0.06 | 1.12 |
| Lipid II binding $K_d$, $\mu M$ | 3.9±0.4 | 2.9±0.3 | 1.6±0.2 | 60±11 | 27.9±2 | 7.89±0.2 | 16.1±0.3 | 0.6±0.1 | 30.3±0.5 | 32.7±2 | 1.81±0.3 |

FIG. 10D

| | 6jc67 | 6jc67A | 6jc69-1 | 6jc69-3 | 6jc69-4 | 6jc69-5 | 6jc76-1 | 6jc76-2 | 6jc77-1 | 6jc77-2 | BAS-001127538 |
|---|---|---|---|---|---|---|---|---|---|---|---|
| S. aureus MRSA 1094 | 0.5 | 1 | 2 | 4 | 8 | >=64 | 2 | 4 | 1.41 | 2 | 0.5 |
| S. aureus HFH-30123 (MRSA) | 0.5 | 1 | 2 | 4 | 8 | 64 | 2 | 4 | 2 | 4 | 0.5 |
| E. faecium EF1509 (VRE) | 2 | 2 | 2 | 2.83 | 4 | 6 | 2 | 2.83 | 2 | 2 | 2 |
| E. faecium F118 (VRE) | 2 | 1.41 | 2 | 4 | 5.66 | 11.31 | 2 | 2 | 2 | 4 | 2 |
| K. pneumoniae NR-15410 (KPC) | 16 | 16 | >=64 | >=64 | >=64 | >=64 | 64 | >=64 | >=64 | >=64 | 16 |
| K. pneumoniae NR-15411 (KPC) | 16 | 32 | >=64 | >=64 | >=64 | >=64 | 64 | >=64 | >=64 | >=64 | 16 |
| A. baumanii ATCC 19606 | 4 | 4 | 32 | >=64 | >=64 | >=64 | 8 | >=64 | 8 | 64 | 4 |
| P. aeruginosa PA01 | >=64 | 64 | >=64 | >=64 | >=64 | >=64 | 45.25 | >=64 | >=64 | >=64 | >=64 |
| P. aeruginosa X13273 | >=64 | 32 | >=64 | >=64 | >=64 | >=64 | 32 | >=64 | >=64 | >=64 | >=64 |
| P. aeruginosa ATCC 27853 | >=64 | 32 | >=64 | >=64 | >=64 | >=64 | 22.63 | >=64 | >=64 | >=64 | >=64 |
| E. cloacae ATCC 13047 | 32 | 32 | >=64 | >=64 | >=64 | >=64 | 32 | >=64 | >=64 | >=64 | 32 |
| E. aerogenes ATCC 13048 | 16 | 16 | >=64 | >=64 | >=64 | >=64 | 45.25483 | >=64 | >=64 | >=64 | 16 |
| $CC_{50\%}$ (72 h HeLa cells) | <.78125 | <.78125 | <.78125 | <.78125 | 3.09 | 4.43 | <.78125 | <.78125 | <.78125 | 1.995 | 0.56 |
| $CC_{50\%MIC}$ (based on S. aureus) | 1.56 | 0.78 | 0.39 | 0.195 | 0.38 | 0.06 | 0.39 | 0.195 | 0.55 | 0.99 | 1.12 |

FIG. 16

| Strain | EL-1 | EL-2 | EL-3 | EL-4 | | EL-5 | EL-6 | EL-7 | EL-8 | EL-9 | EL-10 | EL-11 | 6[o]4B-1 | BAS-00127538 |
|---|---|---|---|---|---|---|---|---|---|---|---|---|---|---|
| S. aureus MRSA 1094 | 0.5 | 1 | 2 | 4.42 | USA300 | 1.00 | 1.00 | 4.00 | 0.50 | 0.50 | 1.00 | 1.00 | 32.00 | 0.5 |
| S. aureus HFH-30123 (MRSA) | 0.5 | 2 | 2 | 6.23 | | | | | | | | | 32.00 | 0.5 |
| E. faecalis ATCC 51299 (VRE) | 1.00 | 1 | 2 | 1.56 | | | | | | | | | 2.80 | 1 |
| E. faecium EF1509 (VRE) | 1.00 | 1 | 2 | 6.25 | EF1509 | 0.25 | 0.13 | 0.50 | 4.00 | 4.00 | 2.00 | 4.00 | 5.60 | 11.31 |
| K. pneumoniae NR-15410 (KPC) | >=32 | >=32 | >=32 | >=100 | | | | | | | | | >32 | 16 |
| K. pneumoniae NR-15411 (KPC) | >=32 | >=32 | >=32 | >=100 | 2,2,2 | 0.50 | 2.00 | 16.00 | 4.00 | 16.00 | 16.00 | | >32 | 4 |
| A. baumanii ATCC 19606 | 4 | 8 | 16 | >=100 | | | | | | | | >64 | >32 | >=64 |
| P. aeruginosa PA01 | >=32 | >=32 | >=32 | >=100 | | | | | | | | | >32 | >=64 |
| P. aeruginosa X13273 | >=32 | >=32 | >=32 | >=100 | | | | | | | | | >32 | >=64 |
| P. aeruginosa ATCC 27653 | >=32 | >=32 | >=32 | >=100 | | | | | | | | | >32 | 45.25 |
| E. cloacae ATCC 13047 | >=32 | >=32 | >=32 | >=100 | | | | | | | | | >32 | 22.63 |
| E. aerogenes ATCC 13048 | >32 | >32 | >32 | >100 | | | | | | | | | >100 | 0.51 |
| CC50 (72h) | 1.3 | 1.40 | 3.78 | >100 | | 2.00 | 3.00 | 2.00 | 4.50 | 3.00 | 2.00 | 3.00 | | |
| CC50 (24) | 5.00 | 3.00 | 3.00 | 2.00 | | | | | | | | | | |
| Lipid II binding (Kd, M) | | | | | | | | | | | | | | |

FIG. 19A

| | 1 | 59 | 12c | 14b | 30 | 5b | 12a | 5B | 7b | 7B | 3 | 10b | 12b | 39 |
|---|---|---|---|---|---|---|---|---|---|---|---|---|---|---|
| S. aureus MRSA 1094 | 0.5 | 2 | 2 | 1 | 1 | 0.5 | 0.5 | 4 | 1 | 1 | 2 | 2 | 1 | 2 |
| S. aureus HFH-30123 (MRSA) | 0.5 | 4 | 4 | 2 | 1 | 1 | 1 | 4 | 1 | 1 | 2 | 2 | 1 | 2 |
| E. faecalis ATCC 51299 (VRE) | 1 | 8 | 8 | 16 | 8 | 2 | 4 | 8 | 8 | 4 | 4 | 16 | 4 | 8 |
| E. faecium EF1509 (VRE) | 1 | 8 | 8 | 8 | 4 | 2 | 2 | 8 | 4 | 4 | 4 | 16 | 2 | 4 |
| E. faecium F118 (VRE) | 1 | 4 | 8 | 8 | 4 | 2 | 4 | 8 | 4 | 4 | 4 | 8 | 2 | 4 |
| K. pneumoniae NR-15410 (KPC) | >=32 | >=64 | >=64 | >=64 | >=64 | 16 | 64 | >=64 | 64 | >=64 | >=32 | >=64 | 64 | >=64 |
| K. pneumoniae NR-15411 (KPC) | >=32 | >=64 | >=64 | >=64 | >=64 | 32 | >=64 | >=64 | 64 | >=64 | >=32 | >=64 | >=64 | >=64 |
| A. baumanii ATCC 19606 | 4 | >=64 | 32 | 16 | 32 | 4 | 4 | >=64 | 8 | 8 | 16 | 32 | 8 | 32 |
| P. aeruginosa PA01 | >=32 | >=64 | 64 | 16 | 16 | 4 | 8 | >=64 | 8 | 8 | >=32 | 16 | 4 | 16 |
| P. aeruginosa X13273 | >=32 | >=64 | >=64 | >=64 | >=64 | 64 | >=64 | >=64 | 32 | >=64 | >=32 | >=64 | >=64 | >=64 |
| P. aeruginosa ATCC 27853 | >=32 | >=64 | >=64 | >=64 | >=64 | 32 | >=64 | >=64 | 32 | >=64 | >=32 | >=64 | >=64 | >=64 |
| E. cloacae ATCC 13047 | >=32 | >=64 | >=64 | >=64 | >=64 | >=64 | >=64 | >=64 | >=64 | >=64 | >=32 | >=64 | >=64 | >=64 |
| E. aerogenes ATCC 13048 | >=32 | >=64 | >=64 | >=64 | >=64 | >=64 | >=64 | >=64 | >=64 | >=64 | >=32 | >=64 | >=64 | >=64 |
| CC50 | 1.4 | 5.82 | 4.92 | 2.16 | 1.94 | 0.94 | 0.94 | 7.1 | 1.72 | 1.65 | 3.2 | 2.58 | 1.24 | 2.27 |
| CC50/SA | 2.8 | 2.91 | 2.46 | 2.16 | 1.94 | 1.88 | 1.88 | 1.775 | 1.72 | 1.65 | 1.6 | 1.29 | 1.24 | 1.135 |
| Lipid II (Kd, µM) | 0.03 | 0.2 | 0.24 | 0.6 | 1.2 | 0.07 | 0.78 | 2.3 | 0.43 | 0.08 | 1.03 | 3.6 | 0.9 | 1.3 |

FIG. 19B

| | 57 | 8 | 29 | 9a | 56 | 38 | 87 | 36 | 7 | 14a | 22 | 28 | 6jc48-1 | 7jc47-1 |
|---|---|---|---|---|---|---|---|---|---|---|---|---|---|---|
| S. aureus MRSA 1094 | 1 | 1 | 2 | 0.5 | 1 | 1 | 2 | 1 | 1 | 0.5 | 0.5 | 0.5 | 32 | 4.41 |
| S. aureus HFH-30123 (MRSA) | 2 | 2 | 2 | 0.5 | 2 | 1 | 2 | 1 | 1 | 0.5 | 1 | 0.5 | 32 | 6.25 |
| E. faecalis ATCC 51299 (VRE) | 4 | 2 | 8 | 8 | 4 | 4 | 8 | 2 | 2 | 8 | 4 | 2 | 2.82 | 1.56 |
| E. faecium EF1509 (VRE) | 4 | 2 | 8 | 4 | 4 | 2 | 8 | 2 | 2 | 4 | 4 | 2 | 5.65 | 6.25 |
| E. faecium E118 (VRE) | 4 | 2 | 8 | 4 | 4 | 4 | 8 | 2 | 2 | 4 | 4 | 2 | >=64 | >=64 |
| K. pneumoniae NR-15410 (K) | >=64 | >=64 | >=64 | >=64 | >=64 | 32 | >=64 | 8 | >=64 | 32 | 32 | 8 | >=64 | >=64 |
| K. pneumoniae NR-15411 (K) | >=64 | >=64 | >=64 | 64 | >=64 | 64 | >=64 | 16 | >=64 | 32 | 64 | 16 | >=64 | >=64 |
| A. baumannii ATCC 19606 | 16 | 4 | 32 | 8 | 8 | 16 | 16 | 4 | 4 | 8 | 8 | 4 | >=64 | >=64 |
| P. aeruginosa PA01 | 16 | 4 | 16 | 8 | >=64 | 16 | 8 | 4 | 4 | 8 | 8 | 4 | >=64 | >=64 |
| P. aeruginosa X13273 | >=64 | >=64 | >=64 | >=64 | >=64 | >=64 | >=64 | 32 | >=64 | 64 | 64 | 8 | >=64 | >=64 |
| P. aeruginosa ATCC 27853 | >=64 | >=64 | 32 | >=64 | >=64 | >=64 | >=64 | 16 | >=64 | 64 | 64 | 8 | >=64 | >=64 |
| E. cloacae ATCC 13047 | >=64 | >=64 | >=64 | >=64 | >=64 | >=64 | >=64 | 64 | >=64 | >=64 | >=64 | >=64 | >=64 | >=64 |
| E. aerogenes ATCC 13048 | >=64 | >=64 | >=64 | >=64 | >=64 | >=64 | >=64 | 32 | >=64 | >=64 | >=64 | 32 | >=64 | >=64 |
| CC50 | 1.0849 | 0.935 | 2.222 | 0.4485 | 0.851 | 0.719 | 1.092 | 0.449 | <0.25 | <0.25 | <0.25 | <0.25 | >100 | >100 |
| CC50/SA | 1.0849 | 0.935 | 1.111 | 0.897 | 0.851 | 0.719 | 0.546 | 0.449 | <0.25 | <0.25 | <0.25 | <0.25 | 35.4 | 22.6 |
| Lipid II (Kd, μM) | 0.27 | 0.14 | 0.56 | 0.11 | 0.14 | 0.54 | 0.78 | 1.06 | 0.06 | 0.09 | 0.12 | 0.04 | 0.15 | 0.34 |

| Organism: | 4890-0291 |
|---|---|
| S. aureus MRSA 1094 | 4 |
| . aureus HFH-30123 (MRS. | 4 |
| E. faecium EF1509 (VRE) | 1 |
| pneumoniae NR-15410 (K | >=64 |
| pneumoniae NR-15411 (K | >=64 |
| A. baumanii ATCC 19606 | >=64 |
| P. aeruginosa PA01 | >=64 |
| P. aeruginosa X13273 | >=64 |
| P. aeruginosa ATCC 2785 | >=64 |
| E. cloacae ATCC 13047 | >=64 |
| E. aerogenes ATCC 13048 | >=64 |
| $CC_{50}$ vs. HeLa (µg/ml) | 7 |
| $CC_{50}$/MIC (based on E. | 7 |
| Lipid II binding (Kd µM) | 14.7±3 |

Compound 80

| ID | Strain | 14a | 14b | 22 | 24 | 25 | 27 | 28 | 29 | 30 | 36 | 38 | 39 | 40 | 56 | 57 | 58 |
|---|---|---|---|---|---|---|---|---|---|---|---|---|---|---|---|---|---|
| | | | | | Plate 3 | | | | | Compound 80 | | | | Plate 4 | | | |
| WTBF-13 | S. aureus MRSA 1094 | 0.5 | 1 | 0.5 | 0.5 | 2 | 1 | 0.5 | 2 | 1 | 1 | 1 | 2 | 2 | 1 | 1 | 4 |
| WTBF-133 | S. aureus HFH-30313 (MRSA) | 0.5 | 2 | 1 | 0.5 | 2 | 1 | 0.5 | 3 | 1 | 1 | 1 | 2 | 2 | 2 | 2 | 4 |
| WTBF-23 | E. faecalis ATCC 51299 (VRE) | 8 | 16 | 4 | 2 | 8 | 16 | 2 | 8 | 8 | 2 | 4 | 4 | 4 | 4 | 4 | 8 |
| WTBF-25 | E. faecium EF1509 (VRE) | 4 | 8 | 4 | 2 | 8 | 4 | 2 | 8 | >=64 | 2 | 4 | 4 | 4 | 4 | 4 | 8 |
| WTBF-49 | E. faecium F116 (VRE) | 4 | 8 | 8 | 8 | >=64 | 32 | 8 | >=64 | >=64 | 8 | 4 | >=64 | >=64 | >=64 | >=64 | >=64 |
| WTBF-262 | K. pneumoniae KH-15430 (KPC) | 32 | >=64 | 32 | 16 | >=64 | 32 | 8 | >=64 | >=64 | 16 | 32 | >=64 | >=64 | >=64 | >=64 | >=64 |
| WTBF-284 | K. pneumoniae BR-15411 (KPC) | 32 | >=64 | 64 | 16 | >=64 | 64 | 16 | 32 | 32 | 64 | 64 | 16 | 16 | >=64 | 16 | >=64 |
| WTBF-134 | A. baumannii ATCC 19606 | 8 | >=64 | 8 | 4 | >=64 | 8 | 4 | 16 | 16 | 16 | 16 | 16 | 16 | 8 | 16 | >=64 |
| WTBF-556 | Acinetobacter baumannii-0856 | 64 | >=64 | 64 | 16 | >=64 | 32 | 8 | >=64 | >=64 | 32 | >=64 | >=64 | >=64 | >=64 | >=64 | >=64 |
| WTBF-58 | P. aeruginosa M32278 | >=64 | >=64 | >=64 | >=64 | >=64 | >=64 | >=64 | >=64 | >=64 | >=64 | >=64 | >=64 | >=64 | >=64 | >=64 | >=64 |
| SOS-89 | P. aeruginosa ATCC 27853 | 64 | >=64 | 64 | 64 | >=64 | 32 | 32 | 32 | >=64 | 64 | >=64 | >=64 | >=64 | >=64 | >=64 | >=64 |
| WTBF-139 | C. cloacae ATCC 13047 | 16 | >=64 | 16 | 16 | >=64 | >=64 | 8 | >=64 | >=64 | 64 | >=64 | >=64 | >=64 | >=64 | >=64 | >=64 |
| WTBF-140 | E. aerogenes ATCC 13048 | 8 | >=64 | 8 | 4 | >=64 | 32 | 32 | >=64 | >=64 | 32 | >=64 | >=64 | >=64 | >=64 | >=64 | >=64 |
| CC50 | | <0.25 | 2.155 | <0.25 | <0.25 | 2.330 | <0.25 | <0.25 | 2.221 | 1.942 | 0.449 | 10.719 | 2.273 | 2.186 | 10.850954 | 1.0885 | 7.1002 |
| CC50/MRSA | | #VALUE! | #VALUE! | #VALUE! | #VALUE! | #VALUE! | #VALUE! | #VALUE! | 1.111 | 1.943 | 0.449 | 0.719 | 1.136 | 1.093 | 0.835054 | 1.0885 | 1.77538 |
| CC50/VRE | | #VALUE! | 0.271 | #VALUE! | #VALUE! | 0.267 | #VALUE! | #VALUE! | 0.278 | 0.486 | 0.225 | 0.359 | 0.568 | 0.543 | 0.212263 | 0.272 | 0.885759 |
| CC50/KPC | | #VALUE! | #VALUE! | #VALUE! | #VALUE! | 0.033 | #VALUE! | #VALUE! | 0.069 | 0.061 | 0.112 | 0.045 | 0.071 | 0.135 | #VALUE! | 0.068 | #VALUE! |
| CC50/AB | | <0.25 | 0.135 | <0.25 | <0.25 | 0.033 | <0.25 | <0.25 | 0.069 | 0.061 | 0.112 | 0.045 | 0.071 | 0.135 | #VALUE! | 0.068 | #VALUE! |

FIG. 22C

Compound ID — Plate 5

| Strain | 59 | 76 | 92 | 96 | 106 | 109 | BAS-00127538 | Date performed |
|---|---|---|---|---|---|---|---|---|
| S. aureus MRSA 1094 | 2 | 1 | 0.5 | 0.5 | 1 | 2 | 0.5 | 181024 |
| S. aureus HFH-30123 (MRSA) | 4 | 1 | 0.5 | 1 | 2 | 2 | 0.5 | 181031 |
| E. faecalis ATCC 51299 (VRE) | 8 | 8 | 8 | 2 | 8 | 16 | 4 | 181024 |
| E. faecium EF1509 (VRE) | 8 | 4 | 4 | 2 | 8 | 16 | 4 | 181024 |
| E. faecium F118 (VRE) | 4 | 4 | 4 | 2 | 8 | 8 | 4 | 181024 |
| K. pneumoniae NR-15410 (KPC) | >=64 | 64 | 32 | 32 | >=64 | >=64 | 16 | 181025 |
| K. pneumoniae NR-15411 (KPC) | >=64 | 64 | 32 | >=64 | >=64 | >=64 | 16 | 181025 |
| A. baumannii ATCC 19606 | >=64 | 8 | 4 | 4 | >=64 | 32 | 4 | 181030 |
| Acinetobacter baumannii -0056 | >=64 | 8 | 8 | 4 | 16 | 16 | 2 | 181030 |
| P. aeruginosa X13273 | >=64 | 32 | >=64 | >=64 | >=64 | >=64 | >=64 | 181030 |
| P. aeruginosa ATCC 27853 | >=64 | 32 | 64 | >=64 | >=64 | >=64 | >=64 | 181030 |
| E. cloacae ATCC 13047 | >=64 | >=64 | >=64 | >=64 | >=64 | >=64 | 64 | 181031 |
| E. aerogenes ATCC 13048 | >=64 | >=64 | >=64 | >=64 | >=64 | >=64 | 16 | 181031 |
| CC50 | 5.82735 | 1.722 | <0.25 | <0.25 | <0.25 | 2.581 | 1.166246626 | |
| CC50/SA | 2.91368 | 1.722 | #VALUE! | #VALUE! | #VALUE! | 1.291 | 2.332493252 | |
| CC90/EF | 0.72842 | 0.43 | #VALUE! | #VALUE! | #VALUE! | 0.161 | 0.291561656 | |
| CC50/AB | #VALUE! | 0.215 | #VALUE! | #VALUE! | #VALUE! | 0.081 | 0.291561656 | |

SMALL MOLECULE LIPID II INHIBITORS

CROSS-REFERENCE TO RELATED APPLICATIONS

This application is a continuation-in-part of and claims the benefit of U.S. application Ser. No. 16/064,276, filed Jun. 20, 2018, which is a 371 national stage application of PCT Application No. PCT/US16/067774, filed Dec. 20, 2016, and claims the benefit of provisional application 62/270,184, entitled "Small Molecule Lipid II Inhibitors," filed Dec. 21, 2015. The entire contents of these applications are incorporated herein in their entirety as if fully set forth herein.

GOVERNMENT FUNDING SUPPORT

This invention was made with government support under Grant No. AI092033 awarded by the National Institutes of Health. The government has certain rights in the invention.

BACKGROUND

1. Field of the Invention

The present invention generally relates to the field of medicine, and specifically to Lipid II (LII) binding agents which are novel antibiotic drugs which can be used in pharmaceutical compositions to treat bacterial infections. The disclosures herein relate, inter alia, to these molecules, their preparation, and their use.

2. Background of the Invention

The public is at increasing risk to emerging infectious diseases and resistant strains of bacteria. The development of resistant bacterial pathogens is rendering current antibiotics largely ineffective, making it essential that new drugs be developed to fight infections caused by these agents. LII is an essential precursor in bacterial membrane biogenesis and an established, yet underused target for antibiotics currently in clinical use. This invention, inter alia, provides small molecule LII inhibitors, identified based on the interaction between defensins, a family of natural antimicrobial peptides, and LII. Characterization of a preferred LII inhibitor reveals that it specifically binds to LII, targets bacterial cell wall synthesis, specifically acts against Enterococci and possesses in vivo efficacy in a murine model for sepsis. These findings indicate that small molecule LII inhibitors can serve as a novel class of antibiotic compounds to combat pathogenic infections caused by multi-drug resistant organisms.

The chemical pathway of bacterial cell wall biosynthesis is well studied and a validated target for the development of antibacterial agents. Cell wall biosynthesis involves two major processes: (1) the biosynthesis of cell wall teichoic acids and (2) the biosynthesis of peptidoglycan. Key molecules in these pathways, including enzymes and precursor molecules are attractive targets for the development of novel antibacterial agents.

LII is an amphipathic peptidoglycan named for the bactoprenol hydrocarbon chain which anchors it into the bacterial cell membrane. LII is essential for bacterial cell wall biosynthesis, but is also present in bacteria without a cell wall, and is believed to be a crucial structural molecule in bacteria. LII translocates across the cell membrane to deliver and incorporate a disaccharide-peptide building block to the peptidoglycan mesh.

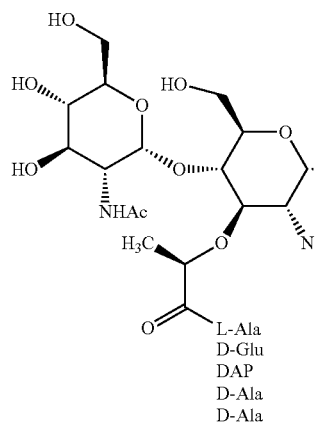
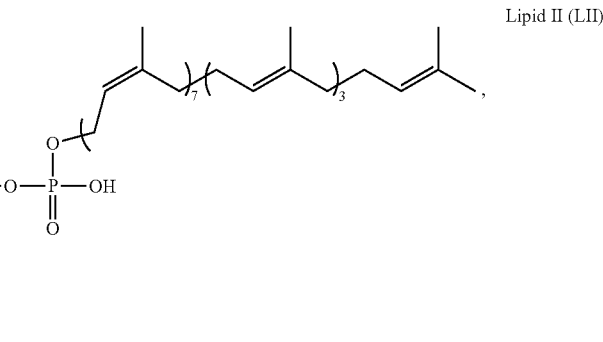
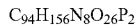

Lipid II (LII)

$C_{94}H_{156}N_8O_{26}P_2$

The cell walls of both Gram-negative and Gram-positive bacteria comprise a peptidoglycan layer which is composed of a polymer of alternating amino sugars (N-acetylglucosamine (GlcNAc) and N-acetylmuramic acid (MurNAc)). On the cytoplasmic side of the plasma membrane, the soluble precursor UDP-MurNAc-pentapeptide is linked to the membrane carrier bactoprenol-phosphate ($C_{55}P$), yielding Lipid I (LI). In a second step, GlcNac is added by the enzyme MurG to yield LII. LII is essential for cell wall biosynthesis, is synthesized in limited amounts, and has a high turnover rate, making it an attractive target for antibacterial compounds.

Various classes of natural antibiotic peptides have been discovered that bind LII, including depsipeptides, lantibiotics, cyclic peptides and glycopeptides. Of these, vancomycin and its more recently developed derivatives daptomycin, oritavancin and telavancin, are approved as first line treatments for Gram-positive infections. However, resistance to these drugs is increasingly reported. Several studies on defensins, effector peptides of innate immunity, revealed specific interactions of defensins with LII, adding another class of natural compounds to the growing list of structurally unrelated peptides that bind this target. Based on the interaction between LII and human neutrophil peptide-1 (HNP1), this study produced, for the first time, low molecular weight synthetic compounds that target LII with high specificity and affinity. The compound, BAS00127538 (also sometimes referred to herein as "6jc67" or "compound 6jc67"), was characterized further and revealed a unique interaction with LII that differs from antibiotics currently in clinical use or development. In this study, the structural and functional relationships of derivatives of BAS00127538, and their uses, are reported.

SUMMARY OF THE INVENTION

The di-benzene-pyrylium-indolene inhibitor of Lipid II, termed BAS00127538 or 6jc67 (1-methyl-2,4-diphenyl-6-((1E,3E)-3-(1,3,3-trimethylindolin-2-ylidene)pro-p-1-en-1yl)pyryl-1-ium) tetrafluoroborate), is the first small molecule LII inhibitor and is structurally different from natural agents that bind LII, such as vancomycin.

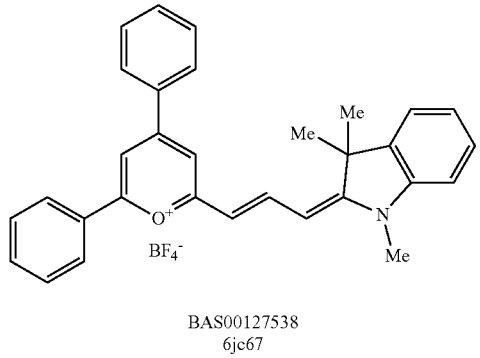

BAS00127538
6jc67

Here, the synthesis and biological evaluation of new analogs of this compound is described. These compounds are designed to investigate the structure-activity relationships of the molecule scaffold. The results provided here indicate an activity map of the scaffold and identify regions of the molecule that affect cytotoxicity, LII binding, and the range of antibacterial action. Compounds according to Formula I and Formula II showed particularly enhanced drug-like properties compared to BAS00127538. Compound 6jc48-1 showed particularly enhanced drug-like properties compared to BAS00127538.

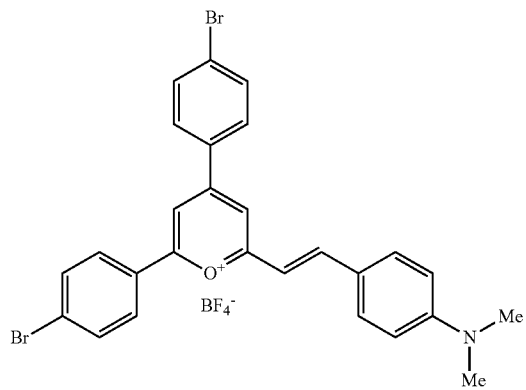

6jc48-1

Compound 6jc48-1 ((E)-2,4-bis(4-bromophenyl)-6-(4-(dimethylamino)styryl)pyrylium boron tetrafluoride salt) has reduced cytotoxicity, but retains specific LII binding and activity against *Enterococcus* spp. in vitro and in vivo. In addition, Compound 6jc48-1 was stable in plasma and had a markedly improved pharmacokinetic profile, with a half-life of over 13 hours upon intravenous administration. These results suggest that scaffolds like that of Compound 6jc48-1 provide a basic structure for small molecule antibiotic drugs that target LII. See Compound 6jc48-1 Scaffold (Formula I) structure below. Active compounds include but are not limited to those compounds according to Formula I.

Formula I

Compound 6jc48-1 Scaffold

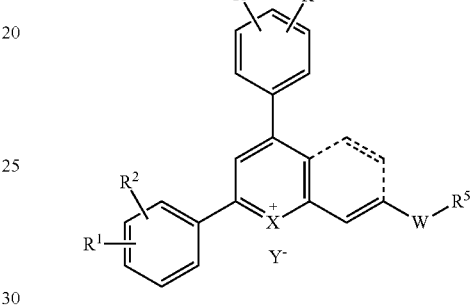

wherein each $R^1$, $R^2$, $R^3$ and $R^4$ independently is H; halogen; trihalomethyl; —$OR^6$; —$NHR^6$; —$NR^6R^6$; $C_1$-$C_6$ alkyl optionally substituted with amino or halo; $C_1$-$C_6$ tert-alkyl; $C_5$-$C_7$ cycloalkyl optionally substituted with amino or halo; $C_4$-$C_6$ cycloheteroalkyl optionally substituted with amino or halo; aryl optionally substituted with amino or halo; or heteroaryl optionally substituted with amino or halo, wherein each $R_6$ independently is H, $C_1$-$C_6$ alkyl, $C_5$-$C_7$ cycloalkyl, $C_4$-$C_6$ cycloheteroalkyl, aryl or heteroaryl and wherein halo is chloride, fluoride or bromide; wherein W is a bond, —$CH_2$—, —CH—, —$CH_2$—CH—, —CH—$CH_2$—, —CH═CH—, —CH═CH—$CH_2$—, or —$CH_2$—CH═CH—; wherein R5 is a mono-, bi- or tri-cyclo group containing 4-18 carbon atoms and optionally containing one or more nitrogen heteroatoms, which optionally is substituted with an amino group, a methyl group, an ethyl group, or a halogen, wherein halo is chloride, fluoride or bromide; wherein X is O, S or $NR_7$, wherein $R_7$ is H, methyl, or ethyl; wherein Y is an anion; and wherein the dotted lines indicate an optional ethenyl group.

Generally preferred compounds are those wherein $R_1$ is H, methyl, ethyl, t-butyl, bromo, fluoro, or chloro; $R^2$ is H, methyl, ethyl, t-butyl, bromo, fluoro, or chloro; W is a bond, methyl, or ethenyl; $R^3$ is a substituted or unsubstituted mono-, bi- or tri-cyclo group containing 4-14 carbon atoms and optionally containing one or more nitrogen heteroatoms, such as a phenyl, indolino, quinolino or pyridoquinolino group, wherein the optional substitution is an amino, methyl, ethyl, methylamino, dimethylamino, halogen or trihalomethyl group; X is oxygen; and Y is $BF_4^-$.

The disclosures herein describe an invention that includes small molecule compounds, methods of synthesis and intermediate compounds, and methods for their use in killing bacteria and treating bacterial infection.

The invention therefore relates to compounds according to:

Formula 1

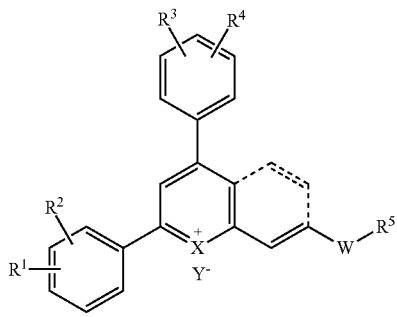

wherein each $R^1$, $R^2$, $R^3$ and $R^4$ independently is H; halogen; trihalomethyl; —$OR^6$; —$NHR^6$; —$NR^6R^6$; $C_1$-$C_6$alkyl optionally substituted with amino or halo; $C_1$-$C_6$ tert-alkyl; $C_5$-$C_7$ cycloalkyl optionally substituted with amino or halo; $C_4$-$C_6$ cycloheteroalkyl optionally substituted with amino or halo; aryl optionally substituted with amino or halo; or heteroaryl optionally substituted with amino or halo, wherein each $R^6$ independently is H, $C_1$-$C_6$ alkyl, $C_{5-7}$ cycloalkyl, $C_4$-$C_6$ cycloheteroalkyl, aryl or heteroaryl and wherein halo is chloride, fluoride or bromide; wherein W is a bond, —$CH_2$—, —CH—, —$CH_2$—CH—, —CH═CH—, —CH═CH—$CH_2$—, or —$CH_2$—CH═CH—; wherein $R^5$ is a mono-, bi- or tri-cyclo group containing 4-18 carbon atoms and optionally containing one or more nitrogen heteroatoms, which optionally is substituted with an amino group, a methyl group, an ethyl group, or a halogen, wherein halo is chloride, fluoride or bromide; wherein X is O, S or $NR^7$, wherein $R^7$ is H, methyl, or ethyl; wherein Y is an anion; and wherein the dotted lines indicate an optional ethenyl group.

Compounds wherein each $R^1$, $R^2$, $R^3$ and $R^4$ independently are in the meta or para position are preferred, as are compounds wherein each $R^1$, $R^2$, $R^3$ and $R^4$ independently are selected from the group consisting of H, bromine, methyl, ethyl, and tert-alkyl. In addition, compounds wherein $R^5$ is p-dimethylaminophenyl optionally substituted with halogen, trihalomethyl, —$OR^4$, —$NHR^4$, —$NR^4R^4$, $C_1$-$C_6$ alkyl, $C_5$-$C_7$ cycloalkyl, $C_4$-$C_6$ cycloheteroalkyl, aryl, heteroaryl; 1H-indol-3-yl; 1-methyl-1H-indol-3-yl; or 1,2,3, 5,6,7-hexahydropyrido(3,2,1-ij)quinolin-9-yl, and 1,3,3-trimethylindolin-2-ylidene also are preferred.

Compounds wherein halo is bromide or wherein W is selected from the group consisting of a bond, —CH═CH— and —CH═CH—CH═, or wherein Y is $BF_4^-$ also are preferred. Specific compounds according to the invention include those selected from the group consisting of compounds 6jc39, 6jc43-1, 6jc48-1, 6jc48-2, 6jc51-1, 6jc51-2, 6jc53-2, 6jc58, 6jc59-1, 6jc59-2, 6jc59-3, 6jc64-1, 6jc64-2, 6jc64-3, 6jc65-1, 6jc65-2, 6jc66-1, 6jc66-2, 6jc66-3, 6jc66-4, 6jc67, 6jc69-1, 6jc69-3, 6jc69-4, 6jc76-1, 6jc76-2, 6jc77-1, 6jc77-2, 7jc46-1, 7jc47-1, and 7jc47-2. More preferred compounds include those selected from the group consisting of compounds 6jc48-1, 6jc58, 6jc66-3, 6jc66-4, 6jc67, 6jc77-1, 6jc77-2, 7jc46-1, 7jc47-1, and 7jc47-2. Most preferred compounds include those selected from the group consisting of compounds 6jc48-1, 6jc67, 7jc46-1, 7jc47-1, and 7jc47-2; and most particularly compound 6jc48-1.

The invention also relates to pharmaceutical compositions comprising a pharmaceutically acceptable vehicle and a compound of Formula I, above, including compounds 6jc39, 6jc43-1, 6jc48-1, 6jc48-2, 6jc51-1, 6jc51-2, 6jc53-2, 6jc58, 6jc59-1, 6jc59-2, 6jc59-3, 6jc64-1, 6jc64-2, 6jc64-3, 6jc65-1, 6jc65-2, 6jc66-1, 6jc66-2, 6jc66-3, 6jc66-4, 6jc67, 6jc69-1, 6jc69-3, 6jc69-4, 6jc76-1, 6jc76-2, 6jc77-1, 6jc77-2, 7jc46-1, 7jc47-1, and 7jc47-2. More preferred compounds for use in a pharmaceutical composition include those selected from the group consisting of compounds 6jc48-1, 6jc58, 6jc66-3, 6jc66-4, 6jc67, 6jc77-1, 6jc77-2, 7jc46-1, 7jc47-1, and 7jc47-2. Most preferred compounds for use in a pharmaceutical composition include those selected from the group consisting of compounds 6jc48-1, 6jc67, 7jc46-1, 7jc47-1, and 7jc47-2; and most particularly compound 6jc48-1.

The invention also involves a method of treating a subject in need for bacterial infection, comprising administering to the subject a compound of Formula I. In preferred embodiments, the subject suffers from infection with *Enterococcus* spp., such as *E. faecalis* and *E. faecium*. In preferred embodiments, the subject suffers from infection with a bacterium selected from the group consisting of *E. faecalis, E. faecium. Staphylococcus aureus, Bacillus anthracia*, and *Acinetobacter baumanii*. In additional preferred embodiments, the bacterial infection is an infection with an antibiotic-resistant bacterial strain.

In further embodiments, the invention comprises a method of synthesizing a compound according to Formula I:

Formula I

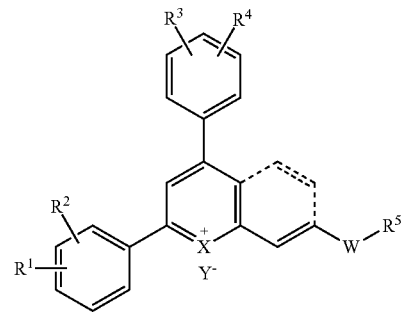

wherein each $R^1$, $R^2$, $R^3$ and $R^4$ independently is H; halogen; trihalomethyl; —$OR^6$; —$NHR^6$; —$NR^6R^6$; $C_1$-$C_6$ alkyl optionally substituted with amino or halo; $C_1$-$C_6$ tert-alkyl; $C_5$-$C_7$ cycloalkyl optionally substituted with amino or halo; $C_4$-$C_6$ cycloheteroalkyl optionally substituted with amino or halo; aryl optionally substituted with amino or halo; or heteroaryl optionally substituted with amino or halo, wherein each $R^6$ independently is H, $C_1$-$C_6$ alkyl, $C_{5-7}$ cycloalkyl, $C_4$-$C_6$ cycloheteroalkyl, aryl or heteroaryl and wherein halo is chloride, fluoride or bromide; wherein W is a bond, —$CH_2$—, —CH—, —$CH_2$—CH—, —CH═CH—, —CH═CH—$CH_2$—, or —$CH_2$—CH═CH—; wherein $R^5$ is a mono-, bi- or tri-cyclo group containing 4-18 carbon atoms and optionally containing one or more nitrogen heteroatoms, which optionally is substituted with an amino group, a methyl group, an ethyl group, or a halogen, wherein halo is chloride, fluoride or bromide; wherein X is O, S or $NR^7$, wherein $R^7$ is H, methyl, or ethyl; wherein Y is an anion; and wherein the dotted lines indicate an optional ethenyl group; comprising the steps:

(1) condensing a compound of Formula A, a compound of Formula B and a compound of Formula C, with an acidic reagent to obtain compound of Formula D

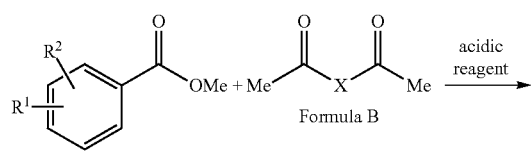

Formula A + Formula B → (acidic reagent)

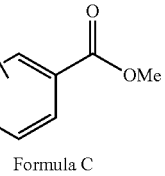

Formula C

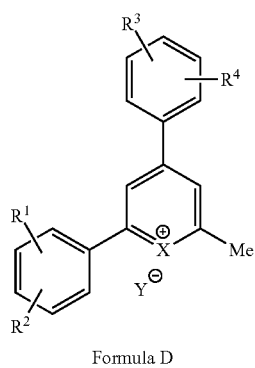

Formula D (2) optionally condensing Formula D with W—R⁵ to obtain compound of Formula I

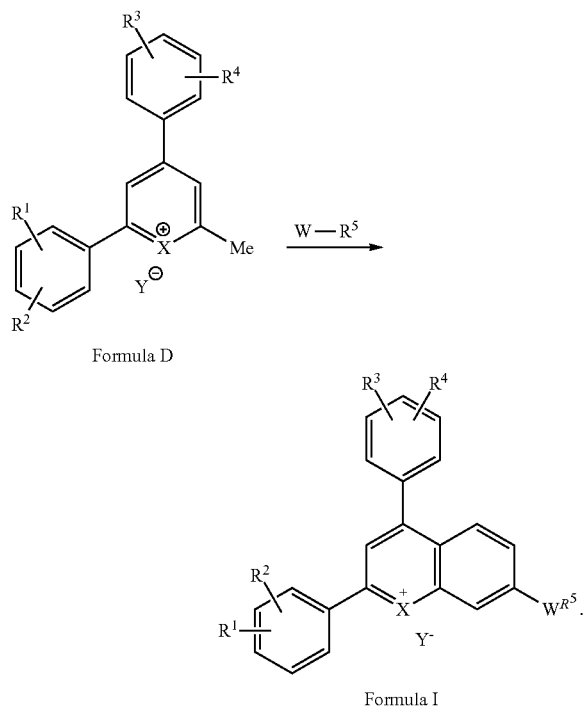

Formula D → (W—R⁵) → Formula I

In preferred embodiments, the acidic reagent is boron trifluoride etherate and/or W is selected from the group comprising: —CH$_2$—, —CH═CH—, —CH═CH—CH—, and —CH═CH—CH═. Yet further embodiments of the invention include a method of killing or reducing bacteria comprising contacting the bacteria with a compound of Formula I, and a method of killing or reducing bacteria on an object comprising contacting the object with a compound of Formula I and a method of protecting an object from colonization by bacteria comprising contacting the object with a compound of Formula I.

Additional compounds according to embodiments of the invention include compounds according to Formula II:

Formula II

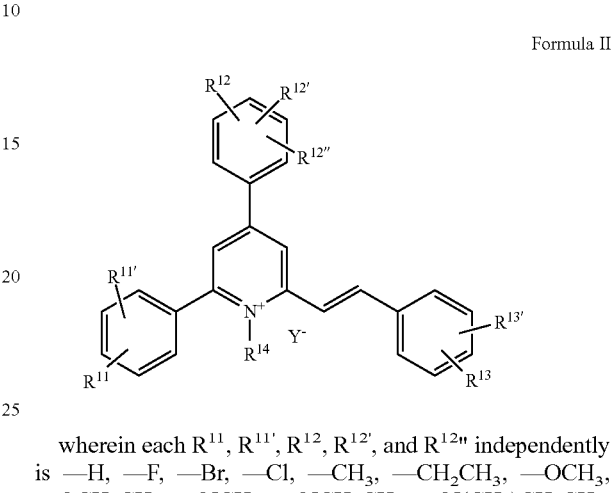

wherein each $R^{11}$, $R^{11'}$, $R^{12}$, $R^{12'}$, and $R^{12''}$ independently is —H, —F, —Br, —Cl, —CH$_3$, —CH$_2$CH$_3$, —OCH$_3$, —OCH$_2$CH$_3$, —NCH$_3$, —NCH$_2$CH$_3$, —N(CH$_3$)CH$_2$CH$_3$, —N(CH$_3$)CH$_2$CH$_2$OH, or —N(CH$_3$)CH$_2$CH$_2$CN;

wherein $R^{13}$ and $R^{13'}$ independently is —CH$_3$, —NCH$_3$, —NCH$_2$CH$_3$, —N(CH$_3$)CH$_3$, —N(CH$_3$)CH$_2$CH$_3$, —N(CH$_2$CH$_3$)CH$_2$CH$_3$, —N(CH$_3$)CH$_2$CH$_2$OH, or —N(CH$_3$)CH$_2$CH$_2$CN;

wherein $R_{14}$ is —CH$_3$, —CH$_2$CH$_3$, —CH$_2$CH(CH$_3$)CH$_3$, or -cyclohexyl; and wherein Y is an ion.

Specifically, the embodiments of the invention pertain to compounds according to:

Formula II

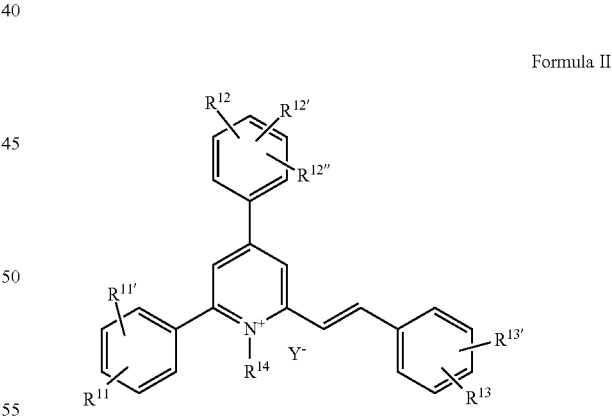

wherein each $R^{11}$, $R^{11'}$, $R^{12}$, $R^{12'}$, and $R^{12''}$ independently is —H, —F, —Br, —Cl, —CH$_3$, —CH$_2$CH$_3$, —OCH$_3$, —OCH$_2$CH$_3$, —NCH$_3$, —NCH$_2$CH$_3$, —N(CH$_3$)CH$_2$CH$_3$, —N(CH$_3$)CH$_2$CH$_2$OH, or —N(CH$_3$)CH$_2$CH$_2$CN;

wherein each $R^{13}$ and $R^{13'}$ independently is —CH$_3$, —NCH$_3$, —NCH$_2$CH$_3$, —N(CH$_3$)CH$_3$, —N(CH$_3$)CH$_2$CH$_3$, —N(CH$_2$CH$_3$)CH$_2$CH$_3$, —N(CH$_3$)CH$_2$CH$_2$OH, or —N(CH$_3$)CH$_2$CH$_2$CN;

wherein $R^{14}$ is —CH$_3$, —CH$_2$CH$_3$, —CH$_2$CH(CH$_3$)CH$_3$, or -cyclohexyl; and wherein Y is an ion.

Preferred compounds of formula II are those wherein wherein each $R^{11}$, $R^{11'}$, $R^{12}$, $R^{12'}$, and $R^{12''}$ independently is —H, —Br, —F, or —N(CH$_3$)CH$_2$CH$_2$OH, or —N(CH$_3$)CH$_2$CH$_2$CN;
wherein $R^{14}$ is —CH$_3$; wherein $R^{13}$ is —NCH$_3$, —NCH$_2$CH$_3$, —N(CH$_3$)CH$_2$CH$_3$, —N(CH$_3$)CH$_2$CH$_2$OH, or —N(CH$_3$)CH$_2$CH$_2$CN; wherein $R^{13'}$ is —H; and
wherein Y is 1.
Preferred compounds include:
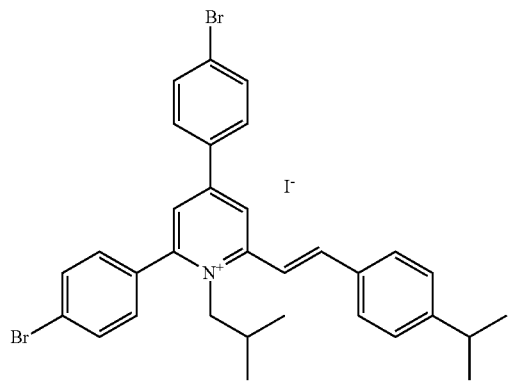
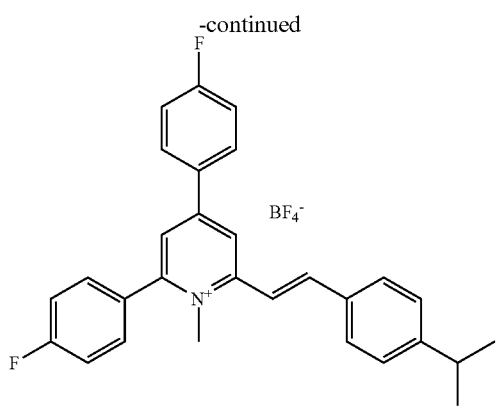
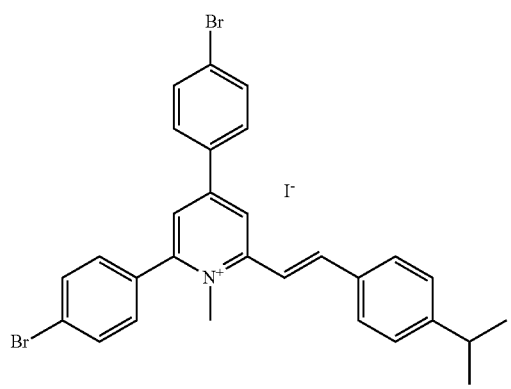
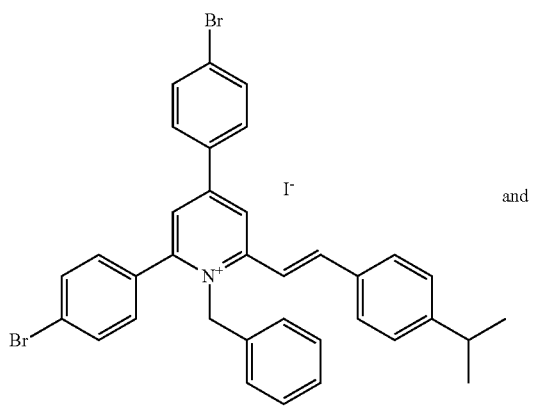
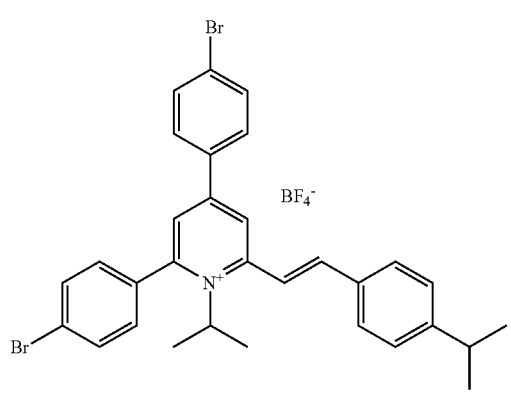
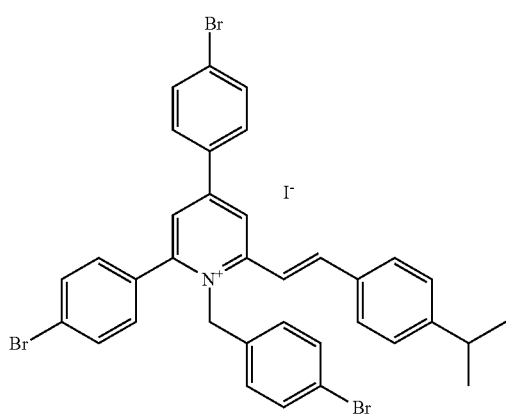
and Most preferred compounds include:

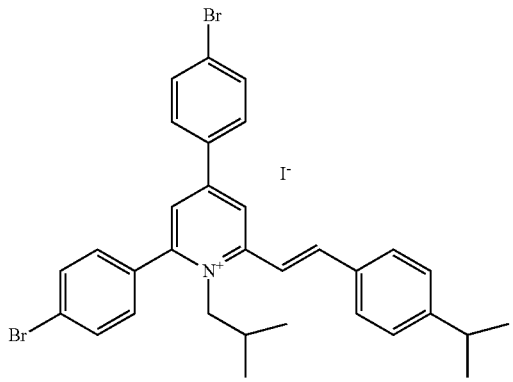

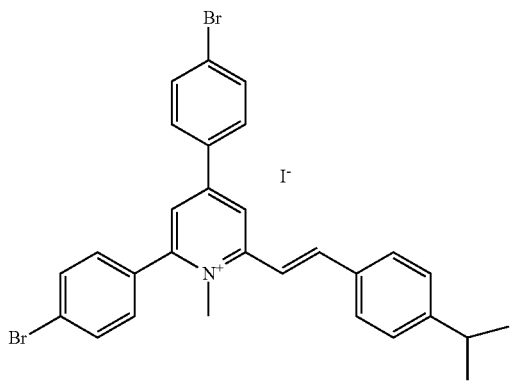

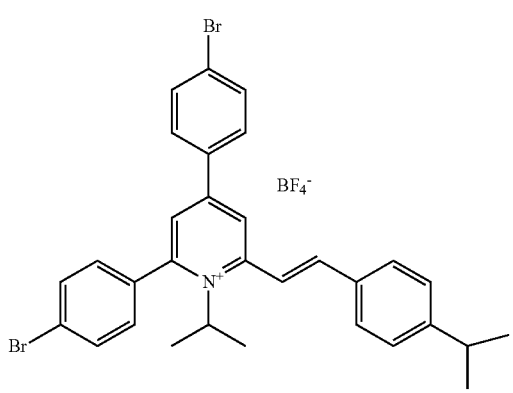

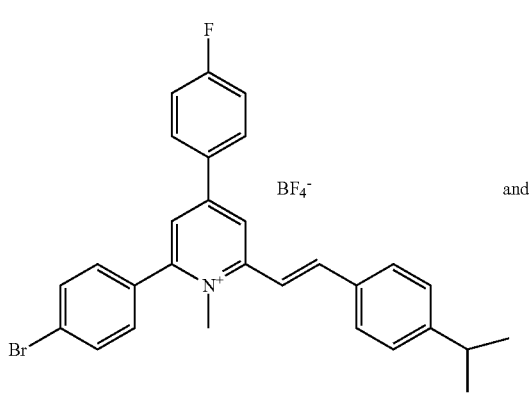

and

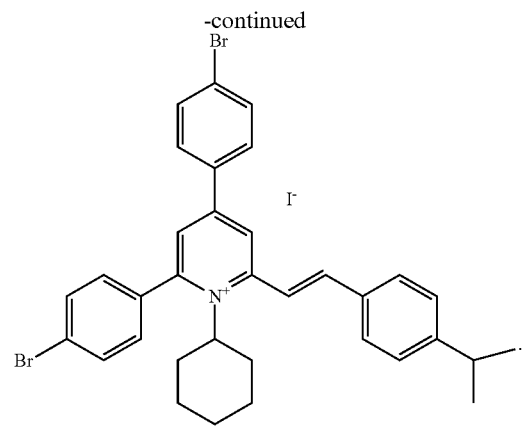

The invention relates to, in certain embodiments, the compound

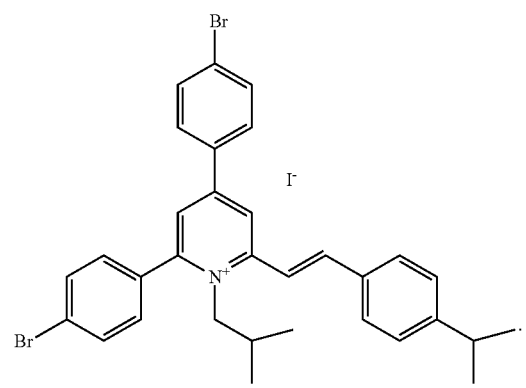 [SMILES: CC(C)C[n+]1c(/C=C/c2ccc(C(C)C)cc2)cc(-c2ccc(Br)cc2)cc1-c1ccc(Br)cc1 ; [I-]]

The invention relates to, in certain embodiments, the compound

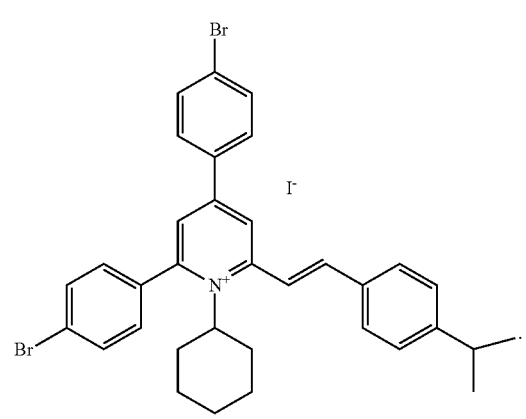 [SMILES: CC(C)c1ccc(/C=C/c2cc(-c3ccc(Br)cc3)cc(-c3ccc(Br)cc3)[n+]2C2CCCCC2)cc1 ; [I-]]

Embodiments of the invention also relate to pharmaceutical compositions comprising a pharmaceutically acceptable vehicle and a compound according to formula II, or any of the above structures.

Embodiments of the invention also relate to a method of treating a subject in need for bacterial infection, comprising administering to the subject a compound according to formula II, or any of the above structures, or a pharmaceutical composition comprising a pharmaceutically acceptable vehicle and a compound according to formula II, or any of the above structures.

Other embodiments of the invention include a method of treating a subject in need for bacterial infection, comprising administering to the subject a compound of formula II or any of the structures above. Preferably, in these embodiments, the subject suffers from infection with bacteria selected from the group consisting of E. faecalis, E. faecium, Staphylococcus aureus, Bacillus anthracis, and Acinetobacter baumanii.

Other embodiments of the invention include a method of killing or reducing bacteria comprising contacting the bacteria with a compound of formula II, a method of killing or reducing bacteria on an object comprising contacting the object with a compound of formula II, and a method of protecting an object from colonization by bacteria comprising contacting the object with a compound of formula II.

BRIEF SUMMARY OF THE DRAWINGS

The following drawings form part of the present specification and are included to further demonstrate certain embodiments of the present invention. The invention may be better understood by reference to one or more of these drawings in combination with the detailed description of specific embodiments presented herein.

FIG. 10A, FIG. 10B, FIG. 10C and FIG. 10D are a table showing the antibacterial activity of the indicated compounds.

FIG. 11A) and 6jc67 (BAS00127538) (MIC 2.mu·g/ml; FIG. 11B) on the macromolecular synthetic pathways for DNA, cell wall, protein, and lipid.

FIG. 16 is a table showing binding data for selected compounds to Lipid II.

FIG. 19A and FIG. 19B are a table presenting data on bacterial killing for the indicated compounds.

FIG. 22A, FIG. 22B, and FIG. 22C are tables containing a summary of MIC and CC50 data for the indicated compounds.

DETAILED DESCRIPTION OF EMBODIMENTS OF THE INVENTION

Figure 1A:
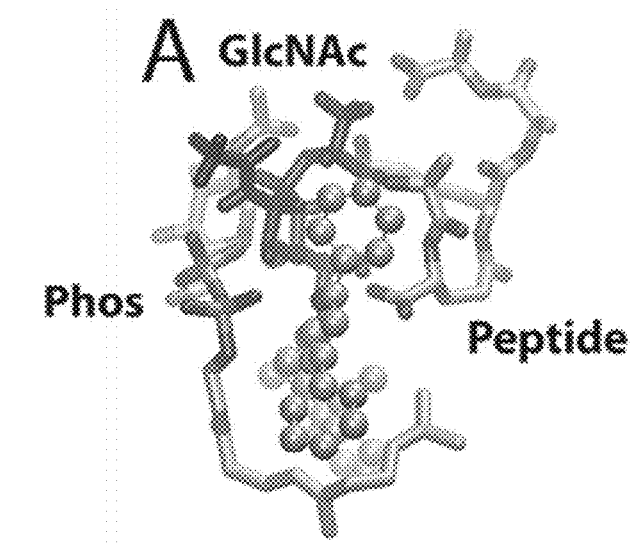
FIG. 1A and FIG. 1B are models of BAS00127538 (FIG. 1A) and compound 6jc48-1 (FIG. 1B), in complex with a LII analog. The compounds are shown in standard CPK atom format, with the Br atoms for compound 6jc48-1 shown as vdW spheres. The LII is in licorice representation. The phosphate (Phos), sugars (GlcNAc) and pentapeptide (Peptide) are indicated. The upper and lower panels of each of FIG. 1A and FIG. 1B are approximately 180° rotations of the complexes.
Figure 1A:
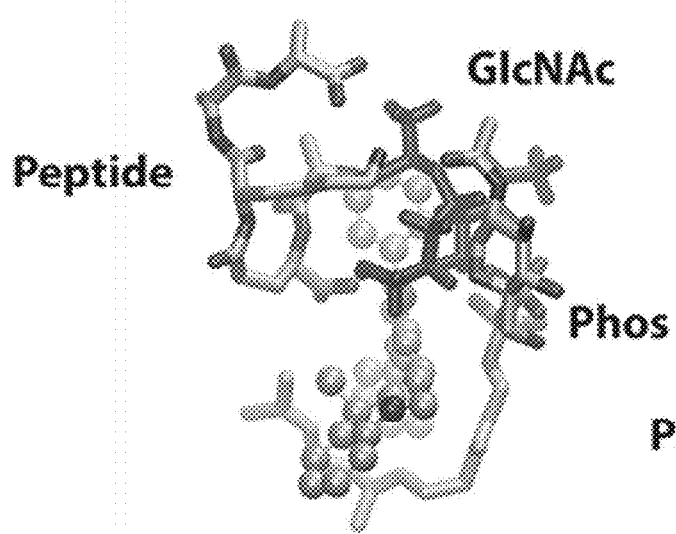
Figure 1B:
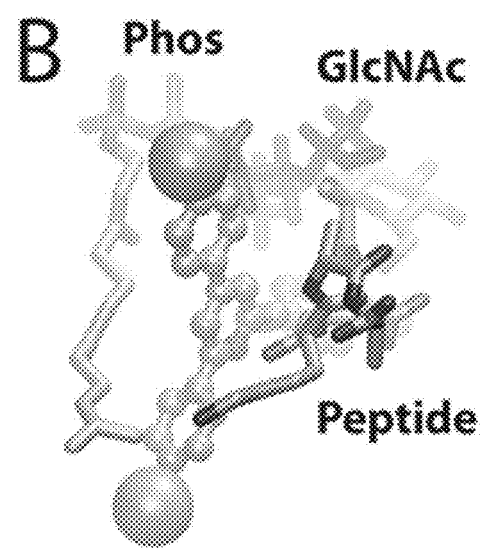
Figure 1B:
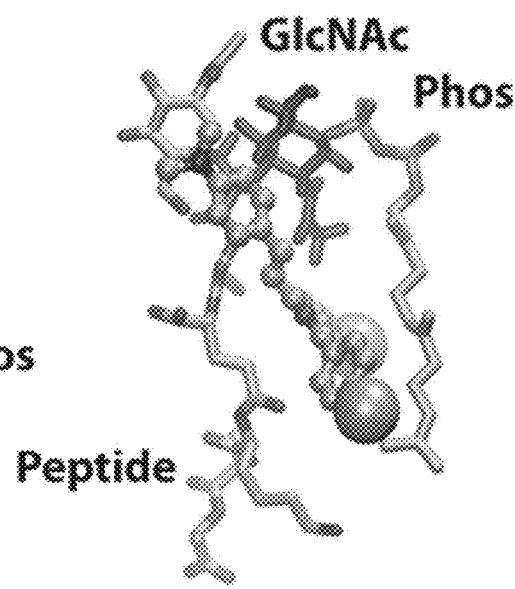

In the following description, for the purposes of explanation, numerous specific details are set forth in order to provide a thorough understanding of the present invention. It will be apparent, however, to one skilled in the art that the present invention may be practiced without these specific details. In order that the invention may be readily understood and put into practical effect, particular preferred embodiments will now be described by way of the text and non-limiting examples below.

1. Definitions

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as:

so dimensioned, about, approximately, substantially, essentially, consisting essentially of, comprising, and effective amount.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and intended to be non-limiting. Furthermore, where the description of one or more embodiments uses the term "comprising," those skilled in the art would understand that, in some specific instances, the embodiment or embodiments can be alternatively described using the language "consisting essentially of" and/or "consisting of."

The term "about," as used herein, means plus or minus 20 percent of the recited value, so that, for example, "about 0.125" means 0.125±0.025, and "about 1.0" means 1.0±0.2.

The term "scaffold" refers to the core region of a compound, or a generic chemical structure based on the compound, which contains the portion of the structure that imparts some or all of the appropriate binding and/or activity to the compound. Additional or modified moieties can be placed on the structure to optimize such binding and activity.

The term "subject" or "subject in need" as used herein refers to animals, such as mammals, or to organs an tissues of an animal, such as for transplant. Animals contemplated as subjects include humans, companion and service animals, farm animals, zoo animals, and the like, including humans; primates; dogs; cats; sheep; cattle; goats; pigs; horses; poultry such as chickens, turkeys, ducks, geese, and the like; mice; rats; rabbits; guinea pigs; and the like. The terms "subject," "patient," and "host" are used interchangeably. Preferably, the subject suffers from or is susceptible to a condition caused by or involving infection by bacteria. Most preferably, the subject suffers from or is subject to a condition that does lead or could lead to bacteremia of the blood (sepsis), of the urinary tract, of the intra-abdominal and pelvic region, of the heart valve (endocarditis), of the lungs, of the central nervous system, or lead to complicated or acute soft skin and tissue infections (SSTIs) and the like. Treatment of infections associated with medical devices and equipment such as ventilator-associated pneumonia (VAP) or central-line associated blood stream infections (CLAB-SIs) and the like obtained in a hospital or community setting are included. These infections generally are caused by bacteria, such as Gram-positive or Gram-negative bacteria, including, but not limited to any species of Actinobacteria, Firmicutes, Tenericutes, Aquificae, Bacteriodetes, Deinococcus, Fusobacteria, Gemmatemonadetes, Nitrospirae, Planctomycetes, Verrucomicrobia, Proteobacteria, Spirochaetes, and Synergistetes. Preferred bacteria are Gram-positive. Most preferred are Enterococci spp., Staphylococci spp., or Streptococci spp.

The compounds and methods of the invention also can be used to reduce or kill bacteria in excised tissues of the animal body, such as organs and tissues for transplant, and can be used on objects that can be subject to undesirable colonization by bacteria, or used to protect food and food service items from colonization and/or infection by bacteria. Therefore, the term subject can loosely refer to the whole organism or to parts thereof.

The term "pharmaceutically acceptable" in respect of salts, ingredients or carriers and the like in pharmaceutical products, and in compounds used in or on the living body or tissues/organs of the body, refers to any convenient compound or group of compounds that are not toxic and that do not destroy or significantly diminish the pharmacological or antibacterial activity of the agent with which it is formulated. Such pharmaceutically acceptable carriers or vehicles encompass any of the standard pharmaceutically accepted solid, liquid, or gaseous carriers known in the art, such as those discussed in the art.

2. Overview

This invention involves identifying and optimizing small molecule antagonists of LII. A lead compound, BAS00127538, was structurally optimized to reduce cytotoxicity, increase in vivo stability and retain activity against Enterococci bacterial pathogens. In the United States, Enterococci infections in hospital settings are the second most common and vancomycin resistance is on the rise. The compound 6jc48-1, a preferred compound, retained activity against Enterococci spp., specifically, a result that is somewhat surprising. The parent scaffold of BAS00127538 is potent against *S. aureus* and Enterococci, yet it displays broad-range antibacterial activity, including activity against Gram-negative species. Without wishing to be bound by theory, one possible explanation could be variations of LII composition between different bacterial species, which would cause differences in binding and/or activity. For example, amidation of the D-iso-glutamine residue of LII has been described in strains of *S. aureus*, resulting in reduced sensitivity to the glycopeptide antibiotics such as vancomycin. This modification has not been found in vancomycin-resistant Enterococci spp.

Additional variations, such as differences in amino acid linkage between peptidoglycan subunits or variations in the MurNac/GlnNac moieties of LII could further potentiate binding of the benzoaldehyde moiety of 6jc48-1, but not the indolene moiety in the BAS00127538 scaffold. This is consistent with the model of the 6jc48-1 interactions shown in FIG. 1. The second major difference between parent BAS00127538 structure and compound 6jc48-1 is reduced cellular cytotoxicity. Mechanism-of-action studies revealed that compound 6jc48-1 does not inhibit protein synthesis to the same extent as BAS00127538. Since the incorporation of bromines in the para positions of the phenyl rings of the parent scaffold did not reduce cytotoxicity (compound 6jc67A), the indolene moiety in BAS00127538 likely contributes to cytotoxicity. The model revealed similar interactions of the parent scaffold and compound 6jc48-1 with LII, possibly suggesting that the indolene moiety in the parent BAS00127538 molecule contributes to the interference of protein synthesis as a cause for cytotoxicity. Studies showed that in the interaction of BAS00127538 with LII, the pyrylium interacts with phosphate; the indolene interacts with isoprenyl; and the diphenyl interacts with muramic acid. These three distinct interactions are referred to as: (a) a phosphate-pyrylium ionic interaction; (b) N-acetyl muramic acid-phenyl stacking; and (c) alkyl chain-indolene hydrophobic interactions.

The present in vitro and in vivo data indicate that the oxonium moiety in compound 6jc48-1 is chemically stable.

In a previous study, replacement of the positively charged oxygen with nitrogen increased antibacterial activity and LII binding, but did not lead to an improvement of cytotoxicity in the BAS00127538 scaffold. Introducing this change in the compound 6jc48-1 scaffold could further enhance its antibacterial spectrum while maintaining low cytotoxicity.

3. Summary of Results

A structure-to-activity (SAR) study of the small molecule LII antagonist BAS00127538 has identified compound 6jc48-1, which displays improved drug-like properties compared to the parent scaffold. Compound 6jc48-1 is stable and efficacious in vivo, has low toxicity and can be administered intravenously and orally. Synthesized BAS00127538 (compound 6jc67) was found to have the same activity as the commercially available product. Compound 6jc67-A, the methyl analog of BAS00127538, also had the same activity. Using an optimized scaffold, compound 6jc48-1 was produced and found to have a 50-fold reduction in cytotoxicity compared to the parent BAS00127538 compound while retaining antimicrobial activity against vancomycin-resistant (VRE) Enterococci spp.

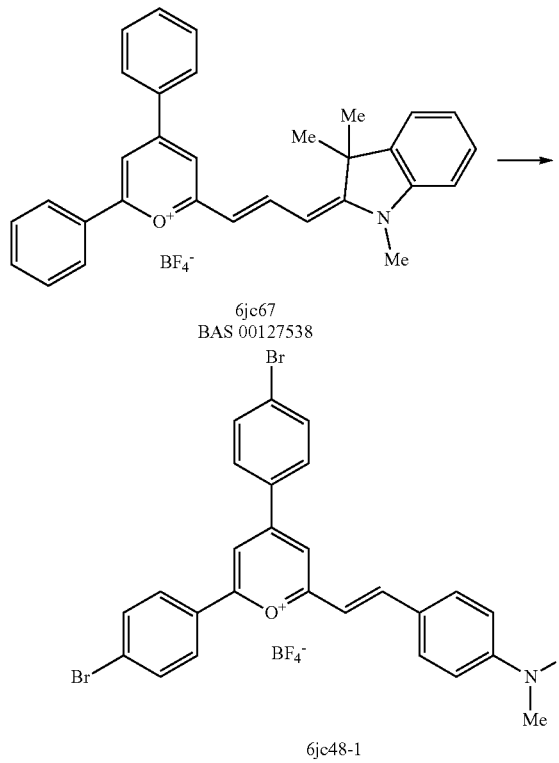

Molecular models of BAS00127538 and compound 6jc48-1 complexed with LII, while qualitative in nature, indicate that the overall interaction pattern of the two compounds with LII are similar, though specific differences are present, suggesting that variations of the scaffold can lead to further improvements or changes in activity. The compound 6jc48-1 scaffold, together with increased understanding of scaffold functionality that impact LII interactions as well as bioavailability considerations, facilitate the development of the first small molecule antibiotic that targets LII. Therefore, the following compounds are preferred compounds contemplated as part of this invention, and are useful as antibiotic compounds for use in treatment: 6jc39, 6jc43-1, 6jc48-1, 6jc48-2, 6jc51-1, 6jc51-2, 6jc53-2, 6jc58, 6jc59-1, 6jc59-2, 6jc59-3, 6jc64-1, 6jc64-2, 6jc64-3, 6jc65-1, 6jc65-2, 6jc66-1, 6jc66-2, 6jc66-3, 6jc66-4, 6jc67, 6jc69-1, 6jc69-3, 6jc69-4, 6jc76-1, 6jc76-2, 6jc77-1, 6jc77-2, 7jc46-1, 7jc47-1, and 7jc47-2.

Preferred compounds include: 6jc48-1, 6jc58, 6jc66-3, 6jc66-4, 6jc67, 6jc77-1, 6jc77-2, 7jc46-1, 7jc47-1, and 7jc47-2, and most highly preferred compounds include: 6jc48-1, 6jc67, 7jc46-1, 7jc47-1, and 7jc47-2. See Table 5 for structures.

4. Embodiments of the Invention

A. Ligand Design Strategy

A molecular model of the interaction of BAS00127538 with a LII analog was obtained, consistent the NMR data obtained. See Varney et al., Turning defense into offense: defensin mimetics as novel antibiotics targeting lipid II. PLoS Pathog. 9(11):e1003732, 2013. The model is shown in FIG. 1A with LII. In the model, the two phenyl rings and the pyrylium wrap around LII with the positive charge of the pyrylium being in the vicinity of the Lipid II phosphates, one phenyl ring interacting with the sugar moiety and the second interacting with the top of the aliphatic tail. In addition, the indolene moiety also interacts with the aliphatic tail. Based on this interaction motif it can be hypothesized that the increased hydrophobicity of the phenyl groups would lead to more favorable interactions with the sugar moiety and aliphatic tail of lipid II. Similarly, the presence and nature of the indolene was varied as well as the pyrylium to ring linker length and composition to understand their impact the SAR. Throughout, the positively charged pyrylium was maintained given that previous results had shown that pyridinium was not active.

This led to the design, synthesis and experimental validation of the compounds shown in Table 5. Subsequent modeling of the preferred synthesized compound (6jc48-1) showed the binding orientation to be similar to that of BAS00127538 (see FIGS. 1B and 1C), though some variation in the LII conformation upon binding of compounds within the complex does occur. These include additional interactions of the bromophenyl moieties with the sugar and aliphatic moieties. In addition, the dimethylaniline analog in compound 6jc48-1 interacts with the peptidic portion of LII and the ligand is shifted further away from the phosphate moieties. In contrast, the indolene moiety of BAS00127538 seemingly interacts with the aliphatic chain of the C55 only.

The parent scaffold BAS00127538 is most potent against S. aureus and Enterococci, yet displays broad-range antibacterial activity, including activity against Gram-negative species. Compound 6jc48-1 retained activity against Enterococci spp. specifically. Compound EL-1 regained activity specifically against S. aureus, Enterococci and A. baumannii, which is highly desirable. One possible explanation could be variations of Lipid II composition between different bacterial species. For example, amidation of the D-isoglutamine residue of Lipid II has been described in strains of S. aureus resulting in reduced sensitivity to the glycopeptides such as vancomycin. This modification has not been found in vancomycin-resistant Enterococci spp. The Lipid II of A. baumannii contains a meso-2,6-diaminopimeloyl moiety linked to the second amino acid of the pentapeptide. Additional variations, such as differences in amino acid linkage between peptidoglycan subunits or variations in the MurNac/GlnNac moieties of Lipid II could further potentiate binding of analogues. These variations are consequential to antibiotic development, for example, the addition of a halogenated biphenyl group and an epi-vancosamine sugar moiety to oritovancin conferred clinically significant antibacterial activity against vancomycin resistant-Enterococci and *S. aureus* (VRE, VRSA).

B. Chemical Compounds

The compounds of the invention include, but are not limited to, any compounds containing the basic structure according to Formula I or Formula II. In general, structures according to these general formulas that have increased polar surface area are preferred. In addition, structures with a lower C log P (as a measure of hydrophilicity, or solubility) also are preferred. See the Examples for synthetic methods and structures.

C. Pharmaceutical and Other Products

The compounds discussed herein can be present in the form of pharmaceutically acceptable salts, acids, hydrates, and solvates, or as a base. These compounds can exist in amorphous form or in any crystalline form. Preferably, the pharmaceutical compositions comprise a therapeutically effective amount. Any pharmaceutically acceptable salt can be used, as may be convenient. Generally, these salts are derived from pharmaceutically and biologically acceptable inorganic or organic acids and bases or metals. Examples of such pharmaceutically acceptable salts include, but are not limited to: acetate, adipate, alginate, ammonium, aspartate, benzoate, besylate, bicarbonate, bisulfate, butyrate, citrate, camphorate, camphorsulfonate, carbonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, magnesium, maleate, malonate, mesylate, 2-naphthalenesulfonate, nicotinate, nitrate, oxalate, palmoate, pectinate, persulfate, 3-phenylpropionate, phosphate, picrate, pivalate, potassium, propionate, salicylate, sodium, succinate, sulfate, tartrate, thiocyanate, toluenesulfonate (tosylate) and undecanoate salts. The compounds described here are drawn, where appropriate, as boron tetrafluoride salts, which is a preferred salt.

The therapeutic agents of some embodiments are also meant to include any or all stereochemical forms of the therapeutic agents where they exist (i.e., the R and/or S configurations for each asymmetric center). Therefore, single enantiomers, racemic mixtures, and diastereomers of the therapeutic agents are within the scope of the invention. Also within the scope of the invention are steric isomers and positional isomers of the therapeutic agents.

The therapeutic agents of some embodiments are also meant to include compounds which differ only in the presence of one or more isotopically enriched atoms. For example, therapeutic agents in which one or more atom is replaced by, for example, deuterium, tritium, $^{13}$C, $^{14}$C (or any isotopic labels as commonly used in the art such as phosphorus, calcium, iodine, chlorine, bromine, or any other convenient element for isotopic labeling) are within the scope of this invention.

In a preferred embodiment, the therapeutic agents of some embodiments are administered as a pharmaceutical composition that includes a pharmaceutically acceptable carrier or vehicle. The terms "pharmaceutically acceptable carrier" or pharmaceutically acceptable vehicle" refer to any convenient compound or group of compounds that is not toxic and that does not destroy or significantly diminish the pharmacological activity of the therapeutic agent with which it is formulated. Such pharmaceutically acceptable carriers or vehicles encompass any of the standard pharmaceutically accepted solid, liquid, or gaseous carriers known in the art, such as those discussed in the art.

Suitable carriers depend on the route of administration contemplated for the pharmaceutical composition, and are well-known in the art. The forms which the pharmaceutical composition can take include, but are not limited to: tablets, capsules, caplets, lozenges, dragees, pills, oral solutions, powders for dilution, powders for inhalation, vapors, gases, granules, sterile solutions for injection, transdermal patches, buccal patches, inserts and implants, rectal suppositories, vaginal suppositories, creams, lotions, ointments, topical coverings (e.g., wound coverings and bandages, and the like).

The carriers can be liquid, semi-liquid, gaseous, semi-solid, or solid, and serve to contain and deliver the active agent to the subject in a convenient form. Liquid or semi-liquid carriers can be in the form of a solution, suspension, emulsion, oil, gel, and the like, and include, for example aqueous solution (e.g., saline solutions, phosphate-buffered saline solutions, Ringer's, and the like), oil-in-water or water-in-oil suspensions, creams, lotions, ointments, and the like. Gaseous carriers can include, for example air, oxygen, fluorocarbons, dispersing agents, and the like. Solid carriers can include, for example, starch (e.g., corn starch, potato starch, rice starch, and the like), cellulose (e.g., microcrystalline cellulose, methylcellulose, and the like), sugars (e.g., lactose, sucrose, glucose, and the like), clays, minerals (e.g., talc, and the like), gums, and the like.

Extended and sustained release compositions also are contemplated for use with and in the inventive embodiments. Thus, suitable carriers can include any of the known ingredients to achieve a delayed release, extended release or sustained release of the active components. These methods are well known in the art and the present invention is intended to include such carriers.

A non-inclusive list of types of carriers and vehicles contemplated for use with the invention follows: fillers, diluents, adjuvants, pH adjusters, containers (e.g., ampoules, bottles, pre-filled syringes, and the like), flavorings, preservatives, colorings, taste-masking agents, sweeteners, oils, solvents, solvents, solubility enhancers, saline solutions, emulsifiers, suspending agents, wetting agents, dispersants, binders, releasing agents, lubricants, and the like. The person of skill is able to select from the known compounds used in pharmaceutical formulation to achieve the desired qualities and to produce an attractive and useful product.

The compounds discussed here also can be formulated into a liquid, solid or gaseous formulation for application to the surface of objects or impregnated into objects for the purpose of curtailing bacterial growth and the potential for infection. Such formulations can be used to coat medical instruments for use in surgery (e.g., metal or plastic instruments or containers therefor, surgical drapes, sutures, surgical gloves, catheters, trocars, wound dressings and bandages, sponges, and the like, or any object for which protection from or reduction of biofilm or bacterial growth is desirable in a medical or veterinarian medical setting. The compounds can be applied to objects e.g., by coating spraying, soaking or dipping, or any convenient method prior to or during use.

In addition, the compounds are useful in the food industry. The compounds of the invention can be applied to (e.g., by coating spraying, soaking or dipping) an object such as food or food containers, food processing equipment or tools and instruments used in food preparation. Hence the invention also included methods of preventing or reducing bacterial growth on objects by contacting the object with the compounds of the invention or a composition containing the compounds.

Therefore, in general, the compounds of the invention can be used to kill or reduce bacteria on an object by contacting the object with the compound. Such contacting can include soaking, dipping, spraying, and the like with a solution or dispersion/suspension of the compound, or by forming a coating on the object by application of a solution, dispersion, suspension, gel, powder or any convenient form containing the compounds of the invention. The coating can be temporary, semi-permanent, or permanent. Porous materials can be soaked or sprayed with the compounds to impregnate the material.

D. Administration

The products of the invention are contemplated to be administered to a subject in need by any convenient route of administration available to the physician or other person of skill. This can be any route which the practitioner deems to be most effective or convenient using considerations such as the patient, the patient's general condition, and the specific condition to be treated. For example, routes of administration can include, but are not limited to: oral, intravenous injection or infusion, subcutaneous injection, intraarterial injection, intrathecal injection, intraperitoneal injection, local injection into a site of infection, potential infection or injury, injection into a tumor, rectal, vaginal, topical, nasal, buccal, transdermal, sublingual, inhalation, transmucosal, wound covering, and the like. More than one route of administration can be used in one subject or in different subjects undergoing a treatment, for example, topical and intravenous, local injection and oral, and the like.

Appropriate dosages can be determined by the practitioner or any skilled person, based on the size of the subject, the disease condition, the severity of the infection, the bacteria responsible, and other factors. In general, for intravenous administration, intramuscular injection, nasal delivery, or oral delivery, the compounds can be administered every week, every day, twice per day, three times per day, four times per day, six times per day, or more often, at a dose range of about 100 mg to about 4000 mg, or about 200 mg to about 3000 mg, or about 400 mg to about 2000 mg, for example at a dose of about 100 mg, 200 mg, 400 mg, 500 mg, 750 mg, 1000 mg, 1500 mg, 2000 mg, 2500 mg, 3000 mg or 4000 mg. Preferably, a pharmaceutical product containing about 400 mg to about 2000 mg is given every 4-12 hours, or the product is administered at about 1 mg/kg to about 30 mg/kg every 4-12 hours. Therefore, a product designed to deliver or contain these amounts of compound contains a pharmaceutically effective amount of the inventive compound.

When the compound is formulated for topical use, in a gel, lotion, cream, ointment, and the like, a suitable pharmaceutical composition contains about 0.1% to about 10% of the compound in a suitable carrier. Preferred pharmaceutical compositions for topical use contain about 0.5% to about 5% of the compound, or about 1% to about 5% of the compound, including about 0.1%, about 0.5%, about 1%, about 2%, about 3%, about 5%, about 7.5%, or about 10% of the compound. These concentrations can be w/w or w/v. Therefore, a product designed to deliver or contain these amounts of compound contains a pharmaceutically effective amount of the inventive compound. For nasal delivery, the compound is contained in a suitable delivery vehicle for spray, at a concentration of about 25% to about 90% of the compound, or about 50% to about 90% of the compound, or about 60% to about 75% of the compound (w/v). Therefore, a product designed to deliver or contain these amounts of compound contains a pharmaceutically effective amount of the inventive compound.

For application to an object, the compounds can be dissolved or suspended in any convenient solution such as water, sterile water, saline, alcohol, oil, and the like which is convenient for preparing a soaking or dipping solution, a spray, which later optionally can be dried. The compounds can be formulated as a solid, for example a powder, or in a semi-solid, such as a gel, for application to any object. For example a food container or a catheter can be soaked in the composition prior to use, or a wound dressing can be impregnated with the composition. In addition, the compounds can be formulated in a hand wash or hand sanitizer, for example, in order to clean and sanitize skin or other objects. Alternatively, food itself, skin or other objects can be sprayed with the composition, or the composition mixed into the food to reduce bacteria. In such compositions, the compounds preferably comprise about 0.01% (w/w) to about 20% (w/w) of the carrier for soaking or spraying solutions, or food products. More preferably, about 1% (w/w) to about 10% (w/w) is used, or most preferably 2% (w/w) to about 10% (w/w).

The inventive compounds can be used alone, or in combination with other antibiotic or bactericidal compositions such as are known in the art. For example in treatment for an infection, the compound can be administered as a monotherapy, or in combination with another agent, either simultaneously or sequentially administered. The inventive compounds also can be used as part of an antibiotic cocktail. More than one of the inventive compounds can be used together as well, as a treatment for infection in a subject, or as an applied composition for treatment of an object, as well as in combination with other known antibiotics.

E. Treatment

The compounds and pharmaceutical compositions of the invention are contemplated for use in the treatment of disease conditions related to the presence of bacteria in a subject. Primarily, the conditions involve an infection, as discussed above, and the like. Treatment of infections with a Gram positive organism is preferred, but treatment of infections with a Gram-negative organism or multiple organisms is contemplated also. Resistant strains of bacteria also are contemplated to be treated with the compounds and compositions of the invention. Preferably, the bacteria are *Enterococcus* spp., including *E. faecalis, E. faecium, S. aureus* (SA), including vancomycin-resistant *S. aureus* (VRSA), vancomycin intermediate resistant *S. aureus* (VISA) and methicillin resistant *S. aureus* (MRSA) strains, *Bacillus anthracia*, and *Acinetobacter baumannii*, including multi-drug resistant (MDR) strains. Preferably, the bacteria are antibiotic resistant, and most preferably vancomycin resistant.

Conditions which can be treated with the inventive compounds, compositions and methods include, but are not limited to the following: urinary tract infections (asymptomatic bacteriuria, catheter-associated infections, urosepsis, and the like), skin and soft tissue infections (SSTIs), bacteremia, biliary tract infections (e.g., cholecystitis and cholangitis, both community acquired and hospital acquired), diverticulitis, pancreatitis, peritonitis (e.g., spontaneous bacterial peritonitis, secondary peritonitis/GI perforation, peritonitis related to peritoneal dialysis, and the like), pelvic infectious disease, prophylaxis (e.g., pre-operative and pre-procedure use, use in transplantations for donors or recipients, neutropenic patients, and the like), central line-associated blood stream infections, central line associated infections, sepsis, catheter-related blood stream infections, infective endocarditis (native valve or prosthetic valve related), infections related to permanent pacemaker (PPM), infections related to implantable cardioverter-defibrillator (ICD), meningitis, brain abscess, infections related to a central nervous system shunt, pre- and postseptal orbital cellulitis, pneumonia (naturally-occurring, health-care acquired (HAP), or ventilator-associated (VAP), infections related to cystic fibrosis (e.g., treatment of S. aureus), skin infections, soft tissue infections, bone infections, surgical site infections (SSIs), serious, deep tissue infections (such as necrotizing fasciitis), anthrax (cutaneous, inhalational, or gastrointestinal), and the like.

The organisms to be treated with the inventive compounds can include any bacteria, but preferably are Gram-positive bacteria. Such organisms include, but are not limited to: Gram-positive bacteria such as any species of Staphylococcus or Enterococcus, for example Staphylococcus aureus (including methicillin-resistant S. aureus (MRSA), methicillin-sensitive S. aureus (MSSA), vancomycin-resistant S. aureus (VRSA), vancomycin-intermediate S. aureus (VISA), daptomycin-resistant S. aureus, and coagulase-positive S. aureus); coagulase-negative Staphylococci, drug-resistant Staphylococci, S. epidermidis, S. saprophyticus, E. faecalis, E. faecium, drug-resistant Enterococcus spp., vancomycin-resistant Enterococcus (VRE), and the like. Additional preferred organisms include, but are not limited to Bacillus anthracia and Acinetobacter baumannii, including multi-drug-resistant (MDR) A. baumannii.

F. Additional Modifications and Testing

Because the presence of a pyrylium moiety in 6jc48-1 is reactive toward nucleophiles, including water, amines, and thiols, the 6jc48-1 pyrylium scaffold was modified at certain positions as shown in Table 1, below, based on the generic structure of Formula II where Y is iodide or another suitable anion, such as $BF_4^-$.

Formula II

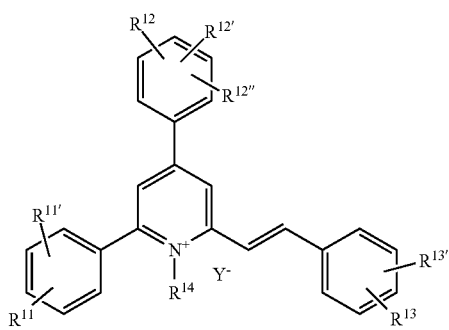

5. Examples

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1: Materials and Methods

A. Bacterial Strains

TABLE 1

Preferred Bacterial Strains.

| Bacterial Species | Accession Number | Source |
|---|---|---|
| Staphylococcus aureus | ATCC 29213 | MicrobiologicsTM (St. Cloud, MN) |
| Escherichia coli | ATCC 25922 | MicrobiologicsTM (St. Cloud, MN) |
| Enterococcus faecalis | ATCC 29212 | MicrobiologicsTM (St. Cloud, MN) |
| Streptococcus pneumonia | ATCC 49619 | MicrobiologicsTM (St. Cloud, MN) |
| Acinetobacter baumanii | ATCC 19606 | MicrobiologicsTM (St. Cloud, MN) |
| Enterococcus faecalis | ATCC 51575 | Laboratory of Pathology, University of Maryland Baltimore School of Medicine |
| Enterococcus faecalis | ATCC 51299 | Laboratory of Pathology, University of Maryland Baltimore School of Medicine |
| Enterococcus faecalis | REMEL C99707 | Laboratory of Pathology, University of Maryland Baltimore School of Medicine |
| Enterococcus faecium | ATCC 51559 (MDR) | Laboratory of Pathology, University of Maryland Baltimore School of Medicine |
| Enterococcus faecium | REMEL IH79985 | Laboratory of Pathology, University of Maryland Baltimore School of Medicine |
| Enterococcus faecium | REMEL C110914 | Laboratory of Pathology, University of Maryland Baltimore School of Medicine |

B. General Methods 1. 3-Lipid II Purification

Short-chain water-soluble LII containing a lipid tail of three isoprene units (3-LII) was generated and purified essentially according to methods known in the art. See Breukink et al., Lipid II is an intrinsic component of the pore induced by nisin in bacterial membranes. J. Biol. Chem. 278(22):19898-19903, 2003, the contents of which are hereby incorporated by reference. Typically, M. flavus vesicles (120 μmol lipid-Pi) were incubated together with 500 μmol UDP-GlcNAc, 500 μmol UDP-MurNAC-pentapeptide and 400 μmol farnesyl phosphate in 100 mM Tris-HCl pH 8.0, 5 mM $MgCl_2$. The incubation period was approximately two hours at room temperature for 3-LII (3-P). The synthesis of 3-Lipid II was followed by RP-8 reversed phase TLC (Merck™) developed with 75% methanol. For purification, the membranes were removed by centrifugation at 40,000×g; the supernatant was collected and loaded on a C18 HPLC column and eluted with a linear gradient from 50 mM ammonium bicarbonate to 100% methanol in 30 minutes. Farnesyl-Lipid II (3-Lipid II) eluted at approximately 60% methanol. Its identity was confirmed by mass spectroscopy.

2. Quality Control

Purity of the synthesized compounds was assessed was performed on a Sciex™ 6500 QTrap™ LC-MS/MS operated in Information Dependent Analysis (IDA) mode. The test compound was prepared at 5 µM and 500 nM in three matrices: 50/50 water/methanol, 50/50 water/methanol+ 0.1% formic acid and 50/50 water/methanol+10 mM ammonium bicarbonate. The IDA mass spectrometric method was designed to perform a full scan (20-700 Da) and obtain a product ion spectrum (MS/MS) from each of the 3 most abundant ions in the full scan. This IDA was run in both positive and negative mode. When operated in negative mode, a mobile phase of 50/50 water/methanol+10 mM ammonium bicarbonate was used. When operated in positive mode, a mobile phase of 50/50 water/methanol+0.1% formic acid was used. No LC column was employed, but an Agilent™ 1290 Infinity Liquid Chromatograph (Agilent Technologies™, Santa Clara, Calif.) was used to produce an isocratic flow for introduction of samples directly into the mass spectrometer. Each sample was directly injected into the mass spectrometer, via the autosampler, and the total run time for each sample was 2 minutes. Peak areas were analyzed using the Analyst software. MS/MS data were compared to full spectrum data to determine if the most abundant peaks were due to the test compound, impurity, or in-source fragmentation of the test compound. A percent purity was calculated from the ratio of the known peak areas to the total peak areas in each positive and negative mode. Calculated percent purities, in positive and negative modes, were weighted according to the total observed signal in the full scans and averaged.

3. Solubility

Solubility of compounds in water can be determined using a NEPHELOstar$^{plus}$™ laser nephelometer (BMG Labtech, Cary, N.C.) at a wavelength of 635 nm and bottom read optics using a 96-well plate format. For example, a solution of compound 6jc48-1 was prepared at a concentration of 2.5 mg/mL in DMSO. The DMSO solution (10 µL) was added to wells containing water (290 µL) for a final concentration of 125 µg/mL. The plate was incubated at room temperature for two hours prior to reading in the nephalometer. All samples were run in triplicate. Control samples (DMSO with no analyte) were prepared and run in parallel.

4. Plasma Protein Binding

Human plasma protein binding was determined using TRANSIL$^{XL}$ PPB™ plates (Sovicell, Leipzig, Germany). The compound 6jc48-1 (15 µL, 32% DMSO stock solution) was added to each well of a column (8 wells total) on a room temperature equilibrated plate. The plate was incubated for twelve minutes on a shaker at 1000 rpm then centrifuged for 10 minutes at 750×g to sediment the beads from the suspension. Aliquots (100 µL) were transferred from the supernatants to 96-well plate for MS analysis. Plasma protein binding data analysis was completed by using the supplied spreadsheet from the manufacturer (Sovicell™, User Guide TRANSIL™ PPB binding kit V2.01, 2013).

5. Animal Care

Care of the mice used in this study met or exceeded the standards set forth by the National Institutes of Health Guide for the care and use of laboratory animals and the AVMA panel on Euthanasia. All procedures in this study were approved by the Institutional Animal Care and Use Committee (IACUC) at the University of Maryland Baltimore School of Medicine. Adult C57BL/6J mice (about 18 grams, 8-10 weeks old) were used for all experiments. Mice were obtained from the Jackson Laboratory.™ (Bar Harbor, Me., USA) and housed in the IHV SPC animal core facility. Mice were fed standard chow (Harlan Laboratories.™) and water ad libitum.

C. Computer-Aided Drug Discovery Modeling and Molecular Dynamics Simulations

Molecular modeling, energy minimization and Molecular Dynamics (MD) simulations were performed with the program CHARMM using the CHARMM36 lipid protein and carbohydrate force field for LII; the TIP3P water model along with the CHARMM General force field was used for the ligands. Using the final snapshot from the 10 nsec MD simulations of the BAS00127538-LII complex in aqueous solution the aromatic rings of the 48-1 analogs were aligned with those of BAS00127538. The system then was subjected to a short energy minimization, following which a 100 ps MD simulation with an integration time step of 0.5 fsec was carried out. The system then was subjected to a 20 nsec MD simulation run with a time step of 1 fsec. Simulations were carried out in the NPT ensemble at 300° K and 1 Atm with SHAKE (an algorithm for applying holonomic constraints in the simulation of semiflexible molecules) of covalent bonds involving hydrogens. There were no restraints in the simulations. Free energies of binding, ΔG, were estimated using the linear interaction energy (LIE) method (see Vanommeslaeghe and Mackerell, Automation of the CHARMM General Force Field (CGenFF) I: Bond Perception and Atom Typing. J. Chem. Inf. Model. 52(12):3144-3154, 2012, the disclosures of which are hereby incorporated by reference), where α=0.5, β=0.16, γ cancels out because only the relative free energies (ΔΔG) were considered, and the unbound interaction energies were computed from 5 nsec MD simulations of the compounds alone in water. The final structures from the simulations were used for visualization of the ligand-LII interactions.

$$\Delta G = \alpha(\langle E_{bound}^{elec}\rangle - \langle E_{unbound}^{elec}\rangle) + \beta(\langle E_{bound}^{vdw}\rangle - \langle E_{unbound}^{vdw}\rangle) + \gamma$$

D. Surface Plasmon Resonance Determination of Lipid II Binding

Surface Plasmon Resonance binding experiments were carried out on a BIAcore T100 system (BIAcore™ Inc., Piscataway, N.Y.) at 25° C. The assay buffer was 10 mM HEPES, 150 mM NaCl, 0.05% surfactant P20, pH 7.4 (+3 mM EDTA) supplemented with 10% DMSO. 3-Lipid II (50 RUs) was immobilized on CM5 sensor chips using the amine-coupling chemistry recommended by the manufacturer. For initial determination of binding, compounds were introduced into the flow-cells (30.mu·1/min) in the running buffer at 10 µM. Resonance signals were corrected for nonspecific binding by subtracting the background of the control flow-cell. Binding to immobilized 3-LII on the chip surface was determined and scored "yes" in Table 5 when more than 20 Resonance Units or RUs were detected. Detection of less than 20 RUs was scored as "no", meaning no significant binding to LII. After each analysis, the sensor chip surfaces were regenerated with 50 mM NaOH for 30 seconds at a flow rate 100 µL/min, and equilibrated with the buffer prior to next injection. For binding kinetics studies, binding isotherms were analyzed with manufacturer-supplied software for BIAcore™ T100.

E. Antibacterial Activity Assay

Determination of the Minimal Inhibitory Concentrations (MIC) by dilution was carried out by broth dilution according to CLSI standards. See CLSI, Methods for Dilution Antimicrobial Susceptibility Tests for Bacteria That Grow Aerobically; Approved Standard—Eighth Edition. 2009, the contents of which are hereby incorporated by reference. Briefly, the minimum inhibitory concentration MIC, is the lowest concentration of a compound that prevents visible growth of a bacterium, in other words at which it has bacteriostatic activity. The lower the MIC, the more active the compound.

F. Cytotoxicity Testing

The cytotoxicity concentration of antibacterial compounds that produces half maximal decrease in viability (CC50) against mammalian cells (HeLa, ATCC CCL-2.2) was determined as described in Butler et al., Antibacterial activity and mechanism of action of a novel anilinouracil-fluoroquinolone hybrid compound. Antimicrob. Agents Chemother. 51(1):119-127, 2007, the contents of which are hereby incorporated by reference. The effect of compounds on HeLa cell viability was assessed in triplicate by measuring the mitochondrial activity using MTS assays according to the manufacturer's instructions (Cell Titer 96 proliferation assay, Promega™). The cells were incubated for 72 hours in RPMI1640 medium containing the compounds at final concentrations ranging from 64 to 0.125 µg/mL. CC50 was determined using a standard curve of serially diluted untreated cells in each experiment.

G. Macromolecular Synthesis (MMS) Assays

The effect of compounds on the macromolecular synthetic pathways of *E. faecalis* EF1509 were measured as follows. Cells were grown at 35° C. overnight on tryptic soy agar broth (Remel™, Lenexa, Kans.). Growth from the plate was used to inoculate 15 mL of Mueller Hinton Broth. The culture was grown to early exponential growth phase ($OD_{600}$=0.2 to 0.3) while incubating in a shaker at 35° C. and 150 rpm. For each macromolecular assay, the test agents 1499-1221 and BAS00127538 were added at either 0, 0.25-, 0.5-, 1-, 2-, or 4-fold their respective MIC values for *S. aureus* ATCC 29213. As positive control drugs, the following antibiotics were added at 8 times MIC in order to validate each assay: vancomycin (which targets cell wall synthesis), ciprofloxacin (which targets DNA synthesis), rifampin (which targets RNA synthesis), cerulenin (which targets lipid synthesis), and linezolid (which targets protein synthesis).

For DNA and protein synthesis experiments, 100 µL of cell culture reaching early exponential phase was added to triplicate wells containing various concentrations of test compound or control antibiotics (2.5 µL) at 40 times the final concentration in 100% DMSO (0.1% methanol in water for Rifampicin). A 2.5% DMSO-treated culture served as the "no drug" control for all experiments. Cells were added in 1.25 times strength MHB to account for the volume of drug added to each reaction, or in M9 minimal medium for protein synthesis reactions. Following a 5 minute incubation at room temperature either [³H]Thymidine (for DNA synthesis) or [³H]leucine (for protein synthesis) was added at 0.5-1.0 µCi per reaction. Reactions were allowed to proceed at room temperature for 15-40 minutes and then stopped by adding 12 µL of cold 5% trichloroacetic acid (TCA) or 5% TCA/2% casamino acids (protein synthesis). Reactions were incubated on ice for 30 minutes and the TCA precipitated material was collected on a 25 mm GF/1.2 pin PES 96 well filter plate (Corning™). After washing five times with 200 µL per well of cold 5% TCA, the filters were allowed to dry, and then counted using a Packard™ Top Count microplate scintillation counter.

For cell wall synthesis experiments, bacterial cells in early exponential growth phase were transferred to M9 minimal medium and added to 1.5 mL Eppendorf tubes (100 µL/tube) containing various concentrations of test compound or control antibiotics (2.5 µL) at 40 times the final concentration in 100% DMSO as described above. Following a 5-minute incubation at 37° C., N-acetyl-glucosamine (0.4 µCi/reaction) was added to each tube and incubated for 45 minutes in a 37° C. heating block. Reactions were stopped by addition of 100 µL of 8% sodium dodecyl(lauryl) sulfate (SDS) to each tube. Reactions were then heated at 95° C. for 30 minutes in a heating block, cooled, briefly subjected to centrifugation, and spotted onto pre-wetted hydroxylapatite (HA) filters (0.45 µM). After washing three times with 5 mL of 0.1% SDS, the filters were rinsed two times with 5 mL deionized water, allowed to dry, and then counted using a Beckman™ LS3801 liquid scintillation counter.

For lipid synthesis, bacterial cells were grown to early exponential growth phase in MHB and 100 µL was added to 1.5 mL Eppendorf tubes (in triplicate) containing various concentrations of test compound or control antibiotics as described above. Following a 5-minute incubation at room temperature, [³H] glycerol was added at 0.5 µCi per reaction. Reactions were allowed to proceed at room temperature for 40 minutes and then stopped by addition of 375 µL of chloroform/methanol (1:2) followed by vortexing for 20 seconds. Chloroform (125 µL) was then added to each reaction and vortexed, followed by the addition of 125 µL $dH_2O$ and vortexing again. Reactions were centrifuged at 13,000 rpm for 10 minutes, and then 150 µL of the organic phase was transferred to a scintillation vial and allowed to dry in a fume hood for at least 1 hour. Samples then were counted using liquid scintillation counting. Each data point provided is the average of three replicates and the error bars represent standard deviation.

Additional methods for performing macromolecular synthesis (MMS) assays includes removing samples of actively growing *S. aureus* NRS 77 cells and incubating them with the appropriate radioactive precursor for DNA (thymidine), RNA (uridine), lipid (glycerol), protein (leucine), or cell wall (N-acetyl-glucosamine) synthesis. Cells are separated from unincorporated radioactivity by filtration and then subjected to liquid scintillation counting. The following concentrations conveniently can be tested in the study: No drug, 0.25×, 0.5×, 1×, 2×, 4× and 8× the MIC (based upon the broth dilution MIC). The following antibiotics can be added at 8× the MIC in order to validate each assay: Vancomycin (cell wall synthesis); ciprofloxacin (DNA synthesis), rifampicin (RNA synthesis), cerulenin (lipid synthesis), and linezolid (protein synthesis).

H. Membrane Perturbation Assays

To examine the possibility that compounds perturbs membrane potential, these effects can be determined in an assay that measures the membrane-potential dependent uptake of the fluorescent dye $DiOC_2$(3). In addition, membrane activity can be confirmed using published assays that employ the fluorescent dyes $DiSC_5$(3) and SYTOX, which measure perturbation of membrane potential and membrane integrity, respectively.

I. In Vitro Absorption, Distribution, Metabolism, Excretion, Toxicity (ADMET) Studies For ADMET studies, liquid chromatography tandem mass spectrometry (LC-MS/MS) was used. Analysis was performed on a Sciex™ 6500 QTrap™ Triple Quadrupole Mass Spectrometer (Sciex™, Ottawa, Ontario) coupled with an Agilent™ 1290 Infinity Liquid Chromatograph (Agilent Technologies™, Santa Clara, Calif.). Separation was performed on a Halo™ C18 Column (2.7 µm, 2.1 mm×50 mm) (Advanced Materials Technology™, Wilmington, Del.) with mobile phase A (methanol with 0.1% formic acid) and mobile phase B (0.1% formic acid in water). A chromatographic ramp consisting of 0 min→3 min: 95% mobile phase B→95% mobile phase A, 3 min→3.1 min: 95% mobile phase A→95% mobile phase B, 3.1 min→6 min: 95% mobile phase B was employed. The chromatographic flow rate was 500 µL/min. The autosampler compartment was held at 10° C. The mass spectrometer was operated in positive, electrospray mode using multiple reaction monitoring (MRM). The following MS settings were employed: ion source temperature, 600° C.; capillary voltage, +5500V; curtain gas, 30; collision assisted dissociation (CAD) gas, medium; ion source gas 1, 50; and ion source gas 2, 70; declustering potential, 45V; entrance potential, 10V. The ion transitions were as follows: 525.9 Da→182.7 Da, collision energy=54 eV, collision cell exit potential=24V and 525.9 Da→155.0 Da, collision energy=94 eV, collision cell exit potential=19V were monitored. Peak areas were integrated using Analyst™ software (Sciex, Ottawa, Ontario).

J. Plasma Stability

Plasma stability of compounds can be determined as follows. For the compound 6jc48-1, plasma stability was determined using heparinized, pooled human plasma (BioreclamationIVT™, Hicksville, N.Y.). The test compound was spiked into plasma at a final concentration of 1 µM. The test compound solution was subsequently incubated at 37° C. for up to 1 hour. Aliquots were removed at 0, 5, 10, 20, 30, 40, 50 and 60 minutes incubation time and diluted 1:2 in cold acetonitrile. Samples were centrifuged at 4000 rpm for 10 minutes. Supernatant was collected and diluted 1:2 in 30% methanol in water. The diluted supernatant was analyzed by LC-MS/MS using the method described above. Stability in plasma was calculated by integrating peak areas of samples using Analyst™ software (Sciex™, Ottawa, Ontario).

K. Cytochrome P450 Inhibition Testing

Cytochrome P450 inhibition testing was conducted according to the method of Paradise et al. (2007) with modifications. Briefly, drug inhibition of the test compound was measured on specific cytochrome P450 enzymes using traditional substrates for CYP3A4, CYP2D6 and CYP2C19. Recombinant human CYP450 3A4, 2D6 and 2C19 enzymes (Supersome™) were obtained from Corning™. Supersomes™ typically have a CYP450 content of 1000-2000 pmol/mL. Standard substrates (mephenytoin, dextromethorphan, testosterone) were prepared at 500 µM in acetonitrile. The final concentration of each substrate was 1 µM. Positive control inhibitors and test compounds were prepared 50 times the final concentration in acetonitrile; 0.25 mM ketoconazole (inhibitor of 3A4), 25 µM quinidine (inhibitor of 2D6) and 5 mM tranylcypromine (inhibitor of 2C19). The typical $IC_{50}$ values for the standard inhibitor/substrate combinations are listed in Table 2, below. Eight concentrations of a positive control inhibitor, eight concentrations of test compound, a no inhibitor control and a background control were tested.

TABLE 2

Cytochrome P450 Inhibitor/Substrate Combinations.

| Enzyme | Substrate | Inhibitor | Time (min) | IC50 |
|---|---|---|---|---|
| CYP2C19 | Mephenytoin | 5 mM Tranycypromine | 45 | 2.5 µM |
| CYP2D6 | Dextromethorphan | 25 µM Quinidine | 30 | 23 nM |
| CYP3A4 | Testosterone | 0.25 mM Ketoconazole | 15 | 60 nM |

The test compound had a final concentration range from 20 µM to single-digit nanomolar. After a 10 minute pre-incubation at 37° C., a 2 times concentrated enzyme/substrate mixture was added to all samples with the exception of the background control. The enzyme/substrate solution contained 100 mM potassium phosphate buffer (pH 7.4), water, substrate, and 50 pmol/mL of the respective enzyme. The reactions were quenched with acetonitrile at the appropriate time points.

All samples were centrifuged for 3 minutes at 13,000×g at room temperature. The supernatant was collected for analysis by LC/MS/MS. For computation of the $IC_{50}$ values, the background of no-enzyme samples was averaged to determine the background value. The positive control or full-reaction samples were averaged to determine the signal value. The percent activity of each sample was calculated using the following equation:

[(Test compound metabolite-average background)/ (average signal-average background)]×100% activity.

GraphPad Prism™ software was used to plot the calculated percent activity values versus the log concentrations of test compound. The $IC_{50}$ value was calculated using non-linear regression. $IC_{50}$ values for standard inhibitors, calculated in-house, are shown in Table 2, above. Although the $IC_{50}$ values may vary slightly, literature reports demonstrate similar values (see Paradise et al., Cytochrome P450 inhibition assays using traditional and fluorescent substrates. Curr. Protoc. Pharmacol., 2007. Chapter 7: p. Unit7 11).

L. Liver Microsome Stability Testing

The in vitro microsome stability assay was performed using human liver microsomes and a Biomek FXP™ liquid handling workstation to deliver reagents to a deep 96-well plate on a shaking peltier with temperature controls. Human liver microsomes were purchased from Corning™. The test compound was incubated in an aqueous reaction mixture (200 µL total volume) consisting of human liver microsomes (150 mixed donor pool) and NADPH Regenerating System Solutions A and B (Corning™) in the presence of 100 mM potassium phosphate buffer (pH 7.4). NADPH Regenerating System Solution A comprises nicotinamide adenine dinucleotide phosphate (NADP+) and glucose 6-phosphate; NADPH Regenerating System Solution B contains glucose-6-phosphate dehydrogenase. Solutions A and B were combined prior to adding to the reaction plate to generate a supply of NADPH. The NADPH was added last to initiate the reactions simultaneously. The final concentration of the test compound was 10 µM and the microsomal protein concentration was 0.5 mg/mL. After incubation at 37° C., the reaction was terminated at 0, 5, 10, 20, 30, 40, 50 and 60 minutes, respectively, by the addition of 600 µL acetonitrile. Three replicates were run for each time point. The quenched reaction plate was centrifuged at 4500 rpm for 10 minutes. The supernatant was diluted 1:2 in 30% methanol in water for LC/MS/MS analyses to monitor substrate depletion. Water was substituted for NADPH for the zero time-point samples. A control plate, without NADPH cofactor, was completed on the same day, using the same conditions.

The half-life (t½) was calculated using the following equation:

$$t_{1/2} = \frac{-0.693}{\text{slope}},$$

where "slope" is the slope of the line formed by ln(% remaining test compound) vs. time. The in vitro intrinsic clearance (CL.sub.int) was calculated using equation:

$$CL_{int} = \left(\frac{0.693}{t_{1/2}}\right)\left(\frac{\text{incubation volume}(ul)}{\text{total microsomal protein(mg)}}\right).$$

The data were compared to a positive control, dextromethorphan, which exhibited a tin of 40 minutes and an intrinsic clearance value of 31 μL/min/mg, consistent with literature values (McNaney et al., ASSAY and Drug Development Technologies, Volume 6, Number 1, 2008).

M. Maximum Tolerated Dose (MTD)

To determine the maximum tolerated dose of a compound, the compound is administered intravenously or orally to groups of 2 male and 2 female ICR mice (23±3 g). Animals receive an initial dose of 10 mg/kg. If the animals survive for 72 hours, the dose for the next cohort is increased to 30 mg/kg. If animals survive for 72 hours, the dose is increased to 100 mg/kg. The testing stops when all animals survive at the upper bound, or when three (3) dose levels have been tested or when the upper or lower bound has been reached. At each dose level, animals will be observed for the presence of acute toxic symptoms (mortality, convulsions, tremors, muscle relaxation, sedation, etc.) and autonomic effects (diarrhea, salivation, lacrimation, vasodilation, piloerection, etc.) during the first 60 minutes then again at 2 hours. Body weights are recorded pre-dose and at 72 hours. The animals are observed and mortality noted daily after compound administration for 3 days. Gross necropsy is performed on all animals without tissue collection.

N. Acute Toxicity In Vivo

To determine acute toxicity, test compounds are administered for 7 days consecutively at a dosage determined by MTD. Three groups of animals (5 male, 5 female ICR mice) are assigned to vehicle, ⅓ of the MTD and 1 times MTD per dose in a suitable vehicle intravenously (iv) or orally (PO) in a volume of 5-10 ml/kg. The estimated animal number is 30 mice per compound per route. Animals are observed closely for mortality or signs of toxicity for 7 days. The following observations will be made up daily during the 7 day period: body weight, routine behavior (water drinking/eating, urination/defecation), gait (normal exploratory locomotion in open field), activity level (alertness in comparison with pre-treatment), grooming behavior after handling and righting reflex after a fall of approximately 2-3 inches. At 8 days post-treatment, surviving animals will be euthanized by $CO_2$ inhalation, followed by determination of clinical pathology (hematology, coagulation, serum chemistry). Macroscopic examination and tissue retention will be done for all animals. Organ weight is determined and tissues will be processed and examined microscopically by pathologists. Study will be performed by PDS Ltd.

O. Toxicokinetic Studies

Serum levels of compounds can be determined at 10, 30, 60, 120, 240, 360, 480 and 1440 minutes (PO) or 3, 10, 30, 60, 120, 240, 360 and 1440 min (IV) following single dose of each compound as determined by the MTD and toxicity studies to groups (12 male, 12 female for IV; 12 male, 12 female plus 3 animals as blank control for PO) of uninfected ICR mice. Blood will be collected by cardiac puncture and converted to plasma for determination of drug levels. The area under the concentration time curve (AUC, mg/h L), maximum concentration of compound in serum ($C_{max}$, mg/L) and terminal half-life ($t_{1/2}$, h) are calculated using serum LC/MS/MS analysis with internals standards determined for each compound. We will determine the MIC, the $C_{max}$/MIC and time during which the serum concentration remains over MIC (T>MIC, h) as selective parameters.

P. Bacterial Infection Models

*S. aureus* VRS-2 strain Hershey (MRSA, VRSA, (MIC>64), quinolones (LVX-R, CIP-R), macrolides (ERY-R, CLI-R), and trimethoprim sulfamethoxazole resistant), thigh infection. Groups of 5 male or female specific-pathogen-free ICR mice weighing 22±2 g are immunosuppressed by two intraperitoneal injections of cyclophosphamide. On day 0, animals are inoculated with pathogens. Vehicle, control antibiotic and compounds are then administered at MTD (IV, PO) 2 and 8 hours later (or per pK results). At 24 hours after treatment, animals are humanely euthanized with $CO_2$ asphyxiation. The muscle of the right thigh is harvested from each test animal. The removed tissues are homogenized and used for serial 10-fold dilutions and plated on nutrient agar plates for colony count (CFU/g) determination.

*Enterococcus faecalis* (ATCC 51575, VRE); peritonitis. Groups of 10 ICR derived male or female mice are inoculated intraperitoneally with a $LD_{90-100}$ dose. Vehicle, control antibiotic and compounds are then administered at MTD (IV, PO) 2 and 8 hours later (or per pK results). Mortality is recorded daily during the following 7 days. Prevention of mortality in 50 percent or more (≥50%) of the animals indicates significant activity. Simultaneously, blood will be collected from infected, satellite animals for pK determination (9 animals per route of administration) as described above.

*A. baumannii* strain that produces TEM-1D, ADC-25, OXA-23, and OXA-66 β-lactamases and is resistant to β-lactam antibiotics, aminoglycosides and quinolones, lung infection. Groups of 5 male or female specific-pathogen-free ICR mice weighing 22±2 g are immunosuppressed by two intraperitoneal injections of cyclophosphamide. On day 0, animals are inoculated with pathogens. Vehicle, control antibiotic and compounds are then administered at MTD (IV, PO) 2 and 8 hours later (or per pK results). At 24 hours after treatment, animals are humanely euthanized with $CO_2$ asphyxiation. Lung tissue is harvested from each test animal. The removed tissues are homogenized and used for serial 10-fold dilutions and plated on nutrient agar plates for colony count (CFU/g) determination.

Example 2: Exemplary General Chemical Syntheses

The general strategy for preparing BAS00127538 and new analogs of BAS00127538 is shown in Schemes 1, 2 and 3 below. This method allows for independent variation of R.sup.1 and the R.sup.2 groups in the scaffold.

General procedure for pyrylium salt synthesis (scheme 1):

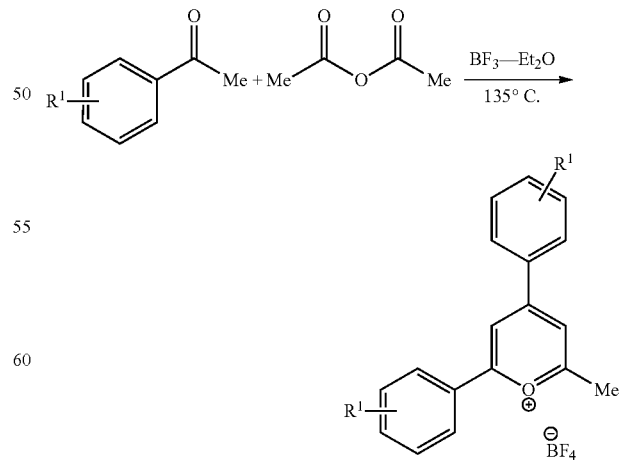

Boron trifluoride etherate (32.0 mmol) was added to a substituted acetophenone and acetic anhydride at room temperature. R' on the acetophenone can signify any desirable group or protected group for inclusion in the final product, but preferably is a halogen such as bromide or fluoride. Other salts can be used, including acetate, adipate, alginate, ammonium, aspartate, benzoate, besylate, bicarbonate, bisulfate, butyrate, citrate, camphorate, camphorsulfonate, carbonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, magnesium, maleate, malonate, mesylate, 2-naphthalenesulfonate, nicotinate, nitrate, oxalate, palmoate, pectinate, persulfate, 3-phenylpropionate, phosphate, picrate, pivalate, potassium, propionate, salicylate, sodium, succinate, sulfate, tartrate, thiocyanate, toluenesulfonate (tosylate) and undecanoate salts. The compounds described here are drawn, where appropriate, as boron tetrafluoride salts, which is a preferred salt. The reaction was heated to 135° C. for 4 hours, cooled, poured into EtOAc and allowed to stand for 1 hour. The resulting solid was filtered and washed with excess EtOAc to give the title compounds as the boron tetrafluoride salts. The $R^1$ groups can be any chemical moiety for testing, but preferably are, each independently, one or more of H, halogen, —$OR^2$, —$NHR^2$, unsubstituted or substituted $C_1$-$C_6$ alkyl, unsubstituted or substituted $C_5$-$C_7$ cycloalkyl, unsubstituted or substituted $C_4$-$C_6$ cycloheteroalkyl, unsubstituted or substituted aryl, or unsubstituted or substituted heteroaryl, and wherein the substitutions are selected from the group consisting of one or more of $C_1$-$C_5$ alkyl, $C_1$-$C_5$ alkenyl, $C_1$-$C_5$ alkynyl, amino, and halo; and wherein $R^2$ is H, alkyl, cycloalkyl, cycloheteroalkyl, aryl or heteroaryl.

General procedure for condensation reaction with aldehydes (scheme 2), wherein $R^1$ is defined as for Formula I:

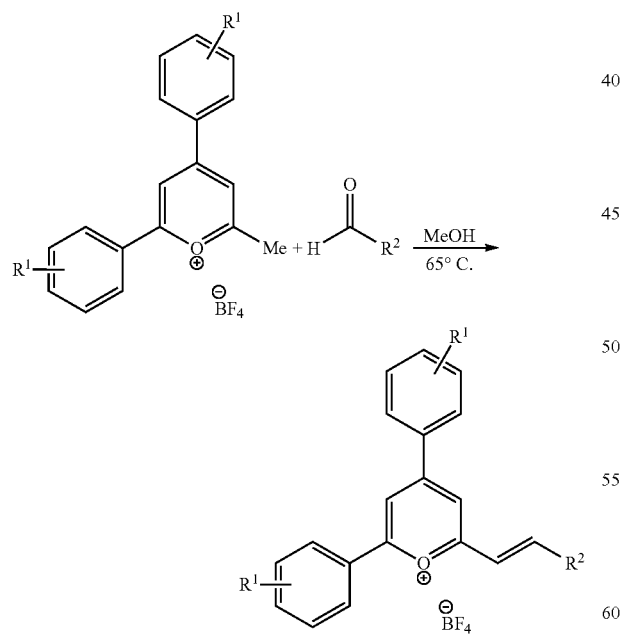

Pyrylium salt (0.28 mmol) and aldehyde (0.34 mmol) in MeOH (8 mL) was heated to reflux for 4 hours. The reaction was cooled, reduced in vacuo, poured into EtOAc and allowed to stand for 1 hour. The dark solid was filtered and washed with excess EtOAc to give the title compounds as the boron tetrafluoride salt. As discussed above, the $R^1$ groups can be any suitable group or protected group which is desired to be part of the final compound, but preferably are, each independently, one or more of H, halogen, —$OR^2$, —$NHR^2$, unsubstituted or substituted $C_1$-$C_6$ alkyl, unsubstituted or substituted $C_5$-$C_7$ cycloalkyl, unsubstituted or substituted $C_4$-$C_6$ cycloheteroalkyl, unsubstituted or substituted aryl, or unsubstituted or substituted heteroaryl, and wherein the substitutions are selected from the group consisting of one or more of $C_1$-$C_5$ alkyl, $C_1$-$C_5$ alkenyl, $C_1$-$C_5$ alkynyl, amino, and halo; and wherein $R^2$ is H, alkyl, cycloalkyl, cycloheteroalkyl, aryl or heteroaryl.

Figure 2:
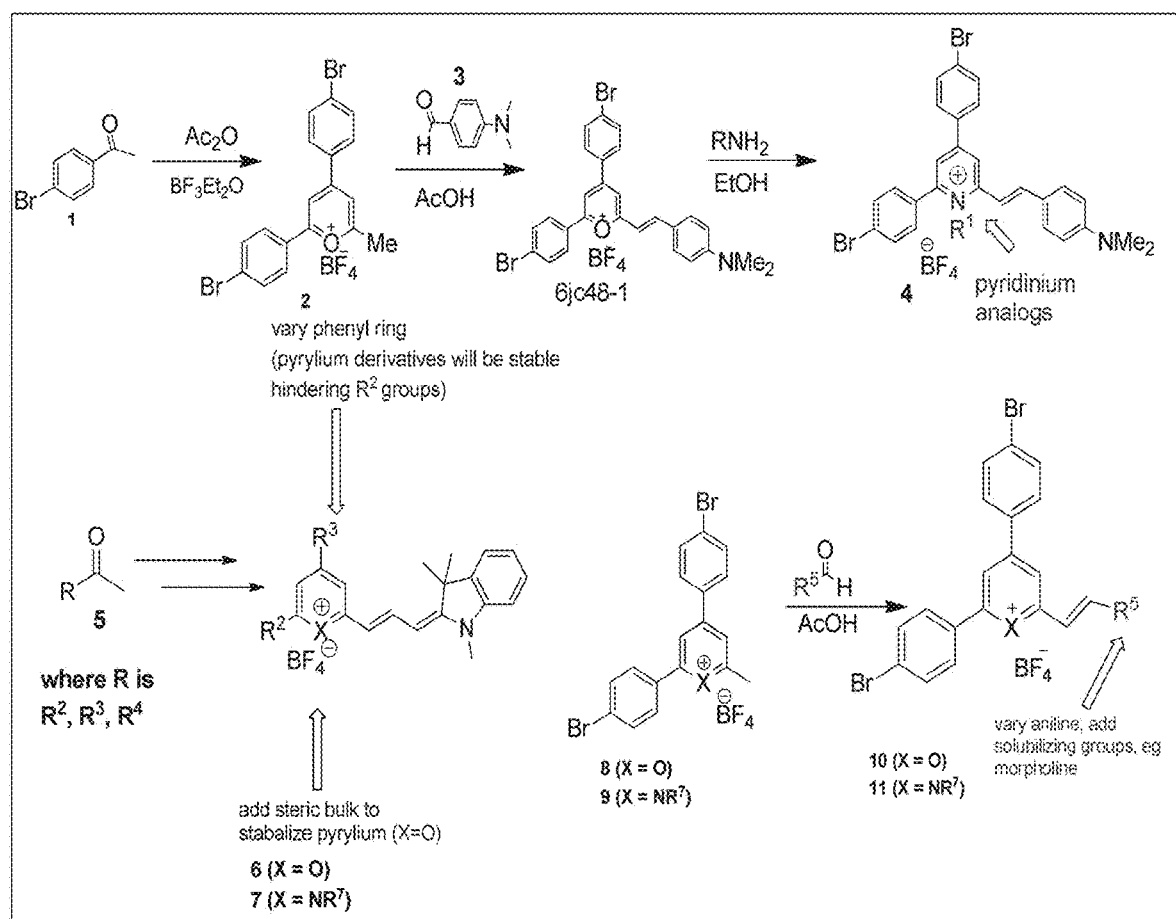
FIG. 2 shows a chemical synthetic scheme for the synthesis of BAS00127538.

General synthesis of the BAS00127538 scaffold showing some non-limiting preferred R group substituents for the indicated compounds is shown below:

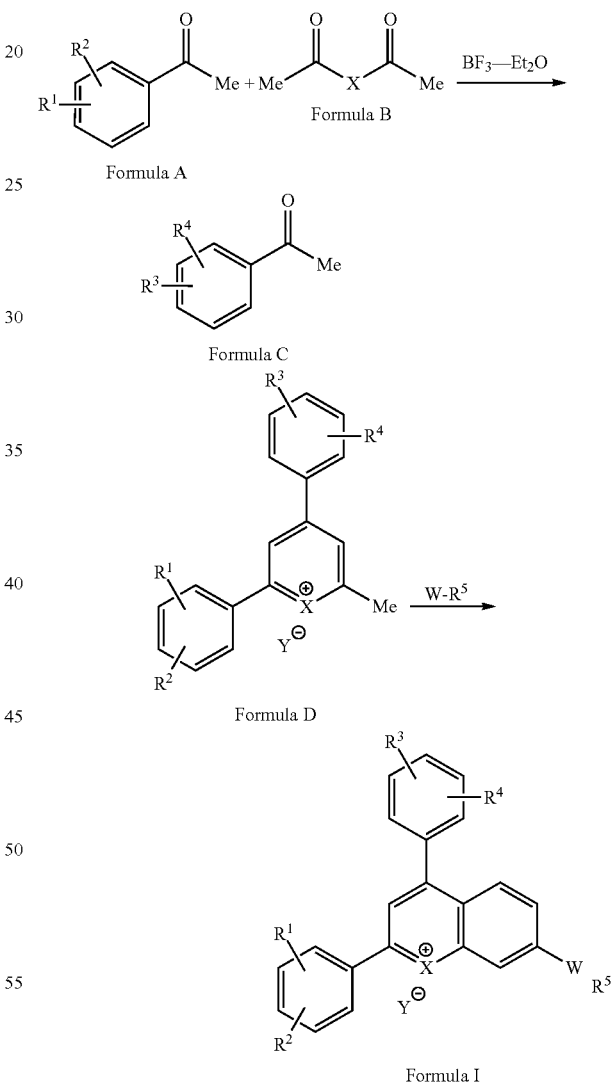

wherein $R^1$, $R^2R^3$ and $R^4$ each preferably are in the meta or para position, and the $R^1$, $R^2$, $R^3$, $R^4$, W, X, and Y substituents are identified as in the general Formula I and in the specific examples presented herein. See FIG. 2. Two examples of the synthesis include:

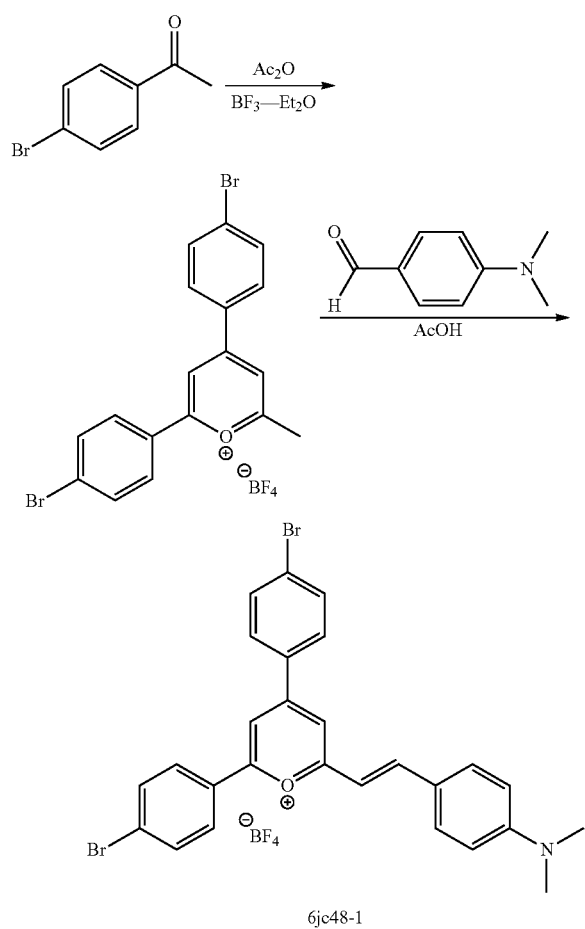

6jc48-1

Boron trifluoride etherate (3.68 mL, 32.0 mmol was added to a mixture of p-bromoacetophenone (2.42 g, 12.12 mmol) and acetic anhydride (1.14 mL, 12.12 mmol) at room temperature. The reaction was heated to 135° C. for 2 hours, cooled, poured into EtOAc, and the resulting yellow solid filtered to give 705 mg. ΔH(MeOH-d.sub.4, 400 MHz) 8.95 (s, 1H, Ar), 8.45 (s, 1H, Ar), 8.30 (d, 2H, J=8.8, Ar), 8.20 (d, 2H, J=8.8), 8.00-7.86 (m, 4H, Ar), 3.03 (s, 3H, Me). (100 mf, 0.20 mmol) p-dimethylamino benzaldehyde (32 mg, 0.02 mmol) in MeOH (10 mL) was added and stirred at room temperature overnight. The solvent was removed and the residue was suspended in ether and filtered to give a blue solid. Recrystallization from EtOH gave 95 mg of the named compound 6jc48-1, a blue solid. $\delta_H$(DMSO-$d_6$, 400 MHz) 8.56 (s, 1H, Ar), 8.47 (s, 1H, Ar), 8.43-8.38 (m, 3H, Ar, HC═), 8.27 (d, 2H, J=8.4, Ar), 8.00-7.90 (m, 4H, Ar), 7.84 (d, 2H, J=8.4, Ar), 7.39 (d, 1H, J=15.6, HC═), 6.94 (d, 2H, J=8.8, Ar), 3.18 (s, δH, 2×Me).

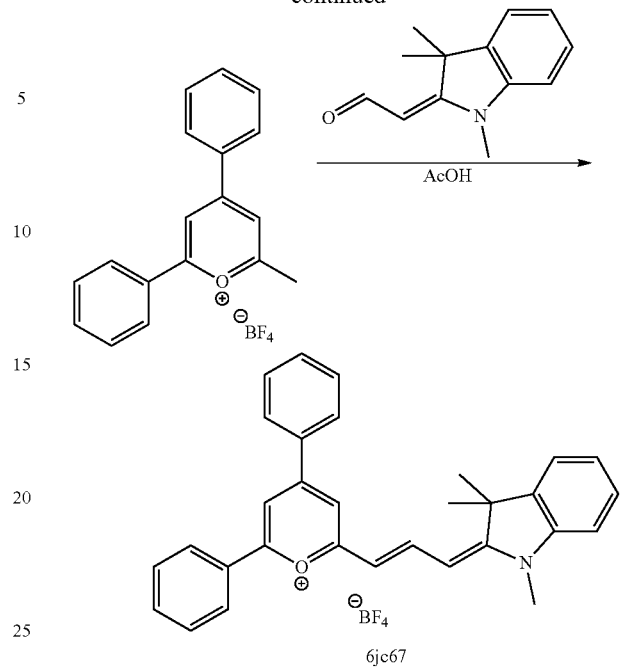

6jc67

To pyrylium salt (50 mg, 0.14 mmol) and 2-(1,3,3-trimethylindolin-2-ylidene)acetaldehyde (28 mg, 0.14 mmol) in acetic anhydride (2 mL) was stirred at reflux for 1 hour. The reaction was cooled and co-evaporated with toluene (×3), washed with ether and decanted (×2). The residue was purified by column chromatography DCM/MeOH and transferred to a vial to give a blue solid 69 mg. $\delta_H$(DMSO-$d_6$, 400 MHz) 8.47 (t, 1H, J=13.2, HC═), 8.26-8.10 (m, 4H, Ar), 7.95 (s, 1H, Ar), 7.90-7.59 (m, 8H, Ar), 7.53-7.44 (m, 2H, Ar), 7.35 (t, 1H, J=7.6, Ar), 6.58 (d, 1H, J=13.2, HC═), 6.39 (br s, 1H, HC═), 3.73 (s, 3H, NMe), 1.74 (s, δH, 2×$CH_3$).

Example 3: De Novo Synthesis of Compound 6jc48-1

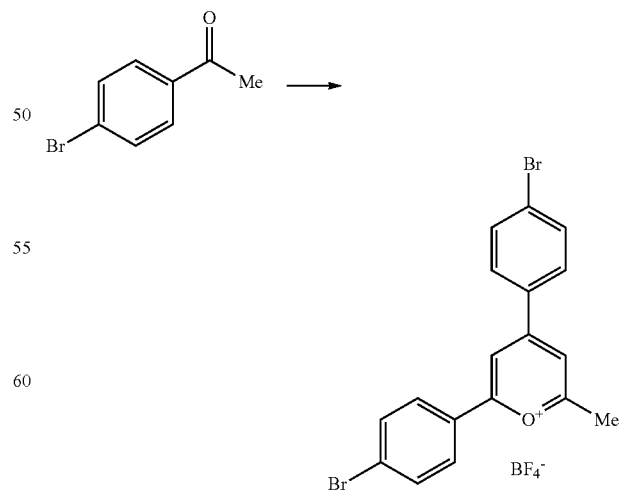

6jc47

Boron trifluoride etherate (3.68 mL, 32.0 mmol was added to a mixture of p-bromoacetophenone (2.42 g, 12.12 mmol) and acetic anhydride (1.14 mL, 12.12 mmol) at room temperature. The reaction was heated to 135° C. for 2 hours, cooled, poured into EtOAc, and the

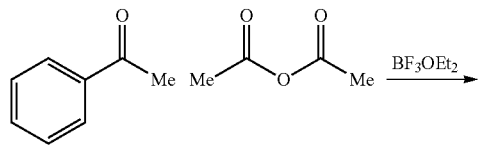

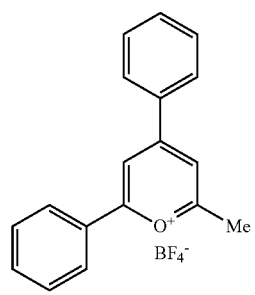

6jc26 resulting yellow solid filtered to give 705 mg $\delta_H$(MeOH-d$_4$, 400 MHz) 8.95 (s, 1H, Ar), 8.45 (s, 1H, Ar), 8.30 (d, 2H, J=8.8, Ar), 8.20 (d, 2H, J=8.8), 8.00-7.86 (m, 4H, Ar), 3.03 (s, 3H, Me). 2,4-bis(4-bromophenyl)-6-methylpyrylium boron tetrafluoride salt, Compound 6jc47.

To compound 6jc47 (100 mf, 0.20 mmol), p-dimethyl-amino benzaldehyde (32 mg, 0.02 mmol) in MeOH (10 mL) was added and stirred at room temperature overnight. The solvent was removed and the residue was suspended in ether and filtered to give a blue solid. Recrystallization from EtOH gave 95 mg of the named compound 6jc48-1, a blue solid. $\delta_H$(DMSO-d$_6$, 400 MHz) 8.56 (s, 1H, Ar), 8.47 (s, 1H, Ar), 8.43-8.38 (m, 3H, Ar, HC══), 8.27 (d, 2H, J=8.4, Ar), 8.00-7.90 (m, 4H, Ar), 7.84 (d, 2H, J=8.4, Ar), 7.39 (d, 1H, J=15.6, HC══), 6.94 (d, 2H, J=8.8, Ar), 3.18 (s, δH, 2×Me).

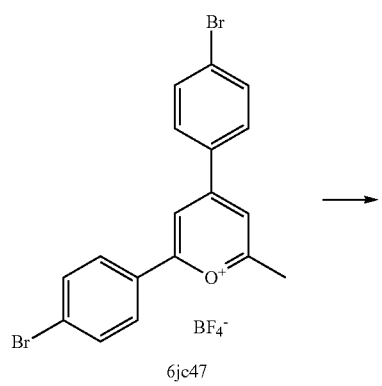

6jc47

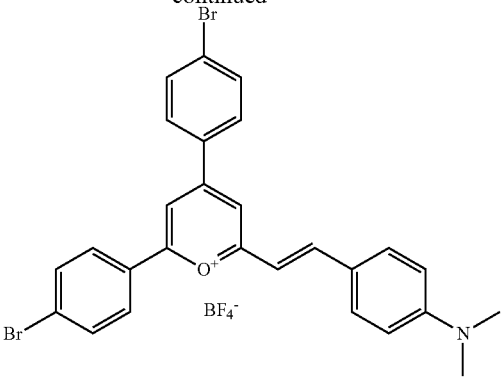

6jc48-1

Example 4: Exemplary Chemical Syntheses

Example 4A: Compound 6jc26; 2-methyl-4,6-diphenylpyrylium boron tetrafluoride salt

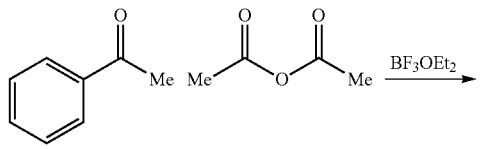

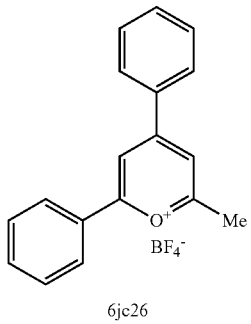

6jc26

Boron trifluoride etherate (3.40 mL, 22.50 mmol) was added to acetophenone (2 g, 1667 mmol) and acetic anhydride (1.57 mL, 16.67 mmol) at room temperature. The reaction mixture was heated to 135° C. for 2 hours, cooled, poured into EtOAc, and the resulting yellow solid filtered. Recrystallization from AcOH gave 813 mg yellow solid.
$\delta_H$(MeOH-d4, 400 MHz) 8.95 (s, 1H, Ar), 8.43 (s, 1H, Ar), 8.41 (d, 2H, J=8.0), 8.30 (d, 2H, J=8.0), 7.82 (t, 2H, J=7.2, Ar), 7.73 (t, 4H, J=7.6, Ar), 3.04 (s, 3H, Me, exchanges with deuterium over time).

Example 4B: Compound 6jc32-1; 2,4-bis(4-chlorphenyl)-6-methylpyrylium boron tetrafluoride salt

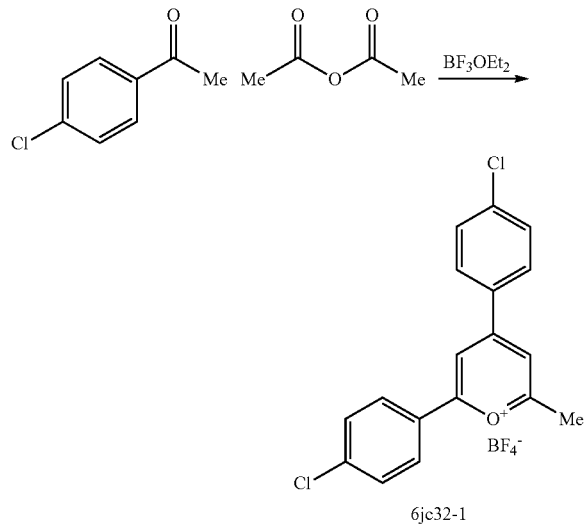

6jc32-1

Boron trifluoride etherate (4 mL, 32.0 mmol) was added to p-chloro-acetophenone (2 g, 13.0 mmol) and acetic anhydride (1.22 mL, 13.0 mmol) at room temperature. The reaction was heated to 135° C. for 2 hours, cooled, poured into EtOAc, and the resulting yellow solid filtered to give 644 mg of the title compound.

$\delta_H$(MeOH-d4, 400 MHz) 8.95 (s, 1H, Ar), 8.44 (s, 1H, Ar), 8.40 (d, 2H, J=8.8), 8.29 (d, 2H, J=8.8), 7.75 (d, 4H, J=7.2, Ar), 3.04 (s, 3H, Me).

Example 4C: Compound 6jc32-2; 2,4-bis(4-methoxyphenyl)-6-methylpyrylium boron tetrafluoride salt Boron trifluoride etherate (4 mL, 32.0 mmol) was added to p-methoxy-acetophenone (2 g,

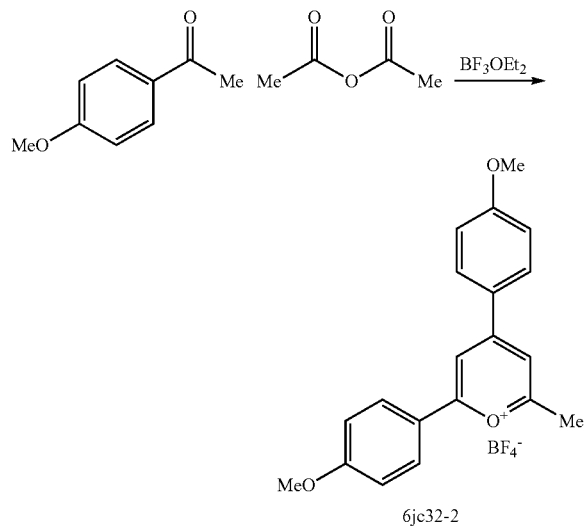

6jc32-2

13.0 mmol) and acetic anhydride (1.22 mL, 13.0 mmol) at room temperature. The reaction was heated to 135° C. for 2 hours, cooled, poured into EtOAc, and the resulting red solid filtered to give 313 mg of the title compound.

$\delta_H$(MeOH-d.sub.4, 400 MHz) 8.67 (s, 1H, Ar), 8.44 (s, 1H, Ar), 8.37 (d, 2H, J=89.6), 8.32 (d, H, J=9.2), 8.15 (s, 1H, Ar), 7.25-7.21 (m, 4H, Ar), 3.97 (s, 3H, OMe), 3.96 (s, 3H, OMe), 2.91 (s, 3H, Me).

Example 4D: Compound 6jc36: 2,4,6-trimethylpyrylium boron tetrafluoride salt

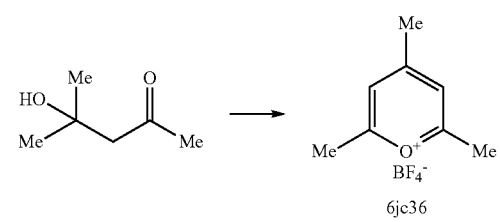

6jc36

Boron trifluoride etherate (2.5 mL, 10.0 mmol) was added to pentanone (1.16 g, 10.0 mmol) and acetic anhydride (9.5 mL, 100.0 mmol) at room temperature. The reaction was heated to 135° C. for 2 hours, cooled, poured into EtOAc, and the resulting white solid filtered to give 980 mg of the title compound.

$\delta_H$(MeOH-d$_4$, 400 MHz) 7.86 (s, 2H, Ar), 2.89 (s, $\delta$H, 2×Me), 2.70 (s, 3H, Me).

Example 4E: Compound 6jc37: (E)-4-(4-(dimethylamino)styryl)-2,6-dimethylpyrylium boron tetrafluoride salt

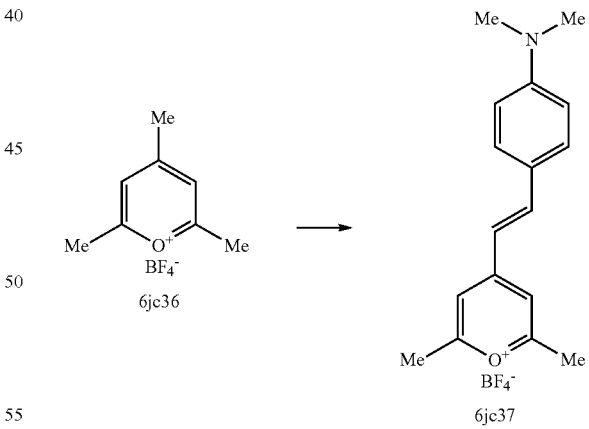

6jc36

6jc37 p-dimethylamino benzaldehyde (150 mg, 1.00 mmol) was added to pyrylium salt 6jc36 (210 mg, 1.00 mmol) in MeOH (10 mL) at room temperature overnight. The solvent was removed and the residue was suspended in ether and filtered to give blue solid. Recrystallization from EtOH yielded 110 mg of the blue solid title compound.

$\delta_H$(DMSO-d.sub.6, 400 MHz) 8.35 (d, 1H, J=14.8, H-vinyl), 7.76 (d, 2H, J=8.4, Ar), 7.69 (s, 2H, Ar), 7.13 (d, 1H, J=14.8, H-vinyl), 6.91 (d, 2H, J=8.4, Ar), 3.16 (s, $\delta$H, 2.times.Me), 2.63 (s, $\delta$H, NMe$_2$).

Example 4F: Compound 6jc38; 4-((1E,3E)-4-(4-(dimethylamino)phenyl)buta-1,3-dien-1-yl)-2,6-dimethylpyr-ylium boron tetrafluoride salt

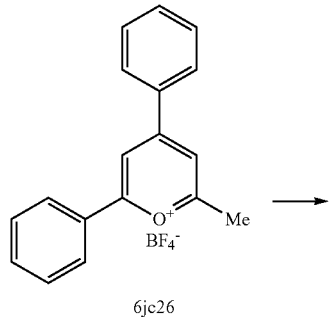

6jc26

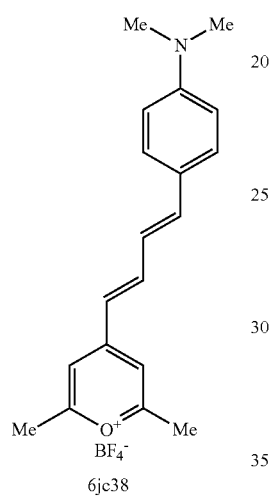

6jc38 p-dimethylamino benzaldehyde)176 mg. 1.00 mmol) and pyrylium salt 6jc36 (210 mg, 1.00 mmol) were stirred in MeOH (10 mL) at room temperature overnight. The solvent was removed and the residue was suspended in ether and filtered to give blue solid. Recrystallization from EtOH gave green solid of 110 mg.

$\delta_H$(DMSO-d.sub.6, 400 MHz) 8.25 (dd, 1H, J=14.8, 14.4, H-vinyl), 7.73 (s, 2H, Ar), 7.65 (d, 2H, J=8.8, Ar), 7.39 (d, 1H, J=14.8, H-vinyl), 7.27 (t, 1H, J=14.8, H-vinyl), 6.81 (d, 2H, J=8.8, Ar), 6.63 (d, 1H, J=14.4, H-vinyl), 3.10 (s, δH, 2.times.Me), 2.64 (s, δH, NMe$_2$).

Example 4G: Compound 6jc39; (E)-2-(4-(dimethylamino)styryl)-4,6-diphenylpyrylium boron tetrafluoride salt

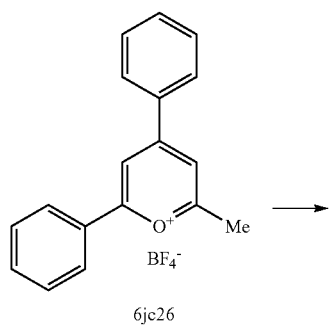

6jc26

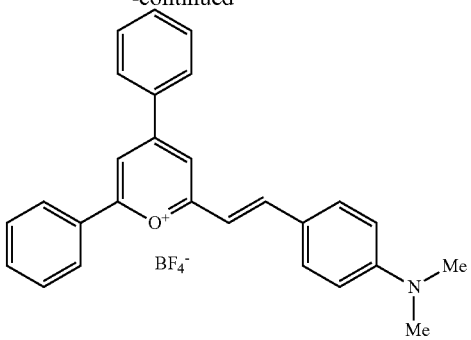

6jc39

Pyrylium salt 6jc26 (100 mg, 0.30 mmol) and p-dimethylamino benzaldehyde (50 mg, 0.32 mmol) in MeOH (6 mL) were stirred at room temperature overnight. The solvent was removed and the residue suspended in ether and filtered to give 81 mg of green solid.

$\delta_H$(DMSO-d.sub.6, 400 MHz) 8.62 (s, 1H, Ar), 8.51-8.42 (m, 4H, Ar, HC=), 8.34 (d, 2H, J=7.2, Ar), 7.86 (d, 2H, J=9.6, Ar), 7.84-7.70 (m, δH, Ar), 7.42 (d, 1H, J=15.6, HC=), 6.93 (d, 2H, J=8.4, Ar), 3.17 (s, δH, 2.times.Me).

Example 4H: Compound 6jc41; (E)-2,4-bis(4-chlorophenyl)-6-(4-(dimethylamino)styryl) pyrylium boron tetrafluoride salt Pyrylium salt 6jc32-1 (134 mg, 0.33 mmol) and p-dimethylamino benzaldehyde (50 mg,

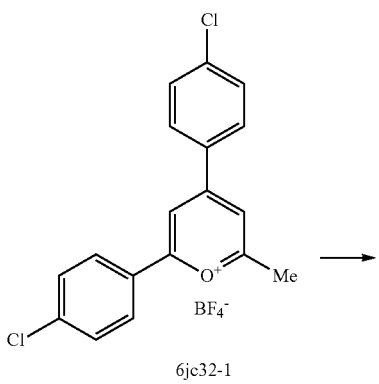

6jc32-1

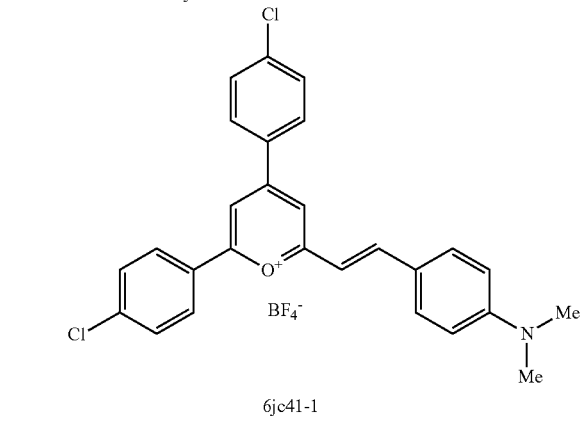

6jc41-1

0.33 mmol) in MeOH (6 mL) were stirred at room temperature overnight. The solvent was removed and the residue suspended in ether and filtered to give dark blue solid of 105 mg.

$\delta_H$(DMSO-$d_6$, 400 MHz) 8.57 (s, 1H, Ar), 8.49-8.40 (m, 4H, Ar, HC=), 8.34 (d, 2H, J=8.4, Ar), 7.84-7.77 (m, δH, Ar), 7.37 (d, 1H, J=15.6, HC=), 6.92 (d, 2H, J=8.4, Ar), 3.17 (s, δH, 2.times.Me).

Example 4I: Compound 6jc43-1; 2-((1E,3E)-4-(4-(dimethylamino)phenyl)buta-1,3-dien-1-yl)-4,6-diphenylpyr-ylium boron tetrafluoride salt

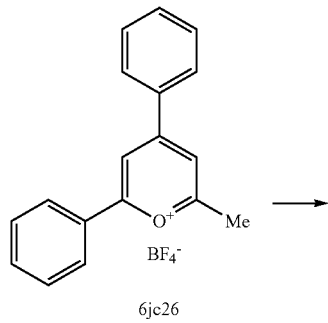

6jc26

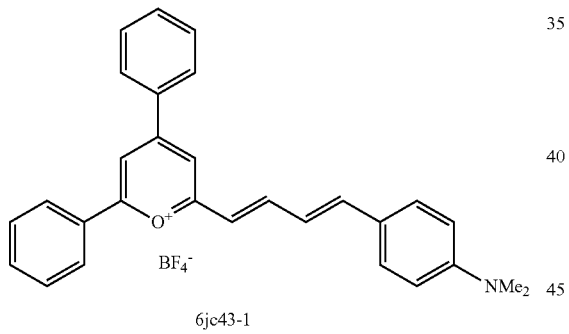

6jc43-1

Pyrylium salt 6jc26 (94 mg, 0.28 mmol) and p-dimethylamino cinnamaldehyde (60 mg, 0.34 mmol) in MeOH (8 mL) were heated to reflux for 2 hours. The reaction was cooled, the solvent removed and the residue was suspended in ether, washed with EtOAc and filtered to give dark blue solid of 55 mg.

$\delta_H$(DMSO-d.sub.6, 400 MHz) 8.67 (s, 1H, Ar), 8.54-8.44 (m, 3H, Ar), 8.36 (d, 2H, J=8.0, Ar), 8.31 (t, 1H, J=14.8, H-vinyl), 7.85-7.70 (m, δH, Ar), 7.65 (d, 2H, J=8.4, Ar), 7.57 (d, 1H, J=14.8, H-vinyl), 7.31 (t, 1H, J=14.8, H-vinyl), 6.88 (d, 1H, J=14.8, H-vinyl), 6.83 (d, 2H, J=8.4, Ar), 3.09 (s, δH, NMe$_2$).

Example 4J: Compound 6jc43-2; 2,4-bis(4-chlorophenyl)-6-((1E,3E)-4-(4-(dimethylamino) phenyl)buta-1,3-dien-1-yl)pyrylium boron tetrafluoride salt

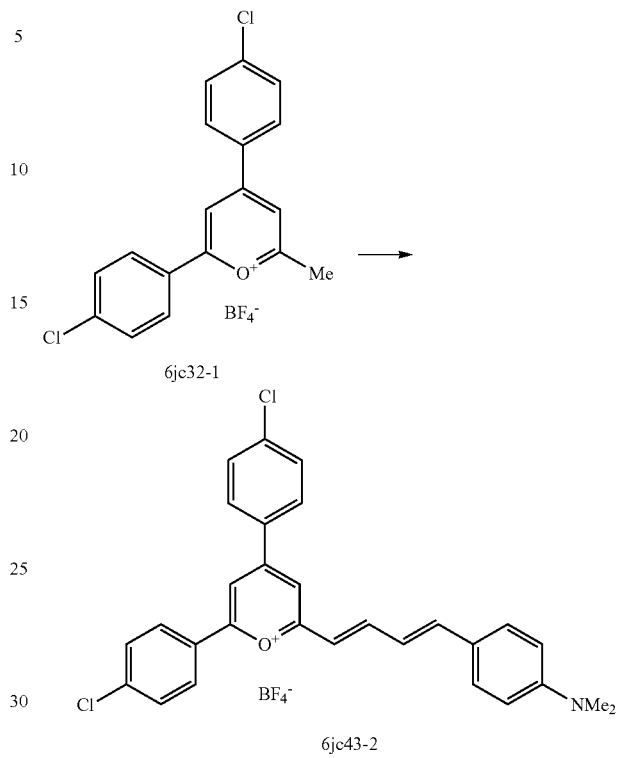

6jc32-1

6jc43-2

Pyrylium salt 6jc32-1 (112 mg, 0.28 mmol) and p-dimethylamino cinnamaldehyde (60 mg, 0.34 mmol) in MeOH (8 mL) were heated to reflux for 2 hours. The reaction was cooled, the solvent removed and the residue suspended in ether, washed with EtOAc and filtered to give dark blue solid of 46 mg.

$\delta_H$(DMSO-$d_6$, 400 MHz) 8.62 (s, 1H, Ar), 8.54-8.44 (m, 3H, Ar), 8.37 (d, 2H, J=7.2, Ar), 8.28 (t, 1H, J=13.6, H-vinyl), 7.89-7.72 (m, 4H, Ar), 7.64 (d, 2H, J=8.0, Ar), 7.55 (d, 1H, J=15.2, H-vinyl), 7.30 (t, 1H, J=13.2, H-vinyl), 6.69-6.73 (m, 3H, Ar, H-vinyl), 3.10 (s, δH, NMe$_2$).

Example 4K: Compound 6jc48-2; 2,4-bis(4-bromophenyl)-6-((1E,3E)-4-(4-(dimethylamino) phenyl)buta-1,3-dien-1-yl)pyrylium boron tetrafluoride salt

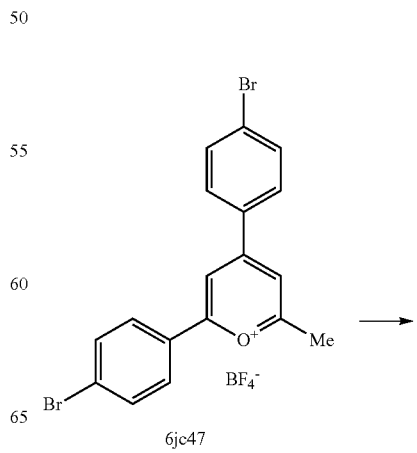

6jc47

-continued

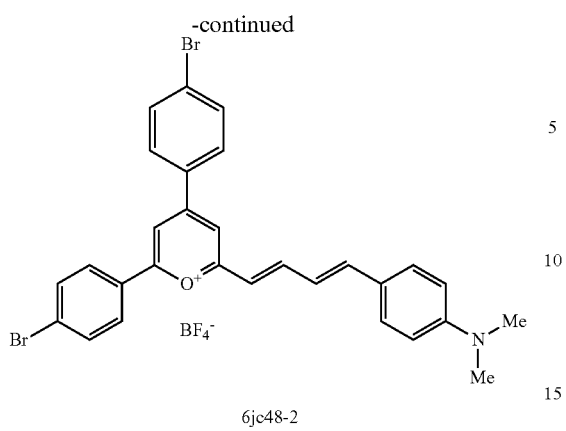

6jc48-2

Pyrylium salt 6jc47 (100 mg, 0.20 mmol) and p-dimethylamino cinnamaldehyde (38 mg, 0.20 mmol) in MeOH (10 mL) was stirred at room temperature overnight. The solvent was removed and the residue was suspended in ether and filtered to give blue solid. Recrystallization from EtOH gave blue solid of 41 mg.

$\delta_H$(DMSO-$d_6$, 400 MHz) 8.64 (s, 1H, Ar), 8.49 (s, 1H, Ar), 8.39 (d, 2H, J=8.4, Ar), 8.35-8.24 (m, 3H, Ar, HC=), 8.00-7.89 (m, 4H, Ar), 7.65 (d, 2H, J=8.4, Ar), 7.56 (d, 1H, J=14.8, HC=), 7.32 (t, 1H, J=14.8, HC=), 6.90-6.81 (m, 3H, Ar, HC=), 3.10 (s, 8H, NMe$_2$).

Example 4L: Compound 6jc49-1; (E)-2-(2-(1H-indol-3-yl)vinyl)-4,6-diphenylpyrylium boron tetrafluoride salt

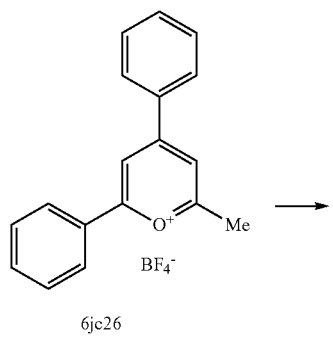

6jc26

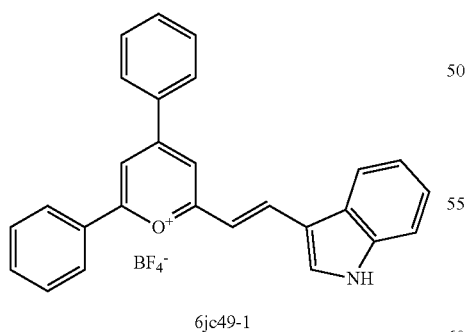

6jc49-1

Pyrylium salt 6jc26 (100 mg, 0.30 mmol) and indole-3-carboxaldehyde (45 mg, 0.30 mmol) in MeOH (8 mL) was stirred at room temperature overnight. The solvent was removed and the residue was suspended in ether and filtered to give blue solid. Recrystallization from EtOH gave blue solid of 32 mg.

δH(DMSO-$d_6$, 400 MHz) 12.65 (br s, 1H, NH), 8.75 (d, 1H, J=16.4, HC=), 8.64 (s, 1H, Ar), 8.60 (s, 1H, Ar), 8.53 (d, 2H, J=7.6, Ar), 8.47 (s, 1H, Ar), 8.40-8.26 (m, 3H, Ar), 7.86-7.70 (m, 8H, Ar), 7.66-7.60 (m, 1H, Ar), 7.54 (d, 1H, J=16.4, HC=), 7.45-7.36 (m, 2H, Ar).

Example 4M: Compound 6jc50-2; 2-methyl-4,6-di-p-tolylpyrylium boron tetrafluoride salt

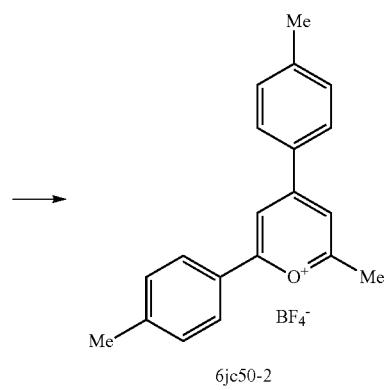

6jc50-2

Boron trifluoride etherate (4.55 mL, 36.9 mmol) was added to p-methyl-acetophenone (2.00 g, 15.0 mmol) and acetic anhydride (1.40 mL, 15.0 mmol) was added at room temperature. The reaction was heated to 135° C. for 2 hours, cooled, poured into EtOAc and the yellow solid filtered to give 609 mg.

$\delta_H$(MeOH-d4, 400 MHz) 8.83 (s, 1H, Ar), 8.32 (s, 1H, Ar), 8.29 (d, 2H, J=8.0, Ar), 8.20 (d, 2H, J=8.0, Ar), 7.59-7.50 (m, 4H, Ar), 2.98 (s, 3H, Me), 2.50 (s, 6H, 2×Me).

Example 4N: Compound 6jc51-1; (E)-2-(4-(dimethylamino)styryl)-4,6-di-p-tolylpyrylium boron tetrafluoride salt

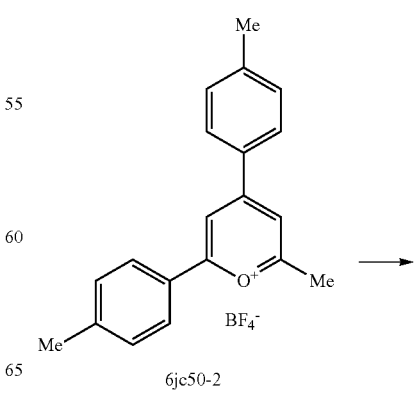

6jc50-2

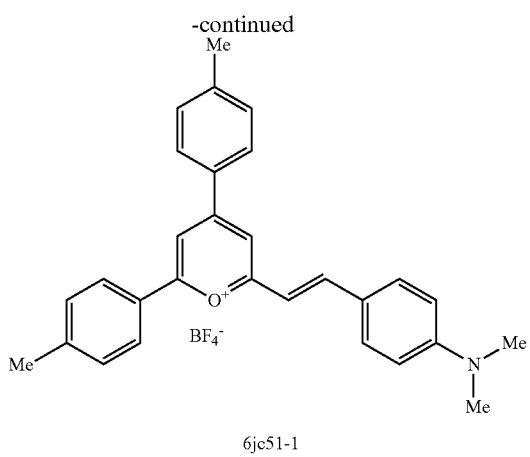

6jc51-1

Pyrylium salt 6jc50-2 (100 mg, 0.27 mmol) and p-dimethylamino benzaldehyde (43 mg, 0.27 mmol) in MeOH (8 mL) were stirred at room temperature overnight. The solvent was removed and the residue was suspended in ether and filtered to give blue solid. Recrystallization from EtOH gave blue solid of 73 mg.

$\delta_H$(DMSO-$d_6$, 400 MHz) 8.58 (s, 1H, Ar), 8.43 (s, 1H, Ar), 8.42-8.35 (m, 3H, Ar, HC=), 8.28 (d, 2H, J=8.0, Ar), 7.83 (d, 2H, J=8.8, Ar), 7.58-7.50 (m, 4H, Ar), 7.38 (d, 1H, J=15.6, HC=), 6.91 (d, 2H, J=8.8, Ar), 3.15 (s, 6H, NMe$_2$), 2.49 (s, 6H, 2×Me).

Example 4O: Compound 6jc51-2; 2-((1E,3E)-4-(4-(dimethylamino)phenyl)buta-1,3-dien-1-yl)-4,6-di-p-tolylpyrylium boron tetrafluoride salt

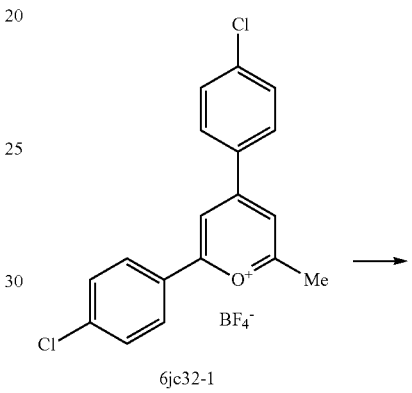

6jc50-2

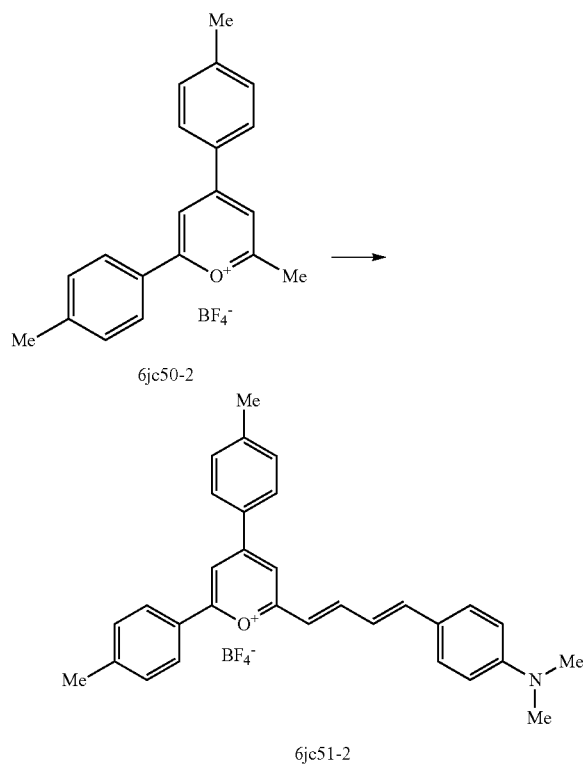

6jc51-2

Pyrylium salt 6jc50-2 (100 mg, 0.27 mmol) and p-dimethylamino cinnamaldehyde (50 mg, 0.27 mmol) in MeOH (8 mL) was stirred at room temperature overnight. The solvent was removed and the residue was suspended in ether and filtered to give blue solid. Recrystallization from EtOH gave blue solid of 58 mg.

$\delta_H$(DMSO-$d_6$, 400 MHz) 8.63 (s, 1H, Ar), 8.44 (s, 1H, Ar), 8.39 (d, 2H, J=7.6, Ar), 8.31 (d, 2H, J=7.6, Ar), 8.24 (t, 1H, HC=), 7.62 (d, 2H, J=8.8, Ar), 7.58-7.43 (m, 5H, Ar, HC=), 7.27 (t, 1H, J=14.8, HC=), 6.90-6.78 (m, 3H, Ar, HC=), 3.08 (s, 6H, NMe$_2$), 2.49 (s, 6H, 2× Me).

Example 4P: Compound 6jc53-1; (E)-2-(2-(1H-indol-3-yl)vinyl)-4,6-bis(4-chlorophenyl) pyrylium boron tetrafluoride salt

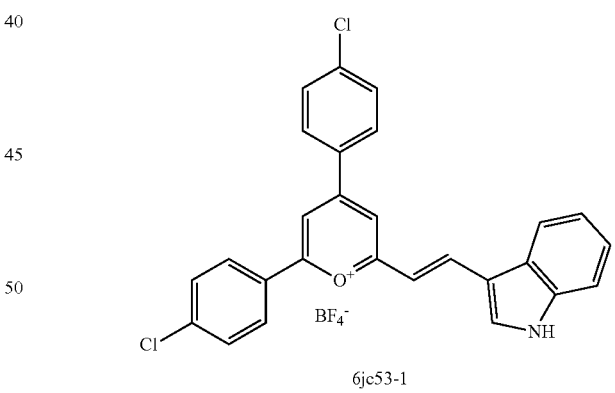

6jc32-1     6jc53-1

Pyrylium salt 6jc32-1 (138 mg, 0.34 mmol) and indole-3-carboxaldehyde (50 mg, 0.34 mmol) in MeOH (8 mL) was stirred at room temperature overnight. The solvent was removed and the residue was suspended in ether and filtered to give blue solid. Recrystallization from EtOH gave purple solid of 53 mg.

$\delta_H$(DMSO-$d_6$, 400 MHz) 12.70 (br s, 1H, NH), 8.78 (d, 1H, J=14.8, HC=), 8.64 (s, 1H, Ar), 8.61 (s, 1H, Ar), 8.53 (d, 2H, J=8.4, Ar), 8.47 (s, 1H, Ar), 8.37 (d, 2H, J=8.8, Ar), 8.31-8.26 (m, 1H, Ar), 7.89-7.80 (m, 4H, Ar), 7.68-7.60 (m, 1H, Ar), 7.52 (d, 1H, J=14.8, HC=), 7.45-7.36 (m, 2H, Ar).

Example 4Q: Compound 6jc53-2; (E)-2-(2-(1H-indol-3-yl)vinyl)-4,6-di-p-tolylpyrylium boron tetrafluoride salt

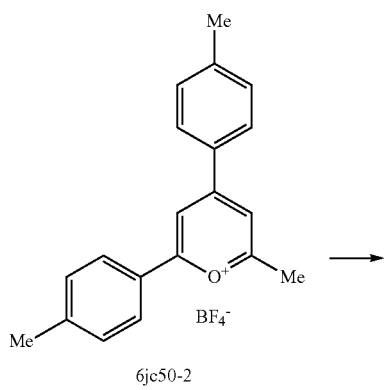

6jc50-2

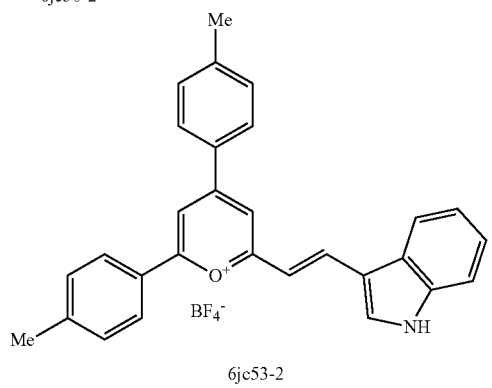

6jc53-2

Pyrylium salt 6jc50-2 (123 mg, 0.34 mmol) and indole-3-carboxaldehyde (50 mg, 0.34 mmol) in MeOH (8 mL) was stirred at room temperature overnight. The solvent was removed and the residue was suspended in ether and filtered to give blue solid. Recrystallization from EtOH gave purple solid of 50 mg.

δ$_H$(DMSO-d$_6$, 400 MHz) 12.55 (br s, 1H, NH), 8.68 (d, 1H, J=15.6 HC═), 8.60 (s, 1H, Ar), 8.55 (s, 1H, Ar), 8.46-8.40 (m, 3H, Ar), 8.30-8.22 (m, 3H, Ar), 7.66-7.53 (m, 5H, Ar), 7.50 (d, 1H, J=15.6, HC═), 7.43-7.35 (m, 2H, Ar), 2.50 (2×Me).

Example 4R: Compound 6jc53-3; (E)-2-(2-(1H-indol-3-yl)vinyl)-4,6-bis(4-bromophenyl) pyrylium boron tetrafluoride salt

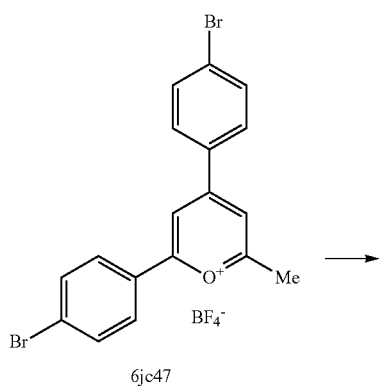

6jc47

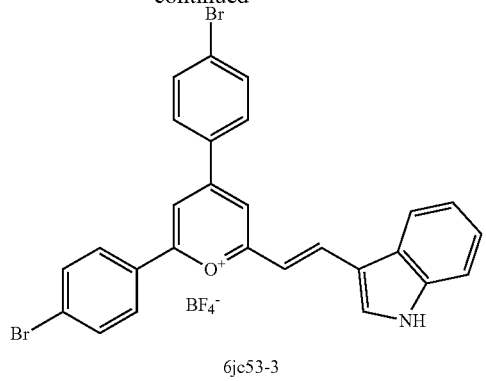

6jc53-3

Pyrylium salt 6jc47 (169 mg, 0.34 mmol) and indole-3-carboxaldehyde (50 mg, 0.34 mmol) in MeOH (8 mL) was stirred at room temperature overnight. The solvent was removed and the residue was suspended in ether and filtered to give blue solid. Recrystallization from EtOH gave purple solid of 38 mg.

δ$_H$(DMSO-d$_6$, 400 MHz) 12.70 (br s, 1H, NH), 8.79 (d, 1H, J=14.8, HC═), 8.64 (s, 1H, Ar), 8.62 (s, 1H, Ar), 8.50-8.42 (m, 3H, Ar), 8.43-8.24 (m, 3H, Ar), 8.04-7.92 (m, 4H, Ar), 7.66-7.60 (m, 1H, Ar), 7.52 (d, 1H, J=14.8, HC═), 7.45-7.36 (m, 2H, Ar).

Example 4S: Compound 6jc56; 2,4-bis(4-(tert-butyl)phenyl)-6-methylpyrylium boron tetrafluoride salt

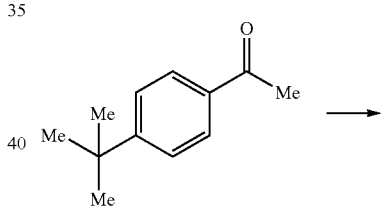

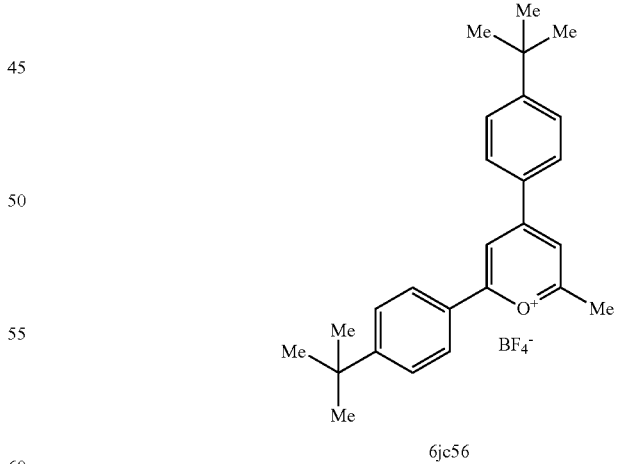

6jc56

Boron trifluoride etherate (3.46 mL, 28.0 mmol) was added to p-tButyl-acetophenone (2.00 g, 11.4 mmol) and acetic anhydride (1.07 mL, 11.4 mmol) at room temperature. The reaction was heated to 135° C. for 2 hours, cooled, poured into EtOAc and the yellow solid filtered to give 494 mg.

δ$_H$(MeOH-d$_4$, 400 MHz) 8.86 (s, 1H, Ar), 8.36-8.32 (m, 3H, Ar), 8.26 (d, 2H, J=8.8, Ar), 7.77 (d, 4H, J=7.6, Ar), 3.00 (s, 3H, Me), 1.40 (s, 18H, 2×tBu).

Example 4T: Compound 6jc57; 2,4-bis(3,4-dimethylphenyl)-6-methylpyrylium boron tetrafluoride salt

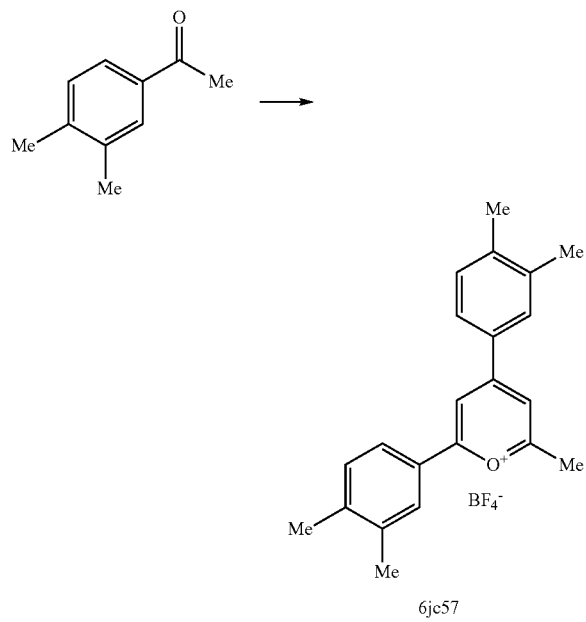

6jc57

Boron trifluoride etherate (4.10 mL, 33.2 mmol) was added to 3,4-dimethyl-acetophenone (2.00 g, 13.5 mmol) and acetic anhydride (1.28 mL, 13.5 mmol) at room temperature. The reaction was heated to 135° C. for 3 hours, cooled, poured into EtOAc and the yellow solid filtered to give 417 mg.

δ$_H$(MeOH-d$_4$, 400 MHz) 8.82 (s, 1H, Ar), 8.30 (s, 1H, Ar), 8.16-8.09 (m, 2H, Ar), 8.05 (d, 1H, J=7.6, Ar), 7.48 (d, 2H, J=8.0, Ar), 2.97 (s, 3H, Me), 2.44 (s, 6H, 2×Me), 2.42 (s, 6H, 2×Me).

Example 4U: Compound 6jc58; (E)-2-(2-(1,2,3,5,6,7-hexahydropyrido[3,2,1-ij]quinolin-9-yl)vinyl)-4,6-diphenylpyrylium boron tetrafluoride salt

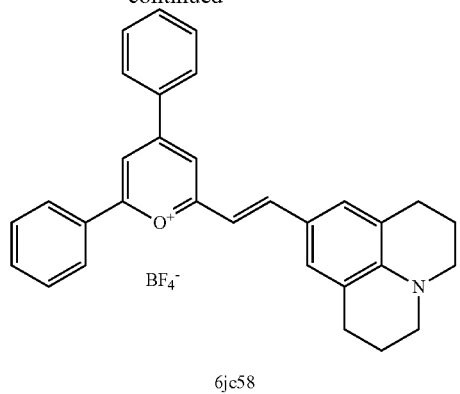

6jc58

Pyrylium salt 6jc26 (120 mg, 0.37 mmol) and 9-CHO-julolidine (34 mg, 0.22 mmol) in MeOH (8 mL) was stirred at room temperature overnight. The solvent was removed and the residue suspended in ether and filtered to give solid. Recrystallization from EtOH gave purple solid of 96 mg.

δ$_H$(DMSO-d$_6$, 400 MHz) 8.44-8.14 (m, 7H, Ar, 7.75-7.60 (m, 6H, Ar), 7.47 (s, 2H, Ar), 7.22 (d, 1H, J=15.2, HC=), 3.50-3.40 (m, 4H, 2×CH$_2$), 2.78-2.70 (m, 4H, 2×CH$_2$), 2.01-1.85 (m, 4H, 2×CH$_2$).

Example 4V: Compound 6jc59-1; (E)-2-(4-(dimethylamino)styryl)-4,6-bis(3,4-dimethylphenyl)pyrylium boron tetrafluoride salt

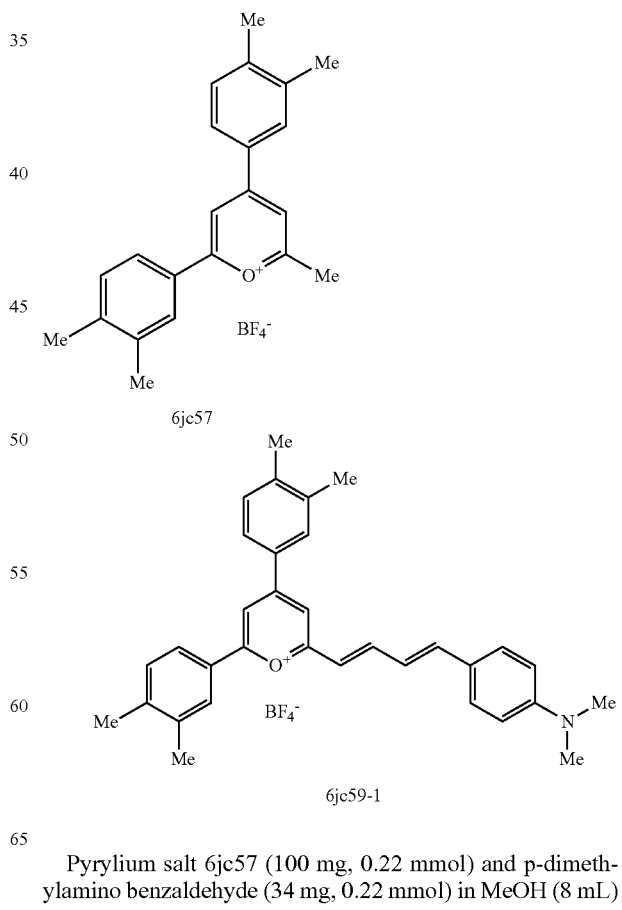

6jc57

6jc59-1

Pyrylium salt 6jc57 (100 mg, 0.22 mmol) and p-dimethylamino benzaldehyde (34 mg, 0.22 mmol) in MeOH (8 mL)

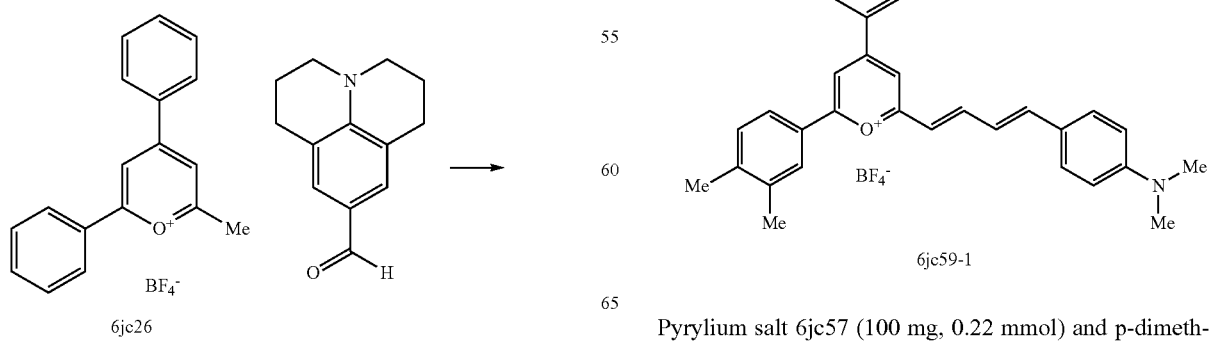

6jc26 was stirred at room temperature overnight. The solvent was removed and the residue suspended in ether and filtered to give blue solid. Recrystallization from EtOH gave green solid of 79 mg.

$\delta_H$(DMSO-$d_6$, 400 MHz) 8.53 (s, 1H, Ar), 8.41 (s, 1H, Ar), 8.36 (d, 1H, J=15.6, HC=), 8.26 (s, 1H, Ar), 8.23 (d, 1H, J=8.8, Ar), 8.16 (s, 1H, Ar), 8.12 (d, 1H, J=7.6, Ar), 7.83 (d, 2H, J=8.8, Ar), 7.52-7.43 (m, 2H, Ar), 7.37 (d, 2H, J=15.6, HC=), 6.91 (d, 2H, J=8.8, Ar), 3.15 (s, 6H, NMe$_2$), 2.43 (s, 3H, Me), 2.42 (s, 3H, Me), 2.40 (s, 6H, 2×Me).

Example 4W: Compound 6jc59-2; 2-((1E,3E)-4-(4-(dimethylamino)phenyl)buta-1,3-dien-1-yl)-4,6-bis(3,4-dimethylphenyl)pyrylium boron tetrafluoride salt Example 4X: Compound 6jc59-3; (E)-2-(2-(1H-indol-3-yl)vinyl)-4,6-bis(3,4-dimethylphenyl)pyrylium boron tetrafluoride salt

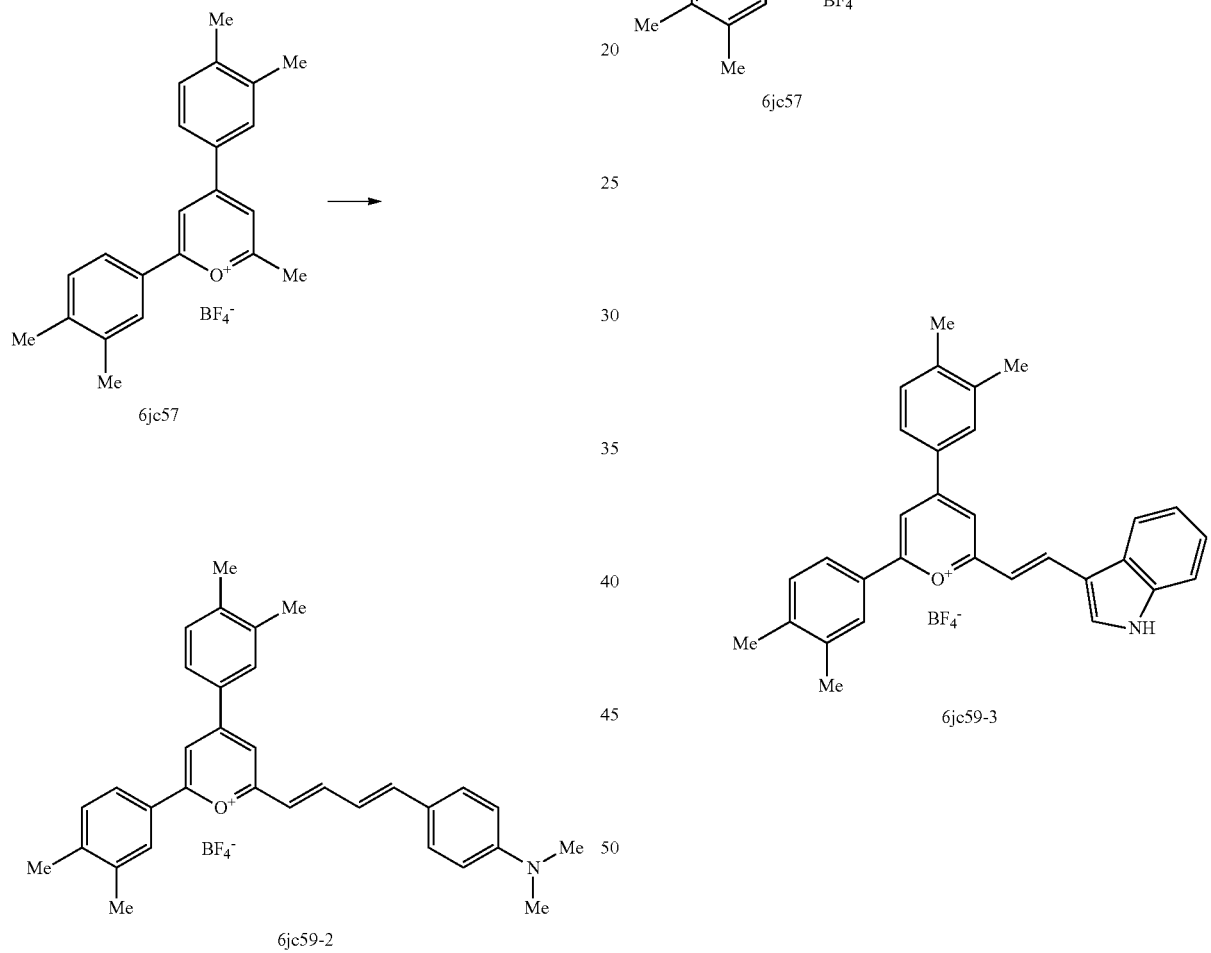

Pyrylium salt 6jc57 (100 mg, 0.22 mmol) and p-dimethylamino cinnamaldehyde 39 mg, 0.22 mmol) in MeOH (8 mL) was stirred at room temperature overnight. The solvent was removed and the residue suspended in ether and filtered to give blue solid. Recrystallization from EtOH gave green solid of 70 mg.

$\delta_H$(DMSO-$d_6$, 400 MHz) 8.58 (s, 1H, Ar), 8.42 (s, 1H, Ar), 8.30-8.16 (m, 4H, Ar, HC=), 8.14 (d, 1H, J=8.0, Ar), 7.62 (d, 2H, J=8.4, Ar), 7.53-7.46 (m, 3H, Ar, HC=), 7.25 (t, 1H, J=14.0, HC=), 6.90-6.77 (m, 3H, Ar, HC=), 3.07 (s, 6H, NMe$_2$), 2.44 (s, 3H, Me), 2.41 (s, 3H, Me), 2.40 (s, 6H, 2× Me).

Pyrylium salt 6jc57 (100 mg, 0.22 mmol) and indole-3-carboxaldehyde (32 mg, 0.22 mmol) in MeOH (8 mL) was stirred at room temperature for 2 days. The solvent was removed and the residue was suspended in ether and filtered to give blue solid. Recrystallization from EtOH gave green solid of 55 mg.

$\delta_H$(DMSO-$d_6$, 400 MHz) 12.54 (br s, 1H, NH), 8.64 (d, 1H, J=15.6, HC=), 8.55 (s, 1H, Ar), 8.52 (s, 1H, Ar), 8.43 (s, 1H, Ar), 8.32-8.22 (m, 3H, Ar), 8.16 (s, 1H, Ar), 8.12 (d, 1H, J=8.4, Ar), 7.63-7.59 (m, 1H, Ar), 7.56-7.45 (m, 3H, Ar, HC=), 7.43-7.34 (m, 2H, Ar), 2.45 (s, 3H, Me), 2.43 (s, 3H, Me), 2.41 (s, 6H, 2× Me).

Example 4Y: Compound 6jc60-1; (E)-2,4-bis(4-(tert-butyl)phenyl)-6-(4-(dimethylamino) styryl) pyrylium boron tetrafluoride salt Example 4Z: Compound 6jc60-2; 2,4-bis(4-(tert-butyl)phenyl)-6-((1E,3E)-4-(4-(dimethylamino)phenyl)buta-1,3-dien-1-yl)pyrylium boron tetrafluoride salt

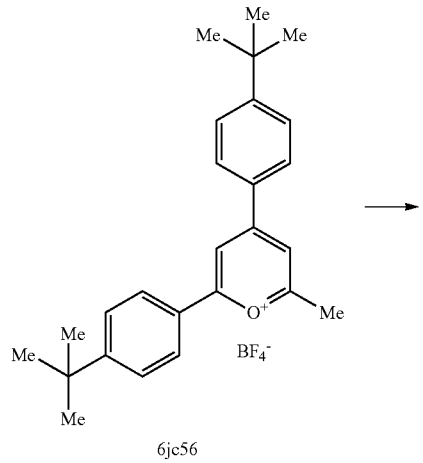

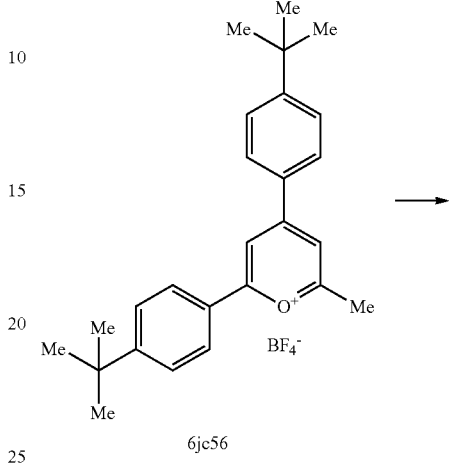

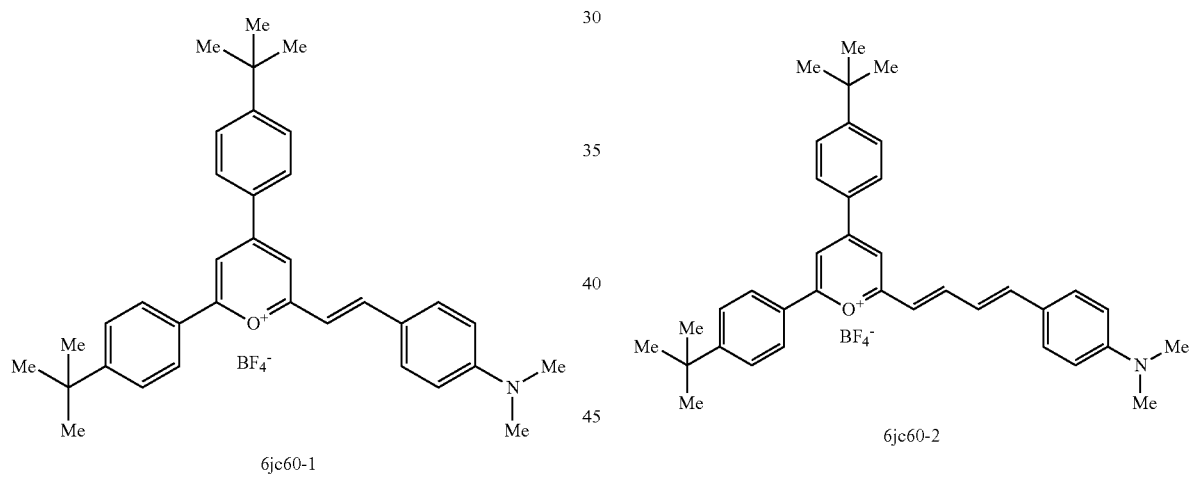

Pyrylium salt 6jc56 (100 mg, 0.22 mmol) and p-dimethylamino benzaldehyde (40 mg, 0.22 mmol) in MeOH (8 mL) were stirred at room temperature overnight. The solvent was removed and the residue suspended in ether and filtered to give solid. Recrystallization from EtOH gave green solid of 67 mg.

$\delta_H$(DMSO-$d_6$, 400 MHz) 8.56 (s, 1H, Ar), 8.41 (s, 1H, Ar), 8.40-8.33 (m, 3H, Ar, HC=), 8.26 (d, 2H, J=8.4, Ar), 7.83 (d, 2H, J=9.6, Ar), 7.78-7.71 (m, 4H, Ar), 7.37 (d, 1H, J=15.6, HC=), 6.91 (d, 2H, J=8.8, Ar), 3.15 (s, 6H, NMe$_2$), 1.39 (s, 9H, tBu), 1.38 (s, 9H, tBu).

Pyrylium salt 6jc56 (100 mg, 0.22 mmol) and p-dimethylamino cinnamaldehyde (44 mg, 0.22 mmol) in MeOH (8 mL) were stirred at room temperature overnight. The solvent was removed and the residue suspended in ether and filtered to give solid. Recrystallization from EtOH gave green solid of 50 mg.

$\delta_H$(DMSO-$d_6$, 400 MHz) 8.61 (s, 1H, Ar), 8.42-8.37 (m, 3H, Ar), 8.29 (d, 2H, J=8.8, Ar), 8.22 (t, 1H, J=14.8, HC=), 7.54 (d, 4H, J=8.0, Ar), 7.62 (d, 2H, J=9.2, Ar), 7.52 (d, 1H, J=14.8, HC=), 7.27 (t, 1H, J=15.2, HC=), 6.86 (d, 1H, J=15.2, HC=), 6.81 (d, 2H, J=8.8, Ar), 3.07 (s, 6H, NMe$_2$), 1.39 (s, 9H, tBu), 1.38 (s, 9H, tBu).

Example 4AA: Compound 6jc60-3; (E)-2-(2-(1H-indol-3-yl)vinyl)-4,6-bis(4-(tert-butyl)phenyl)pyrylium boron tetrafluoride salt

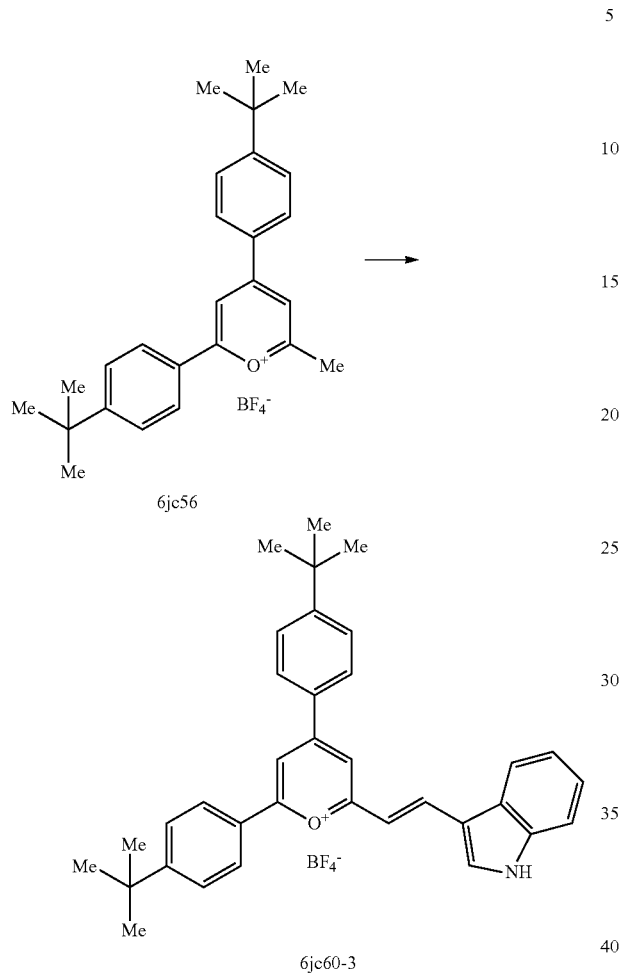

Pyrylium salt 6jc56 (100 mg, 0.22 mmol) and indole-3-carboxaldehyde (32 mg, 0.22 mmol) in MeOH (8 mL) were stirred at room temperature overnight. The solvent was removed and the residue suspended in ether and filtered to give solid. Recrystallization from EtOH gave green solid of 50 mg.

$\delta_H$(DMSO-d$_6$, 400 MHz) 12.56 (br s, 1H, NH), 8.67 (d, 1H, J=15.6, HC═), 8.58 (s, 1H, Ar), 8.52 (s, 1H, Ar), 8.46-8.40 (m, 3H, Ar), 8.32-8.24 (m, 3H, Ar), 7.80-7.72 (m, 4H, Ar), 7.66-7.59 (m, 1H, Ar), 7.51 (d, 1H, J=15.6, HC═), 7.43-7.35 (m, 2H, Ar), 1.39 (s, 18H, 2× tBu).

Example 4BB: Compound 6jc61; 2,4-bis(4-ethylphenyl)-6-methylpyrylium boron tetrafluoride salt

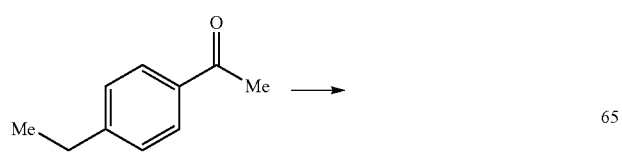

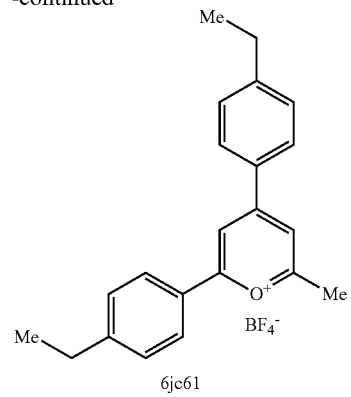

Boron trifluoride etherate (4.17 mL, 33.8 mmol) was added to p-ethyl-acetophenone (2.00 g, 13.51 mmol) and acetic anhydride (1.28 mL, 13.51 mmol) at room temperature. The reaction was heated to 135° C. for 3 hours, cooled, poured into EtOAc and the yellow solid filtered to give 214 mg solid product.

$\delta_H$(MeOH-d$_4$, 400 MHz) 8.85 (s, 1H, Ar), 8.35-8.30 (m, 3H, Ar), 8.24 (d, 2H, J=8.4, Ar), 7.57 (d, 4H, J=8.0, Ar), 2.99 (s, 3H, Me), 2.81 (q, 4H, J=8.0, 2× CH$_2$), 1.30 (t, 6H, J=8.0, 2× CH$_3$).

Example 4CC: Compound 6jc64-1; €-2-(4-(dimethylamino)styryl)-4,6-bis(4-ethylphenyl)pyrylium boron tetrafluoride salt Pyrylium salt 6jc61 (50 mg, 0.13 mmol) and p-dimethylamino benzaldehyde (20 mg, 0.13 mmol) in MeOH (8 mL) were stirred at room temperature overnight. The solvent was removed and the residue suspended in ether and filtered to give blue solid. Recrystallization from EtOH gave brown solid of 41 mg.

$\delta_H$(DMSO-d$_6$, 400 MHz) 8.56 (s, 1H, Ar), 8.46-8.33 (m, 4H, Ar, HC=), 8.29 (d, 2H, J=8.0, Ar), 7.84 (d, 2H, J=8.4, Ar), 7.62-7.54 (m, 4H, Ar), 7.38 (d, 1H, J=16.4, HC=), 6.92 (d, 2H, J=8.4, Ar), 3.15 (s, 6H, NMe$_2$), 2.79 (q, 4H, J=7.2, 2× CH$_2$), 1.28 (t, 6H, J=7.2, 2× CH$_3$).

Example 4DD: Compound 6jc64-2; 2-((1E,3E)-4-(4-(dimethylamino)phenyl)buta-1,3-dien-1-yl)-4,6-bis(4-ethylphenyl)pyrylium boron tetrafluoride salt

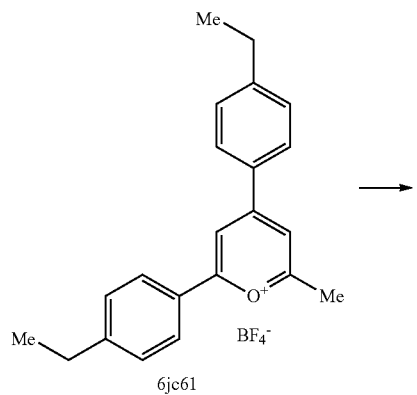

6jc61

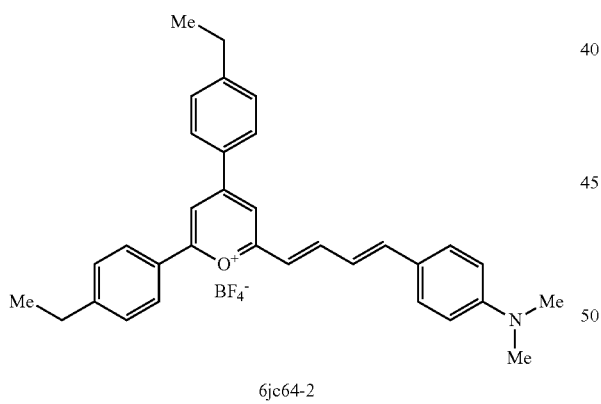

6jc64-2

Pyrylium salt 6jc61 (50 mg, 0.13 mmol) and p-dimethylamino cinnamaldehyde (23 mg, 0.13 mmol) in MeOH (8 mL) were stirred at room temperature overnight. The solvent was removed and the residue suspended in ether and filtered to give blue solid. Recrystallization from EtOH gave brown solid of 31 mg.

$\delta_H$(DMSO-d$_6$, 400 MHz) 8.63 (s, 1H, Ar), 8.43 (s, 1H, Ar), 8.40 (d, 2H, J=7.6, Ar), 8.32 (d, 2H, J=7.6, Ar), 8.24 (t, 1H, J=14.0, HC=), 7.67-7.56 (m, 6H, Ar), 7.52 (d, 1H, J=14.8, HC=), 7.27 (t, 1H, J=14.8, HC=), 6.86 (d, 1H, J=16.0, HC=), 6.81 (d, 2H, J=8.8, Ar), 3.08 (s, 6H, NMe$_2$), 2.79 (q, 4H, J=7.2, 2× CH$_2$), 1.27 (t, 6H, J=7.2, 2× CH$_3$).

Example 4EE: Compound 6jc64-3; (E)-2-(2-(1H-indol-3-yl)vinyl)-4,6-bis(4-ethylphenyl)pyrylium boron tetrafluoride salt

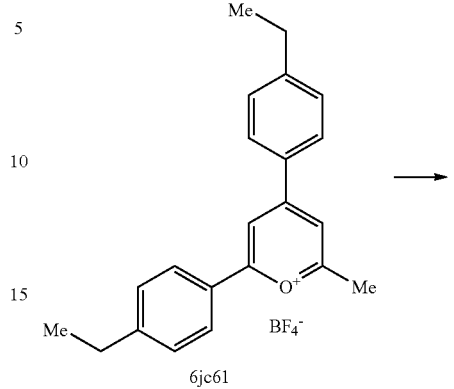

6jc61

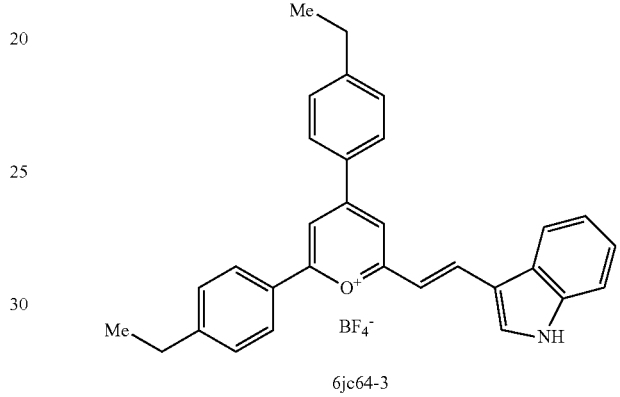

6jc64-3

Pyrylium salt 6jc61 (50 mg, 0.13 mmol) and indole-3-carboxaldehyde (19 mg, 0.13 mmol) in MeOH (8 mL) were stirred at room temperature for 2 days. The solvent was removed and the residue suspended in ether and filtered to give blue solid. Recrystallization from EtOH gave brown solid of 24 mg.

$\delta_H$(DMSO-d$_6$, 400 MHz) 12.56 (br s, 1H, NH), 8.68 (d, 1H, J=15.6, HC=), 8.59 (s, 1H, Ar), 8.54 (s, 1H, Ar), 8.47-8.41 (m, 3H, Ar), 8.34-8.24 (m, 3H, Ar), 7.66-7.57 (m, 5H, Ar), 7.51 (d, 1H, J=15.6, HC=), 7.43-7.37 (m, 2H, Ar), 2.80 (q, 4H, J=8.0, 2× CH$_2$), 1.28 (t, 6H, J=8.0, 2× CH$_3$).

Example 4FF: Compound 6jc65-1; (E)-2-(2-(1,2,3,5,6,7-hexahydropyrido[3,2,1-ij]quinolin-9-yl)vinyl)-4,6-di-p-tolylpyrylium boron tetrafluoride salt

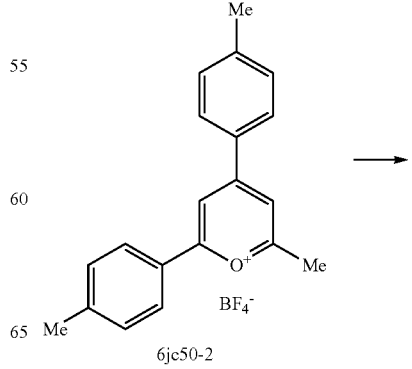

6jc50-2

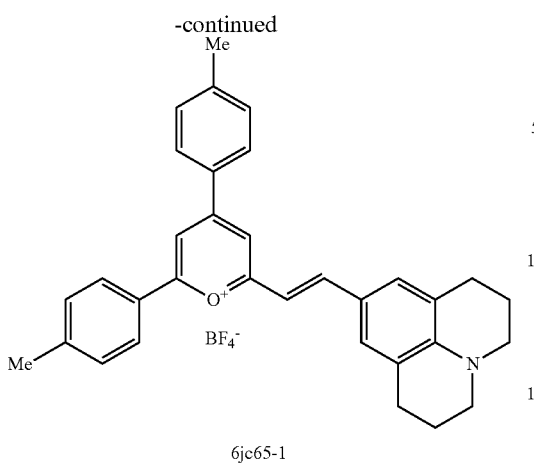

6jc65-1

Pyrylium salt 6jc50-2 (50 mg, 0.14 mmol) and 9-CHO-julolidine (28 mg, 0.14 mmol) in MeOH (8 mL) were stirred at room temperature overnight. The solvent was removed and the residue suspended in ether and filtered to give solid. Recrystallization from EtOH gave red solid of 48 mg.

$\delta_H$(DMSO-d$_6$, 400 MHz) 8.37-8.27 (m, 3H, Ar, HC=), 8.21-8.15 (m, 4H, Ar), 7.54-7.46 (m, 4H, Ar), 7.41 (s, 2H, Ar), 7.17 (d, 1H, J=15.6, HC=), 3.43-3.3.38 (m, 4H, 2× CH$_2$), 2.79-2.70 (m, 4H, 2× CH$_2$), 1.96-1.86 (m, 4H, 2× CH$_2$).

Example 4GG: Compound 6jc65-2; (E)-2-(2-(1-methyl-1H-indol-3-yl)vinyl)-4,6-di-p-tolylpyrylium boron tetrafluoride salt Pyrylium salt 6jc50-2 (50 mg, 0.14 mmol) and N-methyl-indole-3-carboxaldehyde (23 mg, 0.14 mmol) in MeOH (8 mL) was stirred at room temperature for 2 days. The solvent was removed and the residue suspended in ether and filtered to give blue solid. Recrystallization from EtOH gave purple solid of 40 mg.

$\delta_H$(DMSO-d$_6$, 400 MHz) 8.64 (d, 1H, J=15.6, HC=), 8.57 (s, 1H, Ar), 8.53 (s, 1H, Ar), 8.45-8.37 (m, 3H, Ar), 8.32-8.23 (m, 3H, Ar), 7.70 (d, 1H, J=6.8, Ar), 7.56 (t, 4H, J=6.8, Ar), (m, 5H, Ar), 7.50-7.40 (m, 3H, Ar, HC=), 3.97 (s, 3H, NMe), 2.50 (s, 6H, 2× CH$_3$).

Example 4HH: Compound 6jc66-1; (E)-2-(2-(1-methyl-1H-indol-3-yl)vinyl)-4,6-diphenylpyrylium boron tetrafluoride salt

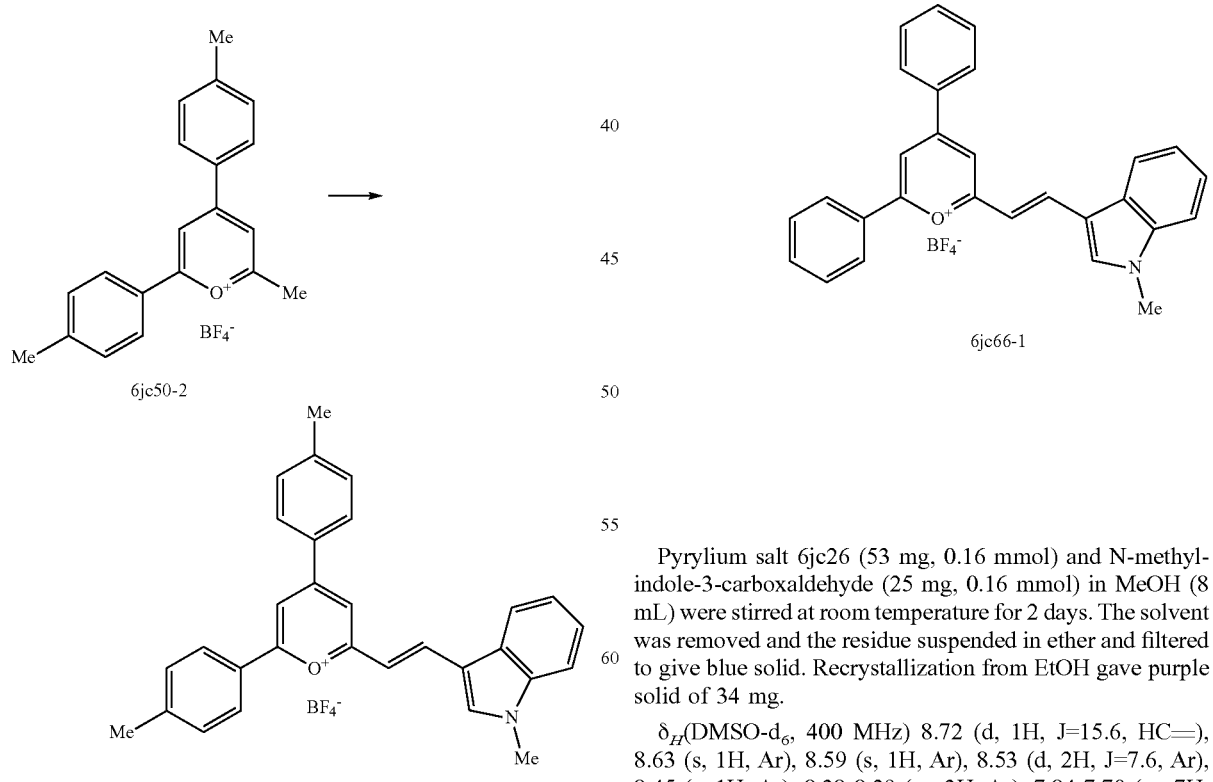

6jc50-2

6jc65-2

6jc66-1

Pyrylium salt 6jc26 (53 mg, 0.16 mmol) and N-methyl-indole-3-carboxaldehyde (25 mg, 0.16 mmol) in MeOH (8 mL) were stirred at room temperature for 2 days. The solvent was removed and the residue suspended in ether and filtered to give blue solid. Recrystallization from EtOH gave purple solid of 34 mg.

$\delta_H$(DMSO-d$_6$, 400 MHz) 8.72 (d, 1H, J=15.6, HC=), 8.63 (s, 1H, Ar), 8.59 (s, 1H, Ar), 8.53 (d, 2H, J=7.6, Ar), 8.45 (s, 1H, Ar), 8.38-8.29 (m, 3H, Ar), 7.84-7.70 (m, 7H, Ar), 7.52 (d, 1H, J=15.6, HC=), 7.49-7.43 (m, 2H, Ar), 3.99 (s, 3H, NMe).

Example 4II: Compound 6jc66-2; (E)-2,4-bis(4-ethylphenyl)-6-(2-(1-methyl-1H-indol-3-yl)vinyl)pyrylium boron tetrafluoride salt

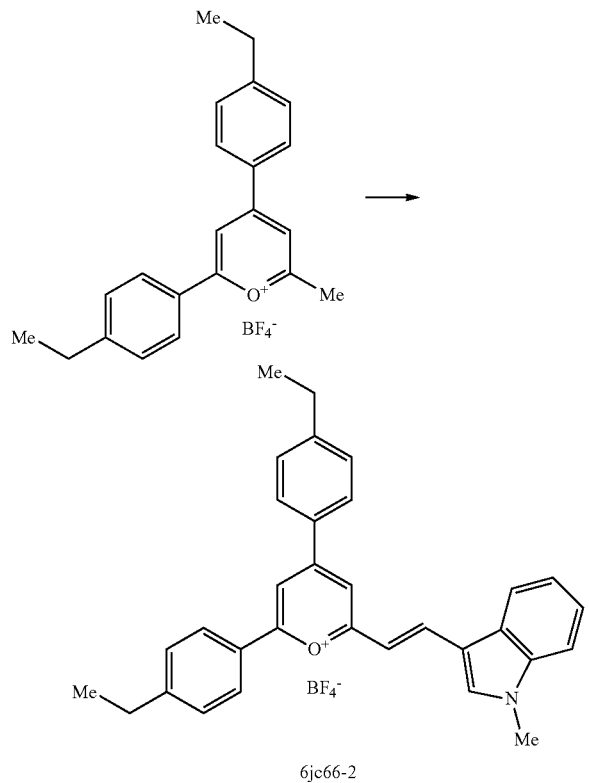

6jc66-2

Pyrylium salt 6jc61 (62 mg, 0.16 mmol) and N-methyl-indole-3-carboxaldehyde (25 mg, 0.16 mmol) in MeOH (8 mL) were stirred at room temperature for 2 days. The solvent was removed and the residue was suspended in ether and filtered to give blue solid. Recrystallization from EtOH gave purple solid of 13 mg.

$\delta_H$(DMSO-$d_6$, 400 MHz) 8.65 (d, 1H, J=15.6, HC=), 8.59 (s, 1H, Ar), 8.54 (s, 1H, Ar), 8.45 (d, 2H, J=7.6, Ar), 8.41 (s, 1H, Ar), 8.34-8.26 (m, 3H, Ar), 7.74-7.68 (m, 1H, Ar), 7.64-7.56 (m, 4H, Ar), 7.52-7.42 (m, 3H, Ar), 3.98 (s, 3H, NMe), 3.00-2.75 (m, 4H, 2× CH$_2$), 1.29 (t, 6H, J=7.2, 2× CH$_3$).

Example 4JJ: Compound 6jc66-3; (E)-2,4-bis(4-(tert-butyl)phenyl)-6-(2-(1-methyl-1H-indol-3-yl)vinyl)pyrylium boron tetrafluoride salt

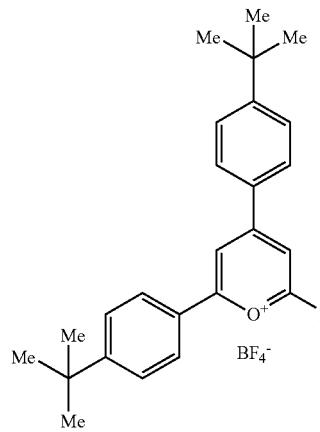

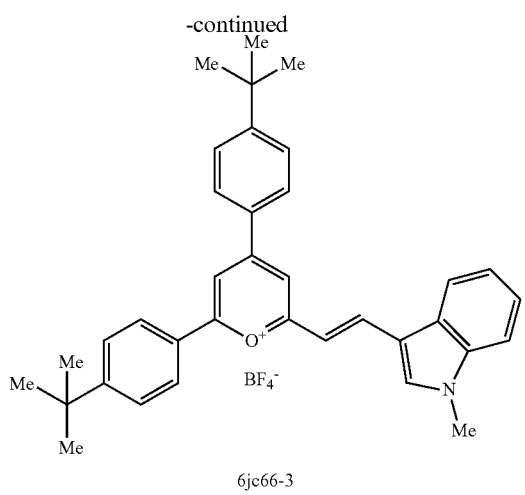

6jc66-3

Pyrylium salt 6jc56 (71 mg, 0.16 mmol) and N-methyl-indole-3-carboxaldehyde (25 mg, 0.16 mmol) in MeOH (8 mL) were stirred at room temperature for 2 days. The solvent was removed and the residue suspended in ether and filtered to give blue solid. Recrystallization from EtOH gave purple solid of 27 mg.

$\delta_H$(DMSO-$d_6$, 400 MHz) 8.64 (d, 1H, J=15.6, HC=), 8.58 (s, 1H, Ar), 8.52 (s, 1H, Ar), 8.47-8.40 (m, 3H, Ar), 8.32-8.24 (m, 3H, Ar), 7.81-7.68 (m, 5H, Ar), 7.53-7.42 (m, 3H, Ar, HC=), 3.99 (s, 3H, NMe), 1.40 (s, 18H, 6× CH$_3$).

Example 4KK: Compound 6jc66-4; (E)-2,4-bis(3,4-dimethylphenyl)-6-(2-(1-methyl-1H-indol-3-yl)vinyl)pyrylium boron tetrafluoride salt

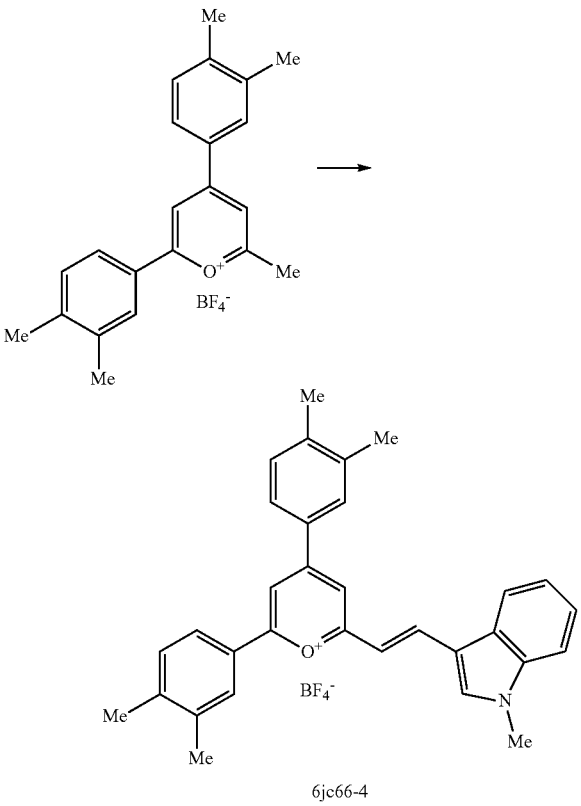

6jc66-4

Pyrylium salt 6jc57 (67 mg, 0.16 mmol) and N-methyl-indole-3-carboxaldehyde (25 mg, 0.16 mmol) in MeOH (8 mL) were stirred at room temperature for 2 days. The solvent was removed and the residue suspended in ether and filtered to give blue solid. Recrystallization from EtOH gave green solid of 38 mg.

$\delta_H$(DMSO-d$_6$, 400 MHz) 8.61 (d, 1H, J=16.0, HC=), 8.54 (s, 1H, Ar), 8.51 (s, 1H, Ar), 8.40 (s, 1H, Ar), 8.34-8.8.22 (m, 3H, Ar), 8.19-8.8.06 (m, 2H, Ar), 7.70 (d, 1H, J=6.8, Ar), 7.58-7.40 (m, 5H, Ar, HC=), 3.97 (s, 3H, NMe), 2.45 (s, 3H, CH$_3$), 2.43 (s, 3H, CH$_3$), 2.41 (s, 6H, 2× CH$_3$).

Example 4LL: Compound 6jc67; 2,4-diphenyl-6-((1E,3E)-3-(1,3,3-trimethylindolin-2-ylidene)prop-1-en-1-yl)pyrylium boron tetrafluoride salt

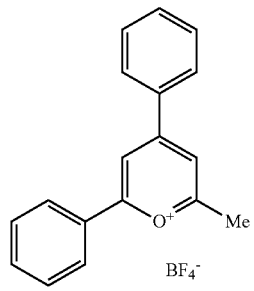

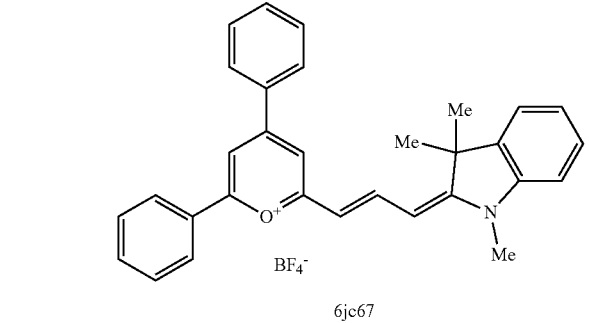

6jc67

Pyrylium salt 6jc26 (50 mg, 0.14 mmol) and 2-(1,3,3-Trimethylindolin-2-ylidene)acetaldehyde (28 mg, 0.14 mmol) in acetic anhydride (2 mL) were stirred at reflux for 1 hour. The reaction was cooled and co-evaporated with toluene (×3), washed with ether and decanted (×2). The residue was purified by column chromatography DCM/MeOH and transferred to a vial to give a blue solid 69 mg.

$\delta_H$(DMSO-d$_6$, 400 MHz) 8.47 (t, 1H, J=13.2, HC=), 8.26-8.10 (m, 4H, Ar), 7.95 (s, 1H, Ar), 7.90-7.59 (m, 8H, Ar), 7.53-7.44 (m, 2H, Ar), 7.35 (t, 1H, J=7.6, Ar), 6.58 (d, 1H, J=13.2, HC=), 6.39 (br s, 1H, HC=), 3.73 (s, 3H, NMe), 1.74 (s, 6H, 2× CH$_3$).

Example 4MM: Compound 6jc67-A; 2,4-di-p-tolyl-6-((1E,3E)-3-(1,3,3-trimethylindolin-2-ylidene)prop-1-en-1-yl)pyrylium boron tetrafluoride salt

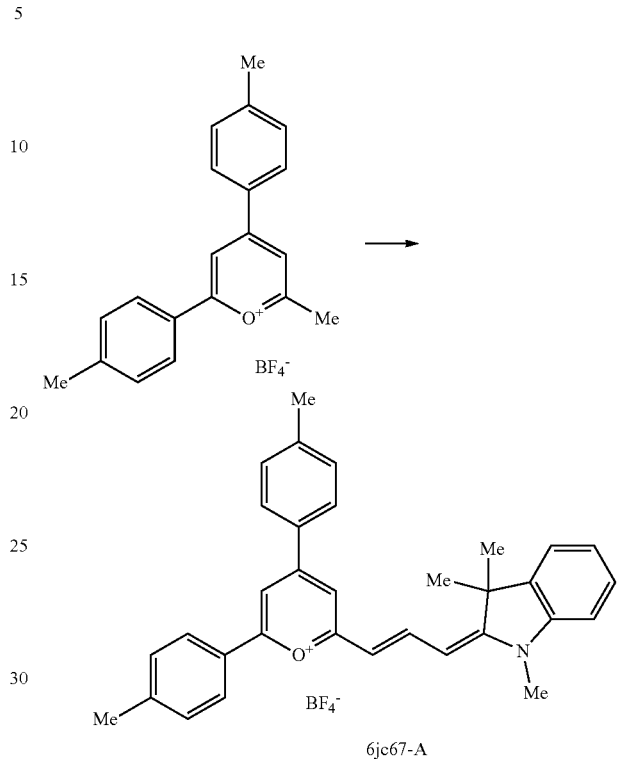

6jc67-A

Pyrylium salt 6jc50-2 (50 mg, 0.14 mmol) and 2-(1,3,3-Trimethylindolin-2-ylidene)acetaldehyde (28 mg, 0.14 mmol) in acetic anhydride (2 mL) were stirred at reflux for 30 minutes. The reaction was cooled and co-evaporated with toluene (×3), washed with ether and decanted (×2). The blue solid was transferred to a vial to give 71 mg.

$\delta_H$(DMSO-d$_6$, 400 MHz) 8.41 (t, 1H, J=14.0, HC=), 8.09 (d, 1H, J=8.0, Ar), 8.05 (d, 1H, J=8.0, Ar), 7.91 (s, 1H, Ar), 7.88-7.72 (m, 1H, Ar), 7.62 (d, 1H, J=8.0, Ar), 7.51-7.37 (m, 6H, Ar), 7.30-7.24 (m, 1H, Ar), 6.45 (d, 1H, J=14.0, HC=), 6.35 (br s, 1H, HC=), 3.65 (s, 3H, NMe), 2.43 (s, 3H, ArCH$_3$), 2.40 (s, 3H, ArCH$_3$), 1.69 (s, 6H, 2× CH$_3$).

Example 4NN: Compound 6jc68-1; (E)-2,4-bis(4-chlorophenyl)-6-(2-(1-methyl-1H-indol-3-yl)vinyl) pyrylium boron tetrafluoride salt

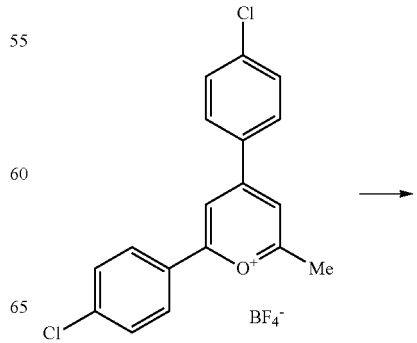

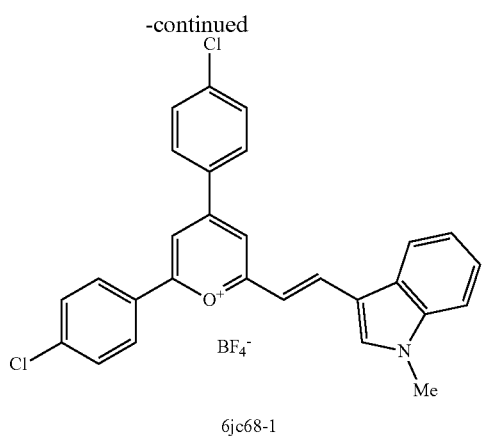

6jc68-1

Pyrylium salt 6jc32-1 (52 mg, 0.14 mmol) and N-methyl-indole-3-carboxaldehyde (23 mg, 0.14 mmol) in MeOH (8 mL) were stirred at room temperature for 2 days. The solvent was removed and the residue was suspended in ether and filtered to give blue solid. Recrystallization from EtOH gave purple solid of 27 mg.

$\delta_H$(DMSO-$d_6$, 400 MHz) 8.75 (d, 1H, J=16.0, HC=), 8.63 (s, 1H, Ar), 8.60 (s, 1H, Ar), 8.54 (d, 2H, J=8.4, Ar), 8.45 (s, 1H, Ar), 8.40-8.28 (m, 3H, Ar), 7.88-7.80 (m, 4H, Ar), 7.76-7.01 (m, 1H, Ar), 7.55-7.43 (m, 3H, Ar, HC=), 4.00 (s, 3H, NMe).

Example 4OO: Compound 6jc68-2; (E)-2,4-bis(4-bromophenyl)-6-(2-(1-methyl-1H-indol-3-yl)vinyl)pyrylium boron tetrafluoride salt

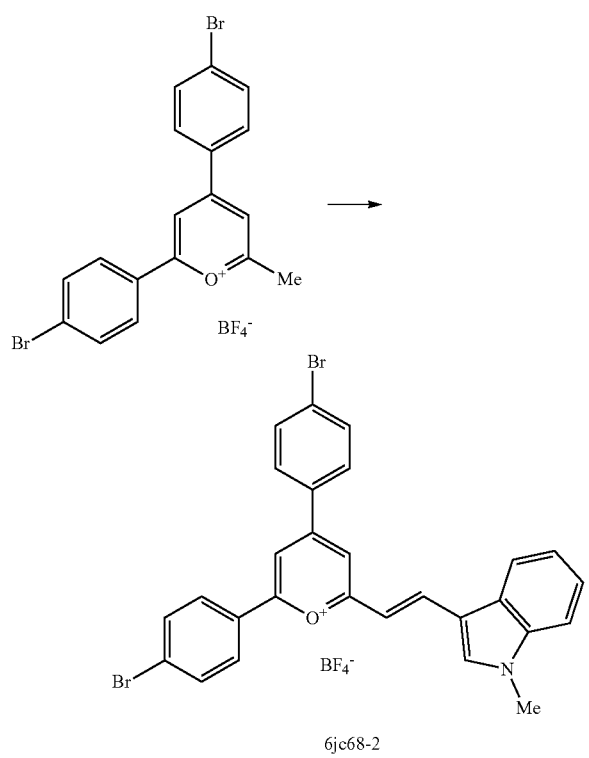

6jc68-2

Pyrylium salt 6jc47 (63 mg, 0.14 mmol) and N-methyl-indole-3-carboxaldehyde (23 mg, 0.14 mmol) in MeOH (8 mL) were stirred at room temperature for 2 days. The solvent was removed and the residue suspended in ether and filtered to give blue solid. Recrystallization from EtOH gave purple solid of 20 mg.

$\delta_H$(DMSO-$d_6$, 400 MHz) 8.74 (d, 1H, J=16.0, HC=), 8.62 (s, 1H, Ar), 8.61 (s, 1H, Ar), 8.48-8.42 (m, 3H, Ar), 8.32-8.23 (m, 3H, Ar), 8.06-7.92 (m, 4H, Ar), 7.76-7.00 (m, 1H, Ar), 7.54-7.42 (m, 3H, Ar, HC=), 4.00 (s, 3H, NMe).

Example 4PP: Compound 6jc69-1; (E)-2,4-bis(4-ethylphenyl)-6-(2-(1,2,3,5,6,7-hexahydropyrido[3,2,1-ij]quinolin-9-yl)vinyl)pyrylium boron tetrafluoride salt

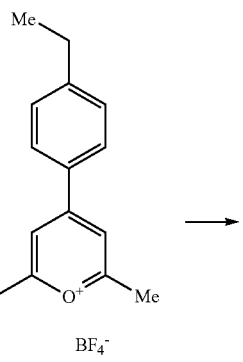

6jc69-1

Pyrylium salt 6jc61 (46 mg, 0.12 mmol) and 9-CHO-julolidine (25 mg, 0.12 mmol) in MeOH (8 mL) were stirred at room temperature overnight. The solvent was removed and the residue suspended in ether and filtered to give solid. Recrystallization from EtOH gave purple solid of 44 mg.

$\delta_H$(DMSO-$d_6$, 400 MHz) 8.40-8.32 (m, 3H, Ar, HC=), 8.27-8.18 (m, 4H, Ar), 7.60-7.52 (m, 4H, Ar), 7.45 (s, 2H, Ar), 7.21 (d, 1H, J=15.6, HC=), 3.50-3.40 (m, 4H, 2× $CH_2$), 2.83-2.70 (m, 8H, 4× $CH_2$), 1.99-1.87 (m, 4H, 2× $CH_2$), 1.27 (t, 6H, J=7.2, 2× $CH_3$).

Example 4QQ: Compound 6jc69-2; (E)-2,4-bis(4-(tert-butyl)phenyl)-6-(2-(1,2,3,5,6,7-hexahydropyrido[3,2,1-ij]quinolin-9-yl)vinyl)pyrylium boron tetrafluoride salt Example 4RR: Compound 6jc69-3; (E)-2,4-bis(3,4-dimethylphenyl)-6-(2-(1,2,3,5,6,7-hexahydropyrido[3,2,1-ij]quinolin-9-yl)vinyl)pyrylium boron tetrafluoride salt

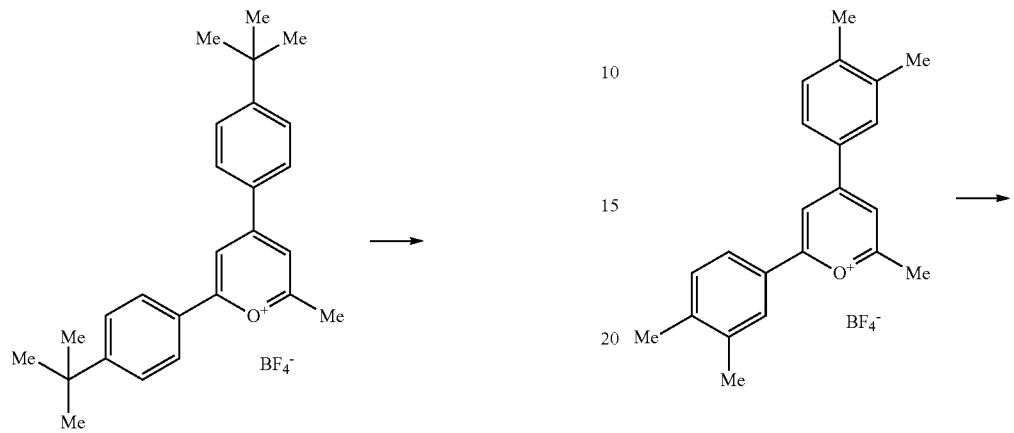

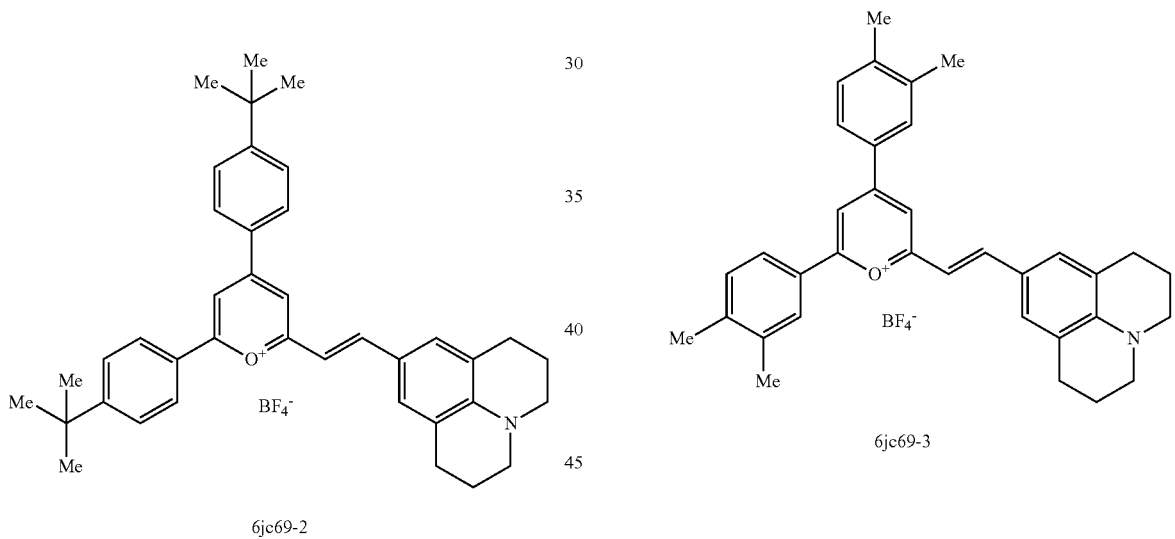

Pyrylium salt 6jc56 (53 mg, 0.12 mmol) and 9-CHO-julolidine (25 mg, 0.12 mmol) in MeOH (8 mL) was stirred at room temperature overnight. The solvent was removed and the residue was suspended in ether and filtered to give solid. Recrystallization from EtOH gave purple solid of 74 mg.

$\delta_H$(DMSO-d$_6$, 400 MHz) 8.38-8.31 (m, 3H, Ar, HC=), 8.24-8.15 (m, 4H, Ar), 7.78-7.67 (m, 4H, Ar), 7.45 (s, 2H, Ar), 7.19 (d, 1H, J=15.6, HC=), 3.49-3.40 (m, 4H, 2× CH$_2$), 2.80-2.72 (m, 4H, 2× CH$_2$), 1.97-1.88 (m, 4H, 2× CH$_2$), 1.38 (s, 18H, 9×CH$_3$).

Pyrylium salt 6jc57 (50 mg, 0.12 mmol) and 9-CHO-julolidine (25 mg, 0.12 mmol) in MeOH (8 mL) were stirred at room temperature overnight. The solvent was removed and the residue were suspended in ether and filtered to give solid. Recrystallization from EtOH gave green solid of 64 mg.

$\delta_H$(DMSO-d$_6$, 400 MHz) 8.33 (s, 1H, Ar), 8.25-8.10 (m, 4H, Ar, HC=), 8.08 (s, 1H, Ar), 8.04 (d, 1H, J=7.6, Ar), 7.50-7.43 (m, 2H, Ar), 7.42 (s, 2H, Ar), 7.18 (d, 1H, J=16.0, HC=), 3.48-3.40 (m, 4H, 2× CH$_2$), 2.79-2.70 (m, 4H, 2× CH$_2$), 2.42 (s, 3H, CH$_3$), 2.40 (s, 3H, CH$_3$), 2.38 (s, 6H, 2× CH$_3$), 1.99-1.88 (m, 4H, 2× CH$_2$).

Example 4SS: Compound 6jc69-4; (E)-2,4-bis(4-chlorophenyl)-6-(2-(1,2,3,5,6,7-hexahydropyrido[3,2,1-ij]quinolin-9-yl)vinyl)pyrylium boron tetrafluoride salt

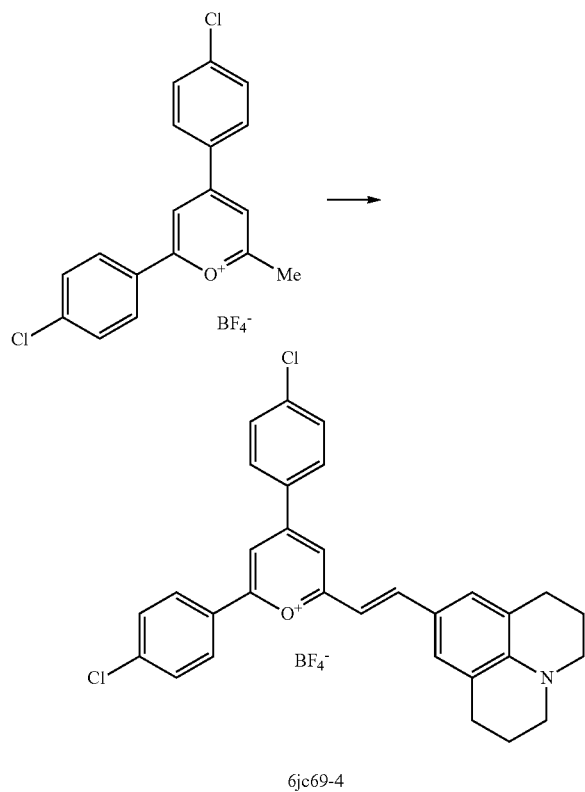

Pyrylium salt 6jc32-1 (48 mg, 0.12 mmol) and 9-CHO-julolidine (25 mg, 0.12 mmol) in MeOH (8 mL) were stirred at room temperature overnight. The solvent was removed and the residue suspended in ether and filtered to give solid. Recrystallization from EtOH gave purple solid of 39 mg.

$\delta_H$(DMSO-$d_6$, 400 MHz) 8.40 (d, 2H, J=8.4, Ar), 8.32 (s, 1H, Ar), 8.30-8.17 (m, 4H, Ar, HC=), 7.83-7.51 (m, 4H, Ar), 7.45 (s, 2H, Ar), 7.18 (d, 1H, J=15.2, HC=), 3.52-3.42 (m, 4H, 2× CH$_2$), 2.81-2.70 (m, 4H, 2× CH$_2$), 1.99-1.86 (m, 4H, 2× CH$_2$).

Example 4TT: Compound 6jc69-5; (E)-2,4-bis(4-bromophenyl)-6-(2-(1,2,3,5,6,7-hexahydropyrido[3,2,1-ij]quinolin-9-yl)vinyl)pyrylium boron tetrafluoride salt

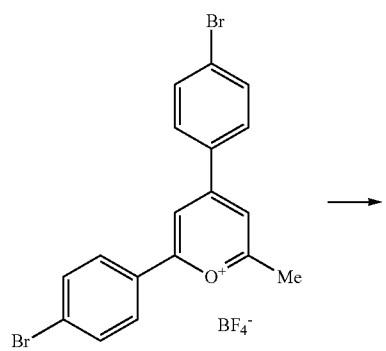

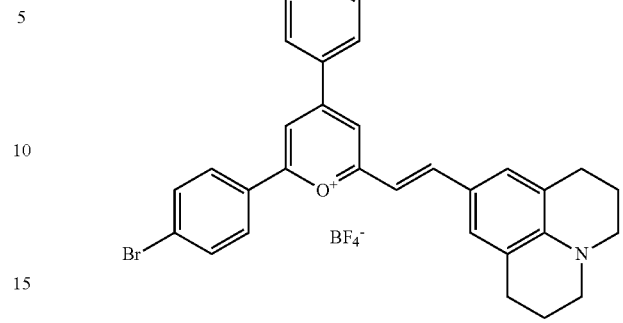

Pyrylium salt 6jc47 (59 mg, 0.12 mmol) and 9-CHO-julolidine (25 mg, 0.12 mmol) in MeOH (8 mL) were stirred at room temperature overnight. The solvent was removed and the residue was suspended in ether and filtered to give solid. Recrystallization from EtOH gave green solid of 47 mg.

$\delta_H$(DMSO-$d_6$, 400 MHz) 8.36-8.13 (m, 7H, Ar, HC=), 7.94-7.85 (m, 4H, Ar), 7.45 (s, 2H, Ar), 7.18 (d, 1H, J=14.8, HC=), 3.52-3.43 (m, 4H, 2× CH$_2$), 2.82-2.71 (m, 4H, 2× CH$_2$), 1.98-1.88 (m, 4H, 2× CH$_2$).

Example 4UU: Compound 6jc76-1; 2,4-bis(4-ethylphenyl)-6-((1E,3E)-3-(1,3,3-trimethylindolin-2-ylidene)prop-1-en-1-yl)pyrylium boron tetrafluoride salt

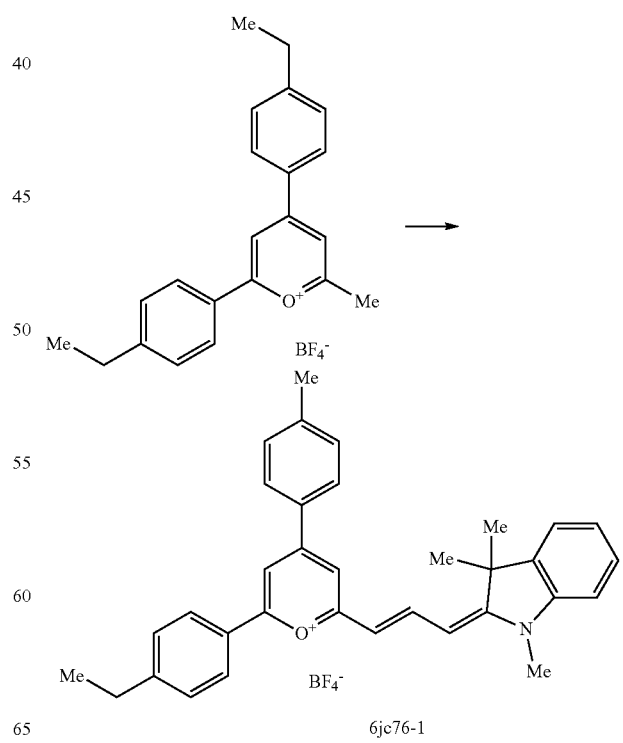

Pyrylium salt 6jc61 (50 mg, 0.13 mmol) and 2-(1,3,3-trimethylindolin-2-ylidene)acetealdehyde (26 mg, 013 mmol) in acetic anhydride (2 mL) was stirred at reflux for 30 minutes. The reaction was cooled and co-evaporated with toluene (×3), washed with ether and decanted (×2). The blue solid was transferred to a vial and lyophilized to give 90 mg.

$\delta_H$(DMSO-d$_6$, 400 MHz) 8.45 (t, 1H, J=14.0, HC=), 8.15 (d, 1H, J=8.0, Ar), 8.11 (d, 1H, J=8.0, Ar), 7.95 (s, 1H, Ar), 7.92-7.78 (m, 1H, Ar), 7.67 (d, 1H, J=6.8, Ar), 7.60-7.42 (m, 6H, Ar), 7.36-7.28 (m, 1H, Ar), 6.50 (d, 1H, J=14.0, HC=), 6.40 (br s, 1H, HC=), 3.69 (s, 3H, NMe), 2.81-2.69 (m, 4H, 2× CH$_2$), 2× CH$_2$), 1.74 (s, 6H, 2× CH$_3$), 1.32-1.20 (m, $\delta_H$, 2× CH$_3$).

Example 4VV: Compound 6jc76-2; 2,4-bis(4-tert-butyl)phenyl)-6-((1E,3E)-3-(1,3,3-trimethylindolin-2-ylidene)prop-1-en-1-yl)pyrylium boron tetrafluoride salt

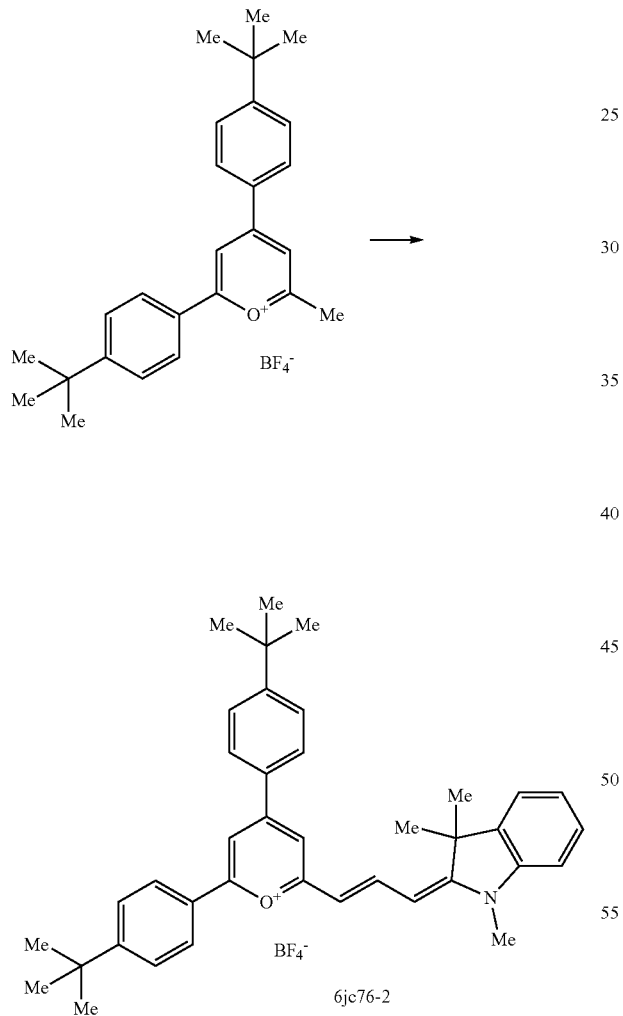

6jc76-2

Pyrylium salt 6jc56 (50 mg, 0.11 mmol) and 2-(1,2,3-trimethylindolin-2-ylidene)acetaldehyde (23 mg, 0.11 mmol) in acetic anhydride (2 mL) were stirred at reflux for 30 minutes. The reaction was cooled and co-evaporated with toluene (×3), washed with ether and decanted (×2). The resulting blue solid was transferred to a vial and lyophilized to give 78 mg.

$\delta_H$(DMSO-d$_6$, 400 MHz) 8.45 (t, 1H, J=13.2, HC=), 8.14 (d, 1H, J=8.0, Ar), 8.09 (d, 1H, J=8.0, Ar), 7.93 (s, 1H, Ar), 7.90-7.78 (m, 1H, Ar), 7.76-7.62 (m, 5H, Ar), 7.54-7.40 (m, 2H, Ar), 7.38-7.29 (m, 1H, Ar), 6.51 (d, 1H, J=13.2, HC=), 6.42 (br s, 1H, HC=), 3.70 (s, 3H, NMe), 1.74 (s, 6H, 2× CH$_3$), 1.38 (s, 9H, 3×CH$_3$), 1.36 (s, 9H, 3×CH$_3$).

Example 4WW: Compound 6jc77-1; 2,4-bis(4-chlorophenyl)-6-((1E,3E)-3-(1,3,3-trimethylindolin-2-ylidene)prop-1-en-1-yl)pyrylium boron tetrafluoride salt

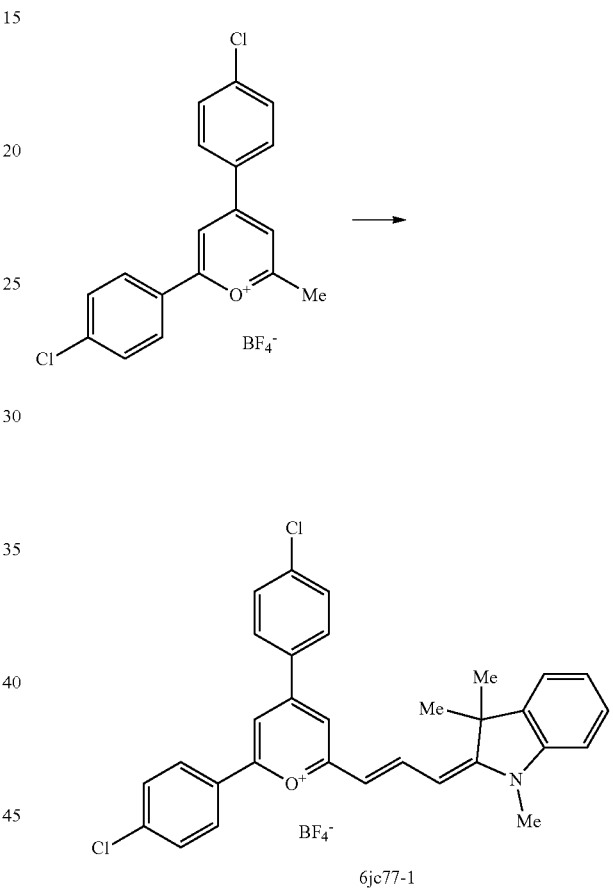

6jc77-1

Pyrylium salt 6jc32-1 (50 mg, 0.12 mmol) and 2-(1,3,3-trimethylindolin-2-ylidene)acetaldehyde (25 mg, 0.12 mmol) in acetic acid (2 mL) were stirred at reflux for 30 minutes. The reaction was cooled and co-evaporated with toluene (×3), washed with ether and decanted (×2). The blue solid was transferred to a vial and lyophilized to give 73 mg. 1H NMR shows desired product but spectrum not clean.

$\delta_H$(DMSO-d$_6$, 400 MHz) 8.44 (t, 1H, J=13.2, HC=), 8.27-8.10 (m, 4H, Ar), 7.92 (s, 1H, Ar), 7.88-7.64 (m, 6H, Ar), 7.60-7.32 (m, 3H, Ar), 6.72-6.55 (m, 2H, 2× HC=), 3.79 (s, 3H, NMe), 1.74 (s, 6H, 2× CH$_3$).

Example 4XX: Compound 6jc77-2; 2,4-bis(4-bromophenyl)-6-((1E,3E)-3-(1,3,3-trimethylindolin-2-ylidene)prop-1-en-1-yl)pyrylium boron tetrafluoride salt

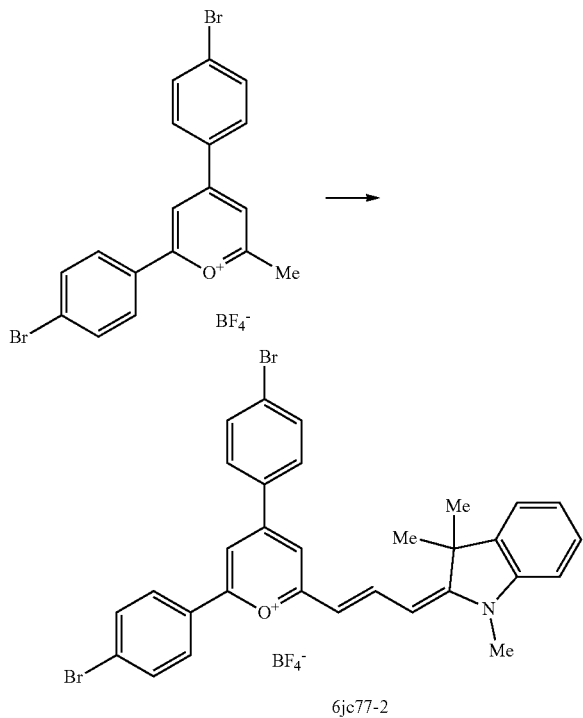

6jc77-2

Pyrylium salt (50 mg, 0.10 mmol) and 2-(1,3,3-trimethylindolin-2-ylidene)acetaldehyde (20 mg, 0.10 mmol) in acetic anhydride (2 mL) was stirred at reflux for 30 minutes. The reaction was cooled and co evaporated with toluene (×3), washed with ether and decanted (×2). The blue solid was transferred to a vial and lyophilized to give 71 mg. 1H NMR shows desired product but spectrum not entirely clean.

$\delta_H$(DMSO-d$_6$, 400 MHz) 8.50-8.38 (m, 1H, HC=), 8.20-8.00 (m, 4H, Ar), 7.96-7.79 (m, 6H, Ar), 7.68 (d, 1H, J=8.0. Ar), 7.60-7.32 (m, 3H, Ar), 6.72-6.55 (m, 2H, 2× HC=), 3.78 (s, 3H, NMe), 1.74 (s, 6H, 2× CH$_3$).

Example 5: X-Ray Based High Ambiguity Driven Protein-Protein Docking (HADDOCK) Model of Human Defensin Peptide 1 (HNP1)

Figure 3:
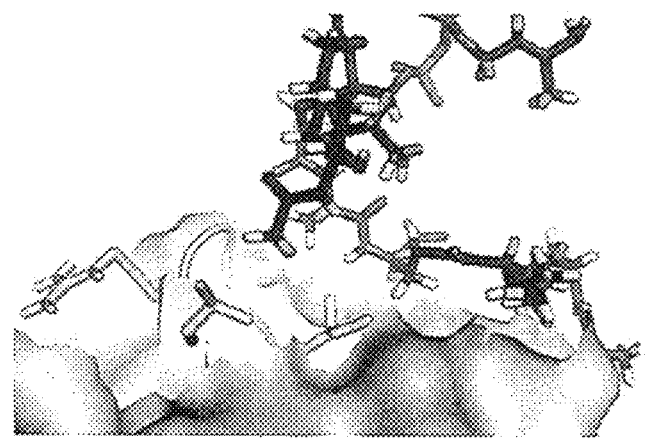
FIG. 3 is an X-ray-based, computer-generated HADDOCK model of human defensin peptide 1 (HNP1) with LII.
Figure 4:
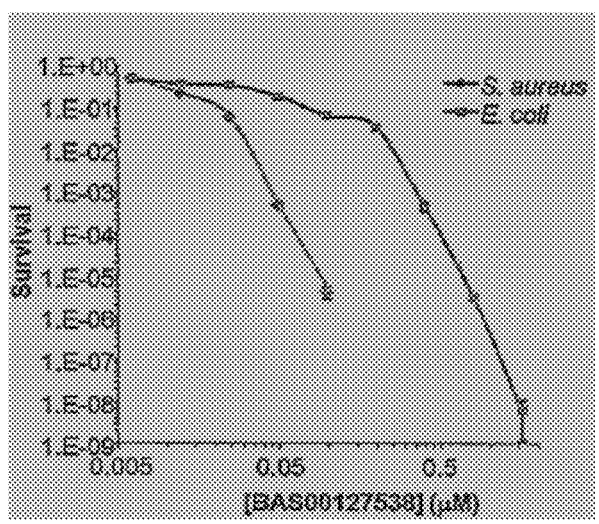
FIG. 4 shows survival data for Staphylococcus aureus and Escherichia coli (bacteria killing) in vitro, after treatment with BAS00127538.
Figure 5:
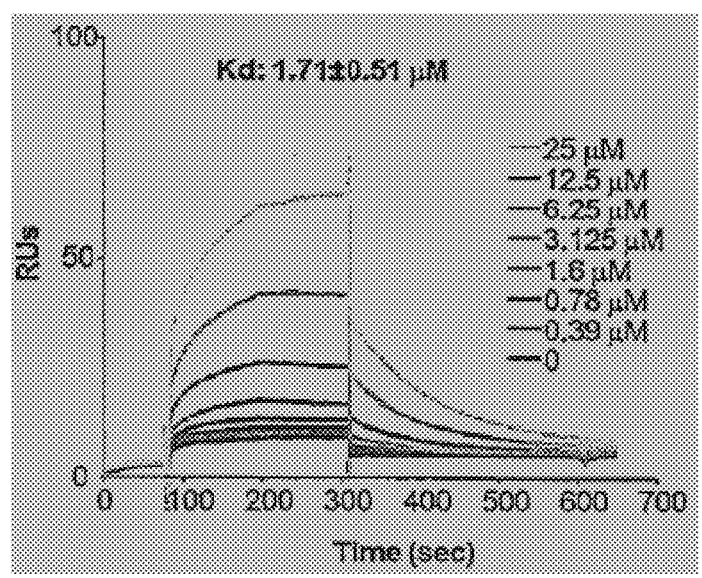
FIG. 5 shows the binding kinetics of BAS00127538 to 3-LII as determined by surface plasmon resonance.
Figure 6A:
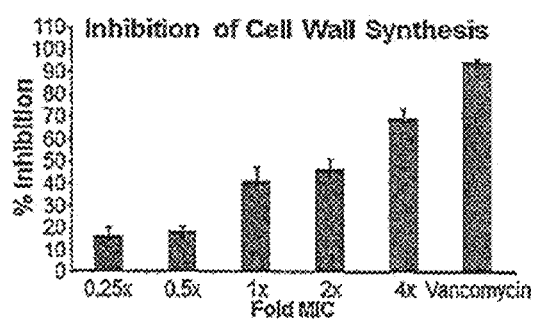
FIG. 6A, FIG. 6B, FIG. 6C, and FIG. 6D show data on the mechanism of action of BAS00127538.
Figure 6B:
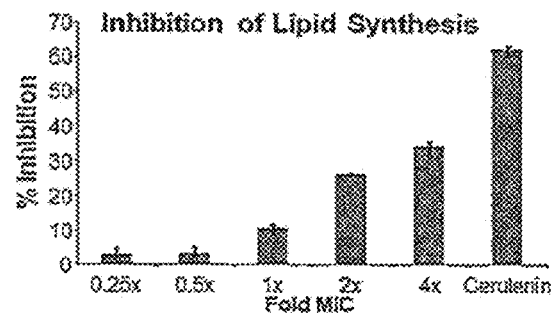
Figure 6C:
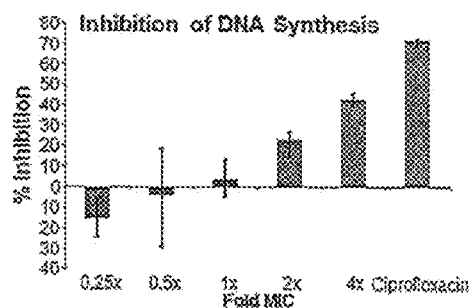
Figure 6D:
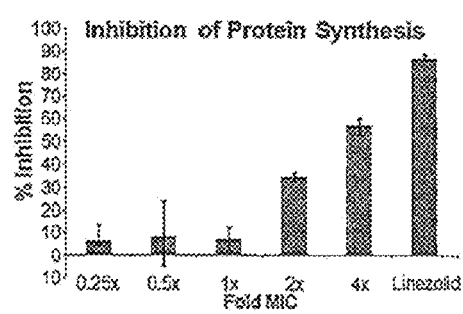

A 3D pharmacophore fingerprinting typed atom triangles (TAT) search was performed to represent specific side-chain structures and properties. See the model pictured in FIG. 3. Approximately 100 compounds of interest were found out of 1.5 million screened. Compound BAS00127538 was tested for survival in vivo against *Staphylococcus aureus* and *Escherichia coli* (FIG. 4) and to determine binding Kd (FIG. 5).

In addition, BAS00127538 and two other compounds were tested for activity against bacterial strains. See results in Table 3, below.

TABLE 3

Antibacterial activity of small molecule LII inhibitors.

| Organism | MMX#-ATCC# | BAS00127538 | 1499-1221 | 1611-0203 | Cipro | Linezolid |
|---|---|---|---|---|---|---|
| *Bacillus anthracis* Sterne | 109-NA | 0.5 | 0.5 | 1 | 0.5 | NA |
| *Bacillus anthracis*\* | Ames | 0.5 | 1 | 0.5 | 0.12 | NA |
| *Bacillus anthracis* (spores)\* | Ames | 0.5 | 1 | 1 | 0.06 | NA |
| *Yersinia pestis*\* | CO92 | 8 | >64 | >64 | <0.06 | NA |
| *Burkholderia mallei*\* | 23344 | >64 | >64 | >64 | 2 | NA |
| *Burkholderia pseudomallei*\* | K96243 | 64 | >64 | >64 | 2 | NA |
| *Staphylococcus aureus* | 100-29213 | 0.5 | 0.25 | 2 | 0.5 | 4 |
| *Staphylococcus aureus* (MRSA) | 757-NA | 0.5 | 0.5 | 2 | >2 | 4 |
| *Enterococcus faecalis* | 101-29212 | 1 | 2 | 1 | 1 | 2 |
| *Enterococcus faecalis* (VRE) | 848-NA | 1 | 2 | 1 | >2 | 2 |
| *Streptococcus pneumoniae* | 1195-49619 | 8 | >8 | >16 | 1 | 2 |
| *Streptococcus pneumoniae* (PRSP) | 884-NA | 8 | >8 | >16 | 2 | 2 |
| *Escherichia coli* | 102.25922 | 4 | >16 | >4 | 0.008 | >64 |
| *Pseudomonas aeruginosa* | 103-27853 | >8 | >16 | >4 | 0.25 | >64 |

Reported MICs were adjusted to reflect instances where drug precipitation obscured the interpretation of the endpoint.
NA—not applicable, MRSA—methicillin-resistant *S. aureus*, VRE—vancomycin-resistant enterococci, PRSP—penicillin-resistant *S. pneumoniae*, Cipro—ciprofloxacin.
\*Carried out according to DOD guidelines.

In order to investigate the mechanism of action of BAS00127538, exponentially growing S. aureus 29213 cells were exposed to the compounds compound and comparators in triplicate using 2.5% DMSO as "no drug" control. Cells were added to Mueller-Hinton broth or M9 medium for protein synthesis and further incubated in the presence of [$^{14}$C]N-acetyl glucosamine (cell wall), [$^{3}$H]glycerol (lipid), [$^{3}$H]thymidine (DNA), or [$^{3}$H] leucine (protein). Following incubation, reactions were stopped by addition of TCA (DNA, protein), 8% SDS (cell wall), or chloroform/methanol (lipid) and analyzed by scintillation counting. See FIG. 6, which shows data on the effects of the BAS00127583 compound on four bacterial parameters, inhibition of cell wall synthesis, lipid synthesis, DNA synthesis, and protein synthesis.

Figure 7A:
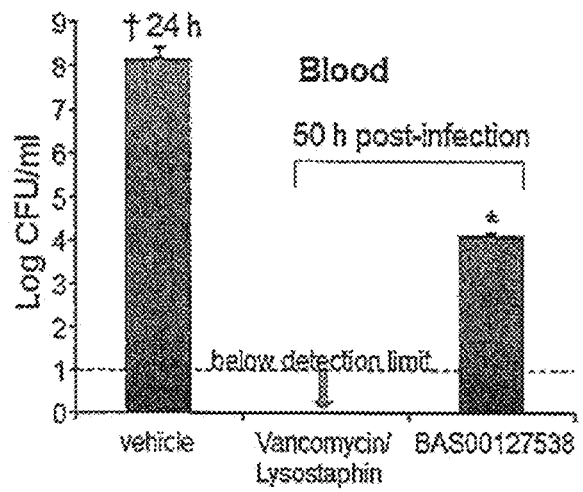
FIG. 7A and FIG. 7B present data on the bacteria present in spleen (FIG. 7A) and in blood (FIG. 7B), showing the efficacy of BAS00127538 in vivo.
Figure 7B:
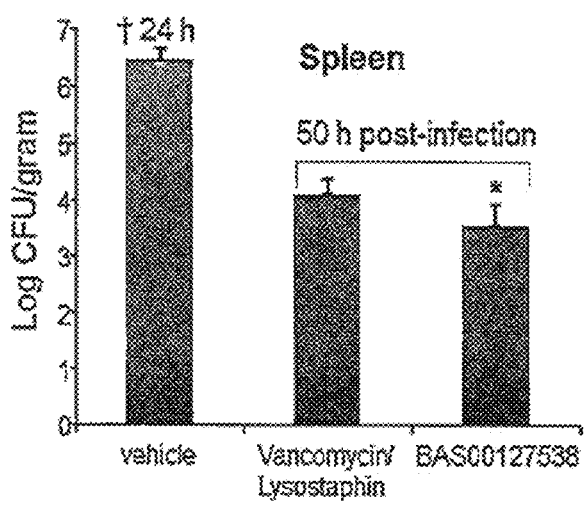

To determine the efficacy of BAS00127583 in vivo, samples were collected from vehicle-treated animals at 20 hours or at 50 hours post-infection from vancomycin- and BAS-treated animals. One animal treated with BAS did not survive beyond 28 hours. Results are presented in FIG. 7A and FIG. 7B.

Example 6: Plasma Stability and Pharmacokinetic Study of Compound 6jc48-1

A 2.5 mg/ml solution of compound 6jc48-1 was prepared in 10% DMSO, 50% PEG in PBS and administered at 2.5 mg/kg intravenous (tail vein) to male CD1 mice (N=3 per group). About 0.02 mL of blood was collected at 5 minutes, 15 minutes, 30 minutes, 1 hour, 2 hours, 4 hours, 6 hours, 8 hours and 14 hours post-treatment in centrifuge tubes containing 2 µL heparin (1,000 units). Compound 6jc48-1 was quantitated by LC/MS/MS using working solutions of 10, 20, 50, 100, 500, 1,000, 5,000 and 10,000 ng/mL compound 6jc48-1 prepared in blank CD1 mouse plasma as internal standards. No adverse clinical observations were observed for the duration of the experiment. For plasma stability measurements, compound 6jc48-1 (10 µg/mL) was incubated for 24 hours in the presence of serum (50%). Samples were taken after 2 minutes, 5 minutes, 15 minutes, 30 minutes, 1 hour, 2 hours and 19 hours. Stability of the compound was determined by LC/MS/MS.

Figure 8:
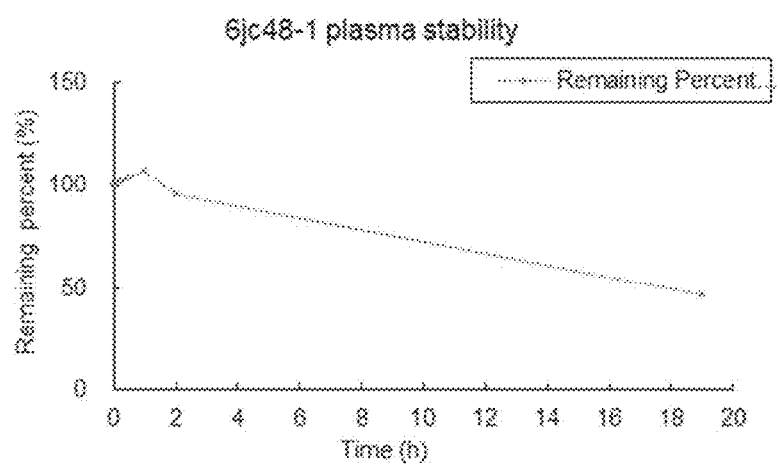
FIG. 8 is a graph showing the plasma stability of compound 6jc48-1 plasma stability, as tested by LC/MS/MS after 2 minutes, 5 minutes, 15 minutes, 30 minutes, 1 hour, 2 hours, and 19 hours in the presence of 50% serum.

The chemical stability of compound 6jc48-1 was tested directly in vivo by determining its stability in plasma as well as its pharmacokinetic profile. Test samples and standard samples (dexamethasone) were prepared and processed simultaneously and analyze under identical conditions. The results indicate that all test samples and standard samples passed acceptance criteria and could be detected by LC/MS/MS with confirmation of correct mass. Compound plasma stability was tested by LC/MS/MS after 2 minutes, 5 minutes, 15 minutes, 30 minutes, 1 hour, 2 hours and 19 hours. The data presented in FIG. 8 show that compound 6jc48-1 was stable after 2 hours in serum; after 19 hours, 46% of compound remained. This indicates that plasma stability is long lasting.

Figure 9:
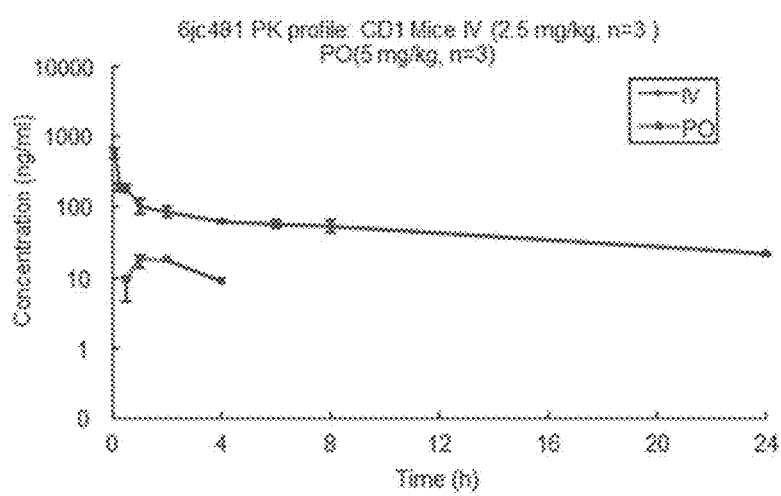
FIG. 9 is a graph showing the pharmacokinetic profile of compound 6jc48-1 in vivo.

Next, the pharmacokinetic (PK) profile of compound 6jc48-1 was compared to the parent compound BAS00127538. To determine the PK parameters, compounds were administered as a single dose of 2.5 mg/kg by intravenous injection (IV) or as a single oral dose (PO) of 5 mg/kg in 10% DMSO and 50% PEG400 in PBS, to mice (n=3), and the plasma concentration over time was determined by LC/MS/MS. Upon intravenous administration, compound 6jc48-1 was very stable in vivo and could be readily detected after 4 hours (PO) or 24 hours (IV). Half-life was determined by measuring the plasma concentration of compound by LC/MS/MS at the time points indicated in the figure. Compound 6jc48-1 had an in vivo half-life of 13.3 hours. See FIG. 8 and FIG. 9.

Based on these observations, the PK parameters were calculated for both compounds, and are presented in Table 4, below ($T_{1/2}$: half-life; $C_{max}$: maximum observed concentration; AUC: area under the curve; D: dose; Vss: volume of distribution; Cl: clearance; MRT: mean residence time; $F_{last}$ (bioavailability at last time point); $F_{inf}$ (inferred bioavailability)). The observed maximum plasma concentration was 1039 ng/mL and decreased slowly over time. The mean residence time (MRT) of the unchanged drug in circulation was 7.29 hours, with an area under the curve (AUCinf of 1769 h·ng·mL per hour. See FIG. 9 and Table 4, below. Volume of distribution at equilibrium (Vs) was 22.8 L·kg with total plasma clearance (CL) of 23.6 mL·min·kg. Compared to BAS00127538, compound 6jc48-1 showed markedly improved half-life (>13 hours vs. 0.22 hours), improved maximum concentration (1039 ng/mL vs. 101 ng/mL), increased volume of distribution (about 23 L/kg vs. 12.2 L/kg) and decreased clearance (23.6 mL/min/kg vs. 711 mL/min/kg). Upon oral administration, compound 6jc48-1 had a half-life of about 3 hours, with a calculated bioavailability of about 2.5%, whereas compound BAS00127538 could not be detected.

TABLE 4

Pharmacokinetic Properties of Compound 6jc48-1 and BAS00127538.

| Pharmacokinetic Parameter | BAS00127538 (IV administration) | Compound 6jc48-1 (IV administration) | Compound 6jc48-1 (PO administration) |
|---|---|---|---|
| $T_{1/2}$ (hours) | 0.227 | 13.3 ± 1.8 | 2.78 |
| $C_{max}$ (ng/mL) | 101 | 1039 ± 323 | 19.1 |
| $AUC_{last}$ (h*ng/mL) | 26.9 | 1340 ± 117 | 46.9 |
| $AUC_{Inf}$ (h*ng/mL) | 27.9 | 1769 ± 120 | 90 |
| $AUC_{Extrap}$ (%) | 4.38 | 24.3 ± 3.1 | 48.6 |
| $AUC_{last}/D$ (h*mg/mL) | 26.9 | 536 ± 47 | 9.4 |
| Vss_obs (L/kg) | 12.2 | 22.8 ± 2.9 | 1.75 |
| Cl_obs (mL/min/kg) | 711 | 23.6 ± 1.7 | NA |
| MRT (hours) | 0.226 | 7.29 ± 0.27 | NA |
| $F_{last}$ (%) | NA | NA | 1.9 |
| $F_{inf}$ (%) | NA | NA | 2.54 |

Example 7: Functional Characterization of Chemically Modified Compounds

The functional consequences of chemical modifications of the substituents around the diphenyl pyrylium core initially were evaluated in two functional assays: (1) antibacterial activity and (2) Lipid II binding as assayed by Surface Plasmon Resonance. See the results in Table 5, below, which provides a chemical and functional overview of some of the compounds generated for this study. In Table 5, a determination of "yes" for Lipid II binding indicates significant binding (binding more than 10 resonance units as determined by SPR), as discussed in Example 1E, above. ND indicates not done.

TABLE 5

Compound Structure and Function.

| Structural Formula and Compound Name | Chemical Formula | MW (g/mol) | IUPAC Name | Lipid II Binding | S. aureus Killing |
|---|---|---|---|---|---|
| 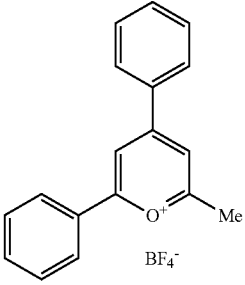 6jc26 | $C_{18}H_{15}BF_4O$ | 334.12 | 2-methyl-4,6-diphenylpyrylium boron tetrafluoride salt | no | >64 |
| 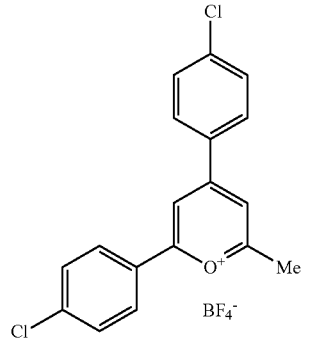 6jc32-1 | $C_{18}H_{13}BCl_2F_4O$ | 403.01 | 2,4-bis(4-chlorophenyl)-6-methylpyrylium boron tetrafluoride salt | no | >64 |
| 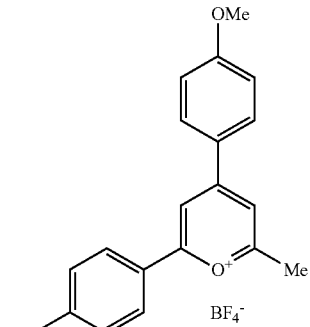 6jc32-2 | $C_{20}H_{19}BF_4O_3$ | 394.17 | 2,4-bis(4-methoxyphenyl)-6-methylpyrylium boron tetrafluoride salt | no | >64 |
| 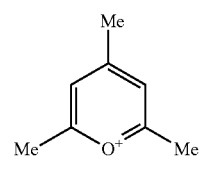 6jc36 | $C_8H_{11}BF_4O$ | 209.98 | 2,4,6-trimethylpyrylium boron tetrafluoride salt | no | >64 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 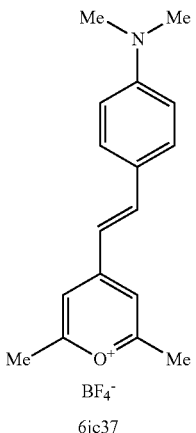 6jc37 | $C_{17}H_{20}BF_4NO$ | 341.15 | (E)-4-(4-(dimethylamino)styryl)-2,6-dimethylpyrylium boron tetrafluoride salt | no | 16 |
| 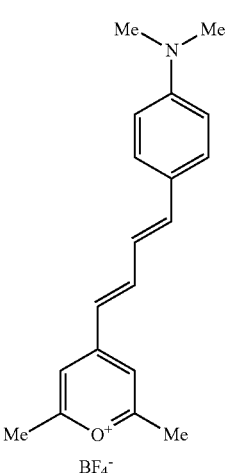 6jc38 | $C_{19}H_{22}BF_4NO$ | 367.19 | 4-((1E,3E)-4-(4-(dimethylamino)phenyl)buta-1,3-dien-1-yl)-2,6-dimethylpyrylium boron tetrafluoride salt | no | 32 |
| 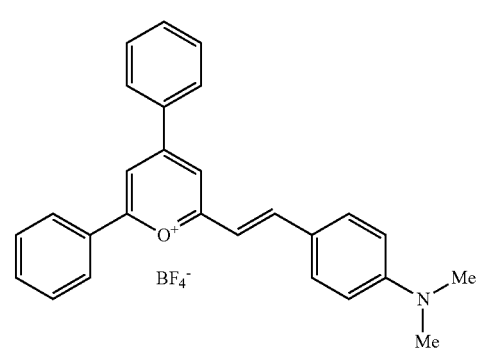 6jc39 | $C_{27}H_{24}BF_4NO$ | 465.29 | (E)-2-(4-(dimethylamino)styryl)-4,6-diphenylpyrylium boron tetrafluoride salt | yes | 2 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 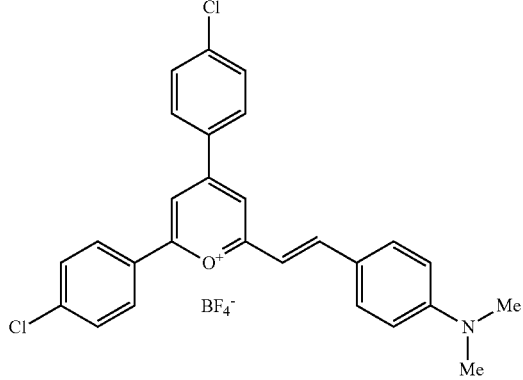 6jc41-1 | $C_{27}H_{22}Cl_2NO$ | 534.18 | (E)-2,4-bis(4-chlorophenyl)-6-(4-(dimethylamino)styryl)pyrylium boron tetrafluoride salt | yes | 32 |
| 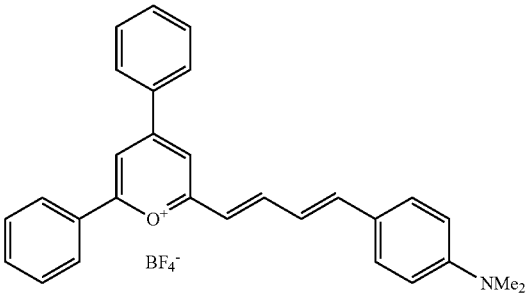 6jc43-1 | $C_{29}H_{26}BF_4NO$ | 491.33 | 2-((1E,3E)-4-(4-(dimethylamino)phenyl)buta-1,3-dien-1-yl)-4,6-diphenyl pyrylium boron tetrafluoride salt | yes | 4 |
| 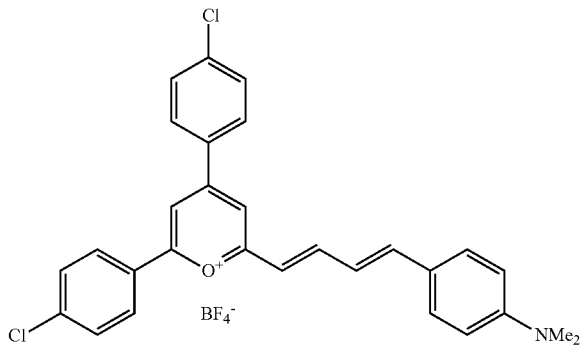 6jc43-2 | $C_{29}H_{24}BCl_2F_4NO$ | 560.22 | 2,4-bis(4-chlorophenyl)-6-((1E,3E)-4-(4-(dimethylamino)phenyl)buta-1,3-dien-1-yl)pyrylium boron tetrafluoride salt | ND | >64 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 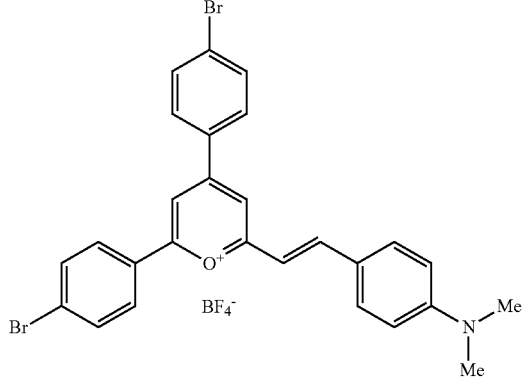 6jc48-1 | $C_{27}H_{22}BBr_2F_4NO$ | 623.08 | (E)-2,4-bis(4-bromophenyl)-6-(4-(dimethylamino)styryl)pyrylium boron tetrafluoride salt | yes | 32 |
| 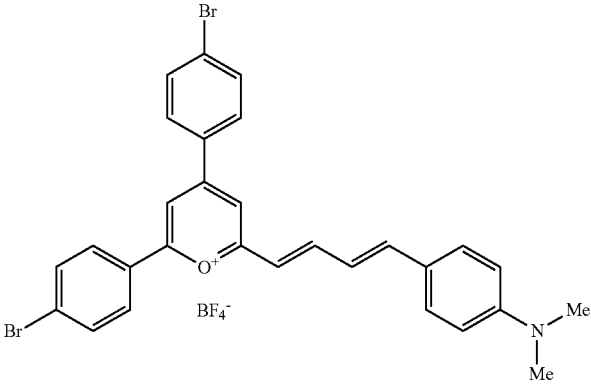 6jc48-2 | $C_{29}H_{24}BBr_2F_4NO$ | 649.12 | 2,4-bis(4-bromophenyl)-6-((1E,3E)-4-(4-(dimetliylamino)phenyl)buta-1,3-dien-1-yl)pyrylium boron tetrafluoride salt | yes | >64 |
| 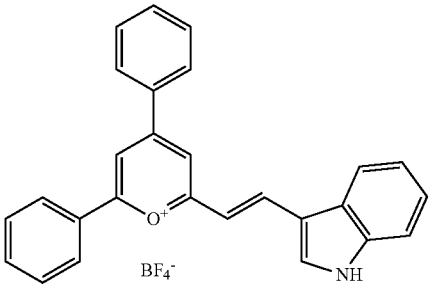 6jc49-1 | $C_{27}H_{20}BF_4NO$ | 461.26 | (E)-2-(2-(1H-indol-3-yl)vinyl)-4,6-diphenylpyrylium boron tetrafluoiide salt | yes | 1 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 6jc50-2 | $C_{20}H_{19}BF_4O$ | 362.17 | 2-methyl-4,6-di-p-tolylpyrylium boron tetrafluoride salt | no | >64 |
| 6jc51-1 | $C_{29}H_{28}BF_4NO$ | 493.34 | (E)-2-(4-(dimethylamino)styryl)-4,6-di-p-tolylpyrylium boron tetrafluoride salt | yes | 0.5 |
| 6jc51-2 | $C_{31}H_{30}BF_4NO$ | 519.38 | 2-((1E,3E)-4-(4-(dimethylamino)phenyl)buta-1,3-dien-1-yl)-4,6-di-p-tolylpyrylium boron tetrafluoride salt | yes | 2 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 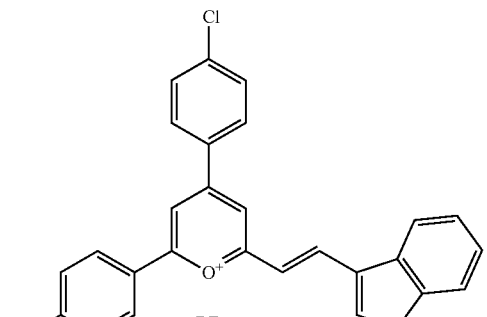 6jc53-1 | $C_{27}H_{18}BCl_2F_4NO$ | 530.15 | (E)-2-(2-(1H-indol-3-yl)vinyl)-4,6-bis(4-chlorophenyl)pyrylium boron tetrafluoride salt | yes | 16 |
| 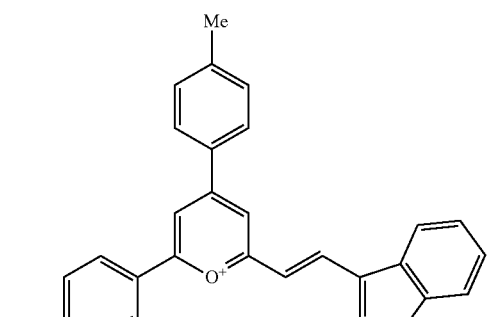 6jc53-2 | $C_{29}H_{24}BF_4NO$ | 489.31 | (E)-2-(2-(1H-indol-3-yl)vinyl)-4,6-di-p-tolylpyiylium boron tetrafluoride salt | yes | 4 |
| 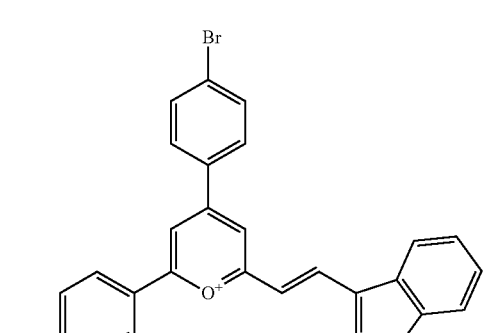 6jc53-3 | $C_{27}H_{18}BBr_2F_4NO$ | 619.05 | (E)-2-(2-(1H-indol-3-yl)vinyl)-4,6-bis(4-bromophenyl)pyrylium boron tetrafluoride salt | yes | >64 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 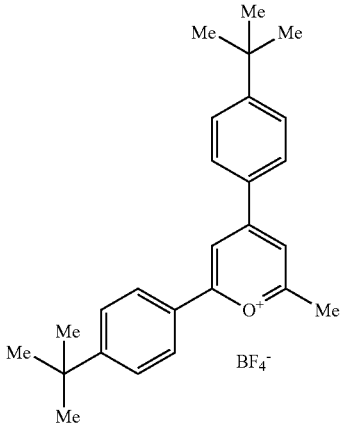<br>6jc56 | $C_{26}H_{32}BF_4O$ | 446.33 | 2,4-bis(4-(tert-butyl)phenyl)-6-methylpyrylium boron tetrafluoride salt | no | >64 |
| 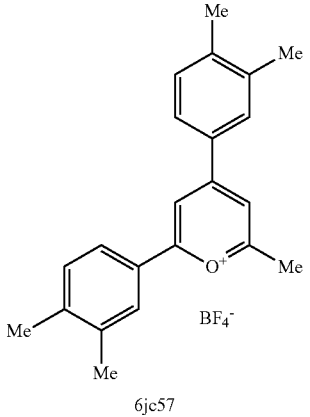<br>6jc57 | $C_{22}H_{23}BF_4NO$ | 390.22 | 2,4-bis(3,4-dimethylphenyl)-6-methylpyrylium boron tetrafluoride salt | no | >64 |
| 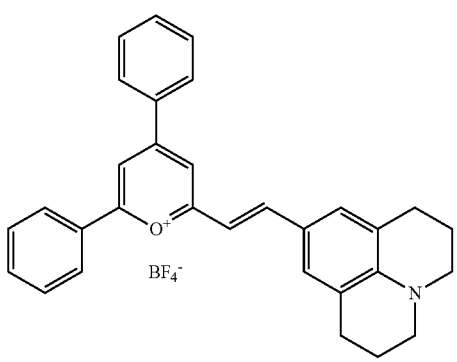<br>6jc58 | $C_{31}H_{28}BF_4NO$ | 517.36 | (E)-2-(2-(1,2,3,5,6,7-hexahydropyrido[3,2,1-ij]quinolin-9-yl)vinyl)-4,6-diphenylpyrylium boron tetrafluoride salt | yes | 1 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 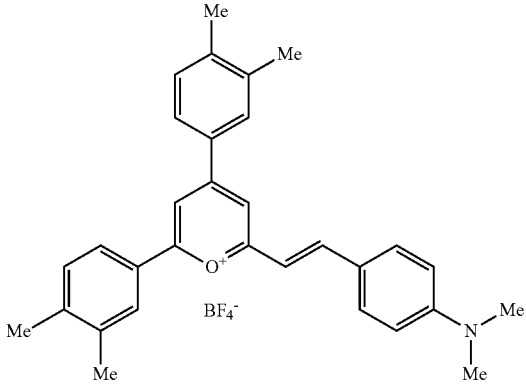 6jc59-1 | $C_{31}H_{32}BF_4NO$ | 521.40 | (E)-2-(4-(dimethylamino)styryl)-4,6-bis(3,4-dimethylphenyl)pyrylium boron tetrafluoride salt | yes | 2 |
| 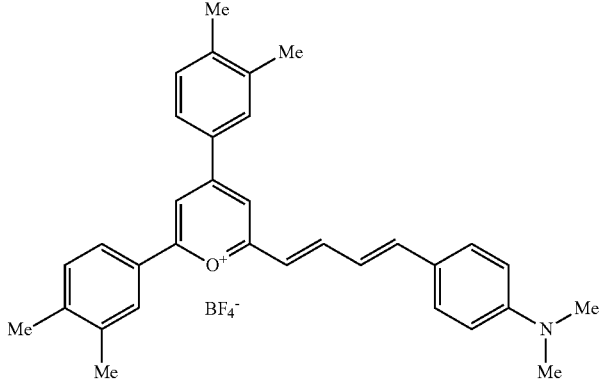 6jc59-2 | $C_{31}H_{28}BF_4NO$ | 547.43 | 2-((1E,3E)-4-(4-(dimethylamino)phenyl)buta-1,3-dien-1-yl)-4,6-bis(3,4-dimethylphenyl)pyrylium boron tetrafluoride salt | yes | 32 |
| 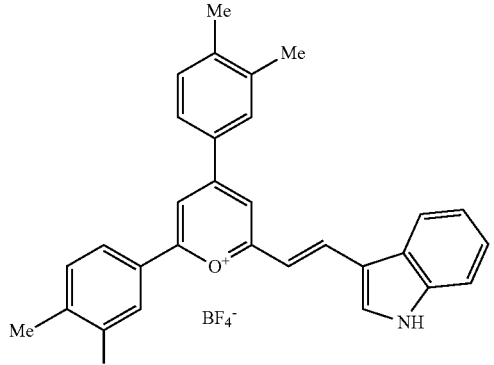 6jc59-3 | $C_{33}H_{34}BF_4NO$ | 517.36 | (E)-2-(2-(1H-indol-3-yl)vinyl)-4,6-bis(3,4-dimethylphenyl)pyrylium boron tetrafluoride salt | yes | 4 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 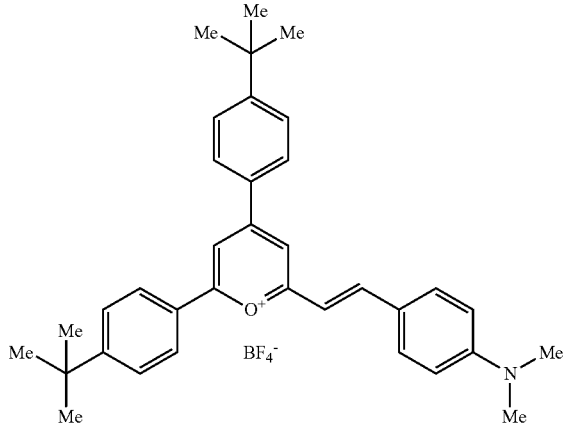 6jc60-2 | $C_{35}H_{40}BF_4NO$ | 577.50 | (E)-2,4-bis(4-(tert-butyl)phenyl)-6-(4-(dimethylamino)styryl)pyrylium boron tetrafluoride salt | yes | 8 |
| 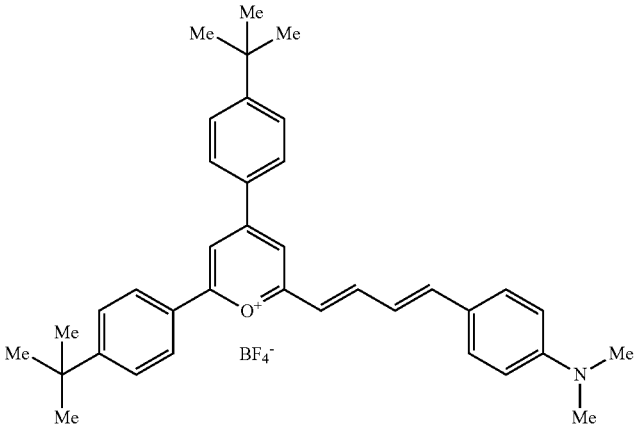 6jc60-2 | $C_{37}H_{42}BF_4NO$ | 603.54 | 2,4-bis(4-(tert-butyl)phenyl)-6-(((1E,3E)-4-(4-(dimethylamino)phenyl)buta-1,3-dien-1-yl)pyrylium boron tetrafluoride salt | yes | 64 |
| 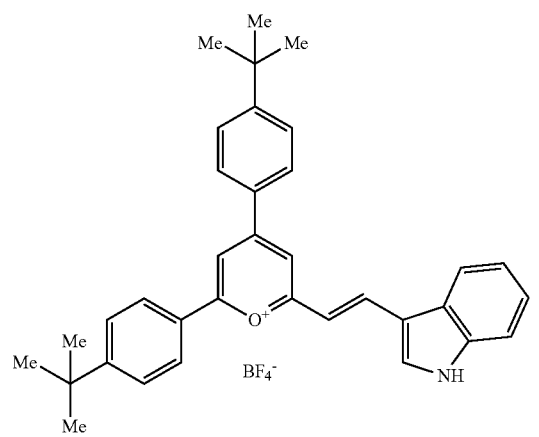 6jc60-3 | $C_{35}H_{36}BF_4NO$ | 573.47 | (E)-2-(2-(1H-mdol-3-yl)vinyl)-4,6-bis(4-(tert-butyl)phenyl)pyrylium boron tetrafluoride salt | yes | 32 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 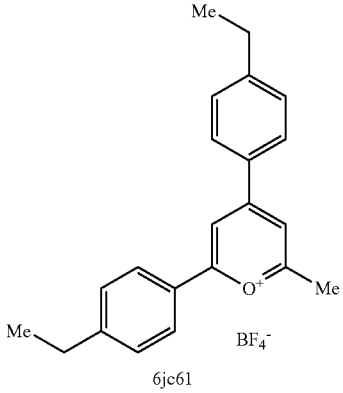<br>6jc61 | C$_{22}$H$_{23}$BF$_4$O | 390.22 | 2,4-bis(4-ethylphenyl)-6-methylpyrylium boron tetrafluoride salt | no | >64 |
| 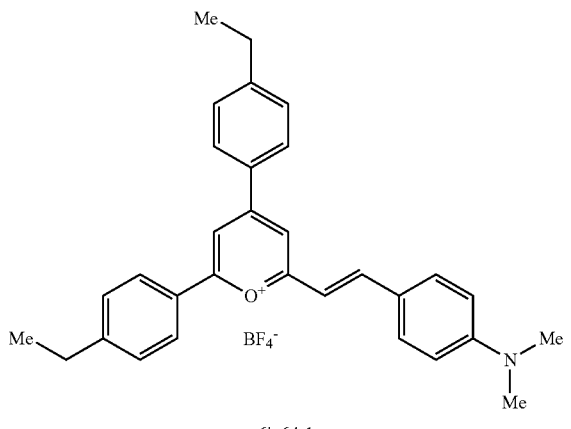<br>6jc64-1 | C$_{31}$H$_{32}$BF$_4$NO | 521.40 | (E)-2-(4-(dimethylamino)styryl)-4,6-bis(4-ethylphenyl)pyrylium boron tetrafluoride salt | yes | 1 |
| 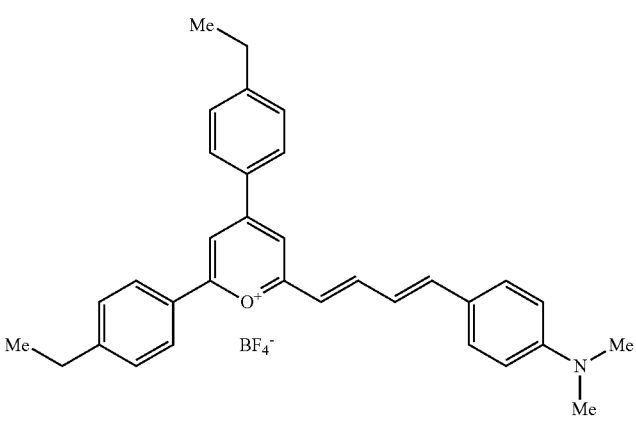<br>6jc64-2 | C$_{33}$H$_{34}$BF$_4$NO | 547.43 | 2-((1E,3E)-4-(4-(dimethylamino)phenyl)buta-1,3-dien-1-yl)-4,6-bis(4-ethylphenyl)pyrylium boron tetrafluoride salt | yes | 8 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 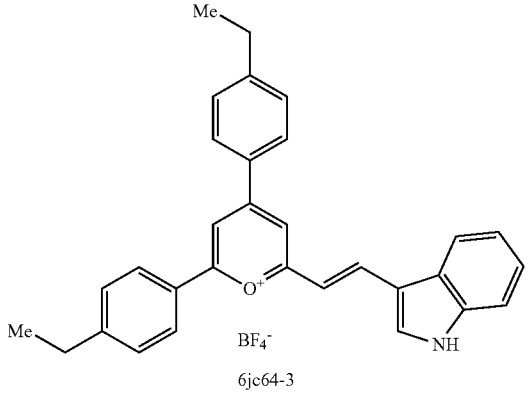 6jc64-3 | $C_{31}H_{28}BF_4NO$ | 517.36 | (E)-2-(2-(1H-indol-3-yl)vinyl)-4,6-bis(4-ethylphenyl)pyrylium boron tetrafluoride salt | yes | 4 |
| 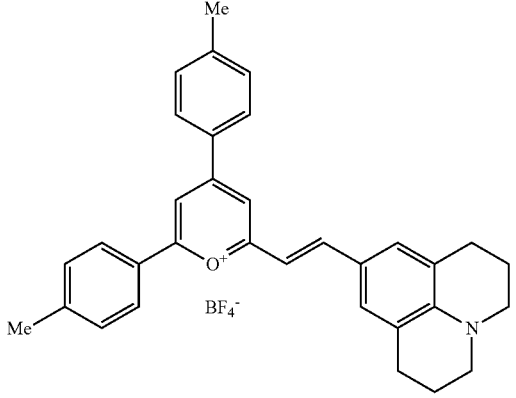 6jc65-1 | $C_{33}H_{32}BF_4NO$ | 545.42 | (E)-2-(2-(1,2,3,5,6,7-hexahydropyrido[3,2,1-ij]quinolin-9-yl)vinyl)-4,6-di-p-tolylpyrylium boron tetrafluoride salt | yes | 1 |
| 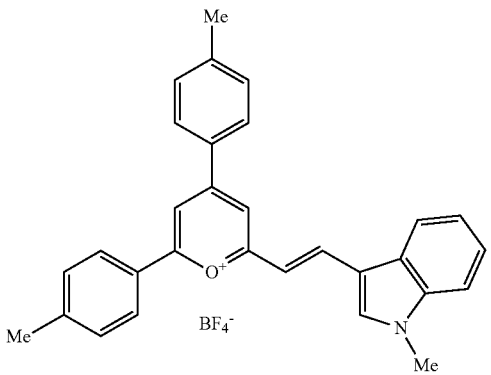 6jc65-2 | $C_{30}H_{26}BF_4NO$ | 503.34 | (E)-2-(2-(1-methyl-1H-indol-3-yl)vinyl)-4,6-di-p-tolylpyrylium boron tetrafluoride salt | yes | 0.5 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 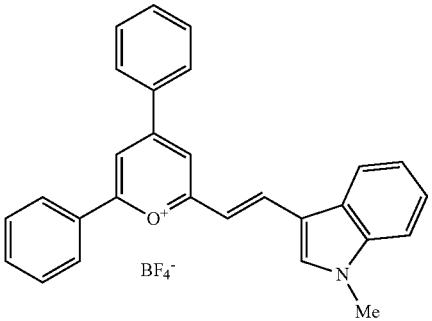 6jc66-1 | $C_{28}H_{22}BF_4NO$ | 475.28 | (E)-2-(2-(1-methyl-1H-indol-3-yl)vinyl)-4,6-diphenylpyrylium boron tetrafluoride salt | yes | 0.5 |
| 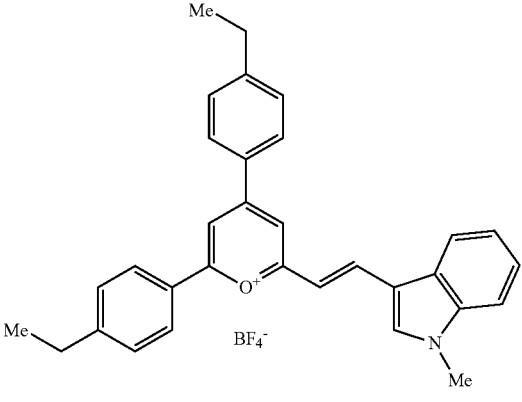 6jc66-2 | $C_{32}H_{30}BF_4NO$ | 531.39 | (E)-2,4-bis(4-ethylphenyl)-6-(2-(1-methyl-1H-indol-3-yl)vinyl)pyrylium boron tetrafluoride salt | yes | 1 |
| 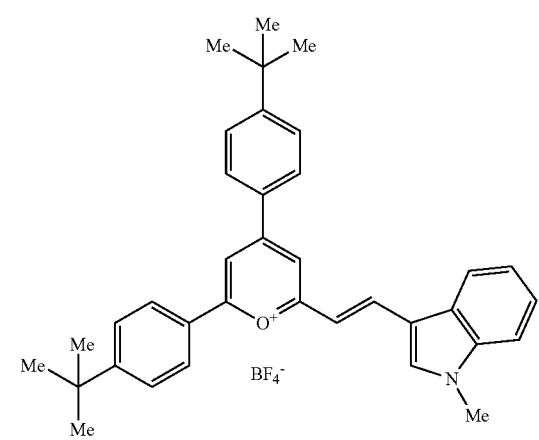 6jc66-3 | $C_{36}H_{38}BF_4NO$ | 587.50 | (E)-2,4-bis(4-(tert-butyl)phenyl)-6-(2-(1-methyl-1H-indol-3-yl)vinyl)pyrylium boron tetrafluoride salt | yes | 16 |

TABLE 5-continued

Compound Structure and Function.

| Structural Formula and Compound Name | Chemical Formula | MW (g/mol) | IUPAC Name | Lipid II Binding | *S. aureus* Killing |
|---|---|---|---|---|---|
| 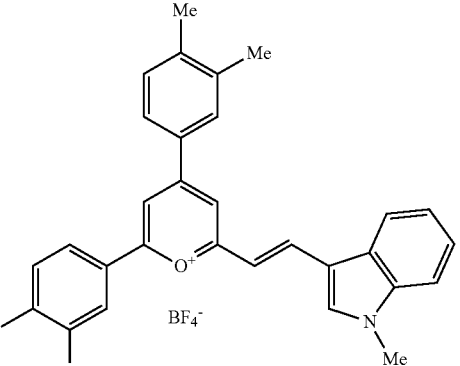<br>6jc66-4 | $C_{32}H_{30}BF_4NO$ | 531.39 | (E)-2,4-bis(3,4-dimethylphenyl)-6-(2-(1-methyl-1H-indol-3-yl)vinyl)pyrylium boron tetrafluoride salt | yes | 1 |
| 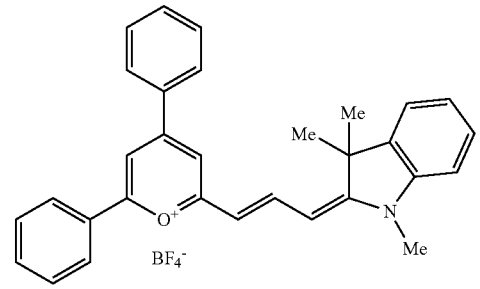<br>6jc67 | $C_{31}H_{28}BF_4NO$ | 430.57 | 2,4-diphenyl-6-((1E,3E)-3-(1,3,3-trimethylindolin-2-ylidene)prop-1-en-1-yl)pyrylium boron tetrafluoride salt | yes | 0.5 |
| 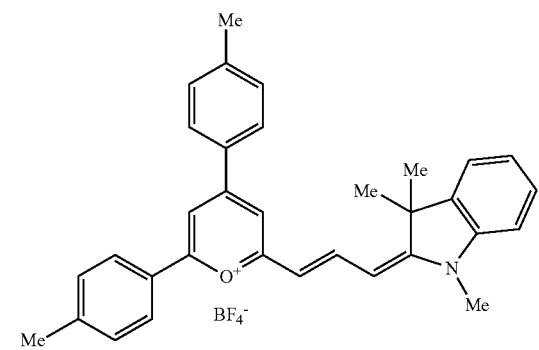<br>6jc67-A | $C_{33}H_{32}BF_4NO$ | 448.57 | 2,4-di-p-tolyl-6-((1E,3E)-3-(1,3,3-trimethylindolin-2-ylidene)prop-1-en-1-yl)pyrylium boron tetrafluoride salt | yes | 1 |
| 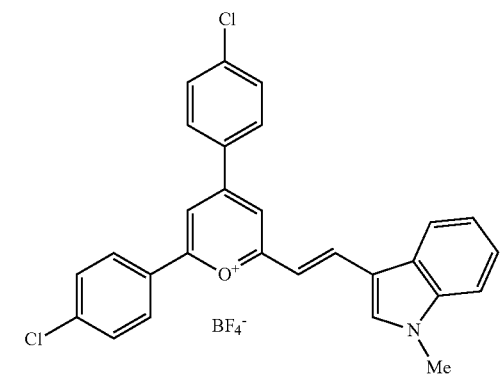<br>6jc68-1 | $C_{28}H_{20}BCl_2F_4NO$ | 544.18 | (E)-2,4-bis(4-chlorophenyl)-6-(2-(1-methyl-1H-indol-3-yl)vinyl)pyrylium boron tetrafluoride salt | ND | 64 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 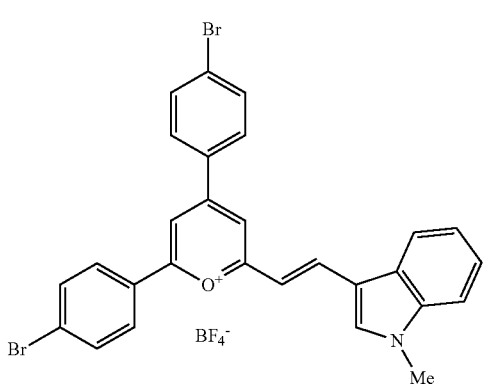<br>6jc68-2 | C$_{28}$H$_{20}$BBr$_2$F$_4$NO | 633.08 | (E)-2,4-bis(4-bromophenyl)-6-(2-(1-methyl-1H-indol-3-yl)vinyl)pyrylium boron tetrafluoride salt | ND | 64 |
| 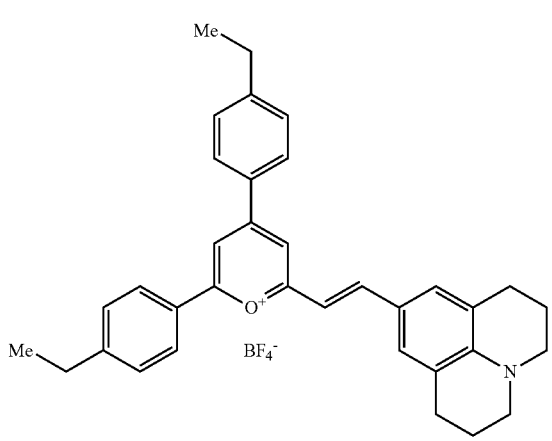<br>6jc69-1 | C$_{35}$H$_{36}$BF$_4$NO | 573.74 | (E)-2,4-bis(4-ethylphenyl)-6-(2-(1,2,3,5,6,7-hexahydropyrido[3,2,1-ij]quinolin-9-yl)vinyl)pyrylium boron tetrafluoride salt | yes | 1 |
| 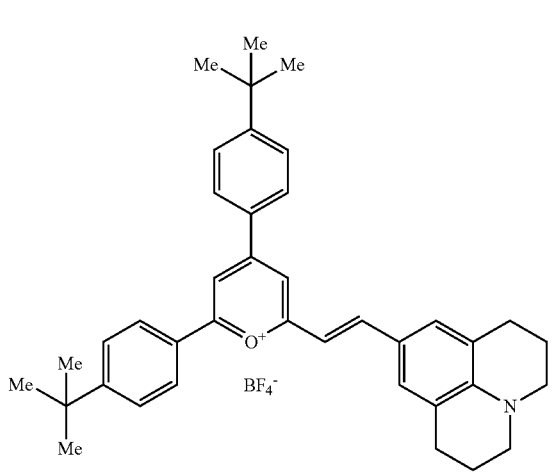<br>6jc69-2 | C$_{39}$H$_{44}$BF$_4$NO | 629.58 | (E)-2,4-bis(4-(tert-butyl)phenyl)-6-(2-(1,2,3,5,6,7-hexahydropyrido[3,2,1-ij]quinolin-9-yl)vinyl)pyrylium boron tetrafluoride salt | yes | 32 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 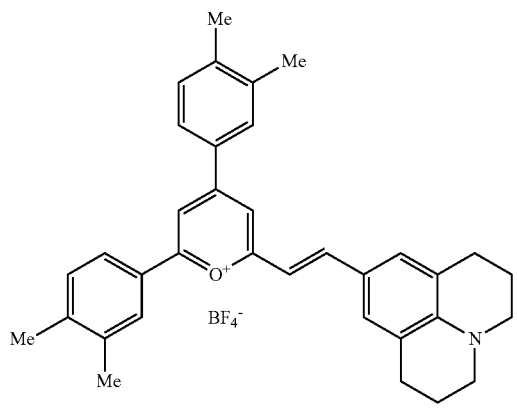 6jc69-3 | C$_{37}$H$_{40}$BF$_4$NO | 573.47 | (E)-2,4-bis(3.4-dimethyiphenyl)-6-(2-(1,2,3,5,6,7-hexahydropyrido[3,2,1-ij]quinolin-9-yl)vinyl)pyrylium boron tetrafluoride salt | yes | 0.5 |
| 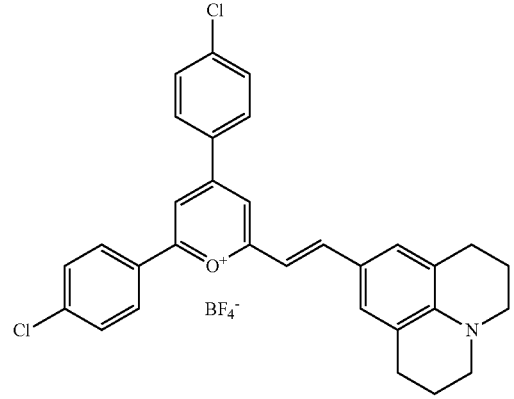 6jc69-4 | C$_{31}$H$_{26}$BCl$_2$F$_4$NO | 586.25 | (E)-2,4-bis(4-chlorophenyl)-6-(2-(1,2,3,5,6,7-hexahydropyrido[3,2,1-ij]quinolin-9-yl)vinyl)pyrylium boron tetrafluoride salt | yes | 1 |
| 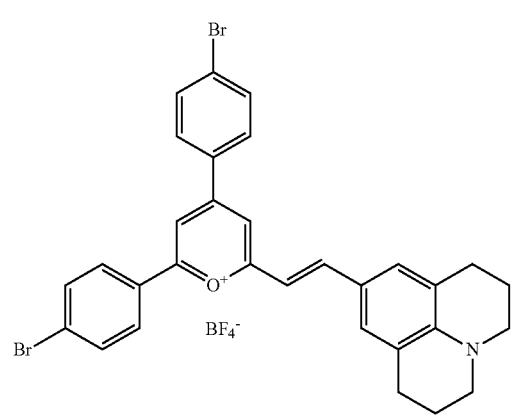 6jc69-5 | C$_{31}$H$_{26}$BBr$_2$F$_4$NO | 675.16 | (E)-2,4-bis(4-bromophenyl)-6-(2-(1,2,3,5,6,7-hexahydropyrido[3,2,1-ij]quinolin-9-yl)vinyl)pyrylium boron tetrafluoride salt | yes | 4 |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 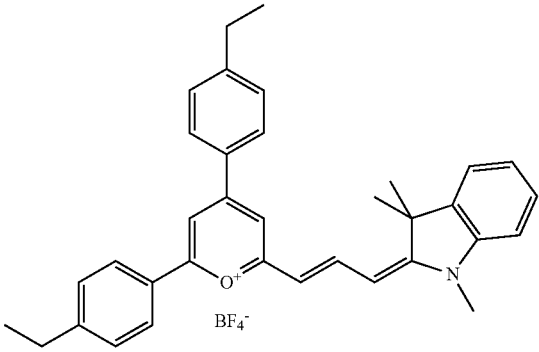 6jc76-1 | C$_{35}$H$_{36}$BF$_4$NO | 573.47 | 2,4-bis(4-ethylphenyl)-6-((1E,3E)-3-(1,3,3-trimethylindolin-2-ylidene)prop-1-en-1-yl)pyrylium boron tetrafluoride salt | | |
| 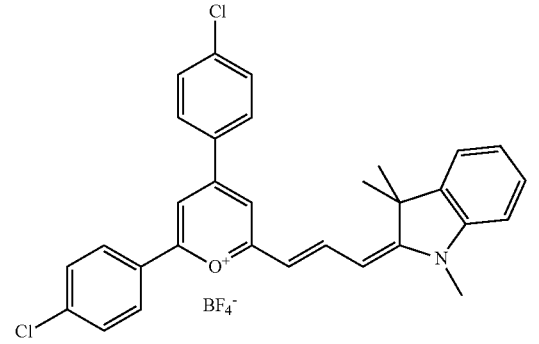 6jc77-1 | C$_{31}$H$_{26}$BCl$_2$F$_4$NO | 586.25 | 2,4-bis(4-chlorophenyl)-6-((1E,3E)-3-(1,3,3-trimethylindolin-2-ylidene)prop-1-en-1-yl)pyrylium boron tetrafluoride salt | | |
| 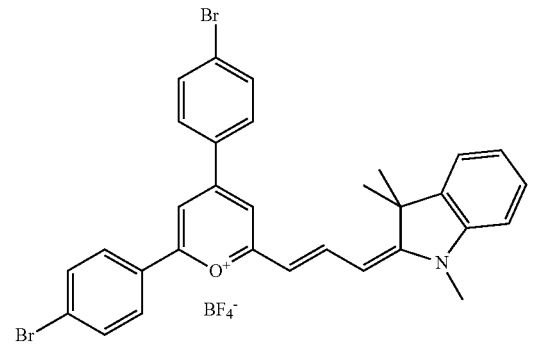 6jc77-2 | C$_{31}$H$_{26}$BBr$_2$F$_4$NO | 675.16 | 2,4-bis(4-bromophenyl)-6-((1E,3E)-3-(1,3,3-trimethylindolin-2-ylidene)prop-1-en-1-yl)pyrylium boron tetrafluoride salt | | |
| 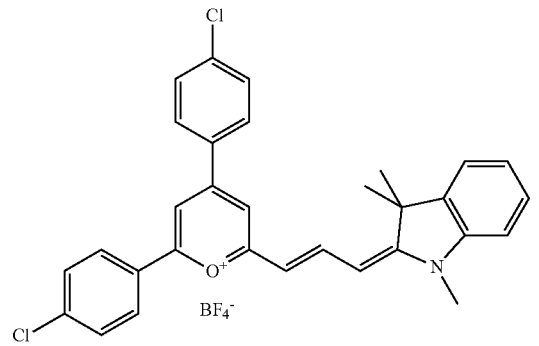 7jc42-1 | C$_{31}$H$_{26}$BCl$_2$F$_4$NO | | 2,4-bis(4-chlorophenyl)-6-((1E,3E)-3-(1,3,3-trimethylindolin-2-ylidene)prop-1-en-1-yl)pyrylium boron tetrafluoride salt | | |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 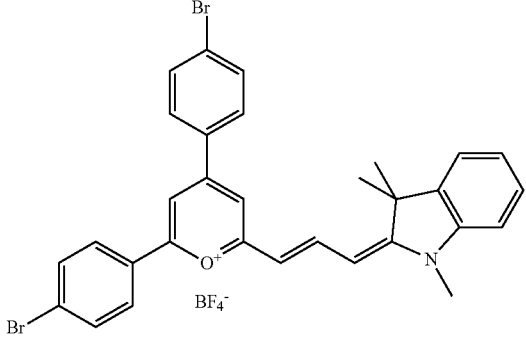 7jc42-2 | $C_{31}H_{26}BBr_2F_4NO$ | | 2,4-bis(4-bromophenyl)-6-((1E,3E)-3-(1,3,3-trimethylindolin-2-ylidene)prop-1-en-1-yl)pyrylium boron tetrafluoride salt | | |
| 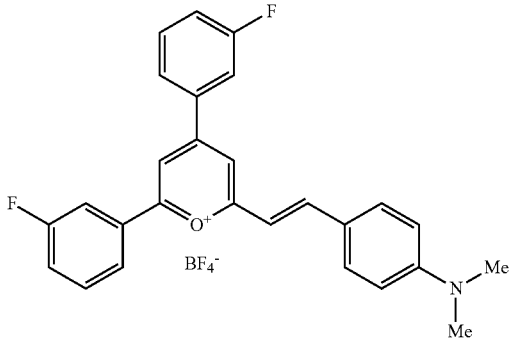 7jc46-1 | $C_{27}H_{22}BF_6NO$ | 501.27 | 2-((1E,3E)-4-(4-(dimethylamino)phenyl)buta-1,3-dien-1-yl)-4,6-bis(4-fluorophenyl)pyrylium boron tetrafluoride salt | | |
| 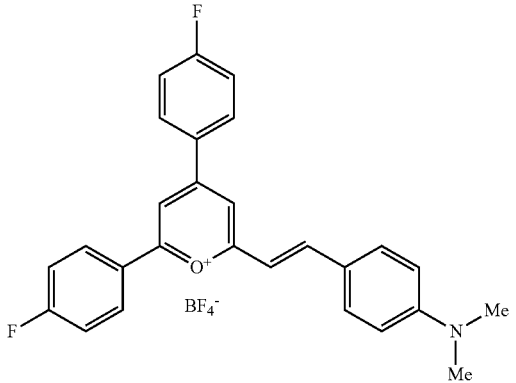 7jc47-1 | $C_{27}H_{22}BF_6NO$ | 501.27 | (E)-2-(4-(dimethylamino)styryl)-4,6-bis(4-fluorophenyl)pyrylium boron tetrafluoride salt | | |

TABLE 5-continued

Compound Structure and Function.

| Structural Formula and Compound Name | Chemical Formula | MW (g/mol) | IUPAC Name | Lipid II Binding | S. aureus Killing |
|---|---|---|---|---|---|
| 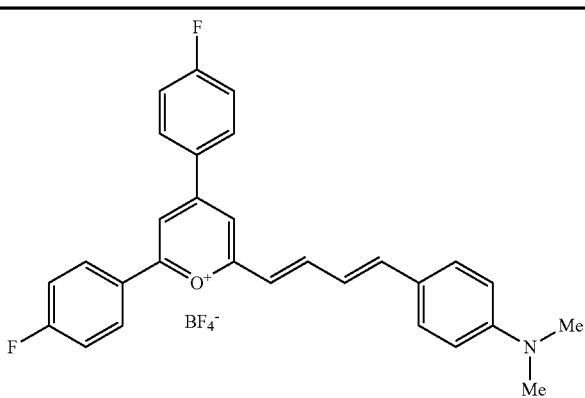<br>7jc47-2 | $C_{29}H_{24}BF_6NO$ | 527.31 | 2-((1E,3E)-4-(4-(dimethylamino)phenyl)buta-1,3-dien-1-yl)-4,6-bis(4-fluorophenyl)pyryliuin boron tetrafluoride salt | | |

Based on the results of these functional assays, selected compounds were further assayed for: (3) broad-range antibacterial activity and (4) cellular cytotoxicity against mammalian cells (HeLa) expressed as the concentration at which cell viability is decreased by 50% (CC.sub.50). The medium used was cation-adjusted Mueller Hinton broth, including 10% BHI for E. faecium spp. Measured Lipid II binding was also further qualified by determining the binding constant of selected compounds. Further data from these assays are presented in Table 6, below, and represent the geomean of 2 samples. Concentrations (minimal inhibitory concentrations (MIC)) are given in .mu·g/mL. The medium used was cation-adjusted Mueller-Hinton broth containing 10% BHI for E. faecium spp.; *CC50 based on E. faecium EF1509.

To explore the role of the indolene group on the potency, toxicity and LII binding of these compounds, a series of analogs were synthesized in which the indolene moiety was replaced by varying aldehydes at the $R^2$ position (see FIG. 10). Based on anti-bacterial activity, substitution of these moieties at the $R^2$ position can be ranked from highest to lowest (antibacterial) potency as: julolidine derivative (6jc65-1)>N-methyl-3-indolyl (6jc53-2)>3-indolyl (6jc53-2)>4-dimethylaminophenyl (6jc51-1)>N,N-dimethyl-4-vinylaniline (6jc51-2). Antibacterial killing potency was correlated with cytotoxicity. Notably, with the exception of compounds 6jc51-1, 6jc58 and 6jc67A, all compounds displayed reduced activity against Gram-negative species.

Effects on activity due to modifications to the $R^2$ positions on the two phenyl rings of the pyrylium core are summarized in FIG. 10. Compared to the parent compound 6jc48-1, none of the $R^1$ substitutions in generic Formula I shown here markedly enhanced potency or breadth of antibacterial activity. Irrespective of variations at the $R^2$ position, para-methyl (compounds: 6jc51-1, 6jc51-2, 6jc53-2, 6jc65-1, 6jc65-2), meta,para-dimethyl (compounds: 6jc59-1, 6jc59-2, 6jc59-3, 6jc66-4, 6jc69-3) or para-ethyl (compounds: 6jc64-1, 6jc64-2, 6jc64-3, 6jc66-2, 6jc69-1) groups at the $R^1$ position retained antibacterial activity most potently. Substitution of the $R^1$ moiety with tert-butyl, tri-methyl, chloride or bromide in the para position significantly reduced antibacterial killing.

Although in general antibacterial activity correlated with LII binding and cellular cytotoxicity, the 6jc48-1 and 6jc48-2 compounds were a notable exception. These compounds revealed high affinity LII binding and markedly reduced cellular cytotoxicity, with a surprisingly specific anti-Enteroccocci activity. These compounds, and their derivatives, are preferred compounds. The following compounds are compounds contemplated as part of this invention, and are useful as antibiotic compounds for use in treatment: 6jc39, 6jc43-1, 6jc48-1, 6jc48-2, 6jc51-1, 6jc51-2, 6jc53-2, 6jc58, 6jc59-1, 6jc59-2, 6jc59-3, 6jc64-1, 6jc64-2, 6jc64-3, 6jc65-1, 6jc65-2, 6jc66-1, 6jc66-2, 6jc66-3, 6jc66-4, 6jc67, 6jc69-1, 6jc69-3, 6jc69-4, 6jc76-1, 6jc76-2, 6jc77-1, 6jc77-2, 7jc46-1, 7jc47-1, and 7jc47-2. Preferred compounds include: 6jc48-1, 6jc58, 6jc66-3, 6jc66-4, 6jc67, 6jc77-1, 6jc77-2, 7jc46-1, 7jc47-1, and 7jc47-2, and most highly preferred compounds include: 6jc48-1, 6jc67, 7jc46-1, 7jc47-1, and 7jc47-2.

Based on its markedly decreased cytotoxicity (see FIG. 10), compound 6jc48-1 was selected for further analysis. First, given its specific potency against Enterococci, compound 6jc48-1 was tested for potency against a wider array of E. faecium and E. faecalis strains (see Table 6, below). For these tests, cation-adjusted Mueller Hinton broth, containing 10% brain-heart infusion (BHI) was used. Concentrations (MIC) are given in µg/mL. The compound was effective in killing the tested drug-resistant strains, confirming its specific activity against these species.

TABLE 6

Activity of Compound 6jc48-1 and Derivatives against *Enterococcus* spp.

| Organism | ATCC# | 6jc48-1 | V | BAS00127538 | 6jc67A | 6jc69-1 | 6jc6913 |
|---|---|---|---|---|---|---|---|
| *E. faecium* | IH79985 | 8 | ND | 2 | 2 | 8 | 4 |
| *E. faecium* | C110914 | 4 | ND | 2 | 1 | 4 | 2 |
| *E. faecium* | S1559 | 2 | ND | 2 | 1 | 2 | 2 |
| *E. faecalis* | 51575 | 2 | ND | 2 | 1 | 2 | 2 |
| *E. faecalis* | 51299 | 4 | ND | 2 | 1 | 1 | 1 |
| *E. faecalis* | C99707 | 2 | ND | 2 | 1 | 1 | 1 |
| *E. faecium** | none | 4-16 | >32 | ND | ND | ND | ND |
| *E. faecalis** | none | 4-16 | >32 | ND | ND | ND | NC |

ND = not determined;
*= clinical isolates sensitive to linezolid and daptomycin, n = 5; V = vancomycin.

Figure 11A:
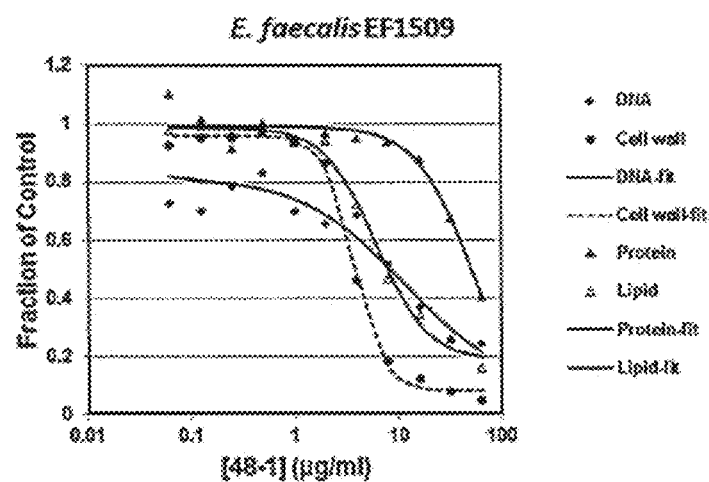
FIG. 11A and FIG. 11B show the effects of 6jc48-1 (MIC 4.mu·g/ml.
Figure 11B:
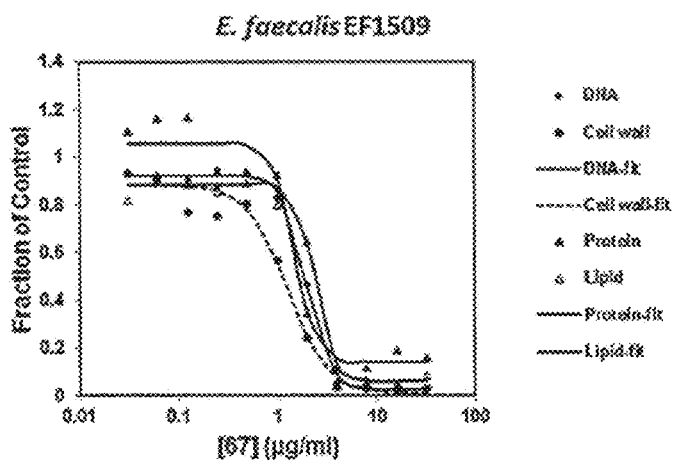

Compound 6jc48-1 (MIC: 4 µg/mL) most potently inhibited cell wall synthesis ($IC_{50}$ of 3.8 µg/mL), followed by inhibition of lipid and DNA synthesis ($IC_{50}$ of 7.8 and 8.3 µg/mL, respectively). See FIG. 11. Compound 6jc67 (MIC: 2 µg/mL), the de novo synthesized parent BAS00127538, also most potently inhibited cell wall synthesis ($IC_{50}$ of 1.1 µg/mL), followed by inhibition of DNA ($IC_{50}$ of 1.8 µg/mL) and lipid synthesis ($IC_{50}$ of 2.3 µg/mL), as previously reported for commercially available BAS00127538. Surprisingly, 6jc48-1 showed a markedly reduced inhibition of protein synthesis ($IC_{50}$ of 50.4 µg/mL) compared to the 6jc67 (BAS00127538) with an $IC_5O$ of 1.6 µg/mL. Interestingly, the methyl analog of BAS00127538 also has the same activity of BAS00127538.

Without wishing to be bound by theory, it is possible that the pyrylium moiety in compound 6jc48-1 causes the compound to be reactive toward nucleophiles, including water, amines, and thiols. Therefore, compound 6jc48-1 was tested for drug-like properties in in vitro assays, including stability and a pharmacokinetic profile.

Compound stability was tested by LC/MS/MS after 2 minutes, 5 minutes, 15 minutes, 30 minutes, 1 hour, 2 hours and 19 hours. The analysis showed that compound 6jc48-1 has favorable purity and solubility, liver microsome stability, and with the exception of CYP3A4/BFC, did not inhibit P450 enzyme activity at ≥10 µM. Further, plasma protein binding was found to be 89%. See the results in Table 7, below. Due to incompatibility with solubilization conditions, membrane permeability and hepatotoxicity could not be determined.

TABLE 7

Drug-like Properties of Compound 6jc48-1, Tested in Vitro.

| Assay | Result |
|---|---|
| Purity (LC-MS-MS) | >95% |
| Solubility in water (laser nephelometry) | >50 µg/mL (n = 3) |
| Liver micosome stability (human; 1 hour; 37° C.) | Half-life > 60 minutes<br>Clearance < 23 µL/min/mg |
| Plasma protein binding (human; Transil ™) | 89%± |
| P450 enzyme inhibition (IC50 fluorescence) CYP3A4/DBF | >10 µM |
| P450 enzyme inhibition (IC50 fluorescence) CYP3A4/BFC | 1.3 µM |
| P450 enzyme inhibition (IC50 fluorescence) CYP2D6/AMMC | >10 µM |

TABLE 7-continued

Drug-like Properties of Compound 6jc48-1, Tested in Vitro.

| Assay | Result |
|---|---|
| P450 enzyme inhibition (IC50 fluorescence) CYP2C19/CEC | >10 µM |

DBF: dibenzylfluorescein; BFC: 7-benzoyloxy-4-trifluoromethyl coumarin; AMMC: 3-[2-(N,N-diethyl-N-methylamino)ethyl]-7-methoxy-4-methylcoumarin; CEC: 3-cyano-7-ethoxycoumarin.

Example 8: Bacterial Killing Activity in Additional Compounds

Ability to kill bacteria was determined as discussed in Example 1E, above. See Table 8, below.

TABLE 8

Bacterial Killing.

| Compound | *S. aureus* | *E. faecium* | *E. coli* |
|---|---|---|---|
| 6jc48-1 | 16 | 4 | >64 |
| 7jc42-1 | 8 | 32 | >64 |
| 7jc42-2 | 32 | 32 | >64 |
| 7jc46-1 | 1 | 2 | >64 |
| 7jc47-1 | 1 | 1 | >64 |
| 7jc47-2 | 1 | 1 | >64 |
| 7jc50 | 8 | >64 | >64 |
| 7jc51 | 64 | >64 | >64 |

Example 9: In Vivo Efficacy of Compound 6jc48-1

General methods for the murine model of sepsis were as follows. To assess the protective potency of defensin mimetic compound 6jc48-1, groups of 5 mice were inoculated intraperitoneally with approximately $5 \times 10^6$ CFU/mL of *Enterococcus faecalis* EF1509 in 500 µL saline solution plus 4.5% (w/v) porcine gastric mucin (Sigma™ Chemical Co., St. Louis, Mo.). Infected animals subsequently were treated by intravenous injection 30 minutes, 120 minutes and 300 minutes post-infection with 5 mg/kg of the compound in 100 µL of one of (1) Tris-buffered saline solution, 50% PEG400, 10% DMSO (v/v), (2) linezolid (50 mg/kg, sterile Tris-buffered saline solution, 50% PEG400, 10% DMSO (v/v) as a positive control) or (3) vehicle (Tris-buffered saline solution, 50% PEG400, 10% DMSO (v/v) as a negative control). Animals were observed closely during a period of 7 days and mice that showed signs of severe sepsis were humanely euthanized. Mice were anesthetized by intraperitoneal injection of ketamine (80-100 mg/kg) and xylazine (10-15 mg/kg). Blood samples were collected by retroorbital puncture using lithium-heparin polystyrene tubes to prevent coagulation. Spleens were harvested aseptically, weighed and homogenized in 500 µL sterile saline solution using an IKA™ basic disperser (IKA™, Wilmington N.C.). Whole blood samples and spleen homogenates were serially diluted and plated onto lysogeny broth (LB) agar plates. Bacterial counts were determined following a 24-hour incubation at 37° C. and expressed as CFU per milliliter for blood and CFU per gram for spleen.

Preliminary maximum tolerated dose studies indicated that compound 6jc48-1 could be safely administered intraperitoneally at doses as high as 100 mg/kg. Solubility of the compound restricted testing concentrations above 100 mg/kg.

Figure 12:
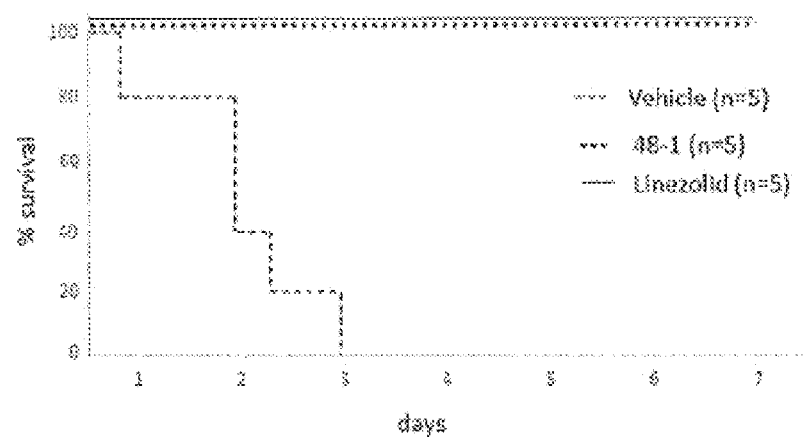
FIG. 12 shows the percent survival of mice with the indicated treatments.

A specific test was performed as follows. Based on the data obtained in the pharmacokinetic analysis, mice (n=5) were inoculated peritoneally with *E. faecalis* EF1509 and treated after 30 minutes and three times every 90 minutes following with compound at 5 mg/kg intravenously. Animals were monitored for survival. Blood and spleen samples were collected and tested for bacteria. Bacterial counts were determined and compared to control treatment with linezolid as measures of efficacy. Animals treated with vehicle (negative control) did not survive the length of the experiment. See FIG. 12, which shows the % survival for the various treatments.

Figure 13:
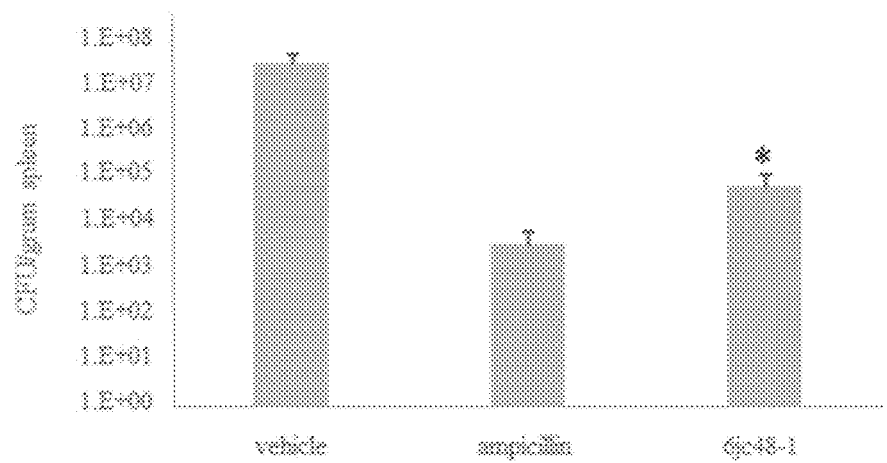
FIG. 13 is bar graph showing the CFU of bacteria per gram of spleen tissue in an animal model of murine sepsis, with the indicated treatments (n=5). The * indicates that one animal treated with compound 6jc48-1 did not survive.

In a separate test, mice (n=5) were inoculated intraperitoneally with *E. faecalis* EF1509 (approximately $5 \times 10^8$ CFU/animal) and treated after 30 minutes with compound 6jc48-1 (100 mg/kg IP), ampicillin (300 mg/kg IP) or a vehicle control. Animals were monitored for survival. After 24 hours, spleen samples were collected and analyzed for the presence of bacteria. Bacterial counts were determined by plating serial dilutions on BHI agar plates and compared to control treatments as measures of efficacy. The results are presented in FIG. 13. None of the animals treated with vehicle survived for the duration of the experiment. Four out of five animals treated with compound 6jc48-1 and all animals treated with ampicillin survived for the duration of the experiment. Bacterial counts measured in spleen revealed significant bacterial clearance for both drugs, indicating in vivo antibiotic efficacy.

Example 10: Additional Compounds

In addition, a second permanently positively charged pyrydinium and/or pyrylium can be synthesized according to scheme 2, below. Our model indicates an interaction between the positive charge in our scaffold and a negatively charged phosphate moeity of Lipid II. Lipid II contains two negatively charged phosphate moieties that together form the so-called phosphate cage. The addition of positive charge in the scaffold is expected to further enhance Lipid II interactions. In addition, variations in linker length could enhance interaction with the first 3 isoprenyl units of Lipid II, which are drug-accesible. SAR that we have established in the pyridinium-based scheme 1 can be applied to alternative scheme 2.

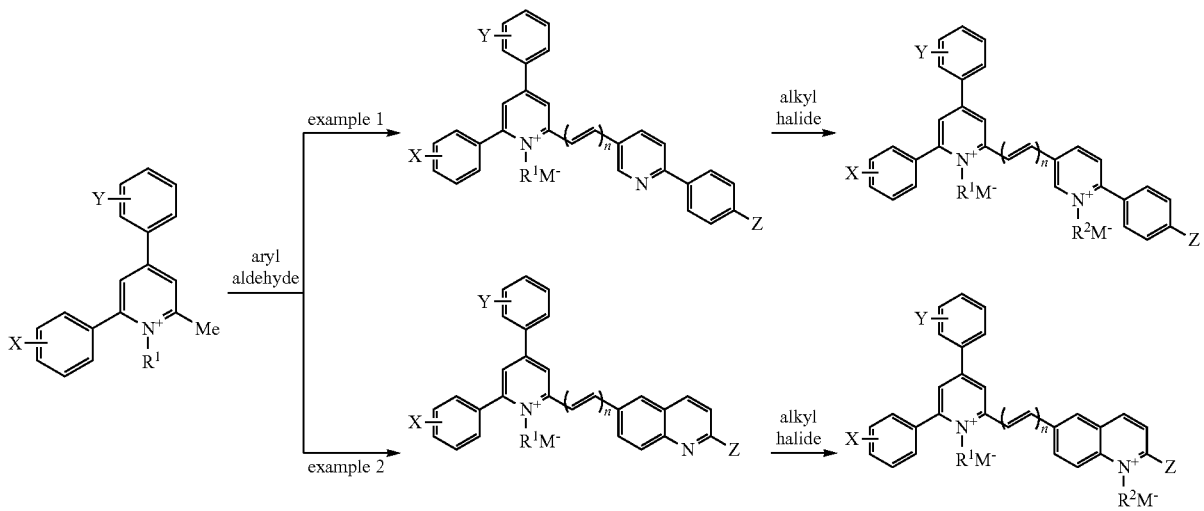

Figure 14:
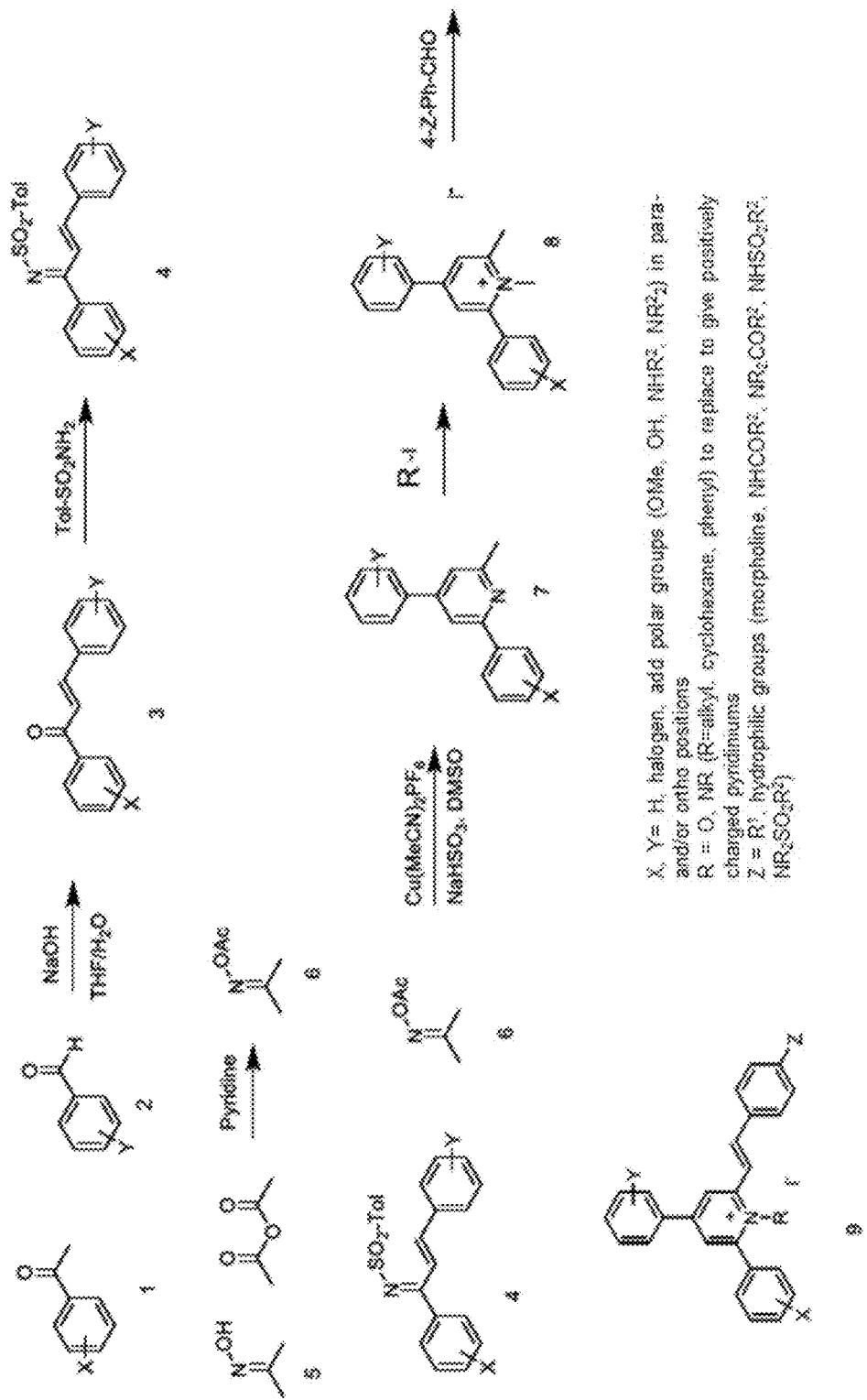
FIG. 14 is a chemical synthetic scheme for certain compounds and intermediates according to the invention.

Models indicate there is an interaction between the positive charge in the scaffold and a negatively charged phosphate moiety of Lipid II. Lipid II contains two negatively charged phosphate moieties that together form the so-called phosphate cage. The addition of positive charge in the scaffold is expected to further enhance Lipid II interactions. In addition, variations in linker length could enhance interaction with the first 3 isoprenyl units of Lipid II, which are drug-accesible. SAR that we have established in the pyridinium-based scheme 1 can be applied to alternative scheme 2. An additional synthetic scheme is shown in FIG. 14.

Example 11: Formula II Scaffold Substitutions

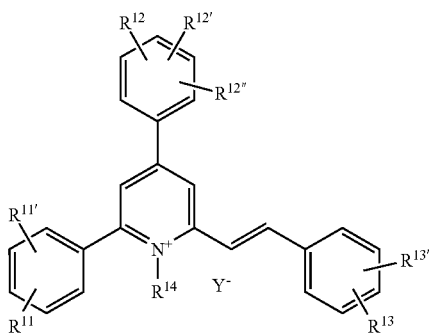

Formula II

Analysis of in vitro drug-like properties for 6jc-48-1 showed that the compound has favorable purity and solubility, liver microsome stability, and with the exception of CYP3A4/BFC, did not inhibit P450 enzyme activity at >10 µM. Since CYP3A4 has a large active site that can bind multiple substrates in different orientation, CYP3A4 can be examined using multiple substrates for lead molecules. Further, plasma protein binding (PPD) of 6jc48-1 was found to be 89%. Binding of a drug to plasma protein reduces free drug available to penetrate from the blood circulation into tissues to reach the therapeutic target or the kidney for elimination. A recent study showed that >45% of FDA-approved drugs between 2003 and 2013 have a PPD of >95% and 24% have a PPD of >99%. In addition, analysis of 222 drugs suggested that a PPD of >90% was selective for favorable lead advancement. However, if the PPD of certain compounds significantly increases and affects the MIC in vitro, the free versus bound fraction can be determined in vitro as a further determinant for in vivo studies.

TABLE 9

Substitutions in the Scaffold of Formula II.

| Cpd | R11 | R11' | R12 | R12' | R12" | R13 | R13' | R14 |
|---|---|---|---|---|---|---|---|---|
| 67 | 4-Br | H | 4-Br | H | H | 4-NMe$_2$ | H | Me |
| 4 | 4-F | H | 4-F | H | H | 4-NMe$_2$ | H | Me |
| 71 | 4-Br | H | 4-Me | H | H | 4-NMe$_2$ | H | Me |
| 85 | 4-Br | H | 3-Br | H | H | 4-NMe$_2$ | H | Me |
| 78 | 4-Br | H | 4-Cl | H | H | 4-NMe$_2$ | H | Me |
| 22 | 4-Me | 2-Me | 4-Br | H | H | 4-NMe$_2$ | H | Me |
| 92 | 4-Me | H | 4-Br | H | H | 4-NMe$_2$ | H | Me |
| 5a | 3-Br | H | 4-Br | H | H | 4-NMe$_2$ | H | Me |
| 9a | 4-Me | H | 4-Cl | H | H | 4-NMe$_2$ | H | Me |
| 56 | 4-Br | H | 3-OMe | 4-Br | 5-OMe | 4-NMe$_2$ | H | Me |
| 38 | 4-Br | H | 2-Cl | 4-Br | H | 4-NMe$_2$ | H | Me |
| 14a | 4-Me | H | 4-Br | H | H | 4-NMe$_2$ | H | Et |
| 7b | 4-Me | H | 4-Br | H | H | 4-NMe$_2$ | H | CH$_2$CH$_2$CH$_3$ |
| 1 | 4-Br | H | 4-Br | H | H | 4-NMe$_2$ | H | CH$_2$CH(CH$_3$)$_2$ |
| 3 | 4-Br | H | 4-Br | H | H | 4-NMe$_2$ | H | CH(CH$_3$)$_2$ |
| 5 | 4-Br | H | 4-Br | H | H | 4-NMe$_2$ | H | Cyclohexyl |
| 6 | 4-Br | H | 4-Br | H | H | 4-NMe$_2$ | H | CH$_2$Ph |
| 7 | 4-Br | H | 4-Br | H | H | 4-NMe$_2$ | H | 4-Br-CH$_2$Ph |
| 87 | 4-Br | H | 4-Br | H | H | 4-Me | H | Me |
| 12a | 4-Br | H | 4-Br | H | H | 4-NMe(Et) | H | Me |
| 96 | 4-Br | H | 4-Br | H | H | 4-NEt$_2$ | H | Me |
| 5b | 3-Br | H | 4-Br | H | H | 4-NEt$_2$ | H | Me |
| 9b | 4-Me | H | 4-Me | H | H | 4-NEt$_2$ | H | Me |
| 24 | 2-Me | 4-Me | 4-Br | H | H | 4-NEt$_2$ | H | Me |
| 28 | 3-Me | 4-Me | 4-Br | H | H | 4-NEt$_2$ | H | Me |
| 57 | 4-Br | H | 3-OMe | 4-Br | 5-OMe | 4-NEt$_2$ | H | Me |
| 36 | 4-Br | H | 2-Cl | 4-Br | H | 4-NEt$_2$ | H | Me |
| 2 | 4-Br | H | 4-Br | H | H | 4-N(Me)CH$_2$CH$_2$OH | H | Me |
| 10a | 4-Me | H | 4-Cl | H | H | 4-N(Me)CH$_2$CH$_2$OH | H | Me |
| 25 | 2-Me | 4-Me | 4-Br | H | H | 4-N(Me)CH$_2$CH$_2$OH | H | Me |
| 29 | 3-Me | 4-Me | 4-Br | H | H | 4-N(Me)CH$_2$CH$_2$OH | H | Me |
| 58 | 4-Br | H | 3-OMe | 4-Br | 5-OMe | 4-N(Me)CH$_2$CH$_2$OH | H | Me |
| 40 | 4-Br | H | 2-Cl | 4-Br | H | 4-N(Me)CH$_2$CH$_2$OH | H | Me |
| 14b | 4-Me | H | 4-Br | H | H | 4-N(Me)CH$_2$CH$_2$OH | H | Et |
| 12c | 4-Br | H | 4-Br | H | H | 4-N(Me)CH$_2$CH$_2$CN | H | Me |
| 10b | 4-Me | H | 4-Cl | H | H | 4-N(Me)CH$_2$CH$_2$CN | H | Me |
| 30 | 3-Me | 4-Me | 4-Br | H | H | 4-N(Me)CH$_2$CH$_2$CN | H | Me |
| 59 | 4-Br | H | 3-OMe | 4-Br | 5-OMe | 4-N(Me)CH$_2$CH$_2$CN | H | Me |
| 39 | 4-Br | H | 2-Cl | 4-Br | H | 4-N(Me)CH$_2$CH$_2$CN | H | Me |
| 12b | 4-Br | H | 4-Br | H | H | 3-F | 4-NEt$_2$ | Me |

Modification of pyrylium into pyridinium on the scaffold resulted in potent restoration of activity against *S. aureus* and *Acinetobacter baumannii*, together with increased in vitro cytotoxicity. Compounds 1, 59 and 12c displayed the most favorable ratio of cytotoxicity over the MIC. Surprisingly, modification of bromides into fluorides in the 6jc48-1 scaffold (7jc47-1) resulted in restoration of *S. aureus* also, with no observable cytotoxicity in vitro.

Studies have revealed that the polyethoxylated excipients Tween-80, PEG-300, and the nonionic Cremophor EL (routinely used for in vivo formulations) can inhibit active P-gp efflux mechanisms in vitro. Inclusion of bile acids (such as taurocholic acid or glycocholic acid) at concentrations of 10 mM may have a beneficial effect in helping to solubilize compounds. Further, using bile salts in formulations to mimic fasted state simulated intestinal fluid (SIF) has shown promise to improve the solubility of highly lipophilic drugs without causing notable toxicity to the Caco-2 monolayer. It is possible that introduction of secondary and tertiary amines at position R17 and R17' decreases oral bioavailability, as suggested by a recent study QSBR study prediciting oral bioavailability of drugs in humans. If there is functional equivalence between compounds with amines and aliphatic nitriles, aliphatic nitriles at this position for membrane permeability can be seen as primary compounds. In addition, cyanoguandine and derivatives at position R16 can be considered.

Compounds were examined for their antibacterial activity and cytotoxicity (Table 10). Compared to the 6jc-48-1, the N-methylated pyridinium-based Compound 2 regained potent antibacterial activity against *S. aureus* and *A. baumannii* (see Table 10), however showed increased in vitro cytotoxicity. MIC data are average of two replicates; SA: *S. aureus* USA300 (MRSA); EF: *E. faecium* EF1509 (VRE); AB: *A. baumannii* 2-2-2 (colistin-resistant clinical isolate). CC50 was determined after exposure of compounds to HeLa cells for 24 hours. Values given are in µg/mL.

Variation in halogens and polar groups at other R positions (such as in Compounds 8 and 22 of Table 10) and addition of branched alkenes at position R13 and R13' (such as in Compounds 28 and 109 of Table 10) in particular further enhanced the antibacterial activity without greatly affecting cytotoxicity. Replacement of the positively charged oxygen by an uncharged nitrogen resulted in loss of antibacterial activity, indicating that charge is functionally important.

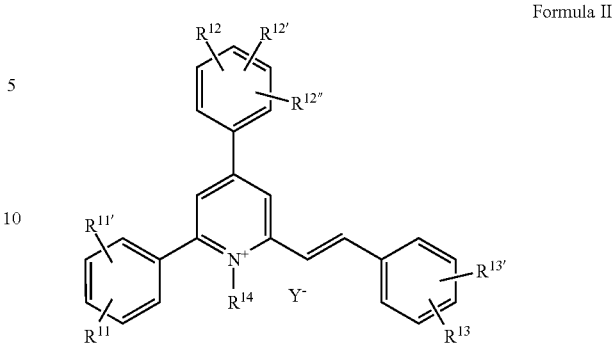

Formula II wherein each $R^{11}$, $R^{11'}$, $R^{12}$, $R^{12'}$, and $R^{12''}$ independently is —H, —F, —Br, —Cl, —CH$_3$, —CH$_2$CH$_3$, —OCH$_3$, —OCH$_2$CH$_3$, —NCH$_3$, —NCH$_2$CH$_3$, —N(CH$_3$)CH$_2$CH$_3$, —N(CH$_3$)CH$_2$CH$_2$OH, or —N(CH$_3$)CH$_2$CH$_2$CN;

wherein $R^{13}$ and $R^{13'}$ independently is —CH$_3$, —NCH$_3$, —NCH$_2$CH$_3$, —N(CH$_3$)CH$_3$, —N(CH$_3$)CH$_2$CH$_3$, —N(CH$_2$CH$_3$)CH$_2$CH$_3$, —N(CH$_3$)CH$_2$CH$_2$OH, or —N(CH$_3$)CH$_2$CH$_2$CN;

wherein $R_{14}$ is —CH$_3$, —CH$_2$CH$_3$, —CH$_2$CH(CH$_3$)CH$_3$, or -cyclohexyl; and wherein Y is an ion.

TABLE 10

Activity of N-methyl-pyridinium analogues of 6jc48-1.

| Cpd | R11/R11' | R12/R12'/R12" | R13/R13' | MIC SA | MIC EF | MIC AB | CC$_{50}$ |
|---|---|---|---|---|---|---|---|
| EL-2 | 4-Br | 4-Br | 4-N(CH$_3$)$_2$ | 1 | 1 | 8 | 5 |
| EL-8 | 4-Me | 4-Br | 4-N(CH$_3$)$_2$ | 0.5 | 4 | 4 | 12 |
| EL-11 | 4-Br | 4-Br | Me | 1 | 4 | >64 | 5 |
| 9s | 3-Me/4-Me | 4-Br | 4-N(CH$_3$)$_2$ | 0.25 | 1 | 16 | 3.5 |
| 9v | 3-Me/4-Me | 4-Br | 4-N(CH$_2$CH$_3$)$_2$ | 2 | 4 | 4 | 5.5 |
| 9p | 4-Me | 4-Cl | 4-N(CH$_3$)CH$_2$CHOH | 0.25 | 2 | 16 | 5.5 |

MIC SA = minimum inhibitory concentration *Staphylococcus aureus* USA 300 strain; MIC EF = minimum inhibitory concentration *Enterococcus faecalis* ATCC 1509; MIC AB = minimum inhibitory concentration *Actinobacter baumannii* clinical isolate; CC50 = cellular toxicity at 50%.

Additional variations were introduced into the compounds, which were then tested for the functional effects. Introduction of increased branching and bulk resulted in increased antibacterial activity compared to the single methyl group, in particular in the case of Compound 5 in Table 11, below. See the results in Table 11, below. MIC data are average of two replicates; SA: *S. aureus* USA300 (MRSA); EF: *E. faecium* EF1509 (VRE); AB: *A. baumannii* 2-2-2 (colistin-resistant clinical isolate). CC50 was determined after exposure of compounds to HeLa cells for 24 hour. Values given are in µg/mL.

TABLE 11

Activity of R-varied pyridinium analogues of 6jc48-1.

| Cpd | R11/R11' | R12/R12'/R12" | R13/R13' | R14 | MIC SA | MIC EF | MIC AB | CC$_{50}$ |
|---|---|---|---|---|---|---|---|---|
| EL-1 | 4-Br | 4-Br | 4-N(CH$_3$)$_2$ | isobutyl | 0.5 | 1 | 4 | 5 |
| EL-2 | 4-Br | 4-Br | 4-N(CH$_3$)$_2$ | Me | 1 | 1 | 8 | 5 |
| EL-3 | 4-Br | 4-Br | 4-N(CH$_3$)$_2$ | isopropyl | 2 | 2 | 16 | 9 |
| EL-5 | 4-Br | 4-Br | 4-N(CH$_3$)$_2$ | cyclohexyl | 1 | 0.25 | 0.5 | 4 |

These data show that the R14 positions influence potency, while the R13 positions primarily affect cytotoxicity.

Example 12: Modification of R Positions of Compounds

Figure 15:
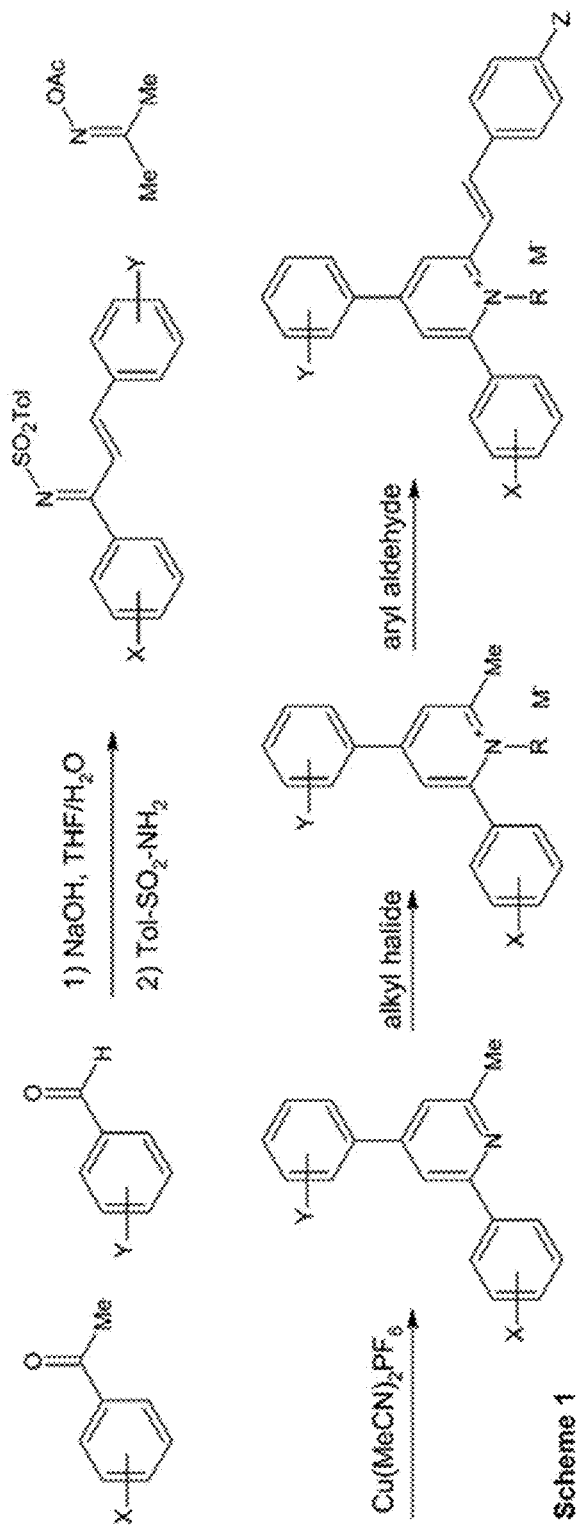
FIG. 15 is a general chemical synthetic scheme for certain compounds and intermediates according to the invention.
Figure 17A:
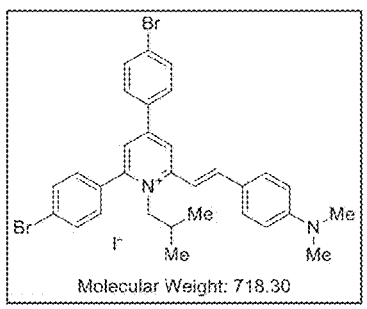
FIG. 17A presents structures of selected compounds: EL-1 (FIG. 17A), EL-2 (FIG. 17B), EL-3 (FIG. 17C), EL-4 (FIG. 17D), EL-5 (FIG. 17E), EL-6 (FIG. 17F), EL-7 (FIG. 17G), EL-8 (FIG. 17H), EL-9 (FIG. 17I), EL-10 (FIG. 17J), and EL-11 (FIG. 17K).
Figure 17B:
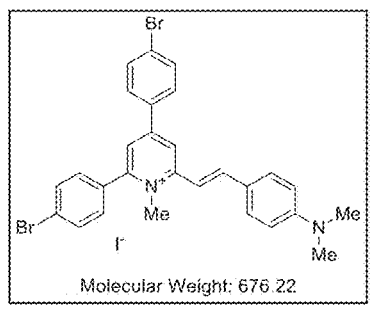
Figure 17C:
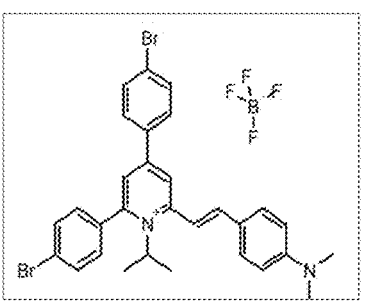
Figure 17D:
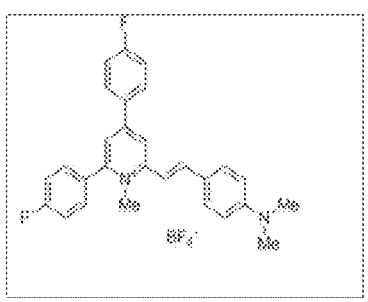
Figure 17E:
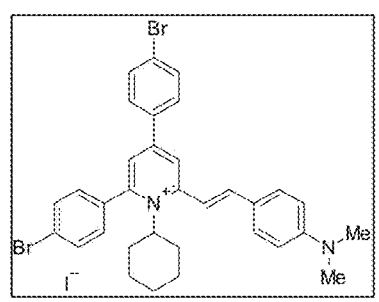
Figure 17F:
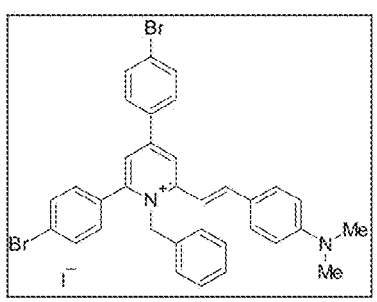
Figure 17G:
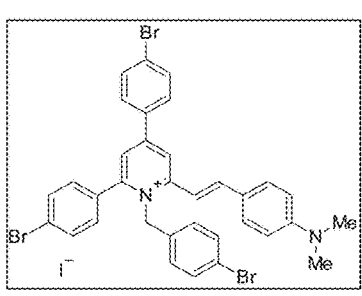
Figure 17H:
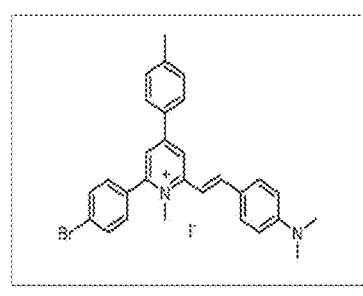
Figure 17I:
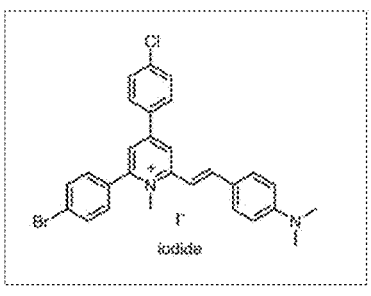
Figure 17J:
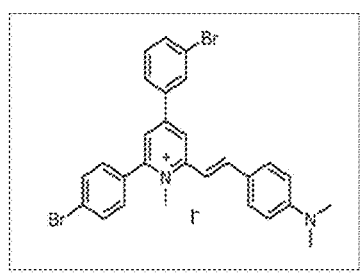
Figure 17K:
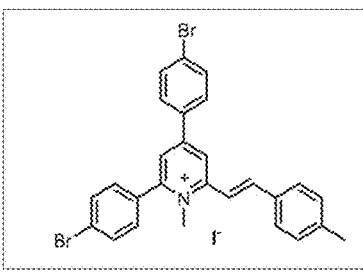

Because the model and preliminary data indicated that ionic interactions between Lipid II phosphates and pyrylium/pyridinium at position R of the scaffold are predominantly important for antibacterial activity, but also affect in vitro cytotoxicity and pharmacokinetics, modified pyridinium moieties were introduced at position R of the 6jc-48-1 scaffold according to the scheme in FIG. 15. Since the data in FIG. 19A and FIG. 19B, discussed below, indicate that addition of steric bulk to positively charged nitrogen such as isopropyl gave better results than isobutyl or methyl, alkyl groups of increasing length and branching were introduced systematically. In addition, cyclic hydrocarbons (cyclo-propyl, -butyl, -pentyl, -hexyl or benzene) were introduced.

The general synthetic approach for the pyridinium core is shown below.

Imidazole core analogs also can be synthesized using the scheme below.

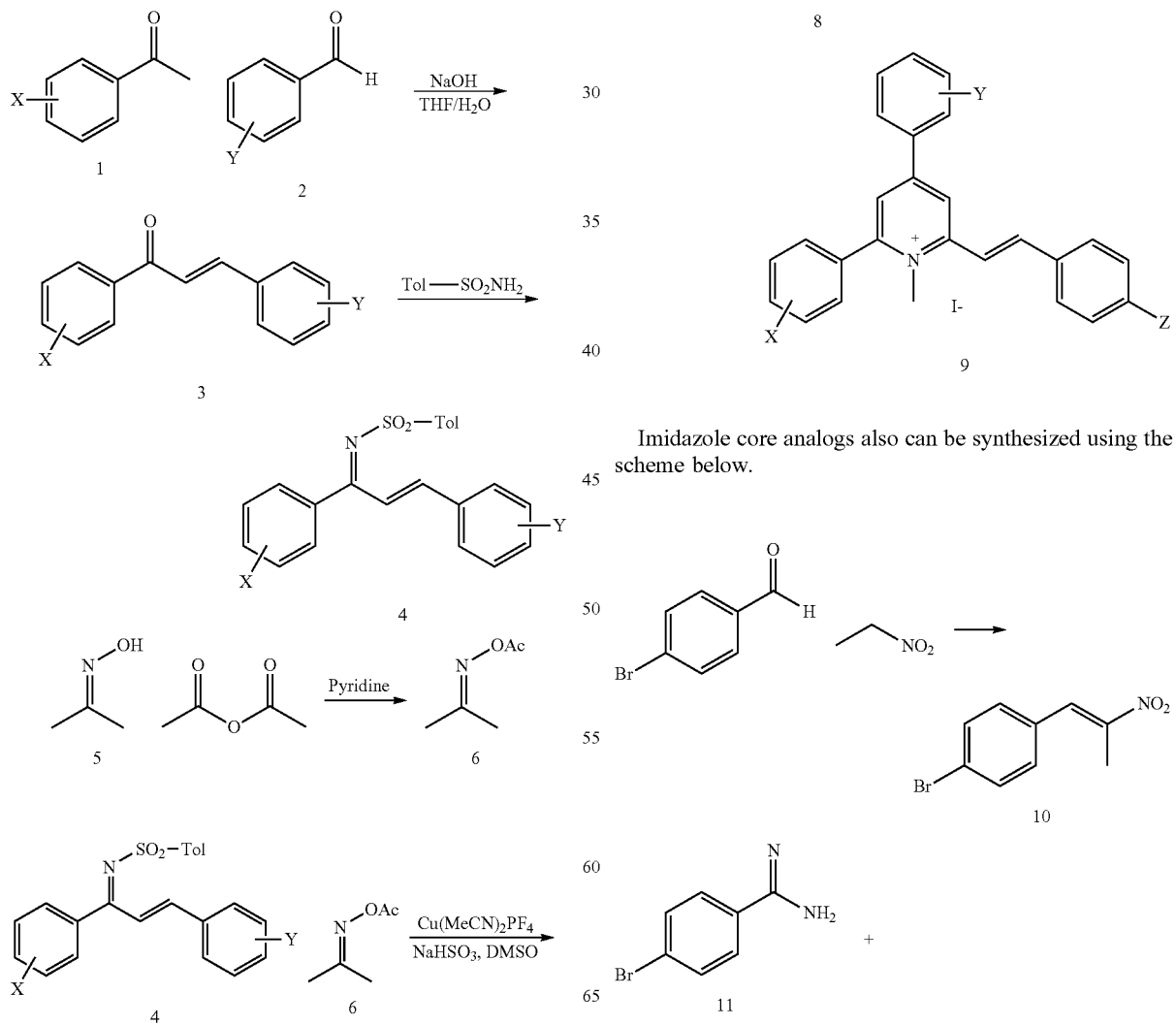

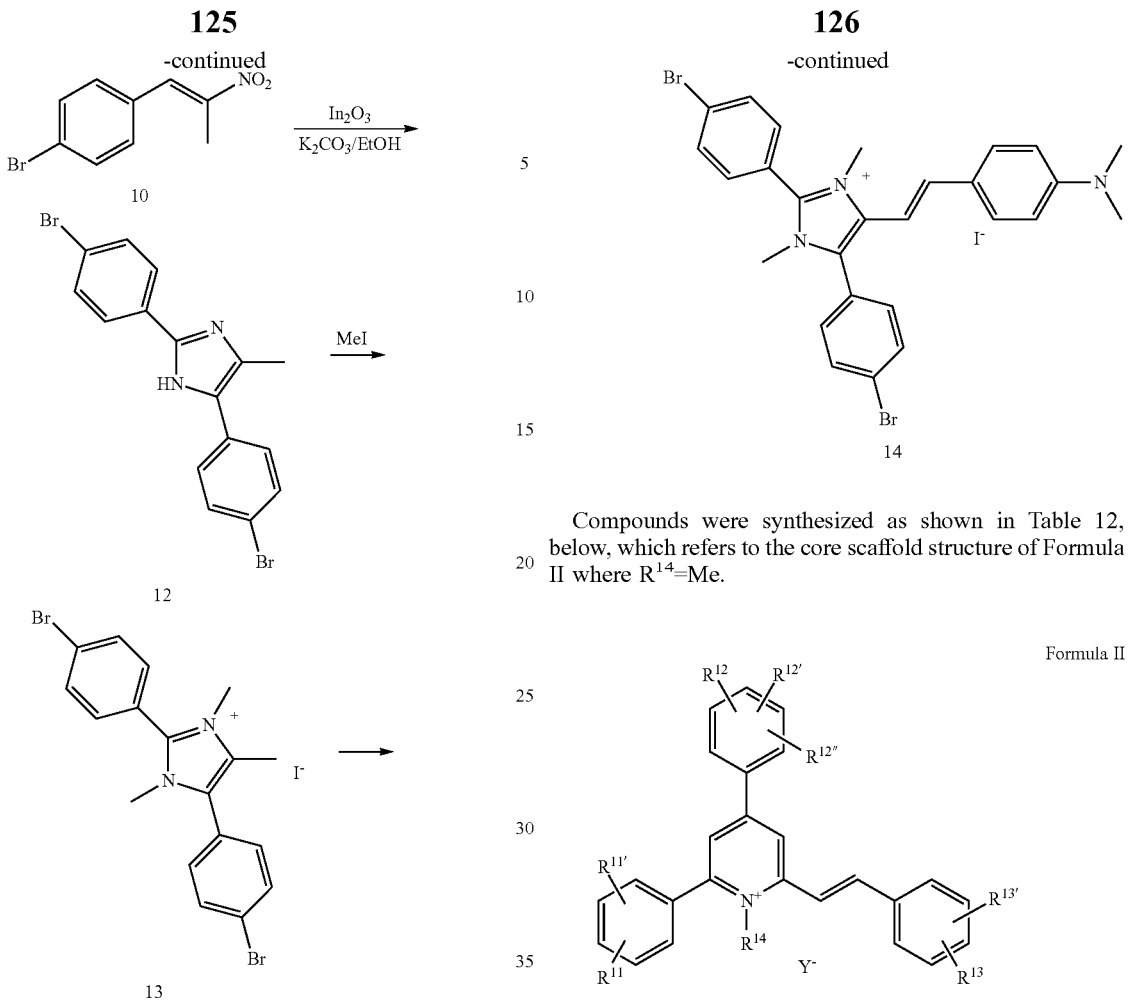

Compounds were synthesized as shown in Table 12, below, which refers to the core scaffold structure of Formula II where $R^{14}$=Me.

TABLE 12

Compounds synthesized on Formula II Scaffold Where $R^1$ is Methyl.

| Cpd No. | Cpd Name | $R^{11}$ | $R^{11'}$ | $R^{12}$ | $R^{12'}$ | $R^{12''}$ | $R^{13}$ | $R^{13'}$ |
|---|---|---|---|---|---|---|---|---|
| 1 | 9 | 4-Br | H | 4-Br | H | H | 4-NMe$_2$ | H |
| 2 | 9a | 4-Br | H | 4-Me | H | H | 4-NMe$_2$ | H |
| 3 | 9b | 4-Br | H | 3-Br | H | H | 4-NMe$_2$ | H |
| 4 | 9c | 4-Br | H | 4-Cl | H | H | 4-NMe$_2$ | H |
| 5 | 9d | 4-Br | H | 4-Br | H | H | 4-Me | H |
| 6 | 9e | 4-Me | H | 4-Br | H | H | 4-NMe$_2$ | H |
| 7 | 9f | 4-Br | H | 4-Br | H | H | 4-NEt$_2$ | H |
| 8 | 9g | 4-Br | H | 4-Br | H | H | 4-N(Me)CH$_2$CH$_2$OH | H |
| 9 | 9h | 4-Br | H | 4-Br | H | H | 4-NMe(Et) | H |
| 10 | 9j | 4-Br | H | 4-Br | H | H | 3-F-4-NEt$_2$ | H |
| 11 | 9k | 4-Br | H | 4-Br | H | H | 4-N(Me)CH$_2$CH$_2$CN | H |
| 12 | 9l | 3-Br | H | 4-Br | H | H | 4-NMe$_2$ | H |
| 13 | 9m | 3-Br | H | 4-Br | H | H | 4-NEt$_2$ | H |
| 14 | 9n | 4-Me | H | 4-Cl | H | H | NMe$_2$ | H |
| 15 | 9o | 4-Me | H | 4-Cl | H | H | NEt$_2$ | H |
| 16 | 9p | 4-Me | H | 4-Cl | H | H | 4-N(Me)CH$_2$CH$_2$OH | H |
| 17 | 9q | 4-Me | H | 4-Cl | H | H | 4-N(Me)CH$_2$CH$_2$CN | H |
| 18 | 9r | 2-Me | 4-Me | 4-Br | H | H | 4-NEt$_2$ | H |
| 19 | 9s | 2-Me | 4-Me | 4-Br | H | H | 4-NMe$_2$ | H |
| 20 | 9t | 2-Me | 4-Me | 4-Br | H | H | 4-N(Me)CH$_2$CH$_2$OH | H |
| 21 | 9u | 3-Me | 4-Me | 4-Br | H | H | 4-N(Me)CH$_2$CH$_2$CN | H |
| 22 | 9v | 3-Me | 4-Me | 4-Br | H | H | 4-NEt$_2$ | H |
| 23 | 9w | 3-Me | 4-Me | 4-Br | H | H | 4-NMe$_2$ | H |
| 24 | 9x | 3-Me | 4-Me | 4-Br | H | H | 4-N(Me)CH$_2$CH$_2$OH | H |
| 25 | 9y1 | 4-Br | H | 3-OMe | 5-OMe | 4-Br | 4-NMe$_2$ | H |
| 26 | 9y2 | 4-Br | H | 3-OMe | 5-OMe | 4-Br | 4-NEt$_2$ | H |
| 27 | 9y3 | 4-Br | H | 3-OMe | 5-OMe | 4-Br | 4-N(Me)CH$_2$CH$_2$CN | H |

TABLE 12-continued

Compounds synthesized on Formula II Scaffold Where $R^1$ is Methyl.

| Cpd No. | Cpd Name | $R^{11}$ | $R^{11'}$ | $R^{12}$ | $R^{12'}$ | $R^{12''}$ | $R^{13}$ | $R^{13'}$ |
|---|---|---|---|---|---|---|---|---|
| 28 | 9y4 | 4-Br | H | 3-OMe | 5-OMe | 4-Br | 4-N(Me)CH$_2$CH$_2$CN | H |
| 29 | 9z1 | 4-Br | H | 2-Cl | 4-Br | H | 4-NMe$_2$ | H |
| 30 | 9x2 | 4-Br | H | 2-Cl | 4-Br | H | 4-NMe$_2$ | H |
| 31 | 9z3 | 4-Br | H | 2-Cl | 4-Br | H | 4-N(Me)CH$_2$CH$_2$CN | H |
| 32 | 9z4 | 4-Br | H | 2-Br | 4-Br | H | 4-N(Me)CH$_2$CH$_2$CN | H |

Compounds were synthesized as shown in Table 13, below, which refers to the core scaffold structure of Formula II above where $R^{14}$=ethyl or propyl.

TABLE 13

Compounds synthesized on Formula II Scaffold.

| Cpd No. | Cpd Name | $R^{11}$ | $R^{11'}$ | $R^{12}$ | $R^{12'}$ | $R^{12''}$ | $R^{13}$ | $R^{13'}$ | $R^{14}$ |
|---|---|---|---|---|---|---|---|---|---|
| 35 | 9e1 | 4-Me | H | 4-Br | H | H | 4-NMe$_2$ | H | ethyl |
|  | 9e2 | 4-Me | H | 4-Br | H | H | 4-NMe(CH2CH2OH) | H | ethyl |
|  | 9e3 | 4-Me | H | 4-Br | H | H | 4-NMe$_2$ | H | propyl |

Example 13: Specific Synthetic Methods for Indicated Compounds

For these syntheses, all reagents and starting materials were purchased from commercial sources and used without further purification. 1H NMR was recorded on a Varian Utility 300 or 400 MHz spectrometer, in deuterated chloroform (CDCl3) or dimethylsulfoxide (DMSO-d6) solvent. Chemical shifts were reported as ppm from solvent reference. Coupling constants (J values) were measured in Hertz. Low resolution electrospray mass spectra (ES-MS) were collected on a Finnigan liquid chromatography quadrupole (LCQ) Duo liquid chromatography tandem mass spectrometer (LCMS-MS). Crude products were purified by recrystallization and silica gel chromatography. Purity was assessed by HPLC and 1H NMR. LCMS: Agilent Pursuit 3 C18, 50×2.5 mm, 300 Å, (5% acetonitrile in 0.1% aqueous formic acid) to (95% acetonitrile in 0.1% formic acid) over 5 min at 0.5 mL/min; positive ion ESI, detection at 254 nm. The temperature of reactions was recorded as internal temperatures. Room temperature was 21-23° C.

Example 13A: Synthesis of (E)-1,3-bis(4-bromophenyl)prop-2-en-1-one (3)

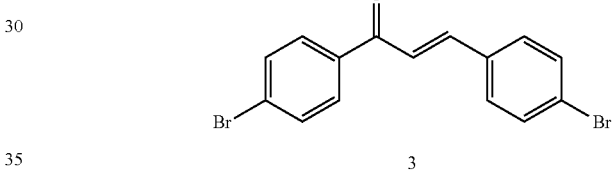

To a mixture of 4-bromoacetophenone (1, 4.18 g, 21 mmol) and 4-bromobenzaldehyde (2.3.7 g, 20 mmol) in 200 mL of MeOH at room temperature (RT) was added NaOH (1.6 g, 2 eq.).

The mixture was stirred at RT over the weekend. The solid precipitate was filtered and washed with Et2O. The desired product (3, white powder) was obtained in 80% yield. 1H NMR (400 MHz, CDCl3): d 7.86 (d, J=8.8 Hz, 2H), 7.72 (d, J=16.0 Hz, 1H), 7.63 (d, J=8.8 Hz, 2H), 7.54 (d, J=8.8 Hz, 2H), 7.48 (d, J=8.4 Hz, 2H), 7.44 (d, J=15.6 Hz, 1H).

Example 13B: Synthesis of N-((1E,2E)-1,3-bis(4-bromophenyl)allylidene)-4-methylbenzenesulfonamide (4)

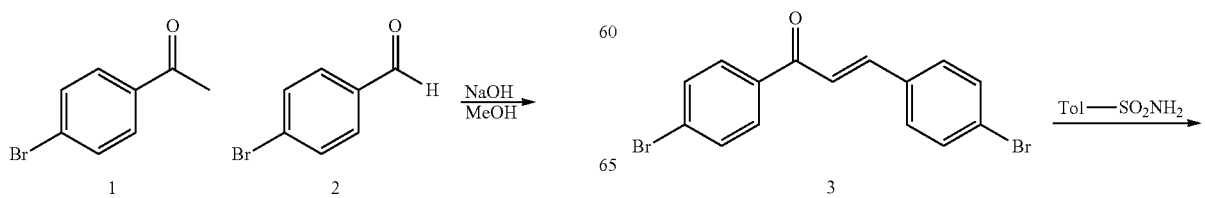

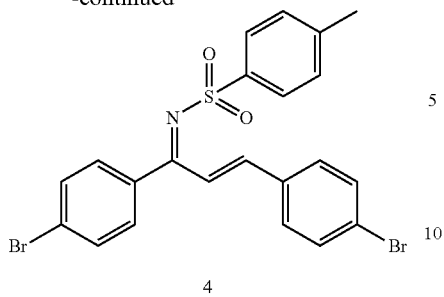

4

To a suspension of (E)-1,3-bis(4-bromophenyl)prop-2-en-1-one (3) (1.92 g, 5 mmol) and 4-toluenesulfonamide (2 eq., 1.71 g) in 40 mL of 1,2-dichloroethane and Et3N (1.9 mL, 3 eq.) at 0° C. was added TiCl4 (1.0 M in DCM, 1.5 eq. 7.5 mL) dropwise. After the addition, the mixture turned from yellow to red and was heated at 80° C. overnight. After it was cooled to RT, it was poured into ice-water and extracted with DCM (2×). The organic layer was washed with brine and dried over Na$_2$SO$_4$. The concentrated crude product mixture was re-dissolved in 15 mL of DCM, was passed through a silica gel pad, and was eluted with 5/4/1 of hexane/DCM/EtOAc. The filtrate was concentrated and the product was triturated with EtOAc, then diluted with hexane. The off-white solid was filtered and dried to give the desired product (4, 1.92 g) in 75% yield. 1H NMR (400 MHz, CDCl3): d 8.10 (br. s. 1H), 7.89 (m, 2H), 7.55 (m, 6H), 7.43 (m, 2H), 7.31 (d, J=8.0 Hz, 2H), 6.94 (d, J=16.0 Hz, 1H), 2.42 (s, 3H). MS: M+1, 517.8, 519.8, 521.8.

Example 13C: Synthesis of propan-2-one O-acetyl oxime (6)

The mixture of propan-2-one oxime (5, 15.2 g, 0.208 mol) and acetic anhydride (120 mL, 6 eq.) in 50 mL of pyridine was stirred at RT overnight. Volatiles were evaporated and the residue was purified on a silica gel column with 1/6/3 of Et2O/hexane/DCM. The desired product (6) was obtained in 79% yield (19 g). 1H NMR (400 MHz, CDCl3): d 2.13 (s. 3H), 2.01 (s, 3H), 1.97 (s, 3H). MS: M+1, 116.06; 2M+1, 231.19.

Example 13D: Synthesis of 2,4-bis(4-bromophenyl)-6-methylpyridine (7)

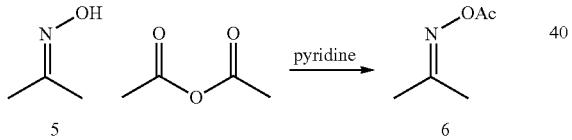

To a solution of N-((1E,2E)-1,3-bis(4-bromophenyl)allylidene)-4-methylbenzenesulfonamide (4) (0.55 g, 1.06 mmol) and propan-2-one O-acetyl oxime (6) (0.366 g, 3 eq.) in 5 mL of DMSO were added Cu(MeCN)$_4$PF$_6$ (0.2 eq. 0.079 g) and NaHSO$_3$ (0.132 g, 1.2 eq.). The mixture was heated at 60° C. for 7 hours. It was cooled to RT and was poured into ice-NaHCO$_3$ (sat. aq.). The product was extracted with EtOAc (2×). The organic layer was washed with brine and dried over Na$_2$SO$_4$. The mixture was purified on a Biotage column eluting with 1-5% EtOAc in hexane to give 0.15 g of the desired product (7) in 36% yield. 1H NMR (400 MHz, CDCl$_3$): δ7.89 (d, J=8.4 Hz, 2H), 7.69 (m, 5H), 7.52 (d, J=8.4 Hz, 2H), 7.27 (s, 1H), 2.67 (s, 3H). MS: M+1, 401.85, 403.87, 406.02.

Example 13E: Synthesis of 2,4-bis(4-bromophenyl)-1,6-dimethylpyridin-1-ium iodide (8)

In a capped vial, the mixture of 2,4-bis(4-bromophenyl)-6-methylpyridine (7) (85 mg, 0.212 mmol) and methyl iodide (60 eq. 0.79 mL) in 1 mL of MeCN was heated at 80° C. for 70 hours. It was cooled and was diluted with Et$_2$O. The precipitate was filtered and washed with Et$_2$O. The desired product (8) was obtained in 91% yield (105 mg). 1H NMR (400 MHz, DMSO-d$_6$): δ8.52 (d, J=2.4 Hz, 1H), 8.25 (d, J=2.4 Hz, 1H), 8.06 (d, J=8.4 Hz, 2H), 7.88 (d, J=8.4 Hz, 2H), 7.82 (d, J=8.4 Hz, 2H), 7.62 (d, J=8.4 Hz, 2H), 3.00 (s, 3H), 2.07 (s, 3H). MS: M+1, 415.91, 417.87, 419.92.

Example 13F: Synthesis of (E)-2,4-bis(4-bromophenyl)-6-(4-(dimethylamino)styryl)-1-methylpyridin-1-ium iodide (9)

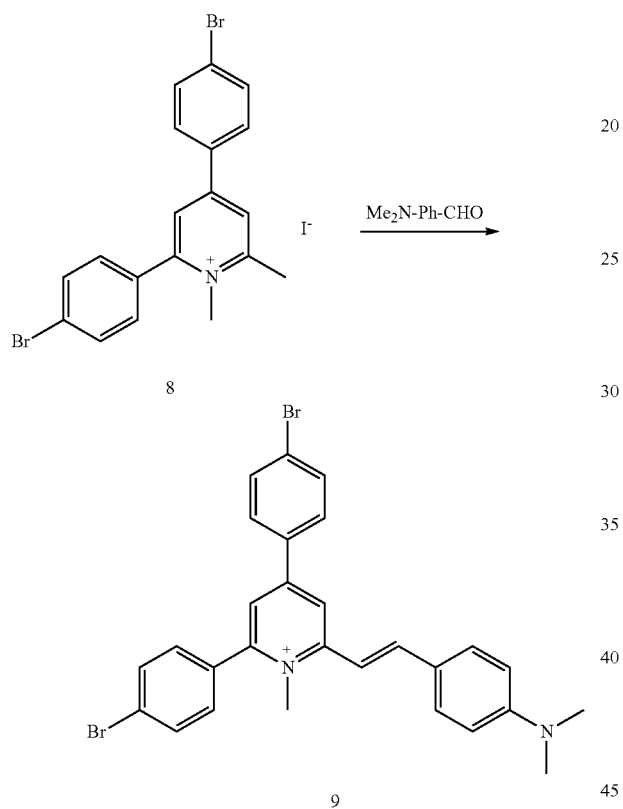

The mixture of 2,4-bis(4-bromophenyl)-1,6-dimethylpyridin-1-ium iodide (8) (90 mg, 0.166 mmol), 4-dimethylaminobenzaldehyde (3 eq. 74 mg) and piperidine (3 eq. 50 μL) in 2 mL of MeOH was heated at 80° C. for 2 hours. It was cooled and was diluted with Et$_2$O. The solid was filtered, washed with Et$_2$O and dried. The desired product (9, deep red solid) was obtained in 92.8% yield (104 mg). 1H NMR (400 MHz, DMSO-d$_6$): δ 8.68 (d, J=2.4 Hz, 1H), 8.15 (d, J=8.4 Hz, 2H), 8.12 (d, J=15.6 Hz, 1H), 8.02 (d, J=2.0 Hz, 1H), 7.87 (d, J=6.8 Hz, 2H), 7.82 (d, J=9.2 Hz, 2H), 7.73 (d, J=9.2 Hz, 2H), 7.66 (d, J=6.8 Hz, 2H), 7.29 (d, J=16.0 Hz, 1H), 6.78 (d, J=9.6 Hz, 2H), 3.94 (s, 3H), 3.02 (s, 6H). MS: (ESI positive ion mode) m/e (M)$^+$ 547.28, 549.24, 551.15. UV: Absorbances at 236.0, 312.0, 483.0 nm. HPLC: Varian C18 4μ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 5.43 min; 99.8%. Similarly, the following final analogs were synthesized based on the synthetic sequence and procedures described above.

Example 13G: Synthesis of (E)-2-(4-bromophenyl)-6-(4-(dimethylamino)styryl)-1-methyl-4-(p-tolyl)-pyridin-1-ium iodide (9a)

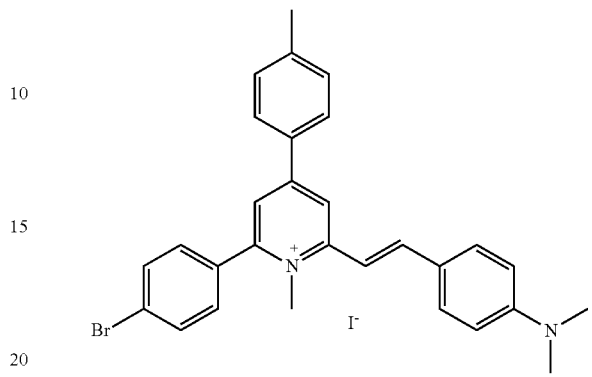

1H NMR (400 MHz) (DMSO-d$_6$): δ 8.64 (d, J=2 Hz, 1H), 8.11 (d, J=8.0 Hz, 2H), 8.10 (d, J=13.6 Hz, 1H), 7.99 (d, J=1.6 Hz, 1H), 7.86 (d, J=8.4 Hz, 2H), 7.73 (d, J=9.2 Hz, 2H), 7.66 (d, J=8.8 Hz, 2H), 7.41 (d, J=8.4 Hz, 2H), 7.28 (d, J=16.0 Hz, 1H), 6.78 (d, J=8.8 Hz, 2H), 3.92 (s, 3H), 3.01 (s, 3H), 2.39 (s, 3H). MS: (ESI positive ion mode) m/e (M)$^+$ 483.36, 485.27 as parent mass. UV: Absorbances at 237.0, 316.0, 475.0 nm. HPLC: Varian C18 4μ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 5.38 min; 99.9%.

Example 13H: Synthesis of (E)-4-(3-bromophenyl)-2-(4-bromophenyl)-6-(4-(dimethylamino)styryl)-1-methylpyridin-1-ium iodide (9b)

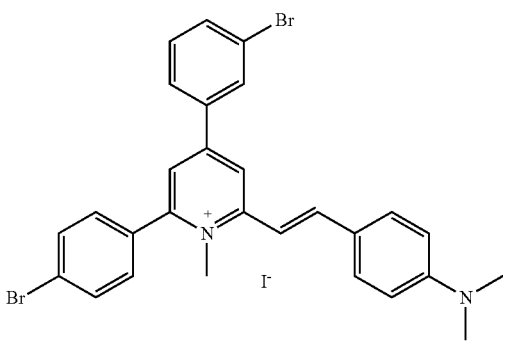

1H NMR (400 MHz, DMSO-d$_6$): δ 8.69 (s, 1H), 8.42 (s, 1H), 8.10 (m, 3H), 7.86 (d, J=7.8 Hz, 2H), 7.80 (d, J=8.0 Hz, 1H), 7.73 (d, J=9.2 Hz, 2H), 7.66 (d, J=8 Hz, 2H), 7.55 (t, J=8 Hz, 1H), 7.28 (d, J=16 Hz, 1H), 6.78 (d, J=9.2 Hz, 2H), 3.94 (s, 3H), 3.01 (s, 6H). MS: (ESI positive ion mode) m/e (M)$^+$ 547.28, 549.20, 551.14. UV: Absorbances at 235.0, 299.0, 488.0 nm. HPLC: Varian C18 4μ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 5.43 min; 98.9%.

Example 13I: Synthesis of (E)-2-(4-bromophenyl)-4-(4-chlorophenyl)-6-(4-(dimethylamino)styryl)-1-methylpyridin-1-ium iodide (9c)

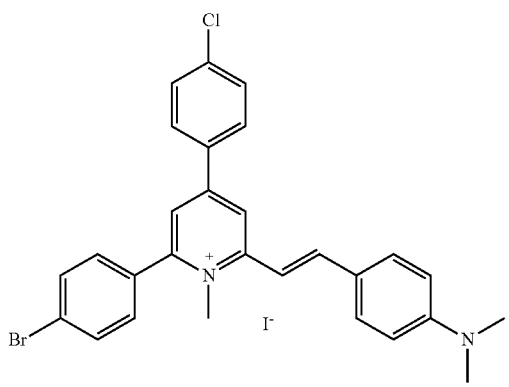

1H NMR (400 MHz, DMSO-d$_6$): δ 8.67 (d, J=2.0 Hz, 1H), 8.22 (d, J=8.8 Hz, 2H), 8.11 (d, J=15.6 Hz, 1H), 8.02 (d, J=2.0 Hz, 1H), 7.86 (d, J=8.4 Hz, 2H), 7.7 (m, 6H), 7.28 (d, J=15.6 Hz, 1H), 6.78 (d, J=9.2 Hz, 2H), 3.94 (s, 3H), 3.01 (s, 6H). MS: (ESI positive ion mode) m/e (M)$^+$ 503.38, 505.29. UV: Absorbances at 235.0, 310.0, 486.0 nm. HPLC: Varian C18 4µ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 5.39 min; 99.3%.

Example 13J: Synthesis of (E)-2,4-bis(4-bromophenyl)-1-methyl-6-(4-methylstyryl)pyridin-1-ium iodide (9d)

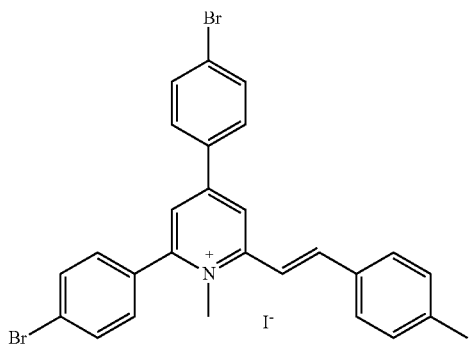

1H NMR (400 MHz, DMSO-d$_6$): δ 8.75 (d, J=2.0 Hz, 1H), 8.22 (d, J=2.0 Hz, 1H), 8.16 (d, J=8.8 Hz, 2H), 8.08 (d, J=16.0 Hz, 1H), 7.88 (d, J=8.8 Hz, 2H), 7.83 (d, J=8.4 Hz, 2H), 7.78 (d, J=8.0 Hz, 2H), 7.67 (d, J=8.4 Hz, 2H), 7.59 (d, J=16.0 Hz, 1H), 7.32 (d, J=8.0 Hz, 2H), 4.00 (s, 3H), 2.35 (s, 3H). MS: (ESI positive ion mode) m/e (M)$^+$ 518.32, 520.24, 522.08. UV: Absorbances at 234.0, 312.0, 368.0 nm. HPLC: Varian C18 4µ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 5.31 min; 99.2%.

Example 13K: Synthesis of (E)-4-(4-bromophenyl)-2-(4-(dimethylamino)styryl)-1-methyl-6-(p-tolyl)-pyridin-1-ium iodide (9e)

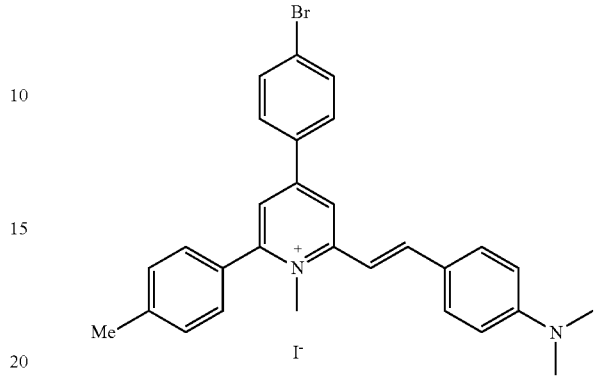

1H NMR (400 MHz, DMSO-d$_6$): δ 8.64 (d, J=2.4 Hz, 1H), 8.13 (d, J=8.8 Hz, 2H), 8.08 (d, J=16.0 Hz, 1H), 7.97 (d, J=2.0 Hz, 1H), 7.80 (d, J=8.8 Hz, 2H), 7.71 (d, J=8.8 Hz, 2H), 7.59 (d, J=8.0 Hz, 2H), 7.44 (d, J=8.0 Hz, 2H), 7.28 (d, J=16.0 Hz, 1H), 6.78 (d, J=8.0 Hz, 2H), 3.95 (s, 3H), 3.01 (s, 6H), 2.41 (s, 3H). MS: (ESI positive ion mode) m/e (M)$^+$ 483.40, 485.33. UV: Absorbances at 235.0, 310.0, 483.0 nm. HPLC: Varian C18 4µ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 5.29 min; 98.6%.

Example 13L: Synthesis of (E)-2,4-bis(4-bromophenyl)-6-(4-(diethylamino)styryl)-1-methylpyridin-1-ium iodide (9f)

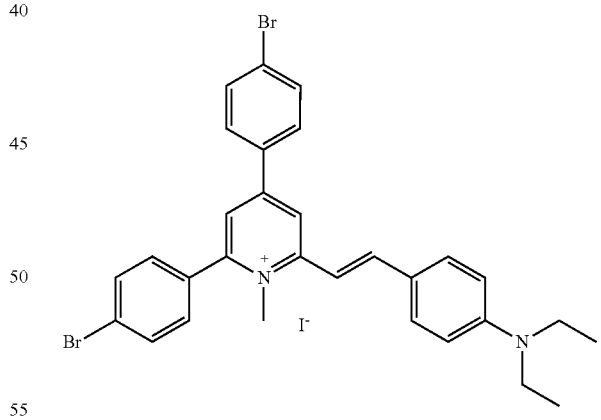

1H NMR (400 MHz, DMSO-d$_6$): δ 8.67 (d, J=2.0 Hz, 1H), 8.13 (m, 3H), 7.99 (d, J=2.0 Hz, 1H), 7.86 (d, J=8.4 Hz, 2H), 7.81 (d, J=9.2 Hz, 2H), 7.70 (d, J=8.8 Hz, 2H), 7.65 (d, J=8.8 Hz, 2H), 7.23 (d, J=15.6 Hz, 1H), 6.74 (d, J=9.6 Hz, 2H), 3.92 (s, 3H), 3.42 (q, J=6.8 Hz, 4H), 1.11 (t, J=6.8 Hz, 6H). MS: (ESI positive ion mode) m/e (M)$^+$ 575.32. 577.28, 579.21. UV: Absorbances at 237.0, 310.0, 502.0 nm. HPLC: Varian C18 4µ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 5.58 min; 98.9%.

Example 13M: Synthesis of (E)-2,4-bis(4-bromophenyl)-6-(4-((2-hydroxyethyl)(methyl)amino)styryl)-1-methylpyridin-1-ium iodide (9g)

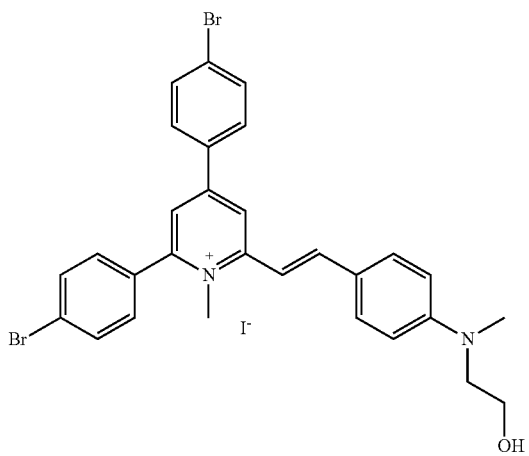

1H NMR (400 MHz, DMSO-$d_6$): δ 8.67 (d, J=2.4 Hz, 1H), 8.13 (m, 3H), 8.01 (d, J=2.0 Hz, 1H), 7.86 (d, J=8.4 Hz, 2H), 7.81 (d, J=9.2 Hz, 2H), 7.70 (d, J=8.8 Hz, 2H), 7.65 (d, J=8.8 Hz, 2H), 7.26 (d, J=15.6 Hz, 1H), 6.78 (d, J=9.6 Hz, 2H), 4.74 (t, J=5.6 Hz, 1H), 3.56 (s, 3H), 3.50 (m, 4H), 1.11 (t, J=6.8 Hz, 6H). MS: (ESI positive ion mode) m/e (M)$^+$ 577.32. 579.12, 581.16. UV: Absorbances at 238.0, 311.0, 490.0 nm. HPLC: Varian C18 4μ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 5.04 min; 98.1%.

Example 13N: Synthesis of (E)-2,4-bis(4-bromophenyl)-6-(4-(ethyl(methyl)amino)styryl)-1-methylpyridin-1-ium iodide (9h)

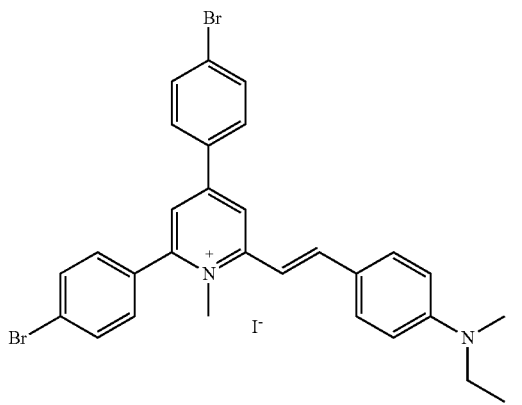

1H NMR (400 MHz, DMSO-$d_6$): δ 8.67 (d, J=2.0 Hz, 1H), 8.13 (m, 3H), 8.01 (d, J=2.0 Hz, 1H), 7.86 (d, J=8.0 Hz, 2H), 7.81 (d, J=8.8 Hz, 2H), 7.71 (d, J=8.8 Hz, 2H), 7.65 (d, J=8.8 Hz, 2H), 7.26 (d, J=15.6 Hz, 1H), 6.77 (d, J=9.2 Hz, 2H), 3.92 (s, 3H), 3.48 (q, J=7.2 Hz, 2H), 2.97 (s, 3H), 1.06 (t, J=7.2 Hz, 3H). MS: (ESI positive ion mode) m/e (M)$^+$ 561.33. 563.28, 565.23. UV: Absorbances at 237.0, 311.0, 495.0 nm. HPLC: Varian C18 4μ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 5.40 min; 99.4%.

Example 13O: Synthesis of (E)-2,4-bis(4-bromophenyl)-6-(4-(diethylamino)-3-fluorostyryl)-1-methyl-pyridin-1-ium iodide (9j)

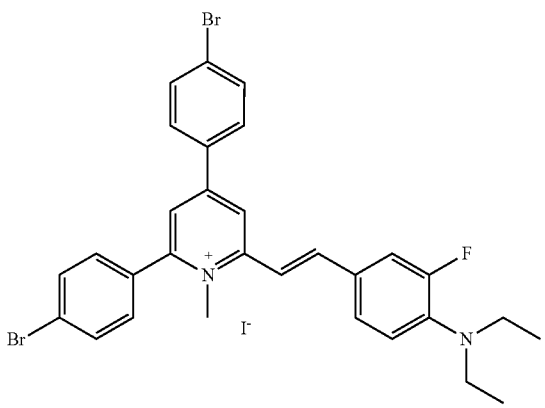

1H NMR (400 MHz, DMSO-$d_6$): δ 8.68 (d, J=2.0 Hz, 1H), 8.14 (m, 3H), 8.04 (d, J=15.6 Hz, 1H), 7.87 (d, J=8.4 Hz, 2H), 7.82 (d, J=8.8 Hz, 2H), 7.76 (d, J=16.4 Hz, 1H), 7.66 (d, J=8.4 Hz, 2H), 7.47 (d, J=8.4 Hz, 1H), 7.41 (d, J=16.0 Hz, 1H), 6.96 (t, J=9.2 Hz, 1H), 3.96 (s, 3H), 3.34 (m, 4H), 1.09 (t, J=7.2 Hz, 6H). MS: (ESI positive ion mode) m/e (M)$^+$ 593.31, 595.37, 597.31. UV: Absorbances at 237.0, 313.0, 466.0 nm. HPLC: Varian C18 4μ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 5.53 min; 99.3%.

Example 13P: Synthesis of (E)-2,4-bis(4-bromophenyl)-6-(4-((2-cyanoethyl)(methyl)amino)styryl)-1-methylpyridin-1-ium iodide (9k)

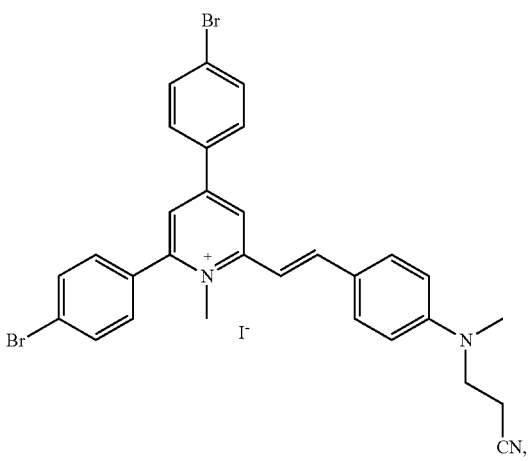

1H NMR (400 MHz, DMSO-$d_6$): δ 8.69 (d, J=2.0 Hz, 1H), 8.13 (m, 3H), 8.05 (d, J=2.0 Hz, 1H), 7.87 (d, J=8.4 Hz, 2H), 7.82 (d, J=8.8 Hz, 2H), 7.74 (d, J=8.8 Hz, 2H), 7.66 (d,

J=8.8 Hz, 2H), 7.33 (d, J=15.6 Hz, 1H), 6.87 (d, J=8.8 Hz, 2H), 3.95 (s, 3H), 3.77 (t, J=6.8 Hz, 2H), 3.04 (s, 3H), 2.75 (t, J=6.8 Hz, 2H). MS: (ESI positive ion mode) m/e (M)+ 586.5, 588.3, 590.2. UV: Absorbances at 237.0, 312.0, 470.0 nm. HPLC: Varian C18 4□ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 5.14 min; 99.9%.

Example 13Q: Synthesis of (E)-2-(3-bromophenyl)-4-(4-bromophenyl)-6-(4-(dimethylamino)styryl)-1-methylpyridin-1-ium iodide (9l)

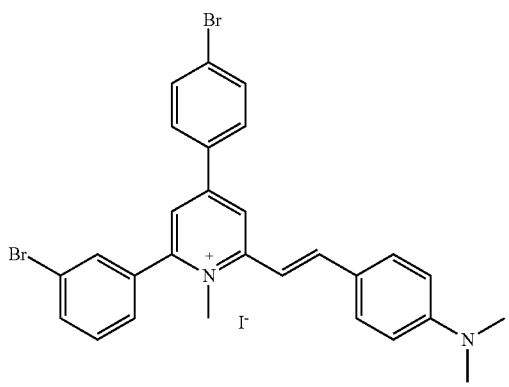

1H NMR (400 MHz, DMSO-d$_6$): δ 8.69 (d, J=2.0 Hz, 1H), 8.14 (m, 3H), 8.05 (m, 2H), 7.86 (m, 3H), 7.74 (m, 3H), 7.60 (t, J=8.0 Hz, 1H), 7.28 (d, J=16 Hz, 1H), 6.78 (d, J=8.8 Hz, 2H), 3.94 (s, 3H), 3.02 (s, 6H). MS: (ESI positive ion mode) m/e (M)+ 547.33, 549.30, 551.19. UV: Absorbances at 234.0, 309.0, 490.0 nm. HPLC: Varian C18 4µ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 5.39 min; 98.8%.

Example 13R: Synthesis of (E)-2-(3-bromophenyl)-4-(4-bromophenyl)-6-(4-(diethylamino)styryl)-1-methylpyridin-1-ium iodide (9m)

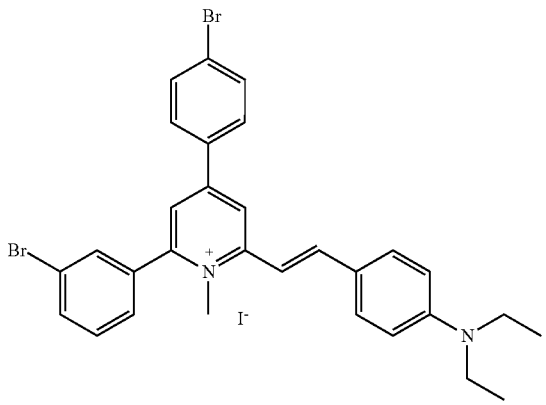

1H NMR (400 MHz, DMSO-d$_6$): δ 8.67 (d, J=2.4 Hz, 1H), 8.14 (m, 3H), 7.97 (m, 2H), 7.84 (m, 3H), 7.71 (m, 3H), 7.59 (t, J=8.0 Hz, 1H), 7.22 (d, J=15.6 Hz, 1H), 6.74 (d, J=9.2 Hz, 2H), 3.92 (s, 3H), 3.25 (m, 4H), 1.11 (t, J=7.2 Hz, 3H). MS: (ESI positive ion mode) m/e (M)+ 575.3, 577.3, 579.2. UV: Absorbances at 235.0, 306.0, 504.0 nm. HPLC: Varian C18 4µ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 5.63 min; 98.5%.

Example 13S: Synthesis of (E)-4-(4-chlorophenyl)-2-(4-(dimethylamino)styryl)-1-methyl-6-(p-tolyl)-pyridin-1-ium iodide (9n)

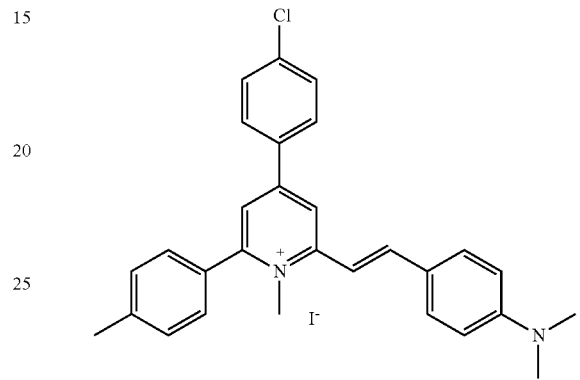

1H NMR (400 MHz, DMSO-d$_6$): δ 8.64 (d, J=2.0 Hz, 1H), 8.21 (d, J=8.4 Hz, 2H), 8.08 (d, J=15.6 Hz, 1H), 7.97 (d, J=2.4 Hz, 1H), 7.72 (d, J=8.8 Hz, 2H), 7.66 (d, J=8.4 Hz, 2H), 7.59 (d, J=7.6 Hz, 2H), 7.44 (d, J=8.4 Hz, 2H), 7.28 (d, J=15.6 Hz, 1H), 6.77 (d, J=9.2 Hz, 2H), 3.96 (s, 3H), 3.01 (s, 6H), 2.41 (s, 3H). MS: (ESI positive ion mode) m/e (M)+ 439.48, 441.33. UV: Absorbances at 236.0, 306.0, 488.0 nm. HPLC: Varian C18 4µ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time, 4.89 min; 96.5%.

Example 13T: Synthesis of (E)-4-(4-chlorophenyl)-2-(4-(diethylamino)styryl)-1-methyl-6-(p-tolyl)pyridin-1-ium iodide (9o)

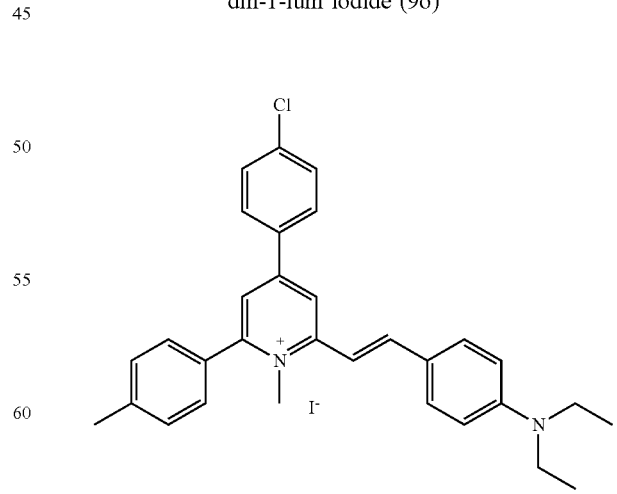

1H NMR (400 MHz, DMSO-d$_6$): δ 8.63 (d, J=2.0 Hz, 1H), 8.21 (d, J=8.4 Hz, 2H), 8.01 (d, J=15.6 Hz, 1H), 7.95 (d, J=2.0 Hz, 1H), 7.68 (m, 4H), 7.59 (d, J=8.0 Hz, 2H), 7.44

(d, J=8.0 Hz, 2H), 7.23 (d, J=15.6 Hz, 1H), 6.75 (d, J=9.2 Hz, 2H), 3.95 (s, 3H), 3.42 (q, J=6.8 Hz, 4H), 2.42 (s, 3H), 1.11 (t, J=6.8 Hz, 6H). MS: (ESI positive ion mode) m/e (M)+ 467.40, 469.37. UV: Absorbances at 237.0, 309.0, 498.0 nm. HPLC: Varian C18 4μ 50×2 mm; flow 0.5 mL/min; Finnigan/Surveyor PDA plus detector (200-600 nm); solvent 5-95% acetonitrile (0.1% TFA) in H₂O (0.1% TFA) over 10 min; retention time, 5.46 min; 99.4%.

Example 13U: Synthesis of (E)-4-(4-chlorophenyl)-2-(4-((2-hydroxyethyl)(methyl)amino)styryl)-1-methyl-6-(p-tolyl)pyridin-1-ium iodide (9p)

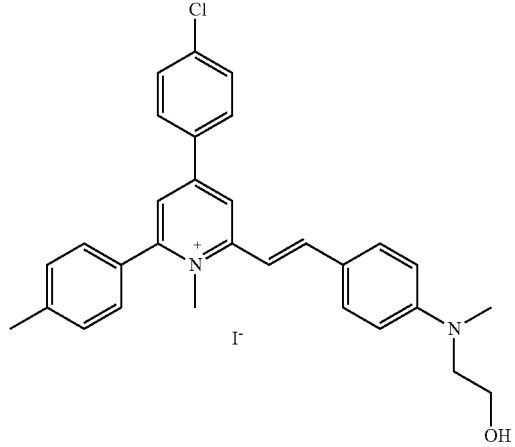

1H NMR (400 MHz, DMSO-d₆): δ 8.64 (d, J=2.0 Hz, 1H), 8.22 (d, J=8.4 Hz, 2H), 8.09 (d, J=15.6 Hz, 1H), 7.97 (d, J=2.0 Hz, 1H), 7.68 (m, 4H), 7.59 (d, J=7.6 Hz, 2H), 7.44 (d, J=8.0 Hz, 2H), 7.26 (d, J=15.6 Hz, 1H), 6.78 (d, J=9.2 Hz, 2H), 4.74 (t, J=5.2 Hz, 1H, OH), 3.95 (s, 3H), 3.55 (t, J=5.6 Hz, 2H), 3.48 (t, J=5.6 Hz, 2H), 3.02 (s, 3H), 2.42 (s, 3H). MS: (ESI positive ion mode) m/e (M)+ 469.40. UV: Absorbances at 235.0, 309.0, 483.0 nm. HPLC: Varian C18 4μ 50×2 mm; flow 0.5 mL/min; Finnigan/Surveyor PDA plus detector (200-600 nm); solvent 5-95% acetonitrile (0.1% TFA) in H₂O (0.1% TFA) over 10 min; retention time, 4.61 min; 99.3%.

Example 13V: Synthesis of (E)-4-(4-chlorophenyl)-2-(4-((2-cyanoethyl)(methyl)amino)styryl)-1-methyl-6-(p-tolyl)pyridin-1-ium iodide (9q)

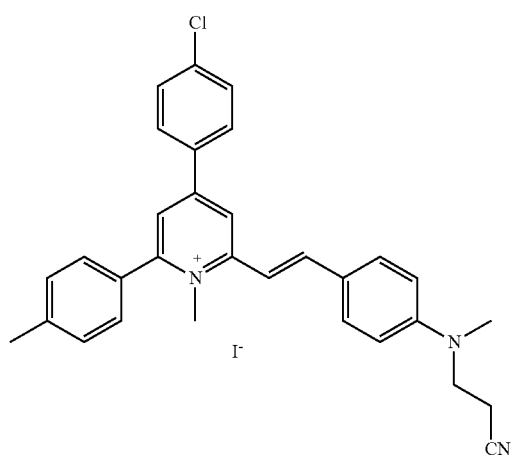

1H NMR (400 MHz, DMSO-d₆): δ 8.66 (d, J=1.6 Hz, 1H), 8.23 (d, J=8.8 Hz, 2H), 8.09 (d, J=15.6 Hz, 1H), 8.01 (d, J=2.0 Hz, 1H), 7.73 (d, J=8.8 Hz, 2H), 7.67 (d, J=8.4 Hz, 2H), 7.59 (d, J=8.0 Hz, 2H), 7.45 (d, J=8.0 Hz, 2H), 7.32 (d, J=15.6 Hz, 1H), 6.87 (d, J=8.8 Hz, 2H), 3.97 (s, 3H), 3.77 (t, J=7.8 Hz, 2H), 3.03 (s, 3H), 2.75 (t, J=7.8 Hz, 2H), 2.42 (s, 3H). MS: (ESI positive ion mode) m/e (M)+ 478.17. UV: Absorbances at 235.0, 308.0, 466.0 nm. HPLC: Varian C18 4μ 50×2 mm; flow 0.5 mL/min; Finnigan/Surveyor PDA plus detector (200-600 nm); solvent 5-95% acetonitrile (0.1% TFA) in H₂O (0.1% TFA) over 10 min; retention time, 4.74 min; purity, 98.6%.

Example 13W: Synthesis of (E)-4-(4-bromophenyl)-2-(4-(diethylamino)styryl)-6-(2,4-dimethylphenyl)-1-methylpyridin-1-ium iodide (9r)

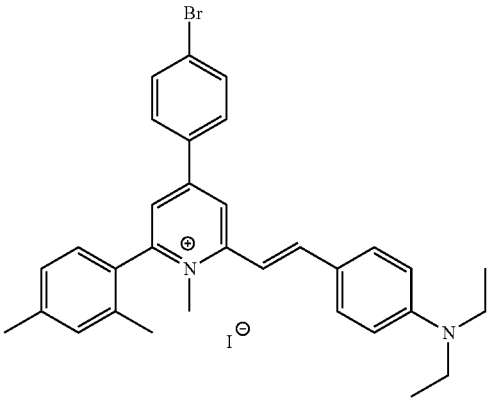 [SMILES: CCN(CC)c1ccc(/C=C/c2cc(-c3ccc(Br)cc3)cc(-c3ccc(C)cc3C)[n+]2C)cc1 ; [I-]]

1H NMR (400 MHz, DMSO-d₆): δ 8.67 (d, J=2.4 Hz, 1H), 8.11 (m, 3H), 7.95 (d, J=2.0 Hz, 1H), 7.80 (d, J=8.8 Hz, 2H), 7.68 (d, J=9.2 Hz, 1H), 7.34 (d, J=8.0 Hz, 1H), 7.26 (m, 3H), 6.75 (d, J=9.2 Hz, 2H), 3.83 (s, 3H), 3.42 (m, 4H), 2.37 (s, 3H), 2.13 (s, 3H), 1.11 (m, 6H). MS: (ESI positive ion mode) m/e (M)+ 264.36, 527.34. UV: Absorbances at 237.0, 308.0, 499.0 nm. HPLC: Varian C18 4μ 50×2 mm; flow 0.5 mL/min; Finnigan/Surveyor PDA plus detector (200-600 nm); solvent 5-95% acetonitrile (0.1% TFA) in H₂O (0.1% TFA) over 10 min; retention time 5.61 min; 98.8%.

Example 13X: Synthesis of (E)-4-(4-bromophenyl)-2-(4-(dimethylamino)styryl)-6-(2,4-dimethylphenyl)-1-methylpyridin-1-ium iodide (9s)

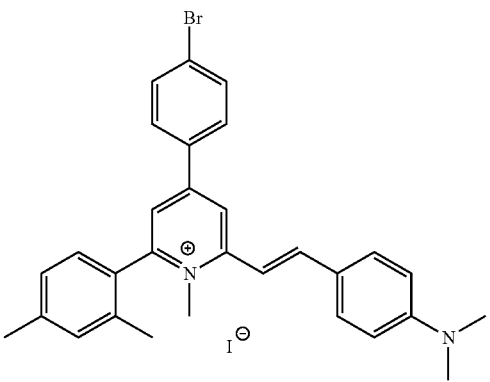

1H NMR (400 MHz, DMSO-d$_6$): δ 8.68 (d, J=2.0 Hz, 1H), 8.11 (m, 3H), 7.98 (d, J=2.0 Hz, 1H), 7.80 (d, J=2.0 Hz, 2H), 7.71 (d, J=8.4 Hz, 2H), 7.29 (m, 4H), 6.78 (d, J=9.2 Hz, 2H), 3.84 (s, 3H), 3.01 (s, 6H), 2.37 (s, 3H), 2.13 (s, 3H). MS: (ESI positive ion mode) m/e (M)$^+$ 497.42, 499.31. UV: Absorbances at 235.0, 307.0, 482.0 nm. HPLC: Varian C18 4μ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 5.43 min; 99.8%.

Example 13Y: Synthesis of (E)-4-(4-bromophenyl)-2-(2,4-dimethylphenyl)-6-(4-((2-hydroxyethyl)(methyl)-amino)styryl)-1-methylpyridin-1-ium iodide (9t)

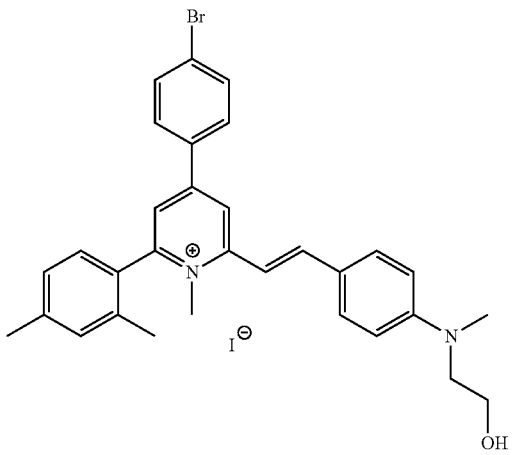 [SMILES: Cc1ccc(-c2cc(-c3ccc(Br)cc3)cc(/C=C/c3ccc(N(C)CCO)cc3)[n+]2C)c(C)c1 ; [I-]]

1H NMR (400 MHz, DMSO-d$_6$): δ 8.68 (d, J=2.0 Hz, 1H), 8.11 (m, 3H), 7.96 (d, J=2.0 Hz, 1H), 7.80 (d, J=8.8 Hz, 2H), 7.68 (d, J=9.2 Hz, 2H), 7.30 (m, 4H), 6.79 (d, J=9.6 Hz, 2H), 4.74 (m, 1H), 3.84 (s, 3H), 3.52 (m, 4H), 3.02 (s, 3H), 2.37 (s, 3H), 2.13 (m, 3H). MS: (ESI positive ion mode) m/e (M)$^+$ 527.62. UV: Absorbances at 237.0, 309.0, 487.0 nm. HPLC: Varian C18 4μ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 5.05 min; 98.2%.

Example 13Z: Synthesis of (E)-4-(4-bromophenyl)-2-(4-((2-cyanoethyl)(methyl)amino)styryl)-6-(3,4-dimethylphenyl)-1-methylpyridin-1-ium iodide (9u)

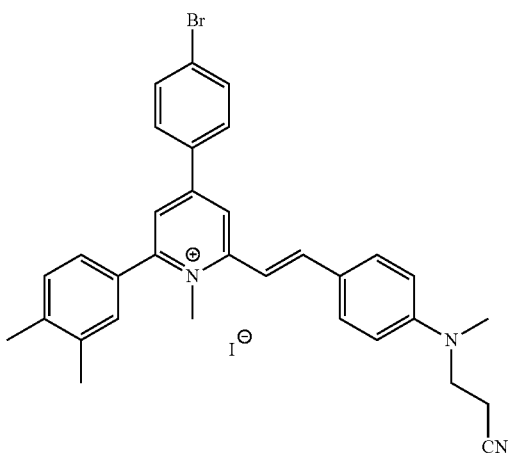 [SMILES: Cc1ccc(-c2cc(-c3ccc(Br)cc3)cc(/C=C/c3ccc(N(C)CCC#N)cc3)[n+]2C)cc1C ; [I-]]

1H NMR (400 MHz, DMSO-d$_6$): δ 8.65 (d, J=2.0 Hz, 1H), 8.11 (m, 3H), 7.95 (d, J=2.0 Hz, 1H), 7.80 (d, J=8.8 Hz, 2H), 7.73 (d, J=9.2 Hz, 2H), 7.48 (s, 1H), 7.40 (m, 2H), 7.32 (d, J=16.0 Hz, 1H), 6.88 (d, J=8.8 Hz, 2H), 3.97 (s, 3H), 3.77 (m, 2H), 3.03 (s, 3H), 2.75 (m, 2H), 2.32 (s, 3H), 2.31 (s, 3H). MS: (ESI positive ion mode) m/e (M)$^+$ 536.06. UV: Absorbances at 254 nm. HPLC: Agilent Pursuit 3 C18, 50×2.5 mm, 300 Å, (5% acetonitrile in 0.1% aqueous formic acid) to (95% acetonitrile in 0.1% formic acid) over 10 min at 0.5 mL/min. Positive Ion ESI, detection at 254 nm. Retention time: 4.90 min; 99.2%.

Example 13AA: Synthesis of (E)-4-(4-bromophenyl)-2-(4-(diethylamino)styryl)-6-(3,4-dimethylphenyl)-1-methylpyridin-1-ium iodide (9v)

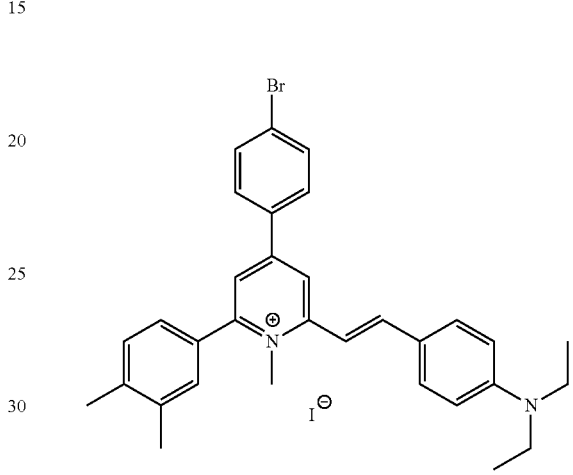

1H NMR (400 MHz, DMSO-d$_6$): δ 8.64 (d, J=2.0 Hz, 1H), 8.10 (m, 3H), 7.94 (d, J=2.0 Hz, 1H), 7.80 (d, J=8.8 Hz, 2H), 7.69 (d, J=9.2 Hz, 2H), 7.48 (s, 1H), 7.41 (m, 2H), 7.23 (d, J=16.0 Hz, 1H), 6.75 (d, J=9.6 Hz, 2H), 3.95 (s, 3H), 3.40 (m, 4H), 2.31 (d, J=4.0 Hz, 6H), 1.11 (m, 6H). MS: (ESI positive ion mode) m/e (M)$^+$ 284.65, 527.12. UV: Absorbances at 254 nm. HPLC: Agilent Pursuit 3 C18, 50×2.5 mm, 300 Å, (5% acetonitrile in 0.1% aqueous formic acid) to (95% acetonitrile in 0.1% formic acid) over 10 min at 0.5 mL/min. Positive Ion ESI, detection at 254 nm. Retention time: 5.19 min; 97.2%.

Example 13BB: Synthesis of (E)-4-(4-bromophenyl)-2-(4-(dimethylamino)styryl)-6-(3,4-dimethylphenyl)-1-methylpyridin-1-ium iodide (9w)

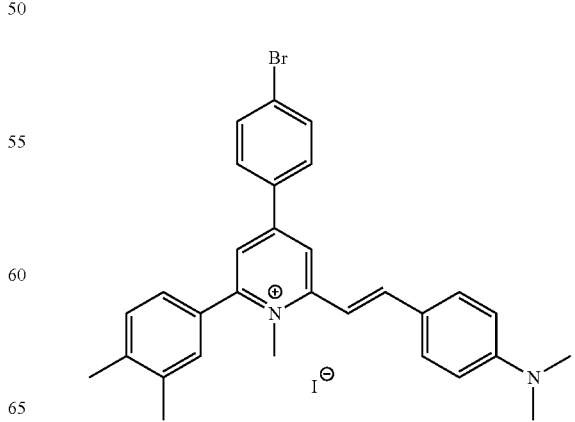

1H NMR (400 MHz, DMSO-d$_6$): δ 8.64 (d, J=2.4 Hz, 1H), 8.11 (m, 3H), 7.96 (d, J=2.0 Hz, 1H), 7.80 (d, J=8.8 Hz, 2H), 7.72 (d, J=8.8 Hz, 2H), 7.48 (s, 1H), 7.40 (m, 2H), 7.28 (d, J=15.6 Hz, 1H), 6.78 (d, J=9.6 Hz, 2H), 3.97 (s, 3H), 3.01 (s, 6H), 2.32 (d, J=4.0 Hz, 6H). MS: (ESI positive ion mode) m/e (M)$^+$ 499.03 UV: Absorbances at 254 nm. HPLC: Agilent Pursuit 3 C18, 50×2.5 mm, 300 Å, (5% acetonitrile in 0.1% aqueous formic acid) to (95% acetonitrile in 0.1% formic acid) over 10 min at 0.5 mL/min. Positive Ion ESI, detection at 254 nm. Retention time: 5.03 min; 96.7%.

Example 13CC: Synthesis of (E)-4-(4-bromophenyl)-2-(3,4-dimethylphenyl)-6-(4-((2-hydroxyethyl)(methyl)-amino)styryl)-1-methylpyridin-1-ium iodide (9x)

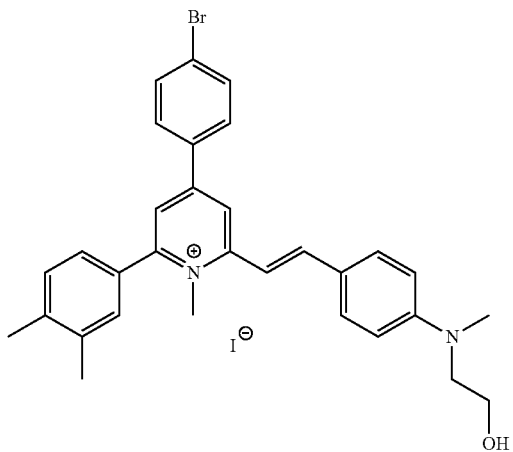 [SMILES: Cc1ccc(-c2cc(-c3ccc(Br)cc3)cc(/C=C/c3ccc(N(C)CCO)cc3)[n+]2C)cc1C ; [I-]]

1H NMR (400 MHz, DMSO-d$_6$): δ 8.63 (s 1H), 8.10 (m, 3H), 7.95 (s 1H), 7.80 (d, J=8.0 Hz, 2H), 7.69 (d, J=8.4 Hz, 2H), 7.44 (m, 3H), 7.25 (d, J=15.6 Hz, 1H), 6.79 (d, J=8.8 Hz, 2H), 4.75 (m, 1H), 3.96 (s, 3H), 3.52 (m, 4H), 3.02 (s, 3H), 2.22 (d, J=2.8 Hz, 6H). MS: (ESI positive ion mode) m/e (M)$^+$ 527.12. UV: Absorbances at 254 nm. HPLC: Agilent Pursuit 3 C18, 50×2.5 mm, 300 Å, (5% acetonitrile in 0.1% aqueous formic acid) to (95% acetonitrile in 0.1% formic acid) over 10 min at 0.5 mL/min. Positive Ion ESI, detection at 254 nm. Retention time: 4.74 min; 95.9%.

Example 13DD: Synthesis of (E)-4-(4-bromo-3,5-dimethoxyphenyl)-2-(4-bromophenyl)-6-(4-(dimethyl-amino)styryl)-1-methylpyridin-1-ium iodide (9y1)

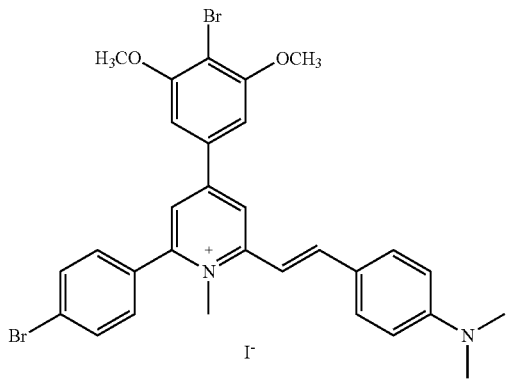

1H NMR (400 MHz, DMSO-d$_6$): δ 8.69 (d, J=2.2 Hz, 1H), 8.13 (d, J=2.2 Hz, 1H), 8.04 (d, J=15.6 Hz, 1H), 7.93-7.84 (m, 1H), 7.74 (d, J=8.8 Hz, 2H), 7.70-7.63 (m, 2H), 7.35 (s, 2H), 7.31 (d, J=15.7 Hz, 1H), 6.82-6.75 (m, 2H), 3.97 (s, 6H), 3.94 (s, 3H), 3.01 (s, 6H). MS: (ESI positive ion mode) m/z 608.8 (M)$^+$. HPLC: Varian C18 4μ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time min; 96%.

Example 13EE: Synthesis of (E)-4-(4-bromo-3,5-dimethoxyphenyl)-2-(4-bromophenyl)-6-(4-(diethyl-amino)-styryl)-1-methylpyridin-1-ium iodide (9y2)

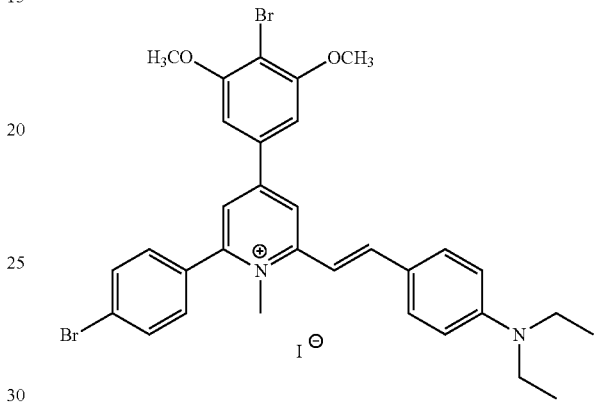

1H NMR (400 MHz, DMSO-d$_6$): δ 8.67 (d, J=2.1 Hz, 1H), 8.10 (d, J=2.1 Hz, 1H), 8.03 (d, J=15.5 Hz, 1H), 7.92-7.84 (m, 2H), 7.70 (d, J=8.7 Hz, 2H), 7.69-7.64 (m, 2H), 7.34 (s, 2H), 7.25 (d, J=15.6 Hz, 1H), 6.74 (d, J=8.9 Hz, 2H), 3.97 (s, 6H), 3.93 (s, 3H), 3.47-3.39 (m, 4H), 1.10 (t, J=7.0 Hz, 6H). MS: (ESI positive ion mode) m/z (M)$^+$ 636.9, 638.9. HPLC: Varian C18 4μ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time: 4.94 min; 95%.

Example 13FF: Synthesis of (E)-4-(4-bromo-3,5-dimethoxyphenyl)-2-(4-bromophenyl)-6-(4-((2-hydroxy-ethyl)(methyl)amino)styryl)-1-methylpyridin-1-ium iodide (9y3)

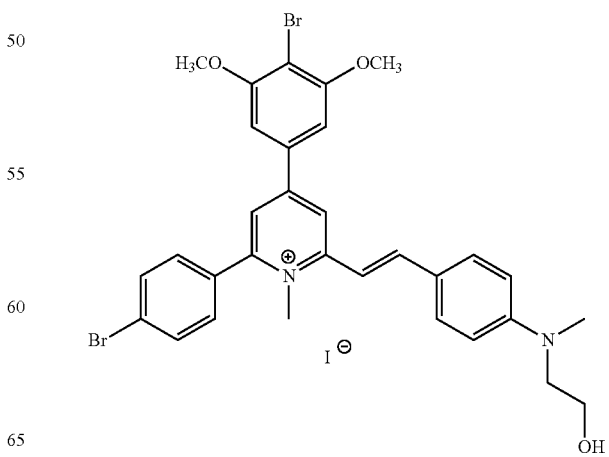

1H NMR (400 MHz, DMSO-d$_6$): δ 8.68 (d, J=2.2 Hz, 1H), 8.11 (d, J=2.1 Hz, 1H), 8.04 (d, J=15.6 Hz, 1H), 7.91-7.85 (m, 2H), 7.71 (d, J=8.7 Hz, 2H), 7.69-7.64 (m, 2H), 7.34 (s, 2H), 7.28 (d, J=15.6 Hz, 1H), 6.78 (d, J=8.8 Hz, 2H), 4.75 (t, J=5.3 Hz, 1H), 3.97 (s, 6H), 3.94 (s, 1H), 3.60-3.53 (m, 2H), 3.51-3.46 (m, 2H), 3.02 (s, 3H). MS: (ESI positive ion mode) m/z 638.9 (M)$^+$. HPLC: Varian C18 4μ 50×2 mm; flow 0.5 mL/min; Finnigan/Surveyor PDA plus detector (200-600 nm); solvent 5-95% Acetonitrile (0.1% TFA) in H$_2$O (0.1% TFA) over 10 min; retention time 4.55 min; 95.6%.

Example 13GG: Synthesis of (E)-4-(4-bromo-3,5-dimethoxyphenyl)-2-(4-bromophenyl)-6-(4-((2-cyano-ethyl)(methyl)amino)styryl)-1-methylpyridin-1-ium iodide (9y4)

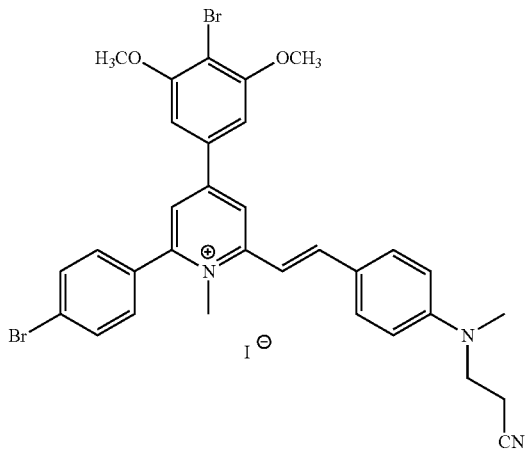 [SMILES: COc1cc(-c2cc(/C=C/c3ccc(N(C)CCC#N)cc3)[n+](C)c(-c3ccc(Br)cc3)c2)cc(OC)c1Br ; [I-]]

1H NMR (400 MHz, DMSO-d$_6$): δ 8.69 (d, J=2.1 Hz, 1H), 8.15 (d, J=2.1 Hz, 1H), 8.03 (d, J=15.7 Hz, 1H), 7.92-7.86 (m, 2H), 7.75 (d, J=8.8 Hz, 2H), 7.71-7.63 (m, 2H), 7.40-7.30 (m, 3H), 6.87 (d, J=8.9 Hz, 2H), 3.97 (s, 6H), 3.95 (s, 3H), 3.77 (t, J=6.6 Hz, 2H), 3.03 (s, 3H), 2.75 (t, J=6.6 Hz, 2H). MS: (ESI positive ion mode) m/z 647.9 (M)$^+$. HPLC: Varian C18 4μ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 4.5 min; 98.5%.

Example 13HH: Synthesis of (E)-4-(4-bromo-2-chlorophenyl)-2-(4-bromophenyl)-6-(4-(dimethylamino)-styryl)-1-methylpyridin-1-ium iodide (9z1)

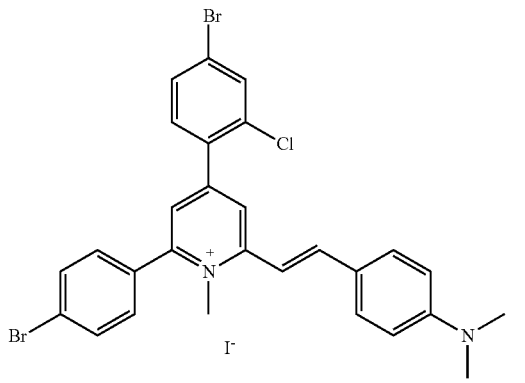

1H NMR (400 MHz, DMSO-d$_6$): δ 8.57 (d, J=2 Hz, 1H), 8.00 (q, J=6 and 8 Hz, 2H), 7.85 (d, J=8.8 Hz, 2H), 7.78 (m, 2H), 7.63 (m, 5H), 7.29 (d, J=16 Hz, 1H), 6.76 (d, J=9.2 Hz, 2H), 3.98 (s, 3H), 3.01 (s, 6H). MS: (ESI positive ion mode) m/e (M)$^+$ 580.80, 582.81, 584.80, 586.67. HPLC: Varian C18 4μ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 5.02 min; 96%.

Example 13II: Synthesis of (E)-4-(4-bromo-2-chlorophenyl)-2-(4-bromophenyl)-6-(4-(diethylamino)-styryl)-1-methylpyridin-1-ium iodide (9z2)

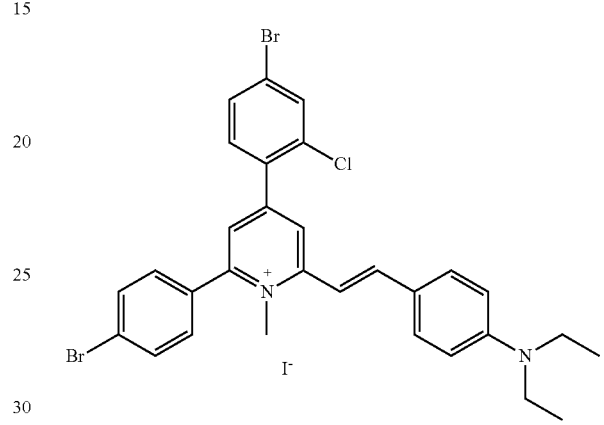

1H NMR (400 MHz, DMSO-d$_6$): δ 8.55 (d, J=2 Hz, 1H), 7.99 (m, 2H), 7.84 (d, J=8.8 Hz, 2H), 7.75 (m, 2H), 7.63 (m, 5H), 7.24 (d, J=15.6 Hz, 1H), 6.72 (d, J=9.2 Hz, 2H), 3.97 (s, 3H), 3.39 (q, J=6.8 and 14 Hz, 4H), 1.08 (t, J=6.8 Hz, 6H). MS: (ESI positive ion mode) m/e (M)$^+$ 608.86, 610.80, 612.88. HPLC: Varian C18 4μ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 5.10 min; 97.6%.

Example 13JJ: Synthesis of (E)-4-(4-bromo-2-chlorophenyl)-2-(4-bromophenyl)-6-(4-((2-hydroxyethyl)-(methyl)amino)styryl)-1-methylpyridin-1-ium iodide (9z3)

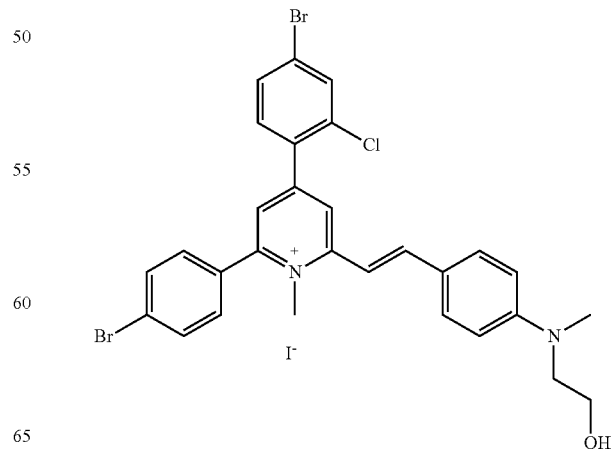

1H NMR (400 MHz, DMSO-d$_6$): δ 8.56 (d, J=2 Hz, 1H), 7.99 (m, 2H), 7.84 (d, J=8.8 Hz, 2H), 7.77 (m, 2H), 7.61 (m, 5H), 7.26 (d, J=15.6 Hz, 1H), 6.76 (d, J=8.8 Hz, 2H), 4.72 (t, J=5.6 Hz, OH), 3.97 (s, 3H), 3.47 (m, 4H), 3.02 (s, 3H). MS: (ESI positive ion mode) m/e (M)$^+$ 610.78, 612.88, 614.83, 615.78. HPLC: Varian C18 4μ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 4.72 min; 95%.

Example 13KK: Synthesis of (E)-4-(4-bromo-2-chlorophenyl)-2-(4-bromophenyl)-6-(4-((2-cyano-ethyl)-(methyl)amino)styryl)-1-methylpyridin-1-ium iodide (9z4)

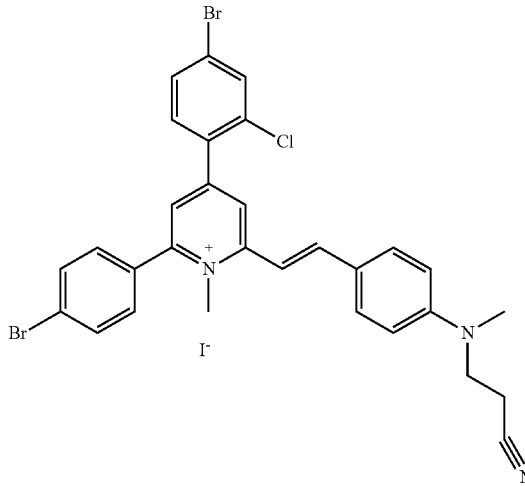

1H NMR (400 MHz, DMSO-d$_6$): δ 8.57 (d, J=2 Hz, 1H), 7.99 (m, 2H), 7.63-7.87 (m, 9H), 7.33 (d, J=16 Hz, 1H), 6.85 (d, J=9.2 Hz, 2H), 3.99 (s, 3H), 3.75 (t, J=6.8 Hz, 2H), 3.03 (s, 3H), 2.73 (t, J=6.4 Hz, 2H). MS: (ESI positive ion mode) m/e (M)$^+$ 619.88, 621.84, 623.83. HPLC: Varian C18 4μ 50×2 mm; flow 0.5 ml/min; Finnigan/Surveyor PDA plus detector (200-600 nm); solvent 5-95% acetonitrile (0.1% TFA) in H$_2$O (0.1% TFA) over 10 min; retention time 4.82 min; 94.5%.

Example 13LL: Synthesis of (E)-4-(4-bromophenyl)-2-(4-(dimethylamino)styryl)-1-ethyl-6-(p-tolyl)pyridin-1-ium iodide (9e1)

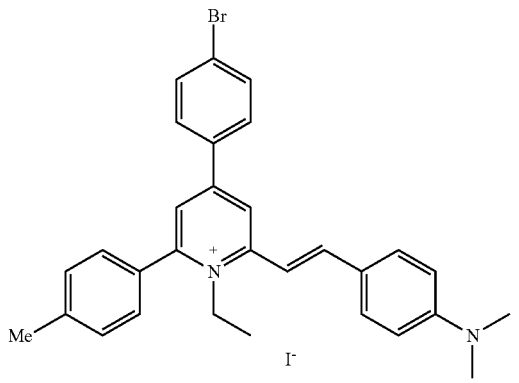

1H NMR (400 MHz, DMSO-d$_6$): δ 8.68 (d, J=2.0 Hz, 1H), 8.12 (m, 3H), 7.95 (d, J=2.0 Hz, 1H), 7.80 (d, J=8.4 Hz, 2H), 7.74 (d, J=8.8 Hz, 2H), 7.55 (d, J=7.6 Hz, 2H), 7.43 (d, J=8.0 Hz, 2H), 7.31 (d, J=15.6 Hz, 1H), 6.78 (d, J=9.2 Hz, 2H), 4.48 (q, J=6.8 Hz, 2H), 3.01 (s, 6H), 2.41 (s, 3H), 1.25 (t, J=7.2 Hz, 3H). MS: (ESI positive ion mode) m/e (M)$^+$ 497.10, 499.10. HPLC: Varian C18 4μ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 4.91 min; 97.3%.

Example 13MM: Synthesis of ((E)-4-(4-bromophenyl)-1-ethyl-2-(4-((2-hydroxyethyl)(methyl)amino)styryl)-6-(p-tolyl)pyridin-1-ium iodide (9e2)

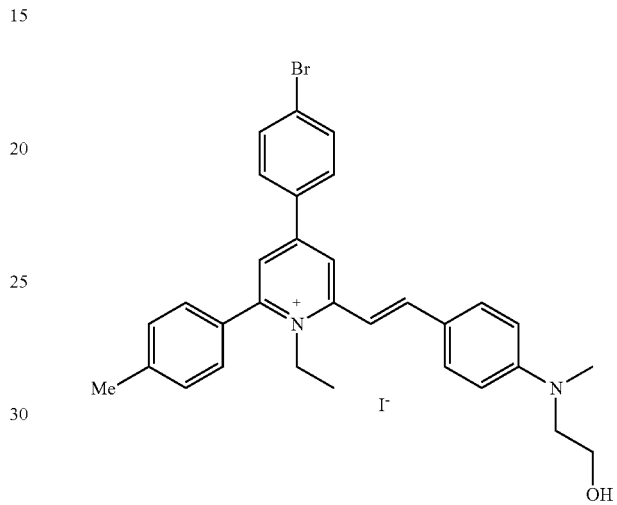

1H NMR (400 MHz, DMSO-d$_6$): δ 8.68 (s, 1H), 8.12 (m, 3H), 7.94 (s, 1H), 7.79 (d, J=8.0 Hz, 2H), 7.72 (d, J=8.4 Hz, 2H), 7.55 (d, J=7.6 Hz, 2H), 7.43 (d, J=7.6 Hz, 2H), 7.28 (d, J=15.6 Hz, 1H), 6.78 (d, J=8.8 Hz, 2H), 4.73 (m, 1H), 4.47 (q, J=6.8 Hz, 2H), 3.51 (m, 4H), 3.01 (s, 3H), 2.41 (s, 3H), 1.25 (t, J=7.0 Hz, 3H). MS: (ESI positive ion mode) m/e (M)$^+$ 527.05, 529.14. HPLC: Varian C18 4μ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 4.62 min; 96.3%.

Example 13NN: Synthesis of (E)-4-(4-bromophenyl)-2-(4-(dimethylamino)styryl)-1-propyl-6-(p-tolyl)-pyridin-1-ium iodide (9e3)

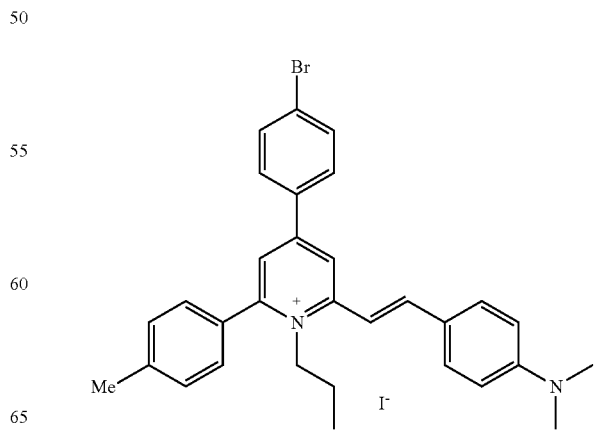

1H NMR (400 MHz, DMSO-d$_6$): δ 8.68 (s, 1H), 8.14 (m, 3H), 7.96 (s, 1H), 7.79 (d, J=8.0 Hz, 2H), 7.75 (d, J=8.4 Hz, 2H), 7.55 (d, J=7.6 Hz, 2H), 7.45 (d, J=7.6 Hz, 2H), 7.31 (d, J=14.8 Hz, 1H), 6.79 (d, J=8.8 Hz, 2H), 4.42 (m, 2H), 3.01 (s, 6H), 1.68 (m, 2H), 1.55 (s, 3H), 0.66 (m, 3H). MS: (ESI positive ion mode) m/e (M)$^+$ 511.05, 513.06. HPLC: Varian C18 4μ 50×2 mm; flow 0.5 mL/min; Finnigan/Surveyor PDA plus detector (200-600 nm); solvent 5-95% acetonitrile (0.1% TFA) in H$_2$O (0.1% TFA) over 10 min; retention time 5.02 min; 95.3%.

Example 13OO: Synthesis of (E)-1-bromo-4-(2-nitroprop-1-en-1-yl)benzene (10)

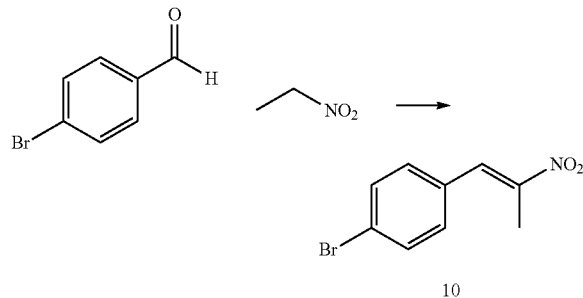

4-Bromobenzaldehyde (1.85 g, 10 mmol) and nitroethane (2 eq. 1.44 ml) was dissolved in 5 ml of MeOH and cooled to 0° C. To the reaction was added NaOH (1.5 eq. 0.6 g in 1 mL of H$_2$O) dropwise. The mixture was stirred overnight. The mixture was poured into ice-water and was acidified with 3N HCl to pH<4. The white precipitated was extracted into EtOAc (2×). The organic layer was washed with brine, dried over Na$_2$SO$_4$ and filtered. The concentrated residue was then dissolved in 10 mL of DCM and 5 mL of Et$_3$N (4 eq.) and cooled at 0° C. To it, MsCl (1.1 eq. 0.85 mL) was added dropwise. The mixture was stirred at 0° C. for 1 hour. It was quenched with water, diluted with DCM. The organic layer was washed with brine, dried and concentrated. The yellow solid crude product (2.5 g) was recrystallized from DCM/hexane to give 1.30 g pure product (10). 1H NMR (400 MHz, CDCl$_3$): δ 7.99 (s, 1H), 7.57 (d, J=8.8 Hz, 2H), 7.28 (d, J=8.4 Hz, 2H), 2.41 (s, 3H).

Example 13PP: Synthesis of 2,5-bis(4-bromophenyl)-4-methyl-1H-imidazole (12)

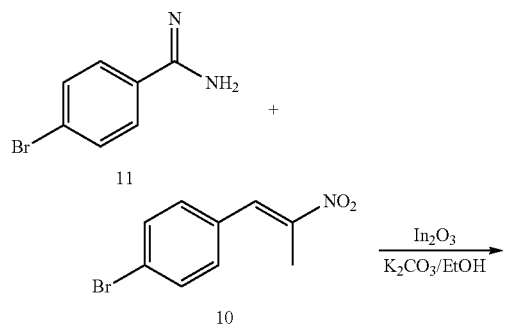

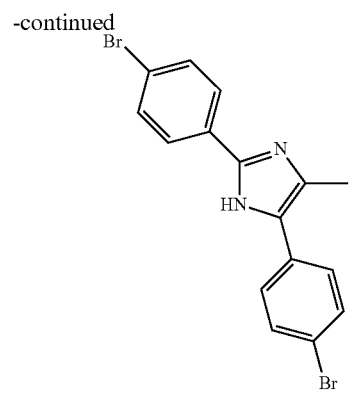

A mixture of 4-bromobenezamidine hydrochloride salt (11, 235.6 mg, 1 mmol), (E)-1-bromo-4-(2-nitroprop-1-en-1-yl)benzene (10, 242 mg, 1 mmol), In$_2$O$_3$ (nano-sized, 83 mg, 0.3 mmol), Na$_2$CO$_3$ (106 mg, 1 mmol) in 10 mL of EtOH was heated at 84° C. in a close-capped vial overnight. It was cooled and the mixture was partitioned between water and EtOAc. The organic layer was washed with brine and dried. The concentrated residue was purified on a Biotage column with 5-35% EtOAc in hexane to give 0.182 g of a mixture of product (12) and other minor impurities, which was used without further purification. LCMS: M+1, 392.74.

Example 13QQ: Synthesis of 2,5-bis(4-bromophenyl)-1,3,4-trimethyl-1H-imidazol-3-ium iodide (13)

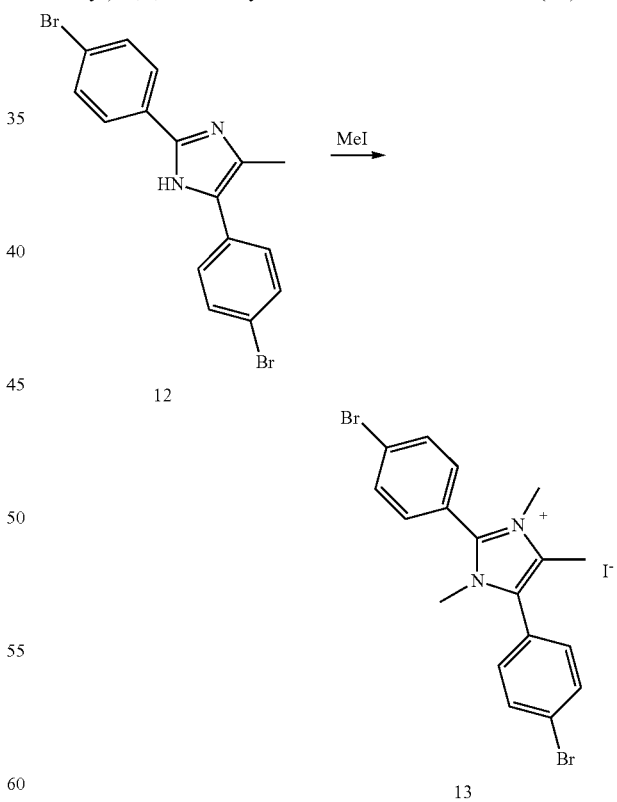

A mixture of 2,5-bis(4-bromophenyl)-4-methyl-1H-imidazole (12) (0.182 g, 0.46 mmol), methyl iodide (1.4 mL, 50 eq.), K$_2$CO$_3$ (0.19 g, 3 eq.) in 2 mL of MeCN was heated at 80° C. in a close-capped vial for 24 hours. It was then cooled and diluted with MeOH. The K$_2$CO$_3$ was removed by filtration. The filtrate was concentrated and re-dissolved in 2 mL of MeCN. It was diluted with Et$_2$O and sonicated. The solid was filtered, washed with Et$_2$O and dried. The desired product (13, 0.19 g) was obtained in 76% yield. 1H NMR (400 MHz, DMSO-d$_6$): δ 7.95 (d, J=8.0 Hz, 2H), 7.82 (d, J=8.4 Hz, 2H), 7.70 (d, J=8.0 Hz, 2H), 7.48 (d, J=8.4 Hz, 2H), 3.61 (s, 3H), 3.43 (s, 3H), 2.30 (s, 3H). LCMS: M$^+$ 418.89, 420.91, 422.89.

Example 14: Lipid II Binding Data and Pharmacokinetic Parameters

See FIG. 16 for Lipid II binding data for selected compounds. Several compounds, EL-1, EL-5, EL-8, EL-10, and EL-11 (structures shown in FIG. 17), were selected for further testing based on below micromolar affinity and low MICs against both *S. aureus* and Enterococci spp.

To examine the functional consequences of these modifications in vivo, compounds 1, 5, 8, and 11 were tested to develop a pharmacokinetic profile (PK) profile which can be compared to that of 6jc48-1, based on their structural and functional variation. To determine the PK parameters, compounds were administered as a single dose of 10 mg/kg by intravenous injection and the plasma concentration at various times after dosing was determined by LC/MS/MS. Compound 6jc48-1 was very stable in vivo with a half-life of 13.3 hours and could be readily detected after 24 hours. Compound EL-1 showed a half-life of greater than 8 hours, whereas Compound 5 showed a markedly increased half-life of greater than 23 hours. Compounds EL-8 and EL-11 had half-lives of >8 hours and >11 hours, respectively. Importantly, at this dose, the maximum concentration of Compounds 1 and 5 was more than 10 times the MIC for *S. aureus* and *E. faecalis*. Surprisingly, Compound 11 appeared toxic in vivo, with all animals showing clinical signs of toxicity and one out of four animals died. These results indicate that modifications at position R16 and R16' affect both the MIC and pK parameters in vivo. Further, modifications at position R17 and R17' affect in vivo toxicity which may not directly correlate to cellular cytotoxicity in vitro. See FIG. 17 for structures.

Table 14, below, presents pharmacokinetic data for the indicated compounds.

TABLE 14

Pharmacokinetic Parameters for Selected Compounds.

| | BAS-00127538 | 6jc48-1 | EL-1 | EL-5 | El-8 | EL-10 | EL-11 |
|---|---|---|---|---|---|---|---|
| T$_{1/2}$ (h) | 0.227 | 13.3 ± 1.8 | 8.33 ± 0.84 | 23.8 ± 0.84 | 9.4 ± 1.01 | 5.94 ± 0.52 | 11 ± 2.37 |
| C$_{max}$ (ng/mL) | 101 | 1039 ± 323 | 5520 ± 850 | 12133.4 ± 850 | 3729 ± 728 | 2842 ± 705 | 3975 ± 739 |
| AUC$_{last}$/D (h*mg/mL) | 26.9 | 1340 ± 117 | 1451 ± 278 | 3001 ± 585 | 729 ± 179 | 685.9 ± 80 | 1853 ± 372 |
| AUC$_{Inf}$ (h*ng/mL) | 27.9 | 1769 ± 120 | 1528 ± 286 | 4125 ± 780 | 764 ± 187 | 695 ± 79.4 | 2137 ± 455 |
| AUC$_{extrap}$ (%) | 4.38 | 24.3 ± 3.1 | 5.15 ± 1.28 | 27.2 ± 1.6 | 4.63 ± 0.51 | 1.31 ± 0.5 | 12.9 ± 5.6 |
| AUC$_{last}$/D (h*ng/mL) | 26.9 | 536 ± 47 | 145 ± 28 | 300 ± 58 | 72.9 ± 17.9 | 68.6 ± 8 | 185.3 ± 37.3 |
| Vss$_{\_obs}$ (L/kg) | 12.2 | 22.8 ± 2.9 | 29.8 ± 8.8 | 46.7 ± 9.7 | 48 ± 13.1 | 28.11 ± 9.8 | 46.3 ± 23.3 |
| Cl$_{\_obs}$ (mL/min/kg) | 711 | 23.6 ± 1.7 | 111 ± 20 | 41.29 ± 7 | 3.53 0.47 | 1.9 0.46 | 80.3 ± 16.6 |
| MRT (h) | 0.226 | 7.29 ± 0.27 | 4.42 ± 0.72 | 18.8 ± 1.62 | 1.74 ± 0.49 | 174 ± 0.49 | 9.13 ± 3.17 |

T$_{1/2}$: half-life; Cmax: Maximum observed concentration; AUC: area under the curve; D; Dose; Vss; volume of distribution; Cl: clearance; MRT: mean residence time.

Example 15: In Vivo Pharmacokinetic Parameters for 6jc48-1 and Derivatives

Figure 18A:
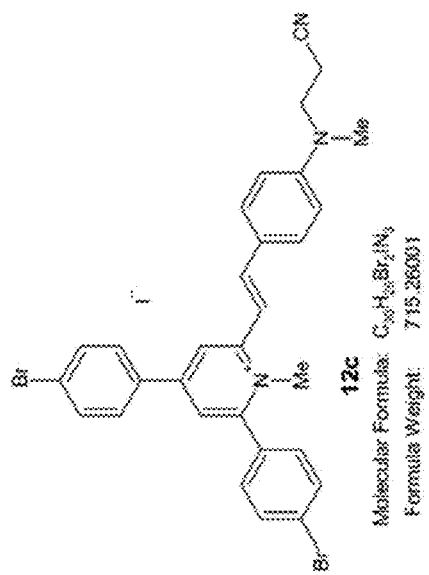
FIG. 18 is a set of chemical structures for Compound 7jc47-1 (FIG. 18A), Compound EL-1 (FIG. 18B), and Compound 12c (FIG. 18C).
Figure 18B:
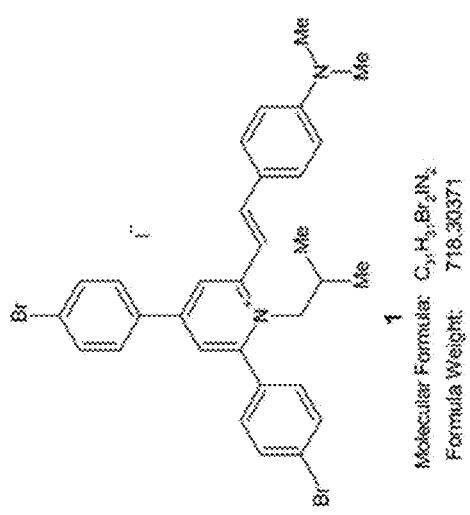
Figure 18C:
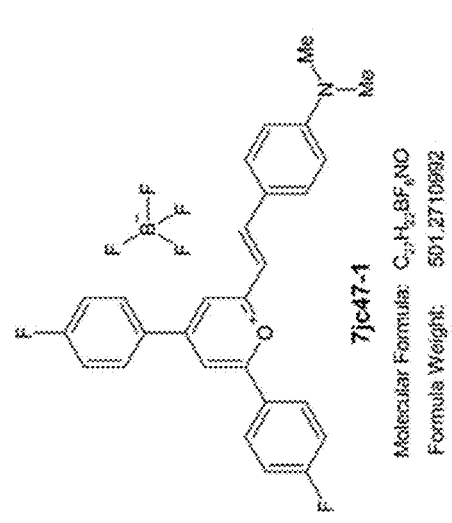

The pharmacokinetic profile (PK) profiles of compounds 7jc47-1, 1 and 12c were determined, based on structural and functional variation and their CC$_5$O to MIC ratio against *S. aureus*. To determine the PK parameters, compounds were administered as a single dose of 10 mg/kg by intravenous injection in CD1 mice (n=3) and the plasma concentration was determined at various times after dosing by LC/MS/MS. See FIG. 18, which provides the chemical formulas. Compound 6jc48-1 was very stable in vivo with a half-life of 13.3 hours and could be readily detected after 24 hours. See Table 15, below. Compound 7c47-1 had a half-life of about 7 hours with 3-fold increase of C$_{max}$ compared to compound 6jc48-1. Compound EL-1 had a half-life of more than 8 hours with a further increase in C$_{max}$, whereas Compound 12c showed a markedly increased half-life of more than 11 hours.

TABLE 15

In Vivo Pharmacokinetic parameters for 6jc48-1 and Derivatives.

|  | 6jc48-1 | 7jc47-1 | EL-1 | 12c |
|---|---|---|---|---|
| $T_{1/2}$ (h) | 13.3 ± 1.8 | 6.81 ± 1.33 | 8.33 ± 0.84 | 11 ± 2.37 |
| $C_{max}$ (ng/mL) | 1039 ± 323 | 3219 ± 1498 | 5520 ± 850 | 3975 ± 739 |
| $AUC_{last}/D$ (h*mg/mL) | 1340 ± 117 | 565 ± 169 | 1451 ± 278 | 1853 ± 372 |
| $AUC_{Inf}$ (h*ng/mL) | 1769 ± 120 | 578 ± 175 | 1528 ± 286 | 2137 ± 455 |
| $AUC_{extrap}$ (%) | 24.3 ± 3.1 | 2.25 ± 1.13 | 5.15 ± 1.28 | 12.9 ± 5.6 |
| $AUC_{last}/D$ (h*ng/mL) | 536 ± 47 | 56.5 ± 16.9 | 145 ± 28 | 185.3 ± 37.3 |
| $Vss_{obs}$ (L/kg) | 22.8 ± 2.9 | 46.3 ± 12.9 | 29.8 ± 8.8 | 46.3 ± 23.3 |
| $Cl_3$ (mL/min/kg) | 23.6 ± 1.7 | 23.6 ± 1.7 | 111 ± 20 | 80.3 ± 16.6 |
| MRT (h) | 7.29 ± 0.27 | 1.74 ± 0.49 | 4.42 ± 0.72 | 9.13 ± 3.17 |

The Maximum Tolerated Dose (MTD) was determined by dose-escalation for Compounds 7jc47-1, 1, and 12c with the goal of examining their antibacterial activity in vivo. The final MTD determined for Compound EL-1 was 25 mg/kg, for Compound 12c 40 mg/kg and for Compound 7jc47-1 the MTD was 60 mg/kg. Next, for all compounds, in vivo toxicity was tested at the MTD upon single(QD), 2QD (2×12 h), TID (3×8 h) and QID (4×6 h) administration IV. In all cases, no clinical observation or mortality was recorded and no significant abnormalities were observed during gross necropsy at termination in all groups.

Example 16: Antibacterial Activity of Selected Compounds

The compounds in Table 16 were examined for their antibacterial activity, in vitro cytotoxicity and Lipid II binding (see results in FIG. 19A and FIG. 19B). $CC_{50}$ was determined after exposure of compounds to HeLa cells for 72 hours. Values given are in μg/ml. Lipid II binding was determined by SPR as described. Compounds were ranked by CC50/MIC ratio. MIC data are an average of two replicates.

Combined, these data show that (1) alterations at position $R^6$ and $R^{6'}$ in this scaffold are a predominant driver for potent MIC against S. aureus, Enterococci and A. baumannii; (2) modification of positions $R^7$ and $R^{7'}$ predominantly reduce cytotoxicity (in agreement with our earlier findings that replacement of the indolene moiety of parent BAS00127538 resulting in 6jc-48-1 negated cytotoxicity); and (3) modifications at positions $R^1$, $R^2$, $R^3$, $R^4$, and $R^5$ primarily negate cytotoxicity of the scaffold.

Example 17: In Vivo Efficacy of Compounds EL-1, 12c, and 7jc47-1

Figure 20A:
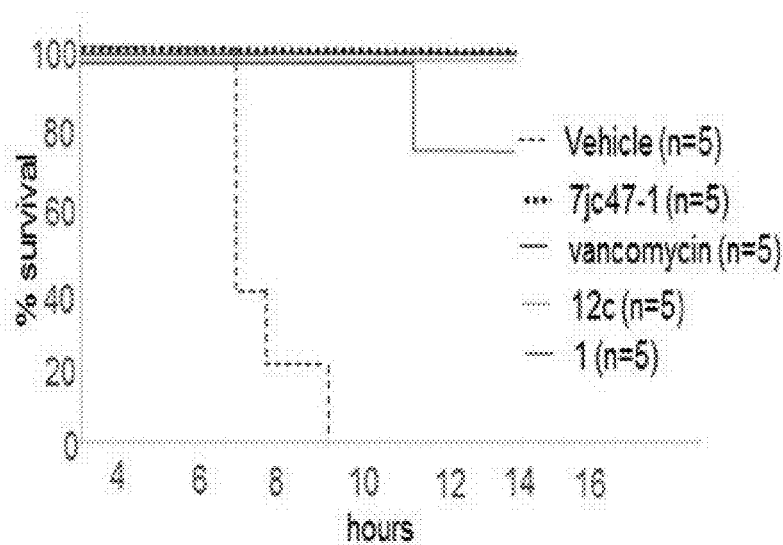
FIG. 20A is a graph showing percent survival of mice treated with the indicated compounds.
Figure 20B:
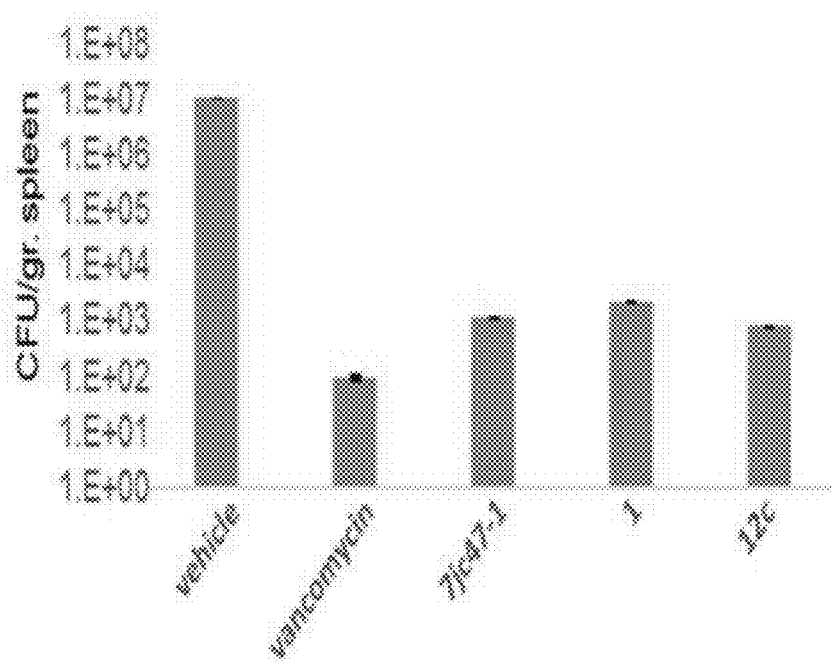
FIG. 20B is a bar graph showing the colony forming units of bacteria in the spleens of treated mice.

Next, the in vivo efficacy of compounds 1, 12c and 7jc47-1 (see FIG. 18) was tested in a MRSA peritonitis model. Animals were monitored for survival and compared to treatment with vehicle or vancomycin as measures of efficacy. Mice (C57/Blk; n=5) were inoculated intraperitoneally with S. aureus USA300 ($10^6$ CFU/mL in 500 μL saline solution with 4.5% hog gastric mucin), and were treated at 2 hours and 8 hours post-infection with the compounds at the MTD. Animals were monitored for survival and spleen was collected. Bacterial counts were determined and compared to control treatment with vancomycin (50 mg/kg) as measures of efficacy. See results in FIG. 20.

None of the animals treated with vehicle alone survived for more than 10 hours. In contrast, all animals treated with vancomycin, Compound 7jc47-1, or Compound 12c survived the length of the experiment. Treatment with compound EL-1 resulted in 80% survival. Treatment with all compounds significantly reduced the bacterial burden in spleen, comparable to vancomycin controls, indicative of in vivo antibiotic efficacy.

A group of chemically diverse small molecule compounds that bind Lipid II have been identified and characterized. 6jc48-1, its analogues, and the other small molecule Lipid II inhibitors potently act against clinically relevant pathogens. Preliminary SAR on the lead scaffold resulted in small molecule Lipid II binders with potent activity against S. aureus, Enterococci and A. baumannii, with significantly improved antibacterial parameters compared to the parent scaffold. Importantly, the optimized Lipid II binders are effective in vivo as antibacterials and can be dosed multiple times without in vivo toxicity. This indicates that small molecule Lipid II binders can be further optimized to create a novel class of antibacterial therapeutics with a spectrum of activity unique to any other compound that interferes with Lipid II.

Example 18: Compound Testing for Minimum Inhibitory Concentration (MIC)

Compounds were tested for MIC by methods known in the art and described in CLSI, *Methods for Dilution Antimicrobial Susceptibility Tests for Bacteria That Grow Aerobically; Approved Standard—Tenth Edition*. CLSI document M07-A10. Wayne, Pa.: Clinical and Laboratory Standards Institute, 2015, which is hereby incorporated by reference for these methods. The results are shown in Table 16, below.

TABLE 16

Minimum Inhibitory Concentration (MIC) of Select Compounds.

| Compound Code | Structural Formula and Compound Name | MIC S. aureus (μg/mL) | MIC E. faecium (μg/mL) | MIC A. baumannii (μg/mL) |
|---|---|---|---|---|
| 9 | 16714-LG-67 | 1 | 8 | 8 |
| 9a | 16714-LG-71 | 0.5 | 4 | 4 |
| 9c | 16714-LG-78 | 0.5 | 4 | 16 |

TABLE 16-continued

Minimum Inhibitory Concentration (MIC) of Select Compounds.

| Compound Code | Structural Formula and Compound Name | MIC S. aureus (μg/mL) | MIC E. faecium (μg/mL) | MIC A. baumannii (μg/mL) |
|---|---|---|---|---|
| 9b | 16714-LG-85 | 1 | 2 | 16 |
| 9d | 16714-LG-87 | 1 | 4 | >64 |
| 9g | 16751-LG-2 | 16 | 8 | 32 |

TABLE 16-continued
Minimum Inhibitory Concentration (MIC) of Select Compounds.
| Compound Code | Structural Formula and Compound Name | MIC S. aureus (µg/mL) | MIC E. faecium (µg/mL) | MIC A. baumannii (µg/mL) |
|---|---|---|---|---|
| 9l | 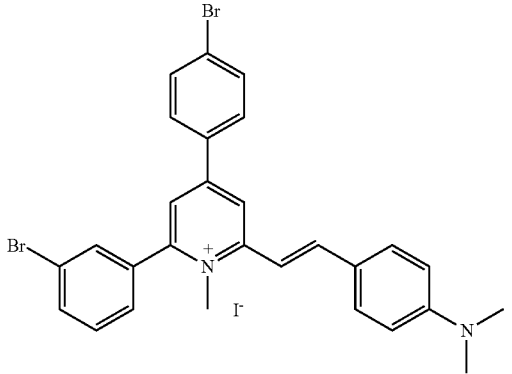<br>16751-LG-5a | 8 | 4 | 16 |
| 9m | 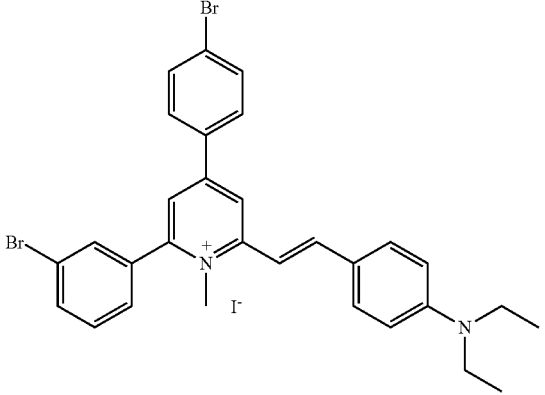<br>16751-LG-5b | 8 | 4 | 8 |
| 9n | 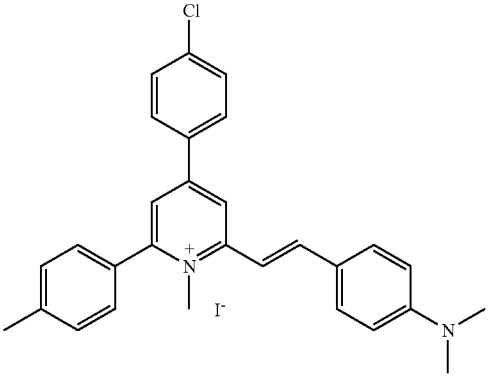<br>16751-LG-9a | 4 | 2 | 4 |

TABLE 16-continued
Minimum Inhibitory Concentration (MIC) of Select Compounds.
| Compound Code | Structural Formula and Compound Name | MIC S. aureus (µg/mL) | MIC E. faecium (µg/mL) | MIC A. baumannii (µg/mL) |
|---|---|---|---|---|
| 9o | 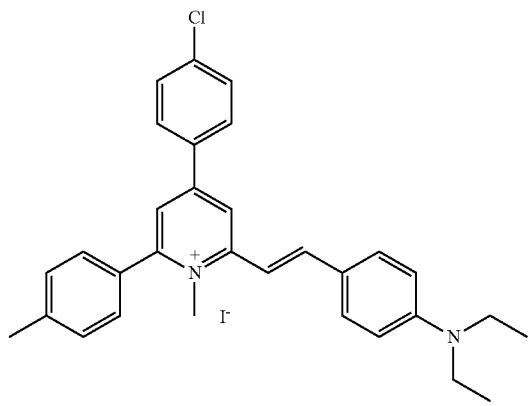<br>16751-LG-9b | 32 | 16 | 16 |
| 9h | 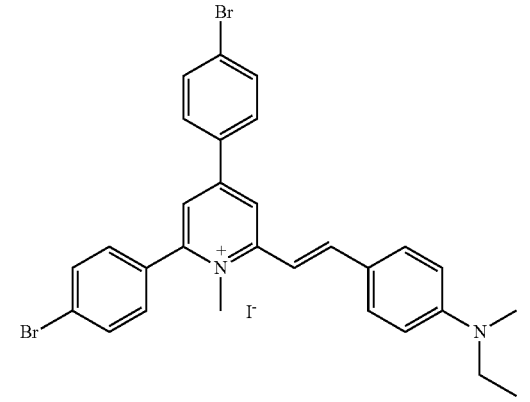<br>16751-LG-12a | 16 | 8 | 8 |
| 9j | 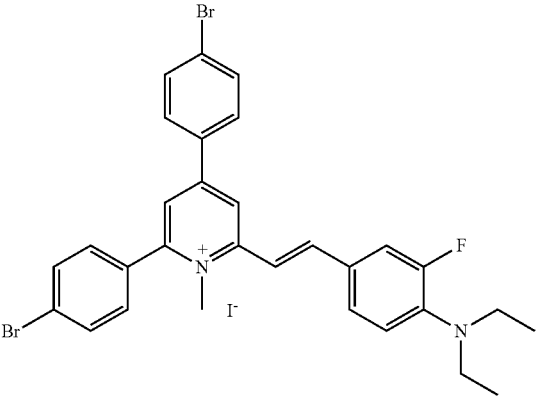<br>16751-12b | 32 | 32 | 64 |

TABLE 16-continued
Minimum Inhibitory Concentration (MIC) of Select Compounds.
| Compound Code | Structural Formula and Compound Name | MIC S. aureus (µg/mL) | MIC E. faecium (µg/mL) | MIC A. baumannii (µg/mL) |
| --- | --- | --- | --- | --- |
| 9k | 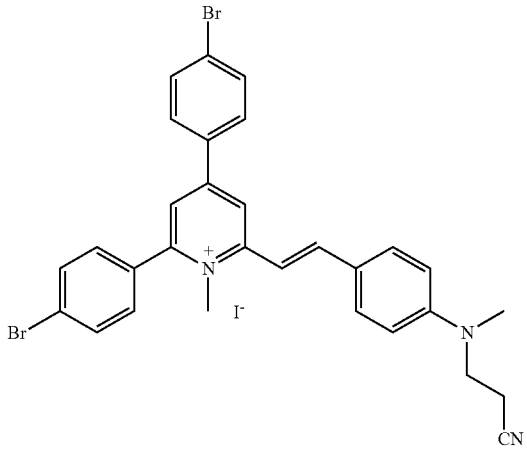 16751-LG-12c | 32 | 32 | 64 |
| 9s | 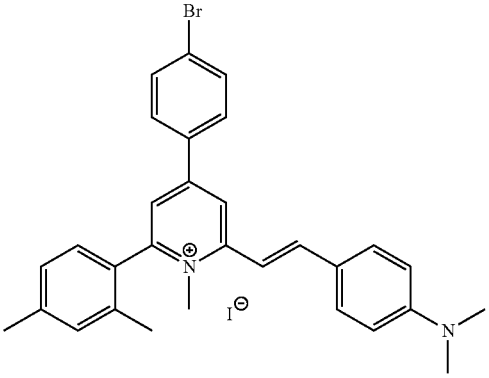 16570-RN-22 | 0.25 | 1 | 16 |
| 9r | 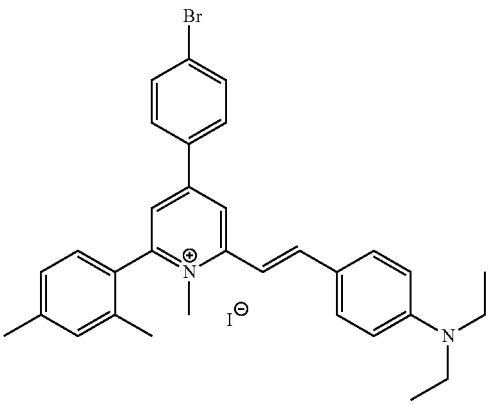 16750-RN-24 | 0.5 | 1 | 8 |

TABLE 16-continued

Minimum Inhibitory Concentration (MIC) of Select Compounds.

| Compound Code | Structural Formula and Compound Name | MIC S. aureus (µg/mL) | MIC E. faecium (µg/mL) | MIC A. baumannii (µg/mL) |
|---|---|---|---|---|
| 9t | 16750-RN-25 | 0.5 | 2 | 16 |
| 9e | 16714-LG-92 | 0.5 | 2 | 8 |
| 9f | 16714-LG-96 | 1 | 2 | 32 |

TABLE 16-continued

Minimum Inhibitory Concentration (MIC) of Select Compounds.

| Compound Code | Structural Formula and Compound Name | MIC S. aureus (µg/mL) | MIC E. faecium (µg/mL) | MIC A. baumannii (µg/mL) |
|---|---|---|---|---|
| 9q | 16751-LG-10b | 0.25 | 2 | 16 |
| 9p | 16751-LG-109 | 0.25 | 2 | 16 |
| 9e1 | 16751-LG-14a | 2 | 2 | 4 |

TABLE 16-continued
Minimum Inhibitory Concentration (MIC) of Select Compounds.
| Compound Code | Structural Formula and Compound Name | MIC S. aureus (µg/mL) | MIC E. faecium (µg/mL) | MIC A. baumannii (µg/mL) |
|---|---|---|---|---|
| 9e2 | 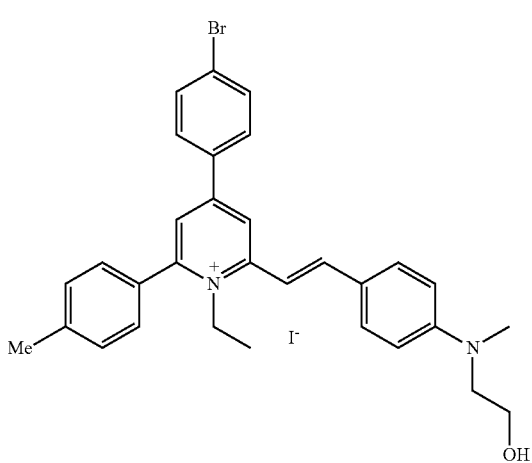<br>16714-RN-27 | 2 | 4 | 4 |
| 9w | 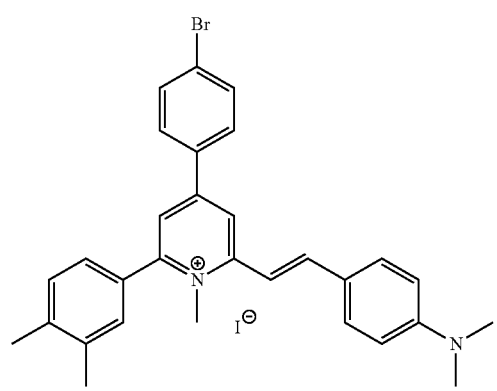<br>16714-RN-27 | 1 | 4 | 8 |
| 9v | 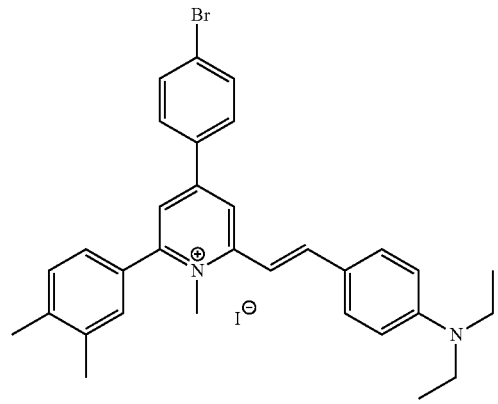<br>16714-RN-28 | 2 | 4 | 4 |

TABLE 16-continued

Minimum Inhibitory Concentration (MIC) of Select Compounds.

| Compound Code | Structural Formula and Compound Name | MIC S. aureus (μg/mL) | MIC E. faecium (μg/mL) | MIC A. baumannii (μg/mL) |
|---|---|---|---|---|
| 9x | 16714-RN-29 | 1 | 8 | 16 |
| 9u | 16714-RN-30 | 2 | 8 | 16 |
| 9z2 | 16754-AD-36 | 0.5 | 1 | 2 |

TABLE 16-continued

Minimum Inhibitory Concentration (MIC) of Select Compounds.

| Compound Code | Structural Formula and Compound Name | MIC S. aureus (µg/mL) | MIC E. faecium (µg/mL) | MIC A. baumannii (µg/mL) |
|---|---|---|---|---|
| 9z1 | 16754-AD-38 | 4 | 8 | 32 |
| 9z4 | 16754-AD-39 | 2 | 4 | 32 |
| 9z3 | 16754-AD-40 | 2 | 4 | 16 |

TABLE 16-continued
Minimum Inhibitory Concentration (MIC) of Select Compounds.
| Compound Code | Structural Formula and Compound Name | MIC S. aureus (µg/mL) | MIC E. faecium (µg/mL) | MIC A. baumannii (µg/mL) |
|---|---|---|---|---|
| 9y1 | 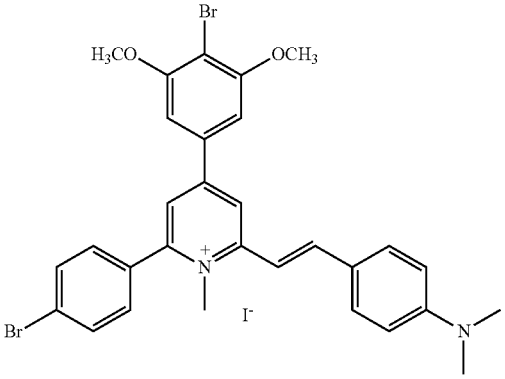 16543-CL-56 | 2 | 8 | 16 |
| 9y2 | 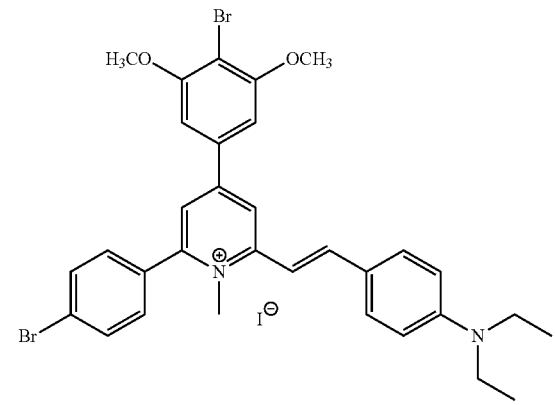 16543-CL-57 | 1 | 4 | 8 |
| 9y3 | 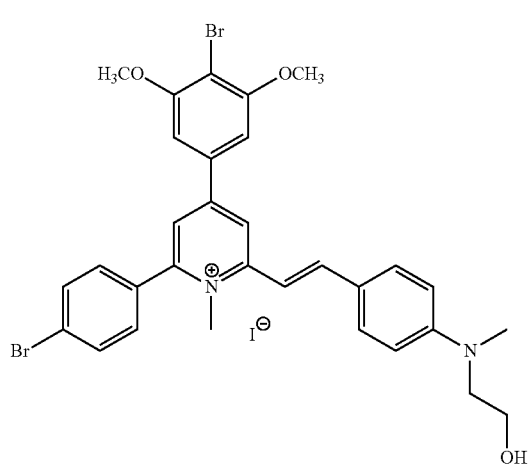 16543-CL-58 | 4 | 8 | 8 |

TABLE 16-continued
Minimum Inhibitory Concentration (MIC) of Select Compounds.
| Compound Code | Structural Formula and Compound Name | MIC S. aureus (µg/mL) | MIC E. faecium (µg/mL) | MIC A. baumannii (µg/mL) |
|---|---|---|---|---|
| 9y4 | 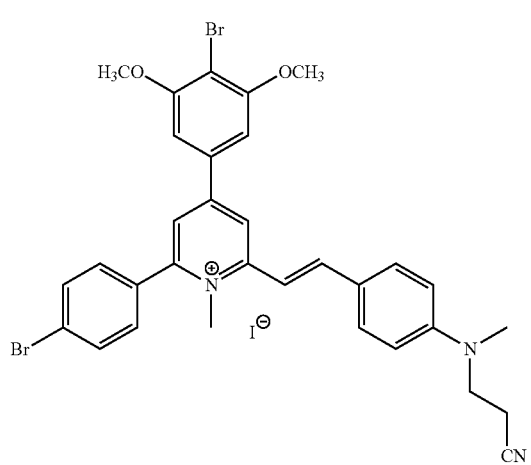 16543-CL-59 | 4 | 8 | 8 |
| 9e3 | 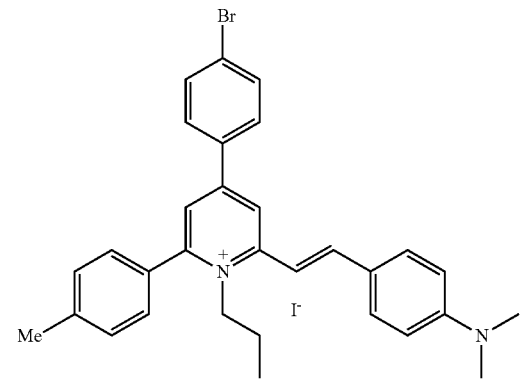 16751-LG-7b | 0.5 | 2 | 2 |

Example 19: Antibacterial Activity of Small Molecule Lipid II Binders

Selected compounds also were tested by broth microdilution methods known in the art and described in CLSI, *Methods for Dilution Antimicrobial Susceptibility Tests for Bacteria That Grow Aerobically; Approved Standard—Tenth Edition.* CLSI document M07-A10. Wayne, Pa.: Clinical and Laboratory Standards Institute, 2015, which is hereby incorporated by reference. Results are provided in Table 18, below. Structures of selected compounds in the tables are listed below.

19A. Compound 2jc39-1: (E)-2-(4-(dimethylamino)styryl)-4,6-bis(4-fluorophenyl)-1-methylpyridin-1-ium iodide salt

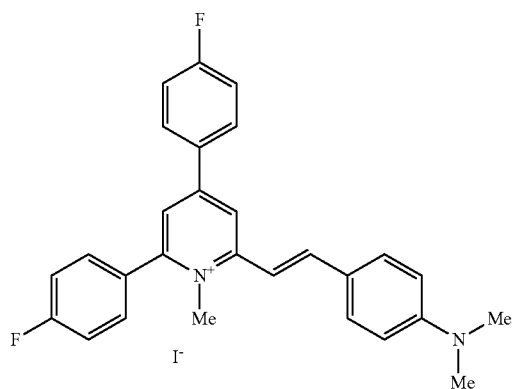 [SMILES: CN(C)c1ccc(/C=C/c2cc(-c3ccc(F)cc3)cc(-c3ccc(F)cc3)[n+]2C)cc1 ; [I-]]

$\delta_H$(DMSO-d, 400 MHz) 8.69 (s, 1H), 8.34-8.31 (m, 2H), 8.14 (d, J=15.6, 1H), 8.05 (s, 1H), 7.84-7.75 (m, 4H), 7.56-7.47 (m, 4H), 7.32 (d, J=15.6, 1H), 6.82 (d, J=8.8, 1H), 3.98 (s, 3H), 3.05 (s, 6H). HPLC retention time (min) 12.14.

19B. Compound 2jc39-2: (E)-2-(4-((2-cyanoethyl)(methyl)amino)styryl)-4,6-bis(4-fluorophenyl)-1-methylpyridin-1-ium iodide salt

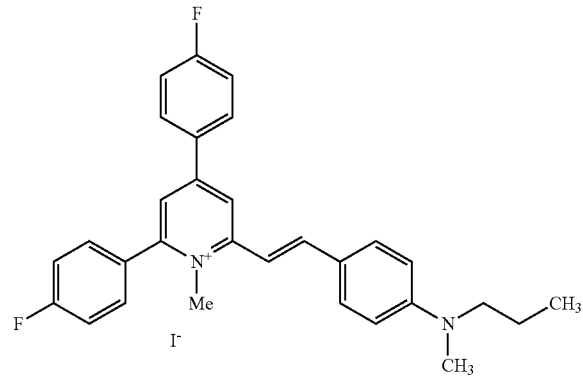 [SMILES: CCCN(C)c1ccc(/C=C/c2cc(-c3ccc(F)cc3)cc(-c3ccc(F)cc3)[n+]2C)cc1 ; [I-]]

$\delta_H$(DMSO-d, 400 MHz) 8.72 (s, 1H), 8.34-8.31 (m, 2H), 8.15 (d, J=15.6, 1H), 8.08 (s, 1H), 7.84-7.75 (m, 4H), 7.57-7.47 (m, 4H), 7.37 (d, J=15.6, 1H), 6.91 (d, J=8.8, 2H), 3.99 (s, 3H), 3.81 (t, J=6.4, 2H), 3.07 (s, 3H), 2.79 (t, J=6.4, 2H). HPLC retention time (min) 9.84.

19C. Compound 2jc39-3: (E)-2-(4-bromophenyl)-6-(4-(dimethylamino)styryl)-4-(4-fluorophenyl)-1-methylpyridin-1-ium iodide salt

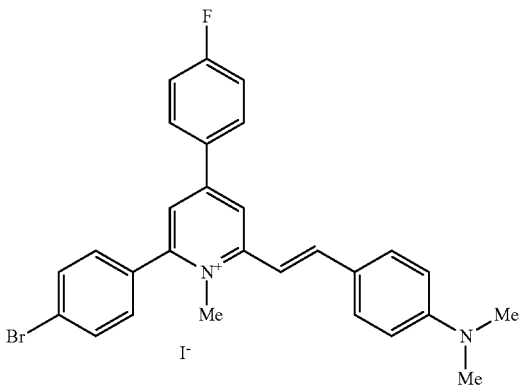 [SMILES: CN(C)c1ccc(/C=C/c2cc(-c3ccc(F)cc3)cc(-c3ccc(Br)cc3)[n+]2C)cc1 ; [I-]]

$\delta_H$(DMSO-d, 400 MHz) 8.70 (s, 1H), 8.34-8.30 (m, 2H), 8.15 (d, J=15.6, 1H), 8.06 (s, 1H), 7.90 (d, J=8.4, 2H), 7.77 (d, J=8.4, 2H), 7.70 (d, J=8.4, 2H), 7.50 (t, J=7.6, 2H), 7.32 (d, J=15.6, 1H), 6.82 (d, J=8.4, 2H), 3.98 (s, 3H), 3.05 (s, 6H). HPLC retention time (min) 12.10.

19D. Compound 2jc39-4: (E)-2-(4-bromophenyl)-6-(4-(2-cyanoethyl)(methyl)amino)styryl)-4-(4-fluorophenyl)-1-methylpyridin-1-ium iodide salt

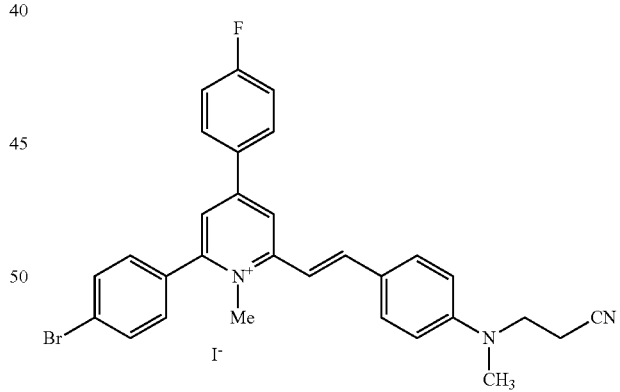

$\delta_H$(DMSO-d, 400 MHz) 8.70 (s, 1H), 8.34-8.30 (m, 2H), 8.15 (d, J=15.6, 1H), 8.08 (s, 1H), 7.91 (d, J=8.8, 2H), 7.78 (d, J=8.8, 2H), 7.71 (d, J=8.8, 2H), 7.50 (t, J=7.6, 2H), 7.36 (d, J=15.6, 1H), 6.91 (d, J=8.4, 2H), 3.99 (s, 3H), 3.81 (t, J=6.4, 2H), 3.07 (s, 3H), 2.79 (t, J=6.4, 2H). HPLC retention time (min) 10.17.

19E. Compound 2jc43-1: (E)-4-(4-chlorophenyl)-2-(4-(dimethylamino)styryl)-6-(4-fluorophenyl)-1-methylpyridin-1-ium iodide salt

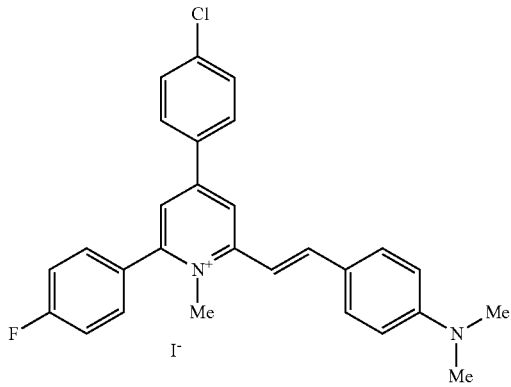 [SMILES: CN(C)c1ccc(/C=C/c2cc(-c3ccc(Cl)cc3)cc(-c3ccc(F)cc3)[n+]2C)cc1 ; [I-]]

$\delta_H$(DMSO-d, 400 MHz) 8.69 (s, 1H), 8.25 (d, J=8.8, 2H), 8.13 (d, J=15.6, 1H), 7.81-7.68 (m, 6H), 7.52 (t, J=7.6, 2H), 7.30 (d, J=15.6, 1H), 6.80 (d, J=8.4, 2H), 3.96 (s, 3H), 3.03 (s, 6H). HPLC retention time (min) 9.89.

19F. Compound 2jc43-2: (E)-4-(4-chlorophenyl)-2-(4-((2-cyanoethyl)(methyl)amino)styryl)-6-(4-fluorophenyl)-1-methylpyridin-1-ium iodide salt

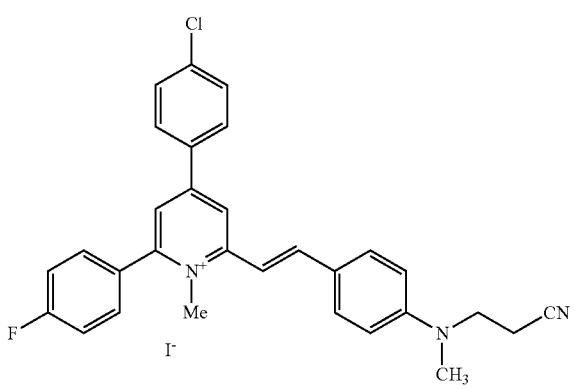 [SMILES: CN(CCC#N)c1ccc(/C=C/c2cc(-c3ccc(Cl)cc3)cc(-c3ccc(F)cc3)[n+]2C)cc1 ; [I-]]

$\delta_H$(DMSO-d, 400 MHz) 8.70 (s, 1H), 8.25 (d, J=8.4, 2H), 8.13 (d, J=15.6, 1H), 7.82-7.68 (m, 6H), 7.53 (t, J=8.8, 2H), 7.35 (d, J=15.6, 1H), 6.89 (d, J=8.8, 2H), 3.97 (s, 3H), 3.79 (t, J=6.4, 2H), 3.05 (s, 3H), 2.77 (t, J=6.4, 2H). HPLC retention time (min) 10.13.

19G. Compound 2jc43-3: (E)-2-(4-bromophenyl)-4-(4-chlorophenyl)-6-(4-(dimethylamino)styryl)-1-methylpyridin-1-ium iodide salt

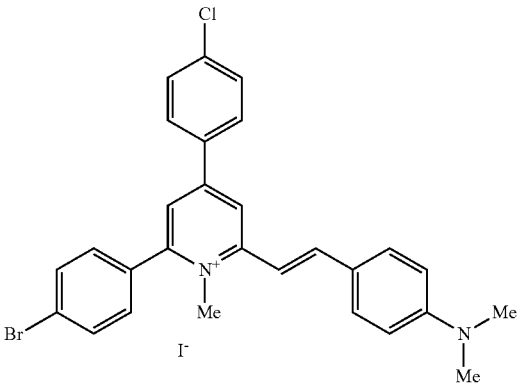 [SMILES: CN(C)c1ccc(/C=C/c2cc(-c3ccc(Cl)cc3)cc(-c3ccc(Br)cc3)[n+]2C)cc1 ; [I-]]

$\delta_H$(DMSO-d, 400 MHz) 8.70 (s, 1H), 8.24 (d, J=8.4, 2H), 8.14 (d, J=15.6, 1H), 8.04 (s, 1H), 7.88 (d, J=8.0, 2H), 7.76-7.67 (m, 6H), 7.30 (d, J=15.6, 1H), 6.80 (d, J=8.8, 2H), 3.96 (s, 3H), 3.03 (s, 3H). HPLC retention time (min) 9.84.

19H. Compound 2jc43-4: (E)-2-(4-bromophenyl)-4-(4-chlorophenyl)-6-(4-((2-cyanoethyl)(methyl)amino)styryl)-1-methylpyridin-1-ium iodide salt

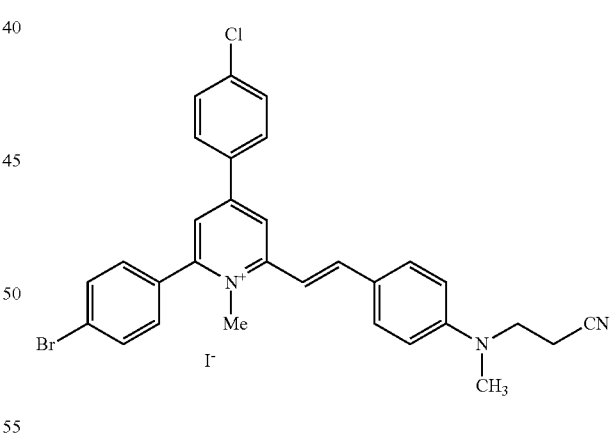

$\delta_H$(DMSO-d, 400 MHz) 8.70 (s, 1H), 8.25 (d, J=8.4, 2H), 8.14 (d, J=16.0, 1H), 8.07 (s, 1H), 7.88 (d, J=8.4, 2H), 7.77-7.67 (m, 6H), 7.34 (d, J=16.0, 1H), 6.90 (d, J=8.4, 2H), 3.97 (s, 3H), 3.79 (t, J=6.4, 2H), 3.05 (s, 3H), 2.77 (t, J=6.4, 2H). HPLC retention time (min) 9.99.

19I. Compound 3jc01-1: (E)-4-(4-(dimethylamino)phenyl)-2-(4-(dimethylamino)styryl)-6-(4-fluorophenyl)-1-methylpyridin-1-ium iodide salt

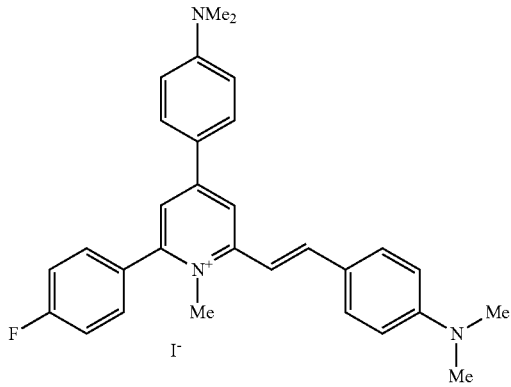 [SMILES: CN(C)c1ccc(/C=C/c2cc(-c3ccc(N(C)C)cc3)cc(-c3ccc(F)cc3)[n+]2C)cc1 ; [I-]]

δ$_H$(DMSO-d, 400 MHz) 8.49 (s, 1H), 8.13 (d, J=8.4, 2H), 8.00 (d, J=16.0, 1H), 7.88 (s, 1H), 7.78-7.70 (m, 6H), 7.23 (d, J=16.0, 1H), 6.84-6.78 (m, 4H), 3.85 (s, 3H), 3.05 (s, 6H), 3.02 (s, 6H). HPLC retention time (min) 10.01.

19J. Compound 3jc01-2: (E)-2-(4-((2-cyanoethyl)(methyl)amino)styryl)-4-(4-(dimethylamino)phenyl)-6-(4-fluorophenyl)-1-methylpyridin-1-ium iodide salt

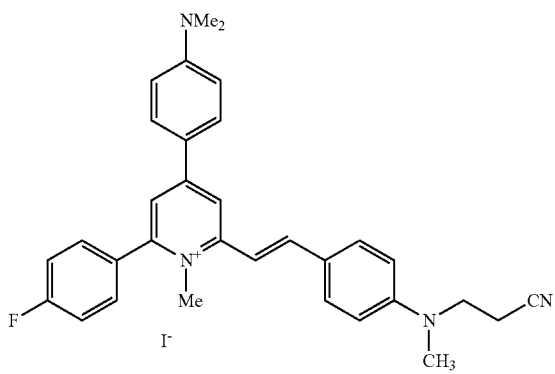

δ$_H$(DMSO-d, 400 MHz) 8.49 (s, 1H), 8.13 (d, J=8.8, 2H), 8.00 (d, J=15.6, 1H), 7.91 (s, 1H), 7.80-7.72 (m, 4H), 7.50 (t, J=8.8, 2H), 7.28 (d, J=15.6, 1H), 6.88 (d, J=8.8, 2H), 6.83 (d, J=8.8, 2H), 3.85 (s, 3H), 3.78 (t, J=6.4, 2H), 3.05 (s, 6H), 3.04 (s, 3H), 2.76 (t, J=6.4, 2H). HPLC retention time (min) 10.27.

19K. Compound 3jc01-3: (E)-2-(4-bromophenyl)-4-(4-(dimethylamino)phenyl)-6-(4-(dimethylamino)styryl)-1-methylpyridin-1-ium iodide salt

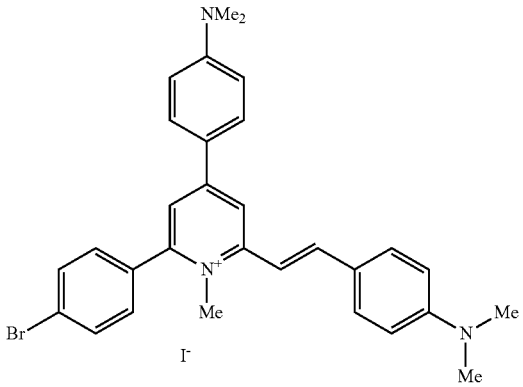 [SMILES: CN(C)c1ccc(/C=C/c2cc(-c3ccc(N(C)C)cc3)cc(-c3ccc(Br)cc3)[n+]2C)cc1 ; [I-]]

δ$_H$(DMSO-d, 400 MHz) 8.48 (s, 1H), 8.12 (d, J=8.4, 2H), 8.00 (d, J=15.6, 1H), 7.89-7.85 (m, 3H), 7.72 (d, J=8.4, 2H), 7.65 (d, J=8.4, 2H), 7.23 (d, J=15.6, 1H), 6.83 (d, J=8.8, 2H), 6.78 (d, J=8.8, 2H), 3.85 (s, 3H), 3.05 (s, 6H), 3.02 (s, 6H). HPLC retention time (min) 10.00.

19L. Compound 3jc01-4: (E)-2-(4-bromophenyl)-6-(4-((2-cyanoethyl)(methyl)amino)styryl)-4-(4-(dimethylamino)phenyl)-1-methylpyridin-1-ium iodide salt

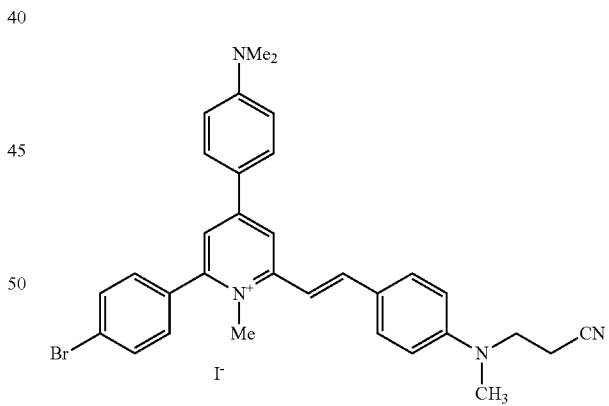

δ$_H$(DMSO-d, 400 MHz) 8.49 (s, 1H), 8.12 (d, J=8.8, 2H), 8.00 (d, J=16.0, 1H), 7.91 (s, 1H), 7.73 (d, J=8.8, 2H), 7.66 (d, J=8.8, 2H), 7.50 (t, J=8.8, 2H), 7.24 (d, J=16.0, 1H), 6.92 (d, J=8.8, 2H), 6.78 (d, J=8.8, 2H), 3.85 (s, 3H), 3.78 (t, J=6.4, 2H), 3.06 (s, 6H), 3.04 (s, 3H), 2.76 (t, J=6.4, 2H). HPLC retention time (min) 10.61.

19M. Compound 3jc01-5: (E)-4-(4-((2-cyanoethyl)(methyl)amino)phenyl)-2-(4-(dimethylamino)styryl)-6-(4-fluorophenyl)-1-methylpyridin-1-ium iodide salt

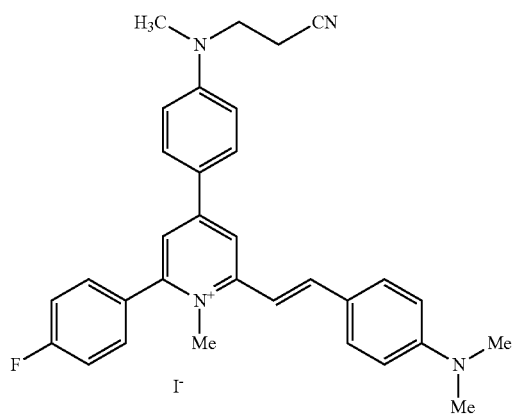 [SMILES: CN(C)c1ccc(/C=C/c2cc(-c3ccc(N(C)CCC#N)cc3)cc(-c3ccc(F)cc3)[n+]2C)cc1 ; [I-]]

$\delta_H$(DMSO-d, 400 MHz) 8.51 (s, 1H), 8.13 (d, J=8.8, 2H), 8.01 (d, J=15.6, 1H), 7.92 (s, 1H), 7.73 (d, J=8.8, 2H), 7.73 (d, J=8.8, 2H), 7.64 (d, J=8.8, 2H), 7.28 (d, J=16.0, 1H), 6.88 (d, J=8.8, 2H), 6.82 (d, J=8.8, 2H), 3.86 (s, 3H), 3.81 (t, J=6.4, 2H), 3.04 (s, 6H), 3.02 (s, 3H), 2.75 (t, J=6.4, 2H). HPLC retention time (min) 10.34.

19N. Compound 3jc01-6: (E)-4-(4-((2-cyanoethyl)(methyl)amino)phenyl)-2-(4-((2-cyanoethyl)(methyl)amino)styryl)-6-(4-fluorophenyl)-1-methylpyridin-1-ium iodide salt

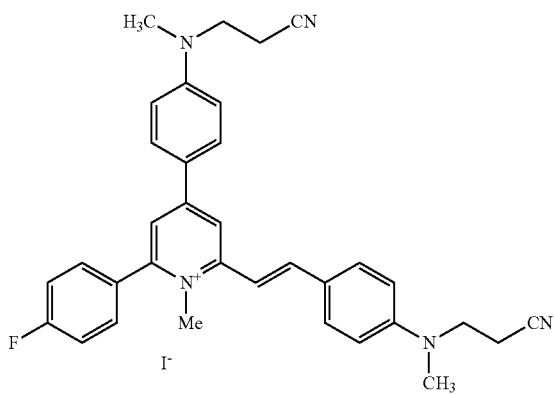 [SMILES: CN(CCC#N)c1ccc(/C=C/c2cc(-c3ccc(N(C)CCC#N)cc3)cc(-c3ccc(F)cc3)[n+]2C)cc1 ; [I-]]

$\delta_H$(DMSO-d, 400 MHz) 8.52 (s, 1H), 8.14 (d, J=9.2, 2H), 8.02 (d, J=15.6, 1H), 7.94 (s, 1H), 7.78-7.72 (m, 4H), 7.50 (t, J=8.8, 2H), 7.28 (d, J=15.6, 1H), 6.93 (d, J=8.8, 2H), 6.88 (d, J=8.8, 2H), 3.87 (s, 3H), 3.84-3.76 (m, 4H), 3.07 (s, 3H), 3.04 (s, 3H), 2.79-2.74 (m, 4H). HPLC retention time (min) 9.90.

19O. Compound 3jc07-1: (E)-2-(4-(dimethylamino)styryl)-6-(4-fluorophenyl)-1-methyl-4-phenylpyridin-1-ium iodide salt

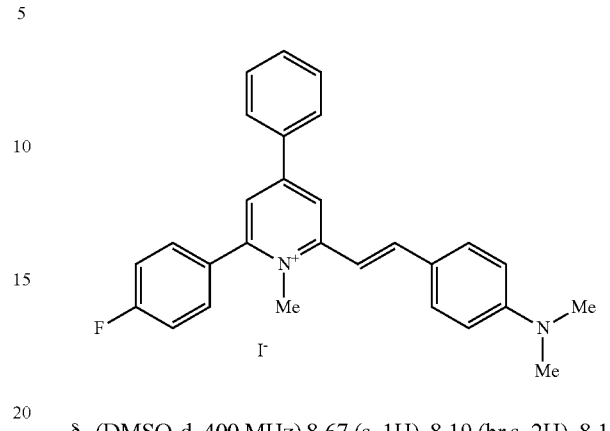

$\delta_H$(DMSO-d, 400 MHz) 8.67 (s, 1H), 8.19 (br s, 2H), 8.14 (d, J=15.6, 1H), 8.02 (s, 1H), 7.82-7.74 (m, 4H), 7.63 (br s, 3H), 7.52 (t, J=8.8, 2H), 7.31 (d, J=15.6, 1H), 6.80 (d, J=8.8, 2H), 3.96 (s, 3H), 3.03 (s, 6H). HPLC retention time (min) 9.92.

19P. Compound 3jc07-2: (E)-2-(4-((2-cyanoethyl)(methyl)amino)styryl)-6-(4-fluorophenyl)-1-methyl-4-phenylpyridin-1-ium iodide salt

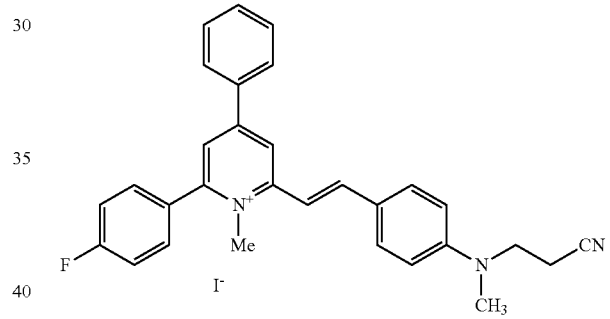

$\delta_H$(DMSO-d, 400 MHz) 8.69 (s, 1H), 8.20 (br s, 2H), 8.13 (d, J=15.6, 1H), 8.05 (s, 1H), 7.82-7.75 (m, 4H), 7.63 (br s, 3H), 7.52 (t, J=8.8, 2H), 7.35 (d, J=15.6, 1H), 6.89 (d, J=8.8, 2H), 3.97 (s, 3H), 3.79 (t, J=6.4, 2H), 3.05 (s, 3H), 2.77 (t, J=6.4, 2H). HPLC retention time (min) 9.81.

19Q. Compound 3jc07-3: (E)-2-(4-bromophenyl)-6-(4-(dimethylamino)styryl)-1-methyl-4-phenylpyridin-1-ium iodide salt

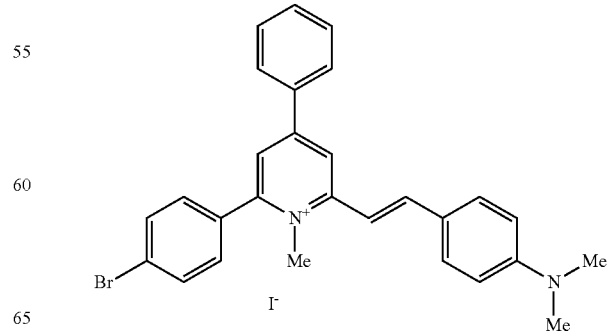

δ$_H$(DMSO-d, 400 MHz) 8.69 (s, 1H), 8.19 (br s, 2H), 8.14 (d, J=15.6, 1H), 8.03 (s, 1H), 7.89 (d, J=8.8, 2H), 7.75 (d, J=8.8, 2H), 7.68 (d, J=8.8, 2H), 7.63 (br s, 3H), 7.31 (d, J=15.6, 1H), 6.80 (d, J=8.8, 2H), 3.96 (s, 3H), 3.03 (s, 6H). HPLC retention time (min) 9.52.

19R. Compound 3jc07-4: (E)-2-(4-bromophenyl)-6-(4-((2-cyanoethyl)(methyl)amino)styryl)-1-methyl-4-phenylpyridin-1-ium iodide salt

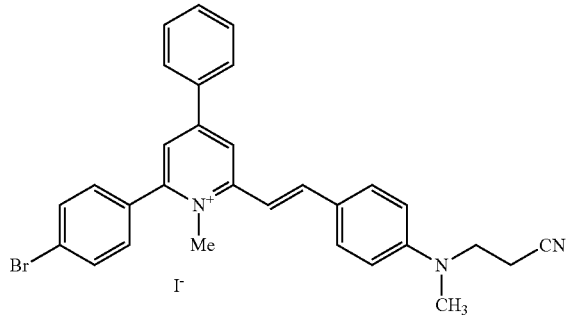 [SMILES: CN(CCC#N)c1ccc(/C=C/c2cc(-c3ccccc3)cc(-c3ccc(Br)cc3)[n+]2C)cc1 ; [I-]]

δ$_H$(DMSO-d, 400 MHz) 8.70 (s, 1H), 8.19 (br s, 2H), 8.13 (d, J=15.6, 1H), 8.05 (s, 1H), 7.88 (d, J=8.0, 2H), 7.76 (d, J=8.4, 2H), 7.68 (d, J=8.0, 2H), 7.62 (br s, 3H), 7.35 (d, J=15.6, 1H), 6.89 (d, J=8.8, 2H), 3.97 (s, 3H), 3.79 (t, J=6.4, 2H), 3.05 (s, 3H), 2.77 (t, J=6.4, 2H). HPLC retention time (min) 10.14.

19S. Compound 3jc07-5: (E)-2-(4-(dimethylamino)styryl)-6-(4-fluorophenyl)-4-(4-methoxyphenyl)-1-methylpyridin-1-ium iodide salt

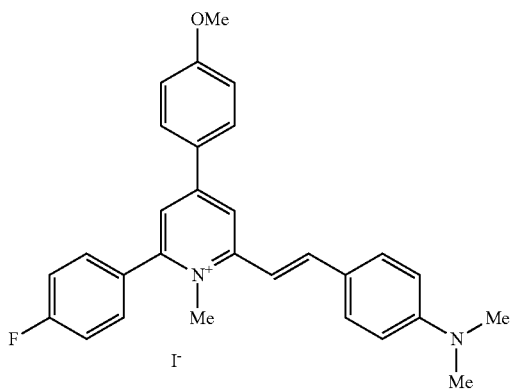 [SMILES: COc1ccc(-c2cc(/C=C/c3ccc(N(C)C)cc3)[n+](C)c(-c3ccc(F)cc3)c2)cc1 ; [I-]]

δ$_H$(DMSO-d, 400 MHz) 8.61 (s, 1H), 8.22 (d, J=8.8, 2H), 8.08 (d, J=15.6, 1H), 7.99 (s, 1H), 7.81-7.73 (m, 4H), 7.52 (t, J=8.4, 2H), 7.28 (d, J=15.6, 1H), 7.14 (d, J=8.8, 2H), 6.80 (d, J=8.4, 2H), 3.92 (s, 3H), 3.87 (s, 3H), 3.03 (s, 6H). HPLC retention time (min) 9.85.

19T. Compound 3jc07-6: (E)-2-(4-((2-cyanoethyl)(methyl)amino)styryl)-6-(4-fluorophenyl)-4-(4-methoxyphenyl)-1-methylpyridin-1-ium iodide salt

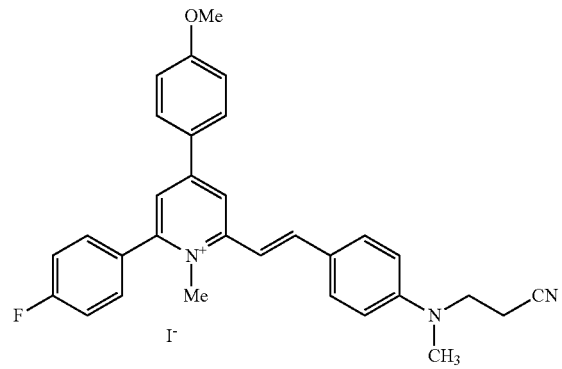

δ$_H$(DMSO-d, 400 MHz) 8.62 (s, 1H), 8.23 (d, J=8.8, 2H), 8.08 (d, J=15.6, 1H), 8.02 (s, 1H), 7.81-7.74 (m, 4H), 7.52 (t, J=8.8, 2H), 7.32 (d, J=15.6, 1H), 7.15 (d, J=8.8, 2H), 6.89 (d, J=8.8, 2H), 3.93 (s, 3H), 3.87 (s, 3H), 3.79 (t, J=6.4, 2H), 3.05 (s, 3H), 2.77 (t, J=6.4, 2H). HPLC retention time (min) 9.94.

19U. Compound 3jc07-7: (E)-2-(4-bromophenyl)-6-(4-(dimethylamino)styryl)-4-(4-methoxyphenyl)-1-methylpyridin-1-ium iodide salt

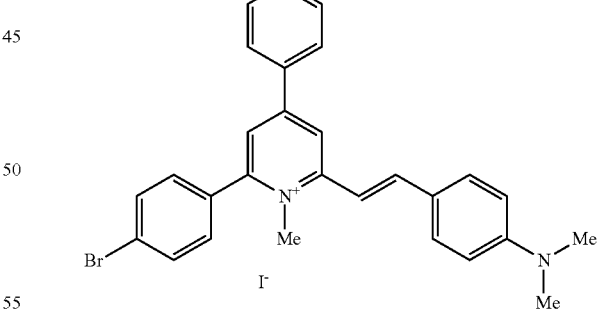

δ$_H$(DMSO-d, 400 MHz) 8.62 (s, 1H), 8.22 (d, J=8.8, 2H), 8.09 (d, J=15.6, 1H), 7.99 (s, 1H), 7.87 (d, J=8.4, 2H), 7.74 (d, J=8.4, 2H), 7.67 (d, J=8.4, 2H), 7.28 (d, J=15.6, 1H), 7.15 (d, J=8.4, 2H), 6.80 (d, J=8.4, 2H), 3.92 (s, 3H), 3.87 (s, 3H), 3.03 (s, 6H). HPLC retention time (min) 9.65.

189

19V. Compound 3jc07-9: (E)-2-(4-(dimethylamino)styryl)-6-(4-fluorophenyl)-4-(4-iodophenyl)-1-methylpyridin-1-ium iodide salt

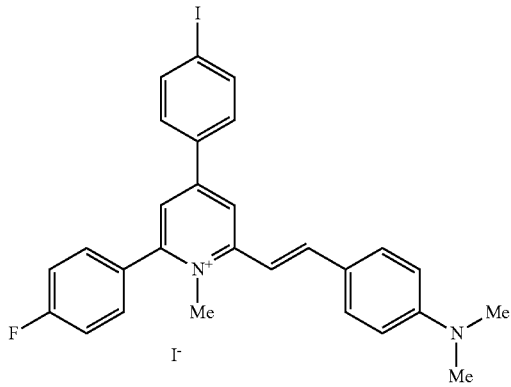 [SMILES: CN(C)c1ccc(/C=C/c2cc(-c3ccc(I)cc3)cc(-c3ccc(F)cc3)[n+]2C)cc1 ; [I-]]

δ$_H$(DMSO-d, 400 MHz) 8.73 (s, 1H), 8.16 (d, J=15.6, 1H), 8.10-8.03 (m, 5H), 7.82-7.78 (m, 4H), 7.56 (t, J=8.4, 2H), 7.34 (d, J=15.6, 1H), 6.84 (d, J=8.4, 2H), 3.09 (s, 3H), 3.07 (s, 6H). HPLC retention time (min) 10.00.

19W. Compound 3jc7-10: (E)-2-(4-((2-cyanoethyl)(methyl)amino)styryl)-6-(4-fluorophenyl)-4-(4-iodophenyl)-1-methylpyridin-1-ium iodide salt

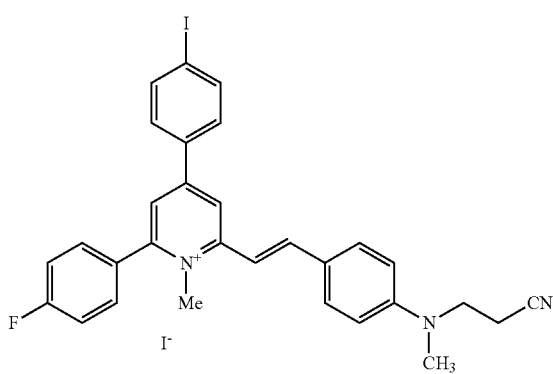

δ$_H$(DMSO-d, 400 MHz) 8.73 (s, 1H), 8.16 (d, J=15.6, 1H), 8.09-8.04 (m, 5H), 7.86-7.79 (m, 4H), 7.57 (t, J=8.4, 2H), 7.38 (d, J=15.6, 1H), 6.94 (d, J=8.4, 2H), 4.00 (s, 3H), 3.83 (t, J=6.4, 2H), 3.10 (s, 3H), 2.81 (t, J=6.4, 2H). HPLC retention time (min) 10.25.

190

19X. Compound 3jc07-11: (E)-2-(4-bromophenyl)-6-(4-(dimethylamino)styryl)-4-(4-iodophenyl)-1-methylpyridin-1-ium iodide salt

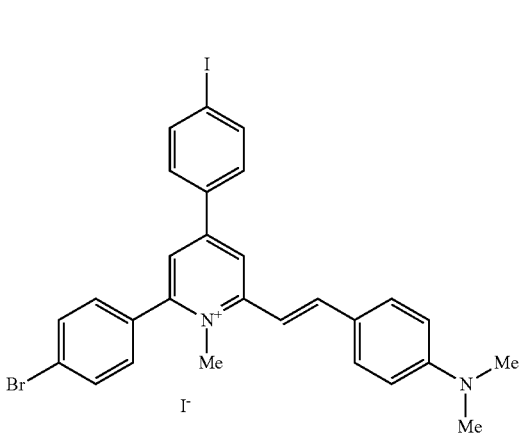 [SMILES: CN(C)c1ccc(/C=C/c2cc(-c3ccc(I)cc3)cc(-c3ccc(Br)cc3)[n+]2C)cc1 ; [I-]]

δ$_H$(DMSO-d, 400 MHz) 8.73 (s, 1H), 8.18 (d, J=15.6, 1H), 8.07-8.03 (m, 5H), 7.92 (d, J=8.4, 2H), 7.79 (d, J=8.4, 2H), 7.72 (d, J=8.4, 2H), 7.34 (d, J=15.6, 1H), 6.84 (d, J=8.4, 2H), 3.99 (s, 3H), 3.08 (s, 6H). HPLC retention time (min) 10.02.

19Y. Compound 3jc07-12: (E)-2-(4-bromophenyl)-6-(4-((2-cyanoethyl)(methyl)amino)styryl)-4-(4-iodophenyl)-1-methylpyridin-1-ium iodide salt

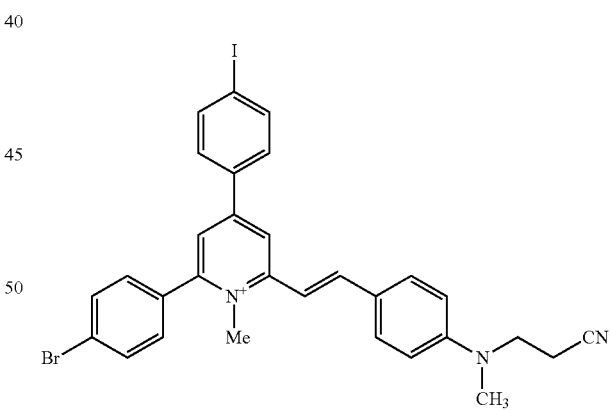

δ$_H$(DMSO-d, 400 MHz) 8.81 (s, 1H), 8.13 (d, J=16.0, 1H), 8.08-7.96 (m, 5H), 7.88 (d, J=8.0, 2H), 7.76 (d, J=8.0, 2H), 7.67 (d, J=8.8, 2H), 7.34 (d, J=16.0, 1H), 6.89 (d, J=8.4, 2H), 3.96 (s, 3H), 3.79 (t, J=6.0, 2H), 3.05 (s, 3H), 2.77 (t, J=6.0, 2H). HPLC retention time (min) 10.63.

19Z. Compound 3jc09-1: (E)-2-(4-((2-cyanoethyl)(methyl)amino)styryl)-4,6-bis(4-fluorophenyl)pyrylium boron tetrafluoride salt

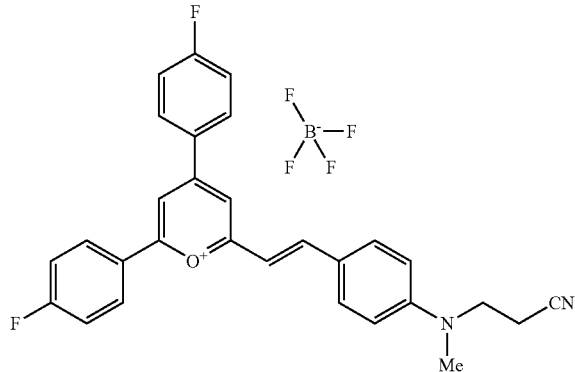 [SMILES: CN(CCC#N)c1ccc(/C=C/c2cc(-c3ccc(F)cc3)cc(-c3ccc(F)cc3)[o+]2)cc1 ; F[B-](F)(F)F]

19AA. Compound 3jc09-2: (E)-2,4-bis(4-bromophenyl)-6-(4-((2-cyanoethyl)(methyl)amino)styryl)pyrylium boron tetrafluoride salt

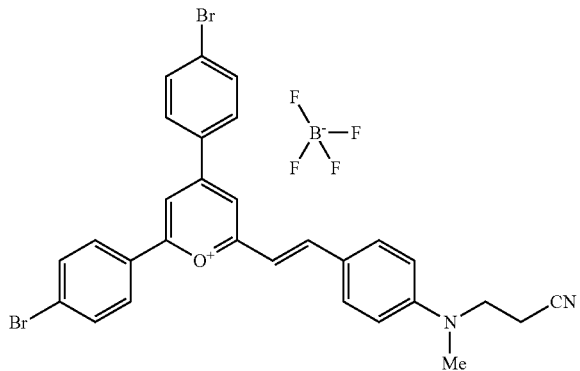 [SMILES: CN(CCC#N)c1ccc(/C=C/c2cc(-c3ccc(Br)cc3)cc(-c3ccc(Br)cc3)[o+]2)cc1 ; F[B-](F)(F)F]

19BB. Compound 3jc12: (E)-2,4-bis(4-bromophenyl)-6-(4-(dimethylamino)styryl)-1-phenylpyridin-1-ium boron tetrafluoride salt

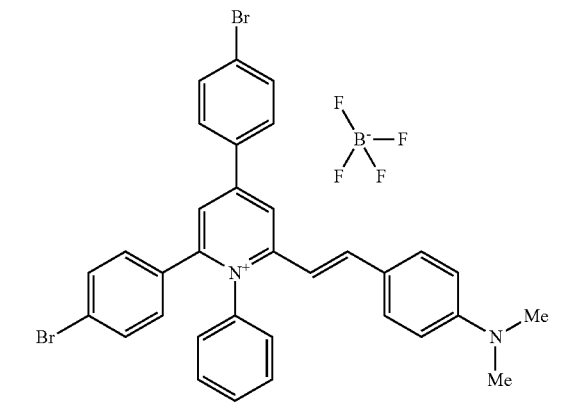 [SMILES: CN(C)c1ccc(/C=C/c2cc(-c3ccc(Br)cc3)cc(-c3ccc(Br)cc3)[n+]2-c2ccccc2)cc1 ; F[B-](F)(F)F]

19CC. Compound 3jc13-1: (E)-2-(4-bromophenyl)-6-(4-((3-cyanopropyl)(methyl)amino)styryl)-4-(4-methoxyphenyl)-1-methylpyridin-1-ium iodide salt

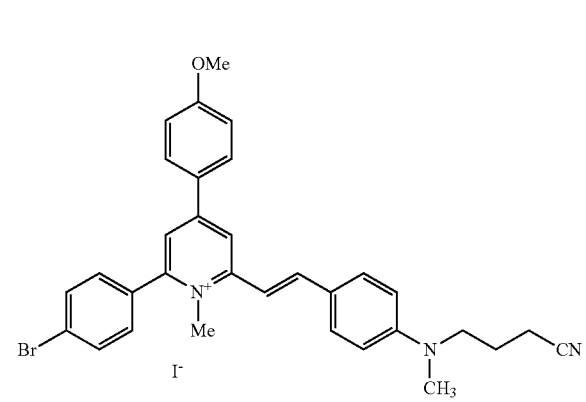 [SMILES: COc1ccc(-c2cc(/C=C/c3ccc(N(C)CCCC#N)cc3)[n+](C)c(-c3ccc(Br)cc3)c2)cc1 ; [I-]]

19DD. Compound 3jc13-2: (E)-2-(4-bromophenyl)-6-(4-((4-cyanobutyl)(methyl)amino)styryl)-4-(4-methoxyphenyl)-1-methylpyridin-1-ium iodide salt

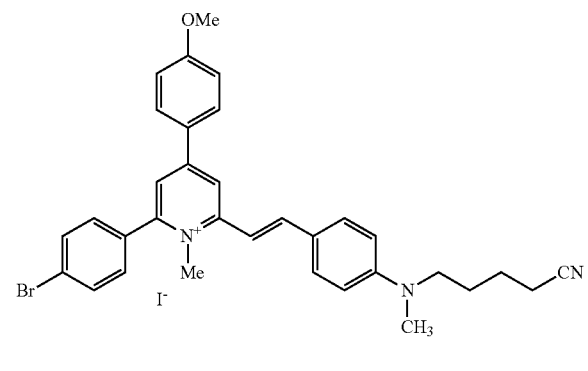

19EE. Compound 3jc13-3: (E)-2-(4-bromophenyl)-6-(4-((5-cyanopentyl)(methyl)amino)styryl)-4-(4-methoxyphenyl)-1-methylpyridin-1-ium iodide salt

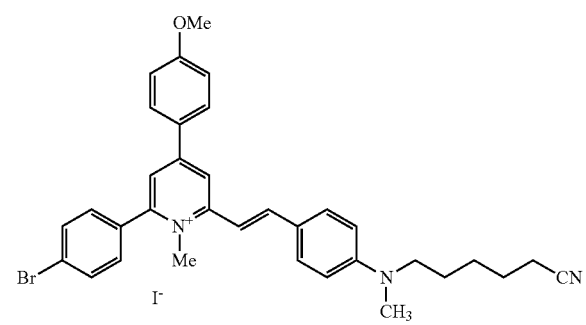 [SMILES: COc1ccc(-c2cc(/C=C/c3ccc(N(C)CCCCCC#N)cc3)[n+](C)c(-c3ccc(Br)cc3)c2)cc1 ; [I-]]

19FF. Compound 3jc14-1: (E)-2-(4-((3-cyanopropyl)(methyl)amino)styryl)-6-(4-fluorophenyl)-4-(4-methoxyphenyl)-1-methylpyridin-1-ium iodide salt 19II. Compound 3jc15-1: (E)-2-(4-bromophenyl)-6-(4-((3-cyanopropyl)(methyl)amino)styryl)-4-(4-(dimethylamino)phenyl)-1-methylpyridin-1-ium iodide salt

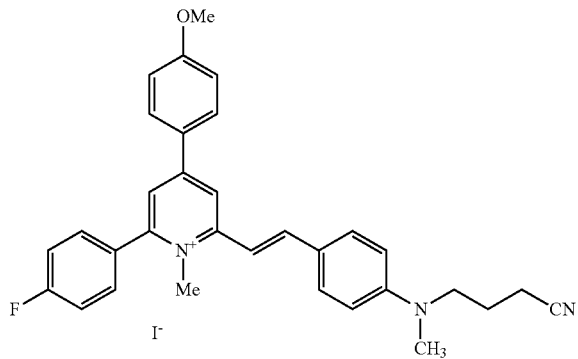 [SMILES: COc1ccc(-c2cc(/C=C/c3ccc(N(C)CCCC#N)cc3)[n+](C)c(-c3ccc(F)cc3)c2)cc1 ; [I-]]

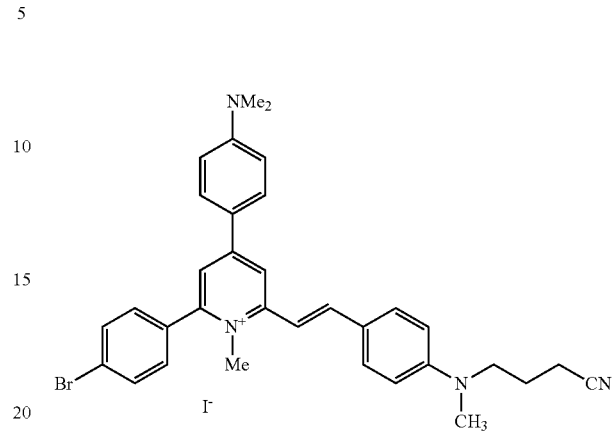

19GG. Compound 3jc14-2: (E)-2-(4-((4-cyanobutyl)(methyl)amino)styryl)-6-(4-fluorophenyl)-4-(4-methoxyphenyl)-1-methylpyridin-1-ium iodide salt 19JJ. Compound 3jc15-2: (E)-2-(4-bromophenyl)-6-(4-((4-cyanobutyl)(methyl)amino)styryl)-4-(4-(dimethylamino)phenyl)-1-methylpyridin-1-ium iodide salt

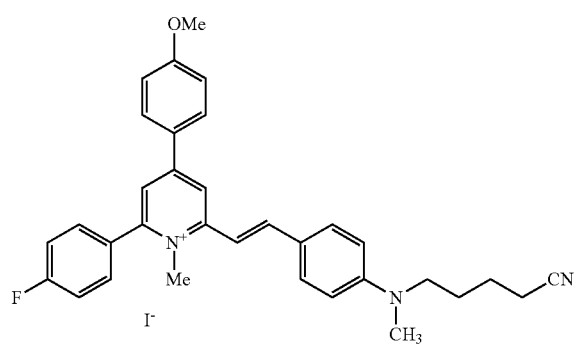 [SMILES: COc1ccc(-c2cc(/C=C/c3ccc(N(C)CCCCC#N)cc3)[n+](C)c(-c3ccc(F)cc3)c2)cc1 ; [I-]]

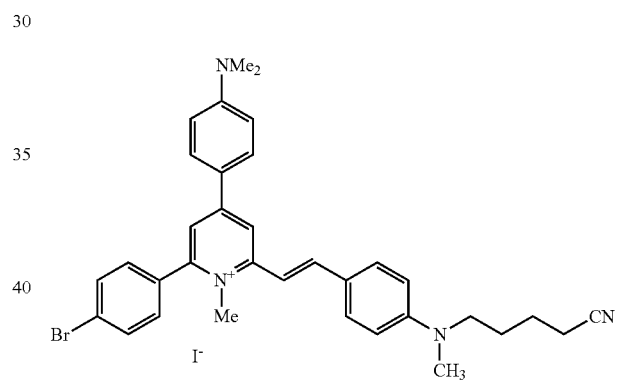

19HH. Compound 3jc14-3: (E)-2-(4-((5-cyanopentyl)(methyl)amino)styryl)-6-(4-fluorophenyl)-4-(4-methoxyphenyl)-1-methylpyridin-1-ium iodide salt 19KK. Compound 3jc15-3: (E)-2-(4-bromophenyl)-6-(4-((5-cyanopentyl)(methyl)amino)styryl)-4-(4-(dimethylamino)phenyl)-1-methylpyridin-1-ium iodide salt

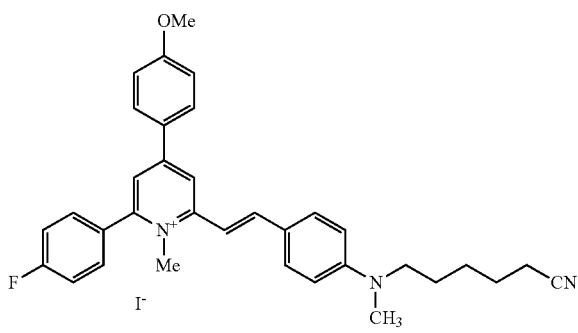

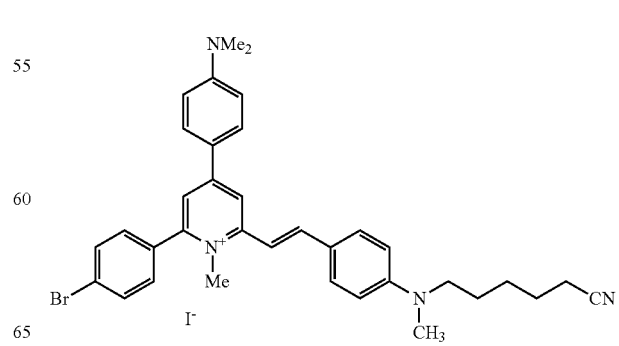

19LL. Compound 3jc16-1: (E)-4-(4-((2-cyanoethyl)(methyl)amino)phenyl)-2-(4-((3-cyanopropyl)(methyl)amino)styryl)-6-(4-fluorophenyl)-1-methylpyridin-1-ium iodide salt

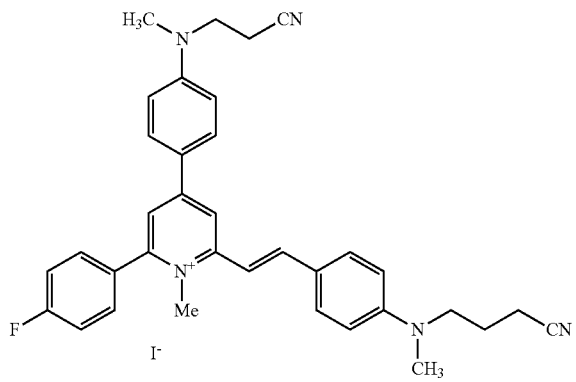 [SMILES: CN(CCC#N)c1ccc(-c2cc(/C=C/c3ccc(N(C)CCCC#N)cc3)[n+](C)c(-c3ccc(F)cc3)c2)cc1 ; [I-]]

19MM. Compound 3jc16-2: (E)-2-(4-((4-cyanobutyl)(methyl)amino)styryl)-4-(4-((2-cyanoethyl)(methyl)amino)phenyl)-6-(4-fluorophenyl)-1-methylpyridin-1-ium iodide salt

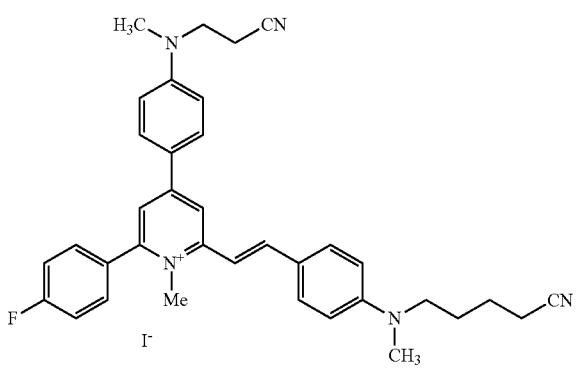 [SMILES: CN(CCC#N)c1ccc(-c2cc(/C=C/c3ccc(N(C)CCCCC#N)cc3)[n+](C)c(-c3ccc(F)cc3)c2)cc1 ; [I-]]

19NN. Compound 3jc16-3: (E)-4-(4-((2-cyanoethyl)(methyl)amino)phenyl)-2-(4-((5-cyanopentyl)(methyl)amino)styryl)-6-(4-fluorophenyl)-1-methylpyridin-1-ium iodide salt

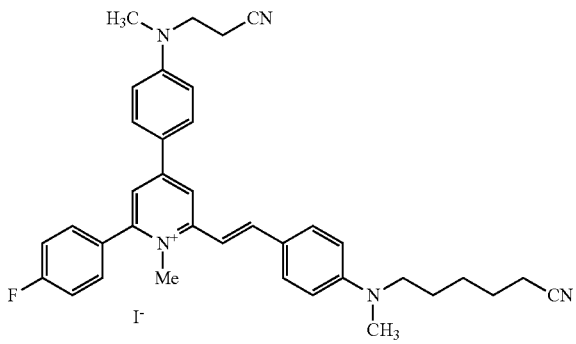 [SMILES: CN(CCC#N)c1ccc(-c2cc(/C=C/c3ccc(N(C)CCCCCC#N)cc3)[n+](C)c(-c3ccc(F)cc3)c2)cc1 ; [I-]]

19OO. Compound 3jc12: (E)-2,4-bis(4-bromophenyl)-6-(4-(dimethylamino)styryl)-1-phenylpyridin-1-ium boron tetrafluoride salt

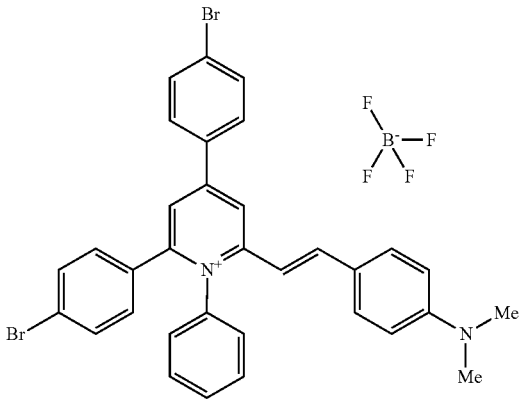 [SMILES: CN(C)c1ccc(/C=C/c2cc(-c3ccc(Br)cc3)cc(-c3ccc(Br)cc3)[n+]2-c2ccccc2)cc1 ; F[B-](F)(F)F]

19PP. Compound 3jc20-1: (E)-2,4-bis(4-bromophenyl)-6-(4-((2-cyanoethyl)(methyl)amino)styryl)pyrylium boron tetrafluoride salt

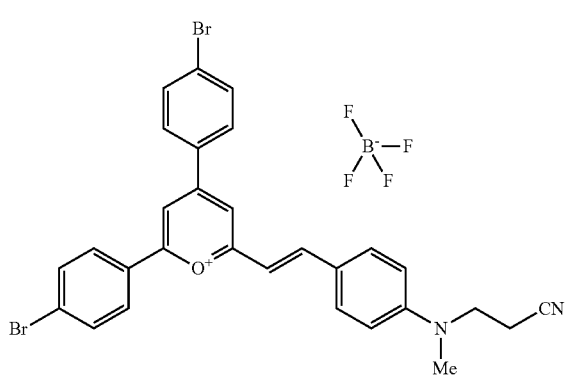 [SMILES: CN(CCC#N)c1ccc(/C=C/c2cc(-c3ccc(Br)cc3)cc(-c3ccc(Br)cc3)[o+]2)cc1 ; F[B-](F)(F)F]

19QQ. Compound 3jc20-2: (E)-2,4-bis(4-bromophenyl)-6-(4-((3-cyanopropyl)(methyl)amino)styryl)pyrylium boron tetrafluoride salt

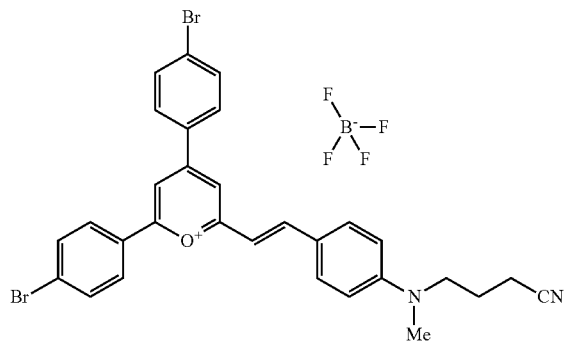 [SMILES: CN(CCCC#N)c1ccc(/C=C/c2cc(-c3ccc(Br)cc3)cc(-c3ccc(Br)cc3)[o+]2)cc1 ; F[B-](F)(F)F]

19RR. Compound 3jc20-3: (E)-2,4-bis(4-bromophenyl)-6-(4-((4-cyanobutyl)(methyl)amino)styryl)pyrylium boron tetrafluoride salt

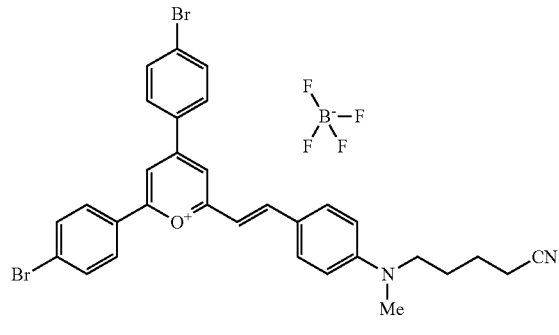 [SMILES: CN(CCCCC#N)c1ccc(/C=C/c2cc(-c3ccc(Br)cc3)cc(-c3ccc(Br)cc3)[o+]2)cc1 ; F[B-](F)(F)F]

19SS. Compound 3jc20-4: (E)-2,4-bis(4-bromophenyl)-6-(4-((5-cyanopentyl)(methyl)amino)styryl)pyrylium boron tetrafluoride salt

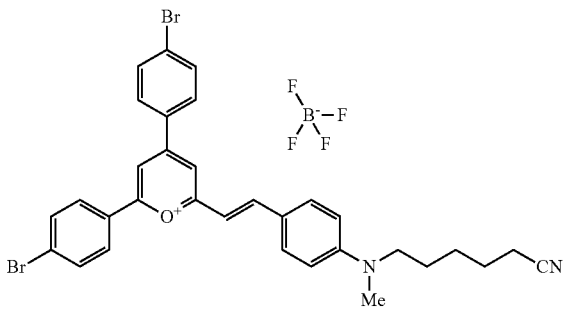 [SMILES: CN(CCCCCC#N)c1ccc(/C=C/c2cc(-c3ccc(Br)cc3)cc(-c3ccc(Br)cc3)[o+]2)cc1 ; F[B-](F)(F)F]

19TT. Compound 3jc21: (E)-2,4-bis(4-bromophenyl)-6-(4-((2-cyanoethyl)(methyl)amino)styryl)-1-phenylpyridin-1-ium boron tetrafluoride salt

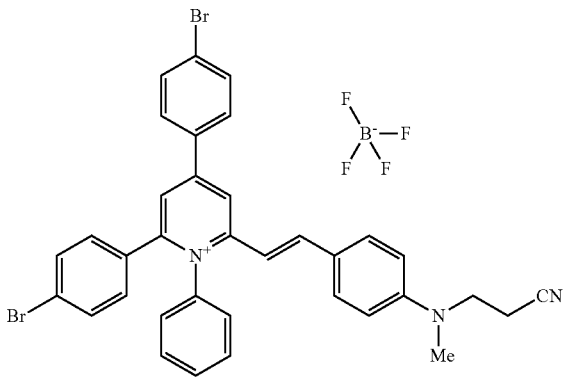 [SMILES: CN(CCC#N)c1ccc(/C=C/c2cc(-c3ccc(Br)cc3)cc(-c3ccc(Br)cc3)[n+]2-c2ccccc2)cc1 ; F[B-](F)(F)F]

19UU. Compound 3jc24-1: (E)-2,4-bis(4-bromophenyl)-6-(4-((3-cyanopropyl)(methyl)amino)styryl)-1-phenylpyridin-1-ium boron tetrafluoride salt

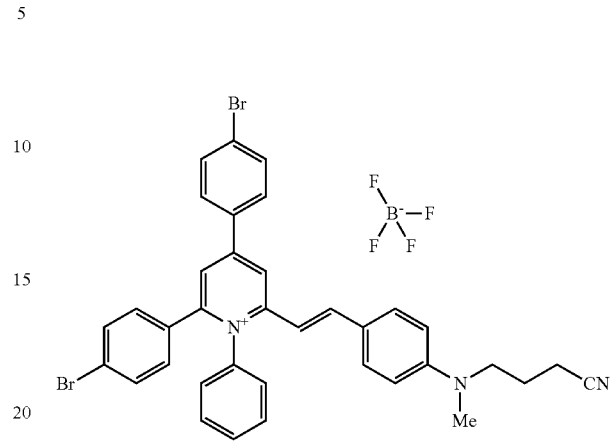

19VV. Compound 3jc24-2: (E)-2,4-bis(4-bromophenyl)-6-(4-((4-cyanobutyl)(methyl)amino)styryl)-1-phenylpyridin-1-ium boron tetrafluoride salt

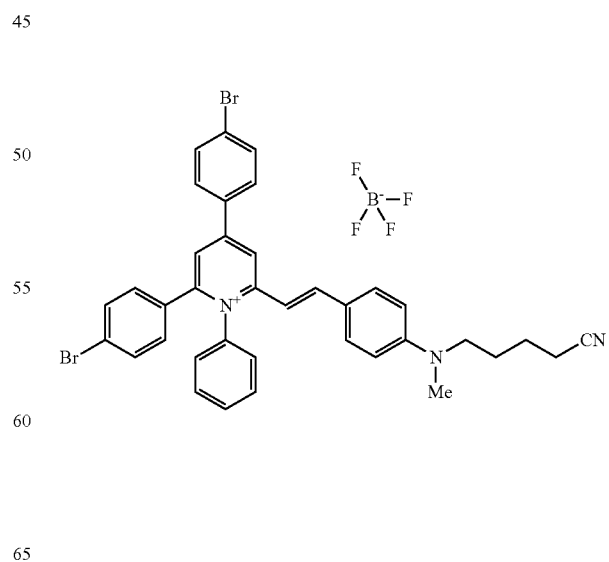

TABLE 17
Structures of Small Molecule Lipid II Binders.
| 19A | 2jc39-1 | 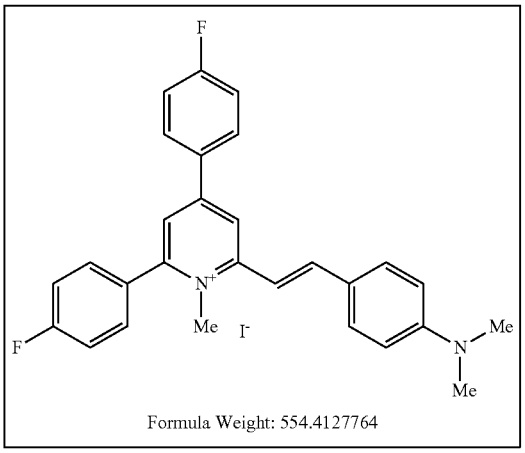 [SMILES: CN(C)c1ccc(/C=C/c2cc(-c3ccc(F)cc3)cc(-c3ccc(F)cc3)[n+]2C)cc1 ; [I-]] |
| 19B | 2jc39-2 | 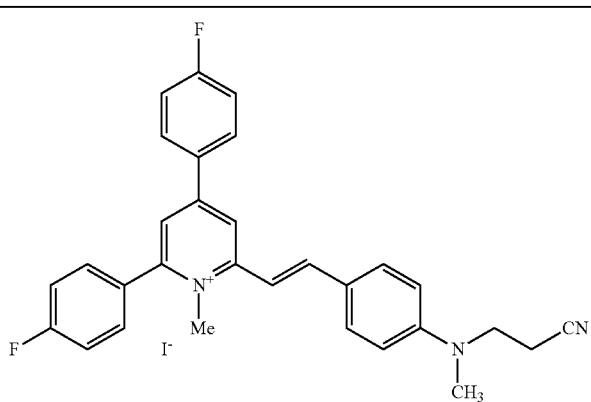 |
| 19C | 2jc39-3 | 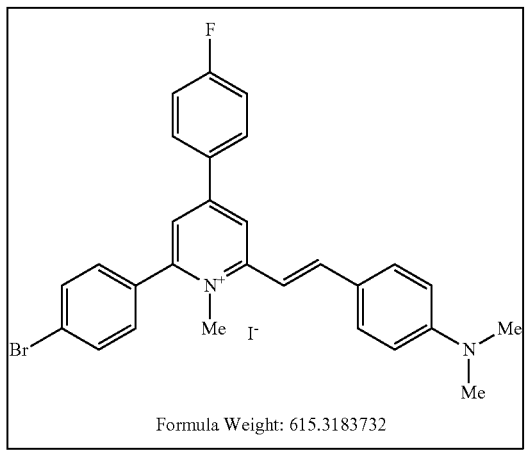 |

TABLE 17-continued
Structures of Small Molecule Lipid II Binders.
19D  2jc39-4
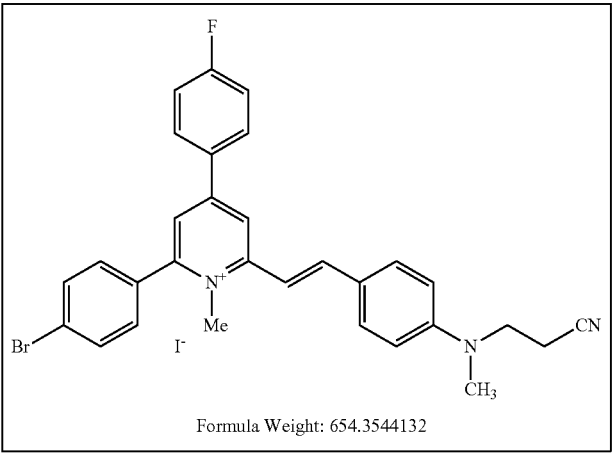 [SMILES: CN(CCC#N)c1ccc(/C=C/c2cc(-c3ccc(F)cc3)cc(-c3ccc(Br)cc3)[n+]2C)cc1 ; [I-]]
Formula Weight: 654.3544132
19E  2jc43-1
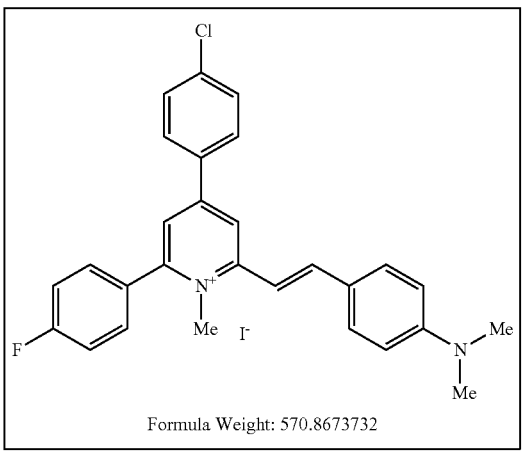 [SMILES: CN(C)c1ccc(/C=C/c2cc(-c3ccc(Cl)cc3)cc(-c3ccc(F)cc3)[n+]2C)cc1 ; [I-]]
Formula Weight: 570.8673732
19F  2jc43-2
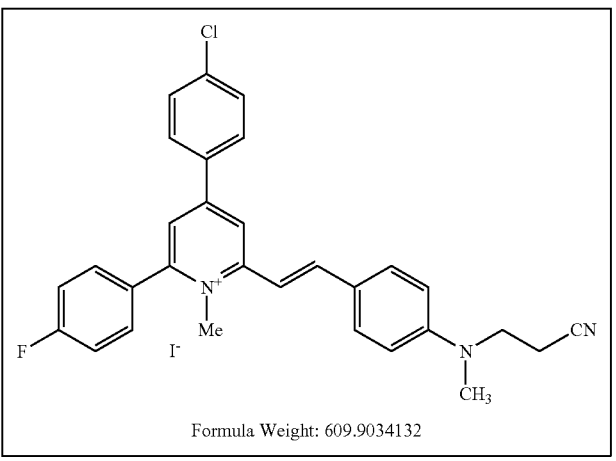 [SMILES: CN(CCC#N)c1ccc(/C=C/c2cc(-c3ccc(Cl)cc3)cc(-c3ccc(F)cc3)[n+]2C)cc1 ; [I-]]
Formula Weight: 609.9034132

TABLE 17-continued
Structures of Small Molecule Lipid II Binders.
19G  2jc43-3
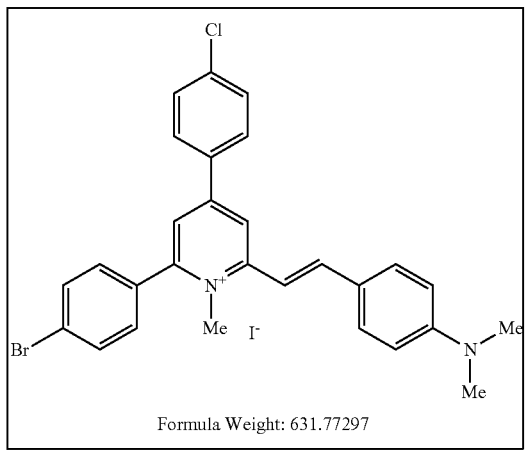 [SMILES: CN(C)c1ccc(/C=C/c2cc(-c3ccc(Cl)cc3)cc(-c3ccc(Br)cc3)[n+]2C)cc1 ; [I-]]
Formula Weight: 631.77297
19H  2jc43-4
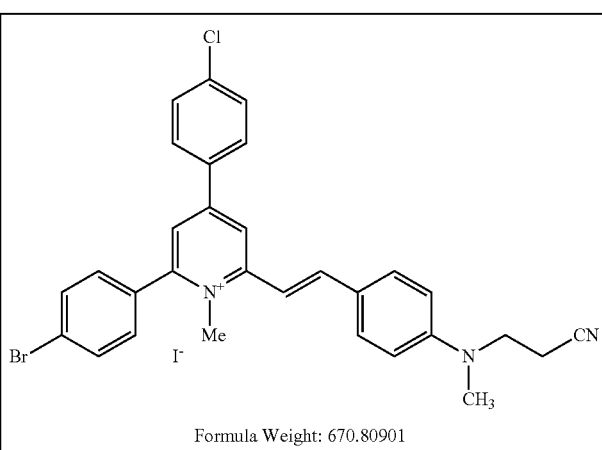
Formula Weight: 670.80901
19I  3jc01-1
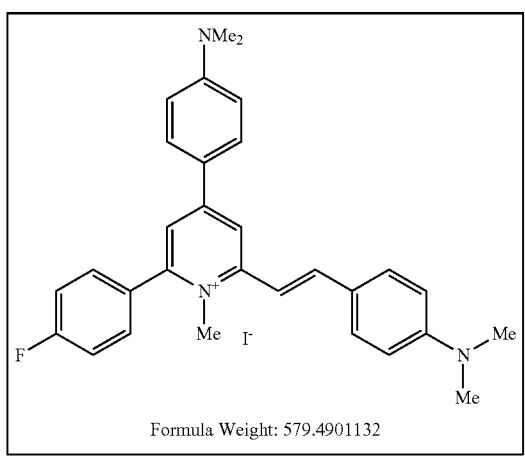 [SMILES: CN(C)c1ccc(/C=C/c2cc(-c3ccc(N(C)C)cc3)cc(-c3ccc(F)cc3)[n+]2C)cc1 ; [I-]]
Formula Weight: 579.4901132

TABLE 17-continued
Structures of Small Molecule Lipid II Binders.
19J  3jc01-2
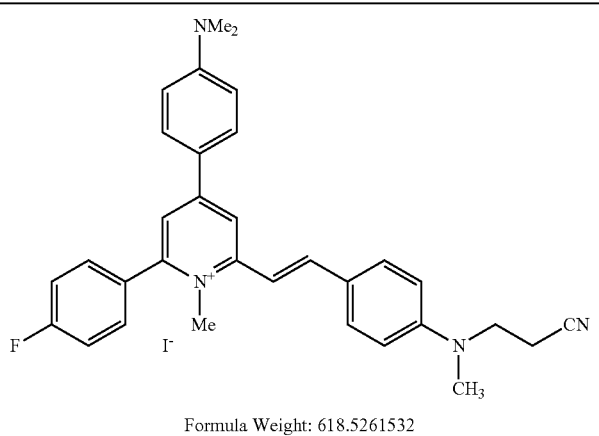
Formula Weight: 618.5261532
19K  3jc01-3
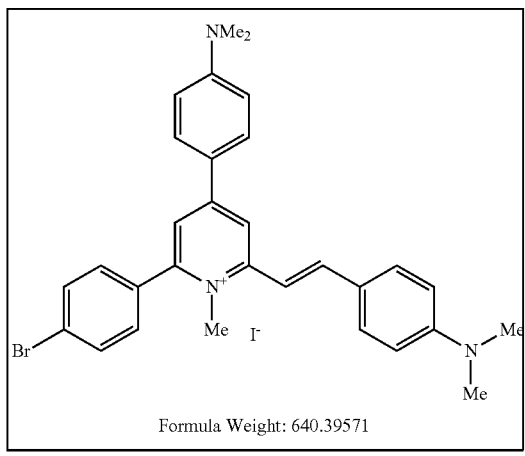 [SMILES: CN(C)c1ccc(/C=C/c2cc(-c3ccc(N(C)C)cc3)cc(-c3ccc(Br)cc3)[n+]2C)cc1 ; [I-]]
Formula Weight: 640.39571
19L  3jc01-4
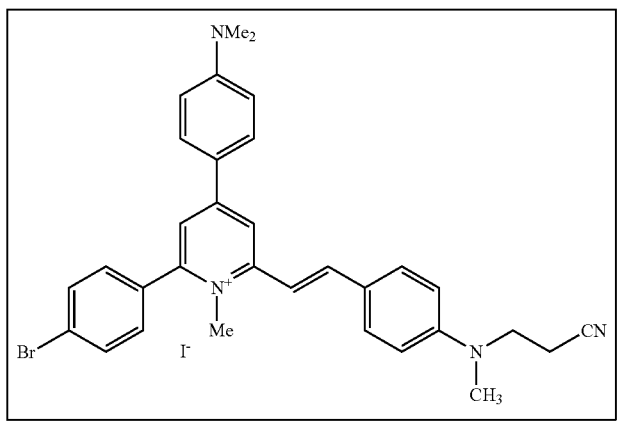 [SMILES: CN(C)c1ccc(-c2cc(/C=C/c3ccc(N(C)CCC#N)cc3)[n+](C)c(-c3ccc(Br)cc3)c2)cc1 ; [I-]]

TABLE 17-continued
Structures of Small Molecule Lipid II Binders.
19M  3jc01-5
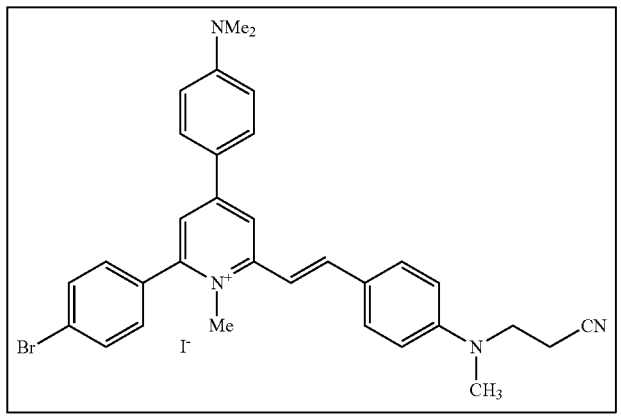 [SMILES: CN(C)c1ccc(-c2cc(/C=C/c3ccc(N(C)CCC#N)cc3)[n+](C)c(-c3ccc(Br)cc3)c2)cc1 ; [I-]]
19N  3jc01-6
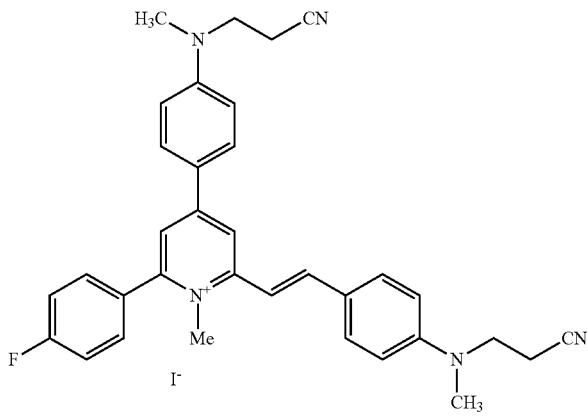
Formula Weight: 657.5621932
19O  3jc01-7
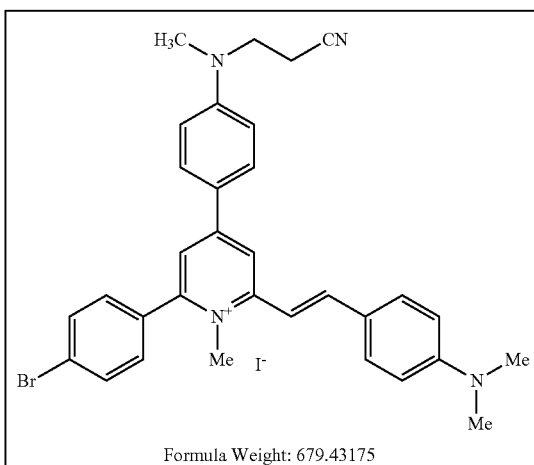
Formula Weight: 679.43175

TABLE 17-continued
Structures of Small Molecule Lipid II Binders.
19P  3jc01-8
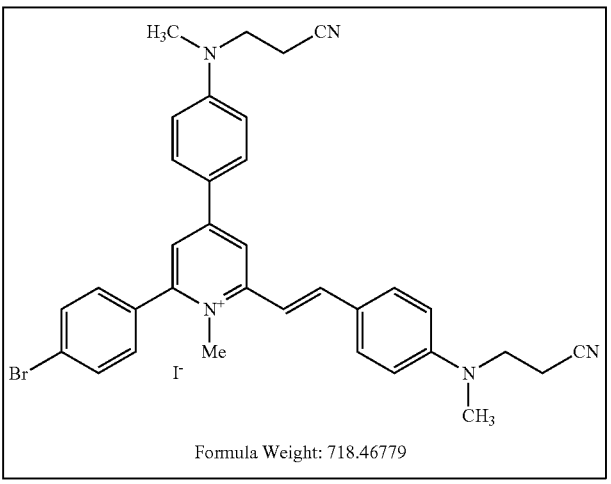 [SMILES: CN(CCC#N)c1ccc(/C=C/c2cc(-c3ccc(N(C)CCC#N)cc3)cc(-c3ccc(Br)cc3)[n+]2C)cc1 ; [I-]]
Formula Weight: 718.46779
19V  3jc07-9
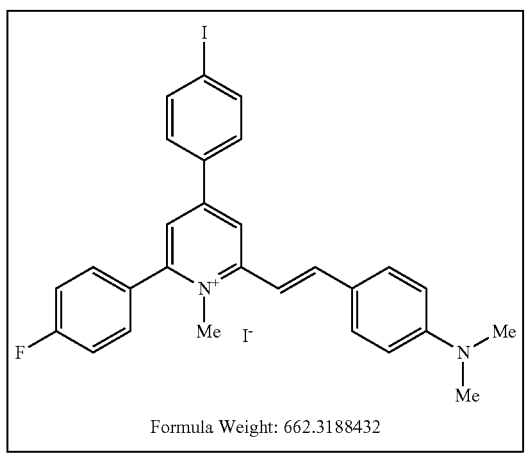 [SMILES: CN(C)c1ccc(/C=C/c2cc(-c3ccc(I)cc3)cc(-c3ccc(F)cc3)[n+]2C)cc1 ; [I-]]
Formula Weight: 662.3188432
19W  3jc07-10
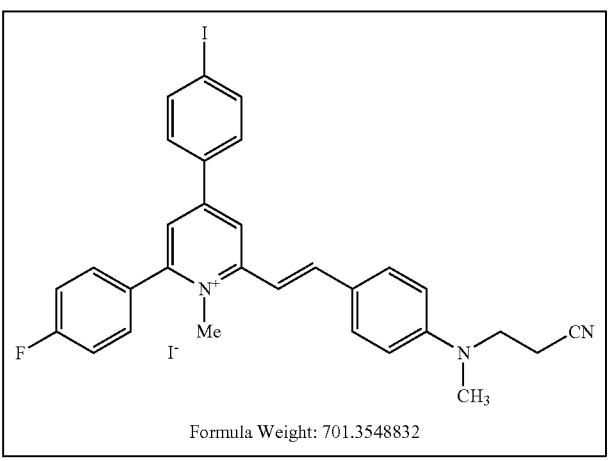 [SMILES: CN(CCC#N)c1ccc(/C=C/c2cc(-c3ccc(I)cc3)cc(-c3ccc(F)cc3)[n+]2C)cc1 ; [I-]]
Formula Weight: 701.3548832

TABLE 17-continued
Structures of Small Molecule Lipid II Binders.
19X  3jc07-11
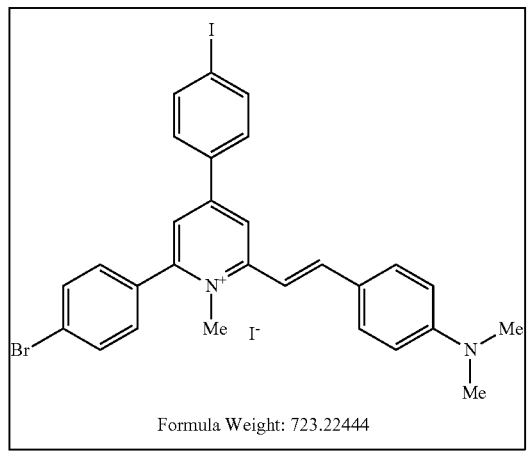
Formula Weight: 723.22444
19Y  3jc07-12
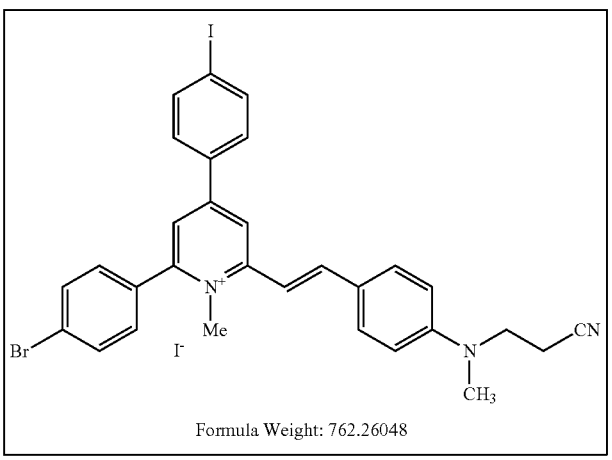 [SMILES: CN(CCC#N)c1ccc(/C=C/c2cc(-c3ccc(I)cc3)cc(-c3ccc(Br)cc3)[n+]2C)cc1 ; [I-]]
Formula Weight: 762.26048
19O  3jc07-1
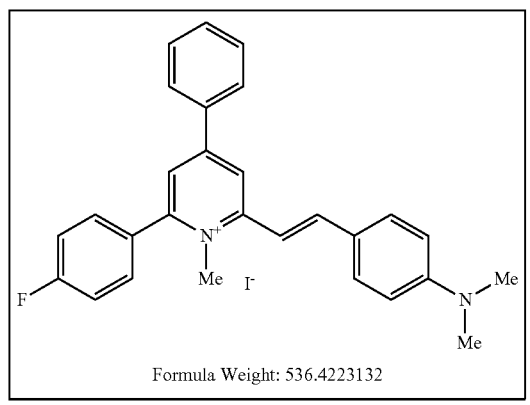 [SMILES: CN(C)c1ccc(/C=C/c2cc(-c3ccccc3)cc(-c3ccc(F)cc3)[n+]2C)cc1 ; [I-]]
Formula Weight: 536.4223132

TABLE 17-continued
Structures of Small Molecule Lipid II Binders.
| 19P | 3jc07-2 | 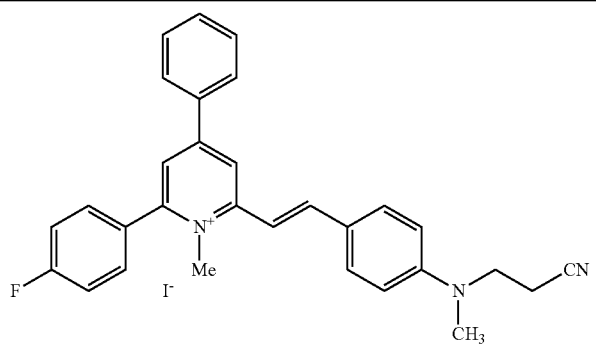 Formula Weight: 575.4583532 |
| 19Q | 3jc07-3 | 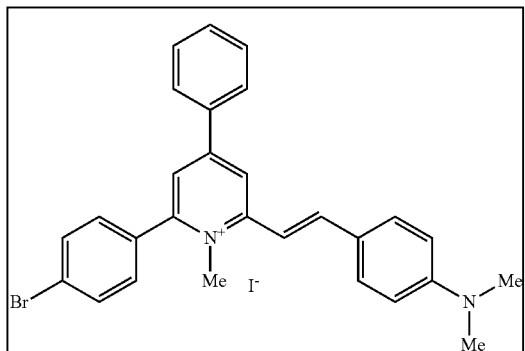 Formula Weight: 597.32791 |
| 19R | 3jc07-4 | 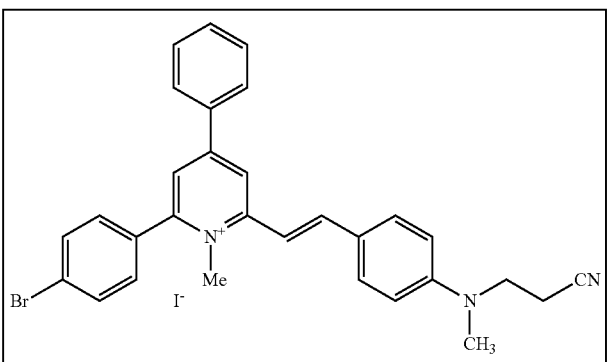 Formula Weight: 636.36395 |

TABLE 17-continued
Structures of Small Molecule Lipid II Binders.
19S  3jc07-5
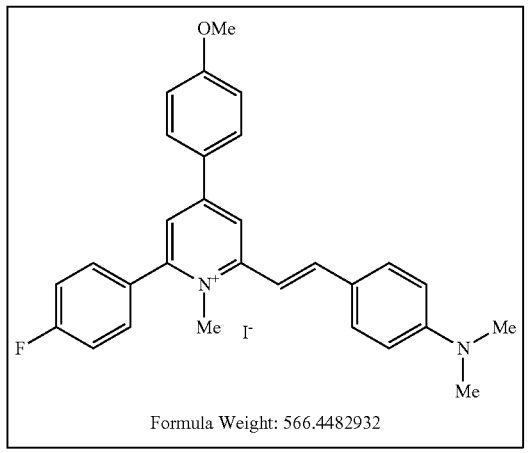
19T  3jc07-6
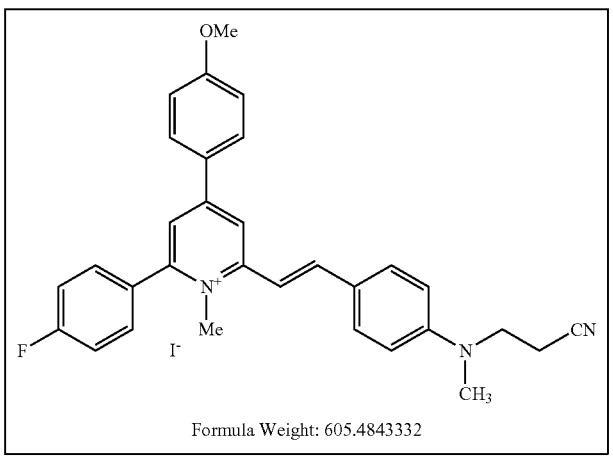 [SMILES: COc1ccc(-c2cc(/C=C/c3ccc(N(C)CCC#N)cc3)[n+](C)c(-c3ccc(F)cc3)c2)cc1 ; [I-]]
19U  3jc07-7
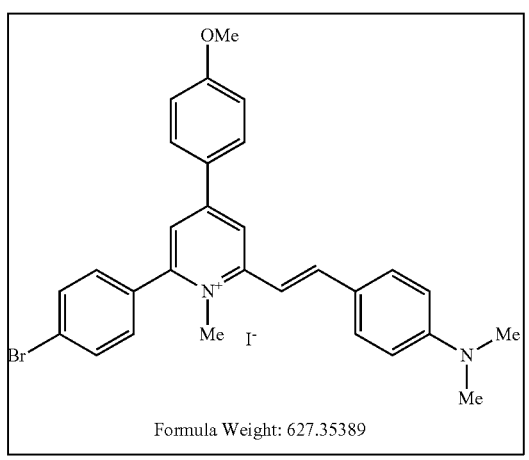 [SMILES: COc1ccc(-c2cc(/C=C/c3ccc(N(C)C)cc3)[n+](C)c(-c3ccc(Br)cc3)c2)cc1 ; [I-]]

TABLE 17-continued
Structures of Small Molecule Lipid II Binders.
19ZZ  3jc07-8
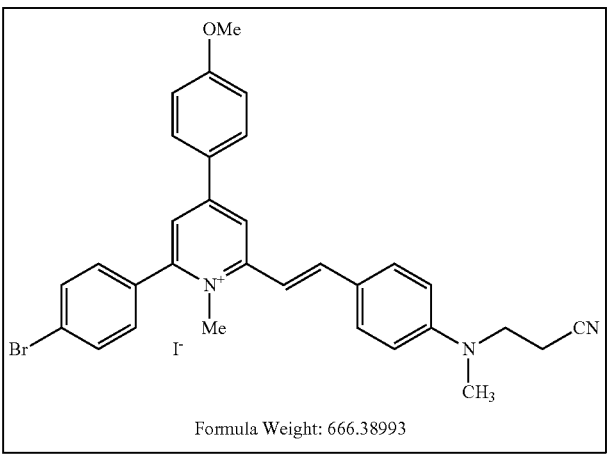 [SMILES: COc1ccc(-c2cc(/C=C/c3ccc(N(C)CCC#N)cc3)[n+](C)c(-c3ccc(Br)cc3)c2)cc1 ; [I-]]
Formula Weight: 666.38993
19ZZ  3jc09-1
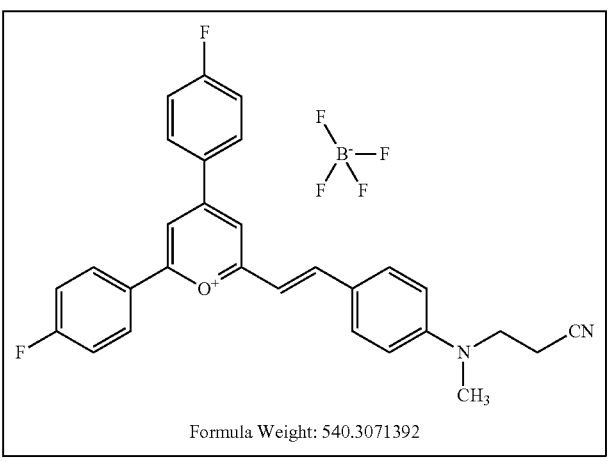 [SMILES: CN(CCC#N)c1ccc(/C=C/c2cc(-c3ccc(F)cc3)cc(-c3ccc(F)cc3)[o+]2)cc1 ; F[B-](F)(F)F]
Formula Weight: 540.3071392
19AA  3jc09-2
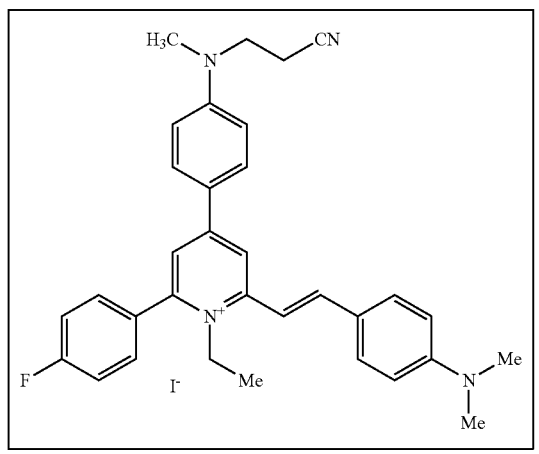 [SMILES: CC[n+]1c(/C=C/c2ccc(N(C)C)cc2)cc(-c2ccc(N(C)CCC#N)cc2)cc1-c1ccc(F)cc1 ; [I-]]

TABLE 17-continued
Structures of Small Molecule Lipid II Binders.
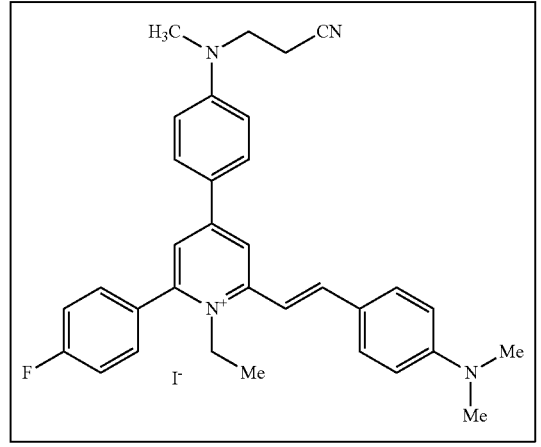 [SMILES: CC[n+]1c(/C=C/c2ccc(N(C)C)cc2)cc(-c2ccc(N(C)CCC#N)cc2)cc1-c1ccc(F)cc1 ; [I-]]
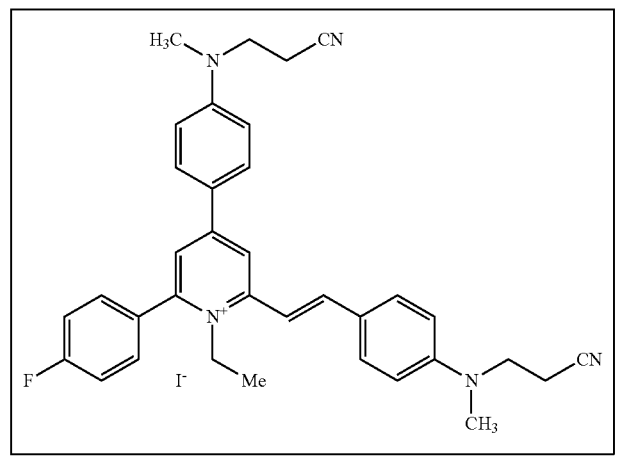 [SMILES: CC[n+]1c(/C=C/c2ccc(N(C)CCC#N)cc2)cc(-c2ccc(N(C)CCC#N)cc2)cc1-c1ccc(F)cc1 ; [I-]]
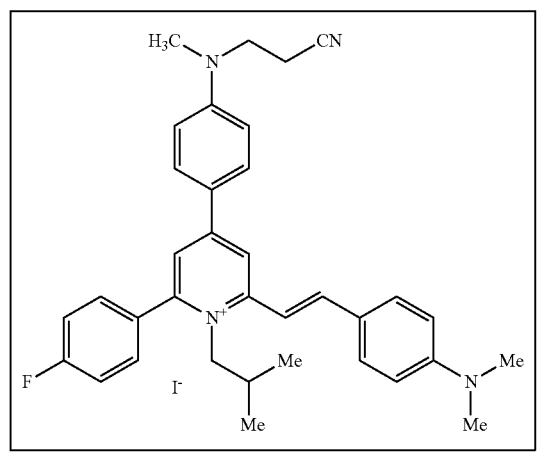 [SMILES: CC(C)C[n+]1c(/C=C/c2ccc(N(C)C)cc2)cc(-c2ccc(N(C)CCC#N)cc2)cc1-c1ccc(F)cc1 ; [I-]]

TABLE 17-continued

Structures of Small Molecule Lipid II Binders.

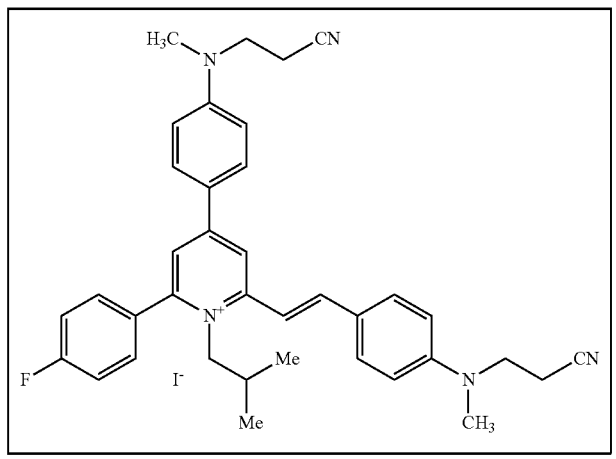 [SMILES: CC(C)C[n+]1c(/C=C/c2ccc(N(C)CCC#N)cc2)cc(-c2ccc(N(C)CCC#N)cc2)cc1-c1ccc(F)cc1 ; [I-]]

TABLE 18

Antibacterial Activity of Small Molecule Lipid II Binders.

| Compound Code | Compound Name | NMR | SA USA300 | EF 15951 |
|---|---|---|---|---|
| 19A | 2jc39-1 | Yes | 4 | 4 |
| 19B | 2jc39-2 | Yes | 16 | 16 |
| 19C | 2jc39-3 | Yes | 4 | 4 |
| 19D | 2jc39-4 | Yes | 16 | 16 |
| 19E | 2jc43-1 | Yes | 4 | 2 |
| 19F | 2jc43-2 | Yes | 2 | 2 |
| 19G | 2jc43-3 | Yes | 2 | 2 |
| 19H | 2jc43-4 | Yes | 32 | 16 |
| 19I | 3jc01-1 | Yes | 2 | 1 |
| 19J | 3jc01-2 | Yes | 32 | 16 |
| 19K | 3jc01-3 | Yes | 1 | 1 |
| 19L | 3jc01-4 | yes | 32 | 32 |
| 19M | 3jc01-5 | Yes | 1 | 4 |
| 19N | 3jc01-6 | Yes | 1 | 8 |
|  | 3jc01-7 | Yes | 1 | 2 |
|  | 3jc01-8 | Yes | 1 | 2 |
| 19V | 3jc07-9 | ND | 4 | ND |
| 19W | 3jc07-10 | ND | 32 | ND |
| 19X | 3jc07-11 | ND | 4 | ND |
| 19Y | 3jc07-12 | ND | 32 | ND |
| 19O | 3jc07-1 | ND | 4 | ND |
| 19P | 3jc07-2 | ND | 32 | ND |
| 19Q | 3jc07-3 | ND | 2 | ND |
| 19R | 3jc07-4 | ND | 32 | ND |
| 19S | 3jc07-5 | ND | 1 | ND |
| 19T | 3jc07-6 | ND | 16 | ND |
| 19U | 3jc07-7 | ND | 1 | ND |
|  | 3jc07-8 | ND | 16 | ND |
| 19Z | 3jc09-1 | ND | >64 | ND |
| 19AA | 3jc09-2 | ND | >64 | ND |

MIC SA USA300 = minimum inhibitory concentration *Staphylococcus aureus* USA 300 strain; MIC EF 15951 = minimum inhibitory concentration *Enterococcus faecalis* 15951.

Example 20: Additional Compound Structures

Selected compounds also were tested to confirm the structure by NMR, as indicated. Results are provided in Table 19.

TABLE 19

Additional Compound Structures.

M1a 2jc31-2 NMR not done

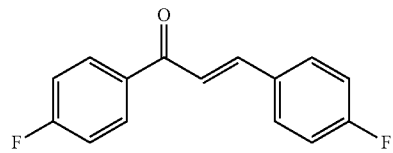

Formula Weight: 244.2361064

M1b 2jc32 NMR not done

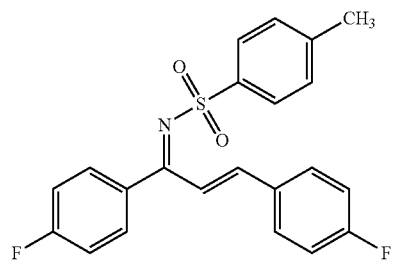

Formula Weight: 397.4376864

TABLE 19-continued
Additional Compound Structures.
M1c 2jc33 NMR not done
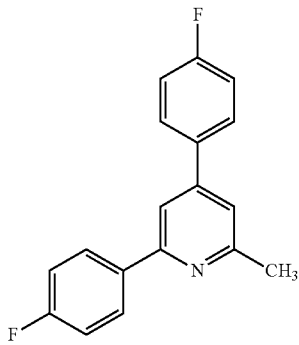
Formula Weight: 281.2993264
M1d 2jc36 NMR not done
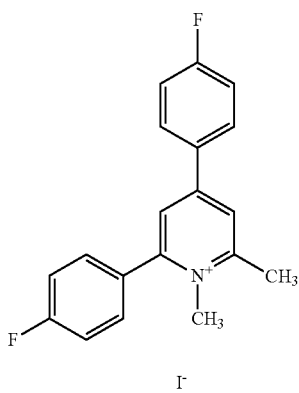
Formula Weight: 423.2383164
19A 2jc39-1 NMR confirmed
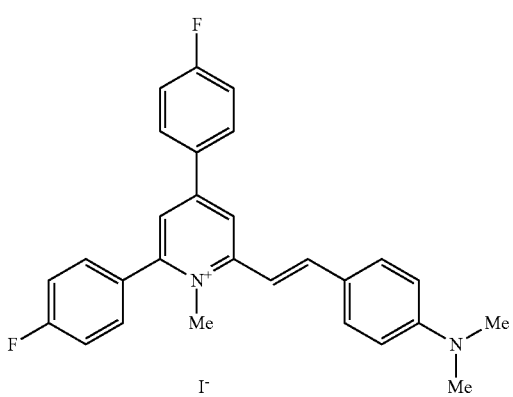
Formula Weight: 554.4127764
TABLE 19-continued
Additional Compound Structures.
19B 2jc39-2 NMR confirmed
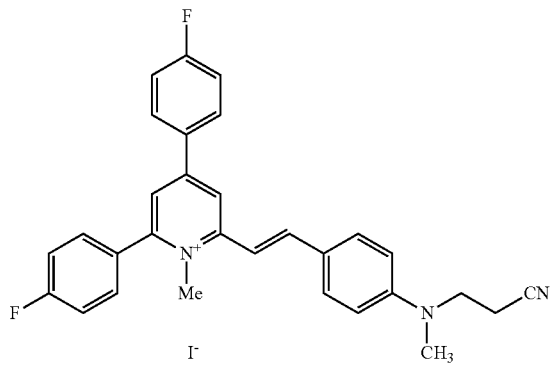
Formula Weight: 593.4488164
M2a 2jc31-1 NMR not done
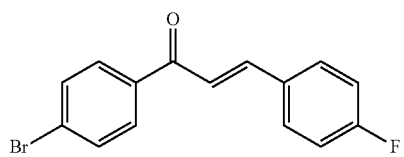
Formula Weight: 305.1417032
M2b 2jc35-1 NMR not done
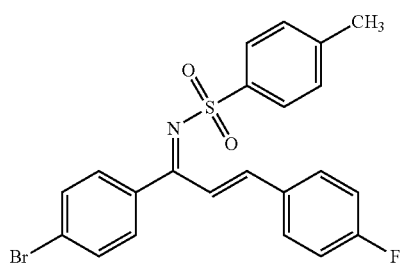
Formula Weight: 458.3432832
M2c 2jc37 NMR not done
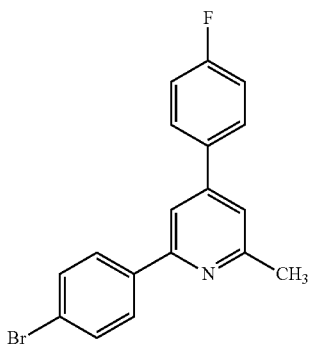
Formula Weight: 342.2049232

TABLE 19-continued
Additional Compound Structures.
M2d 2jc38 NMR not done
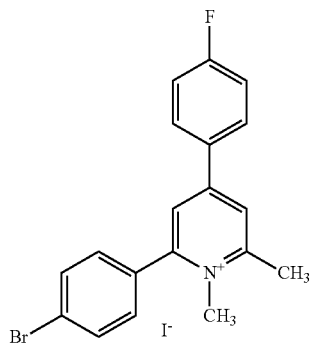
Formula Weight: 484.1439132
19C 2jc39-3 NMR confirmed
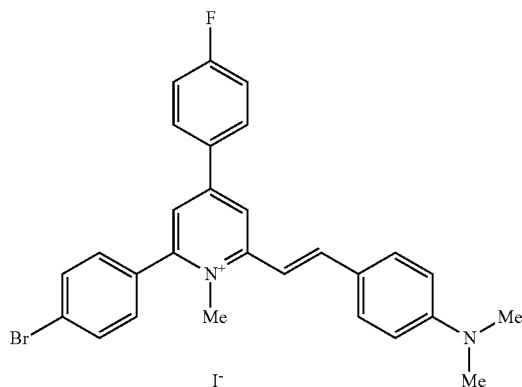
Formula Weight: 615.3183732
19D 2jc39-4 NMR confirmed
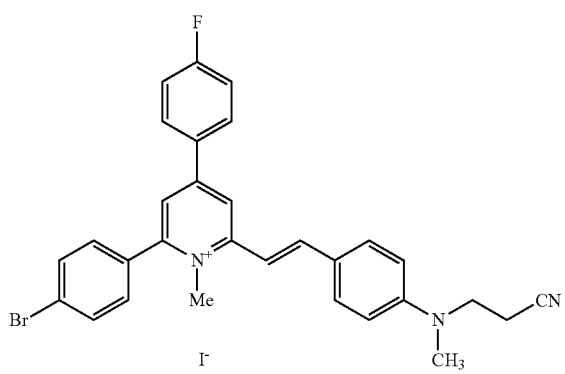
Formula Weight: 654.3544132
TABLE 19-continued
Additional Compound Structures.
M3a 2jc31-4 NMR not done
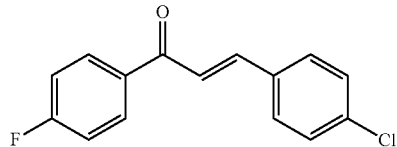
Formula Weight: 260.6907032
M3b 2jc40-1 NMR not done
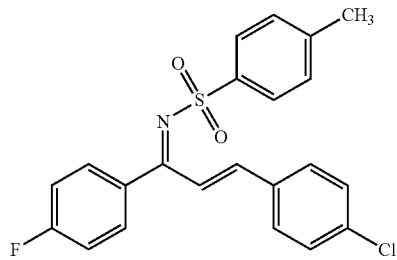
Formula Weight: 413.8922832
M3c 2jc41-1 NMR not done
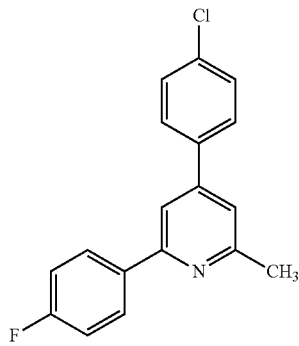
Formula Weight: 297.7539232
M3c 2jc42-1 NMR not done
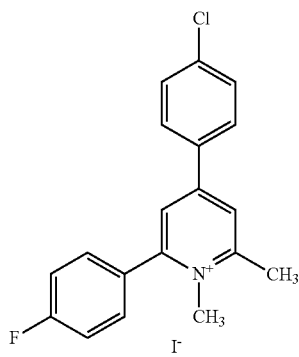
Formula Weight: 439.6929132

TABLE 19-continued
Additional Compound Structures.
19E 2jc43-1 NMR confirmed
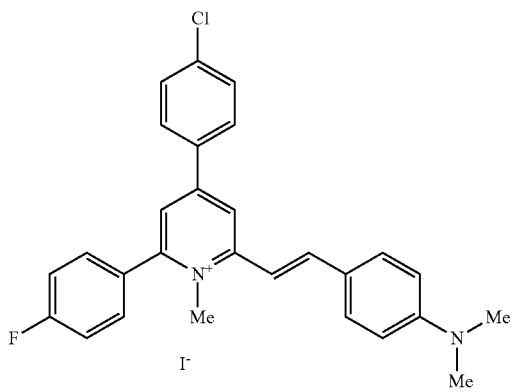
Formula Weight: 570.8673732
19F 2jc43-2 NMR confirmed
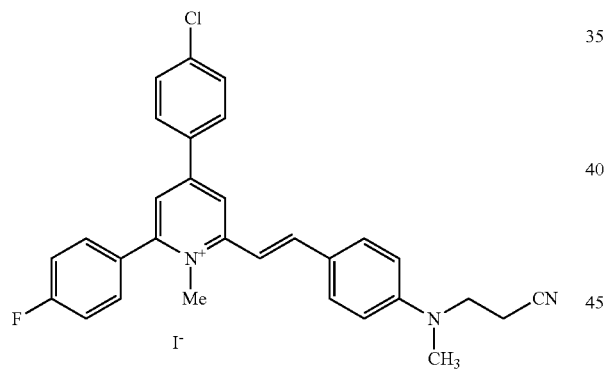
Formula Weight: 609.9034132
M14a 2jc31-3 NMR not done
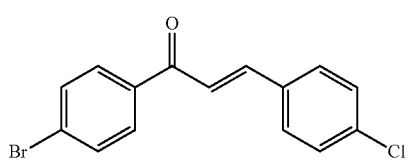
Formula Weight: 321.5963
TABLE 19-continued
Additional Compound Structures.
M4b 2jc40-2 NMR not done
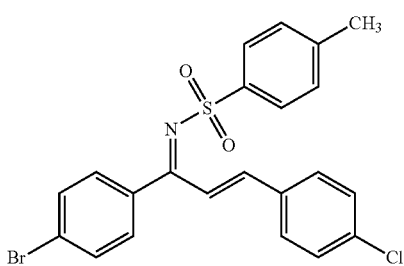
Formula Weight: 474.79788
M4c 2jc41-2 NMR not done
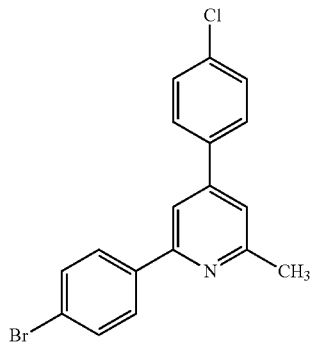
Formula Weight: 358.65952
M4d 2jc42-2 NMR not done
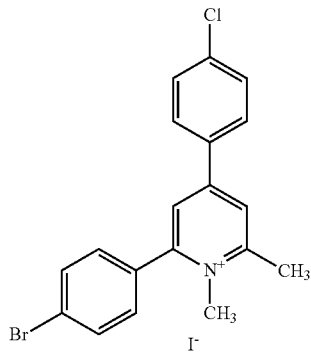
Formula Weight: 500.59851

TABLE 19-continued
Additional Compound Structures.
19G 2jc43-3 NMR confirmed
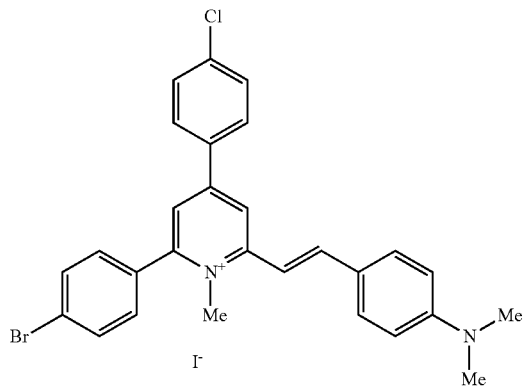
Formula Weight: 631.77297
19H 2jc43-4 NMR confirmed
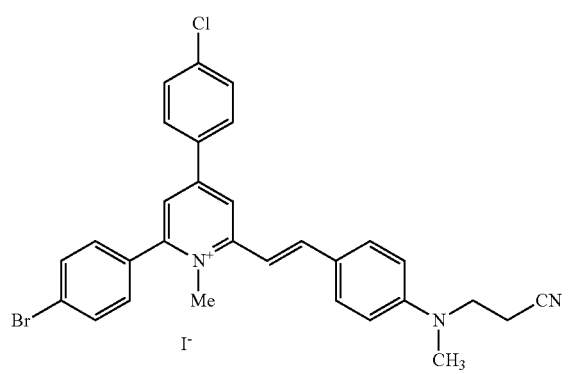
Formula Weight: 670.80901
M5a 2jc44-1 NMR not done
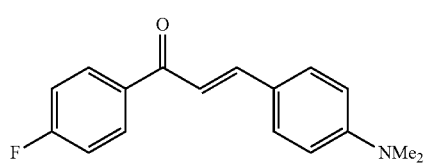
Formula Weight: 269.3134432
TABLE 19-continued
Additional Compound Structures.
M5b 2jc45-1 NMR not done
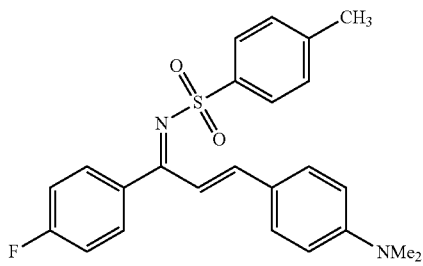
Formula Weight: 422.5150232
M5c 2jc46-1 NMR not done
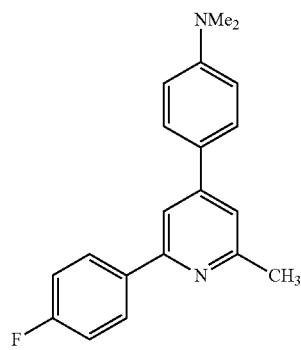
Formula Weight: 306.3766632
M5d 2jc48-1 NMR confirmed
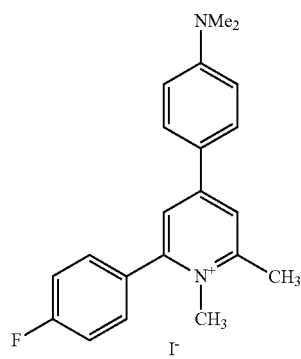
Formula Weight: 448.3156532

TABLE 19-continued
Additional Compound Structures.
19I 3jc01-1 NMR confirmed
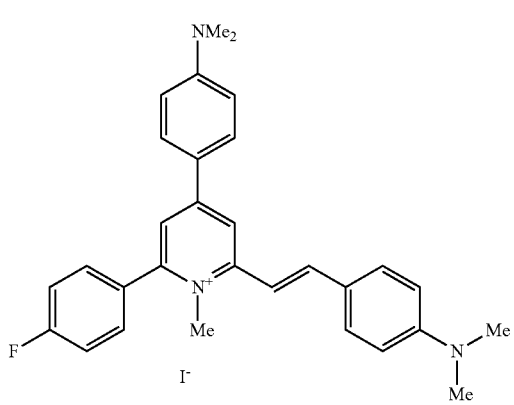
Formula Weight: 579.4901132
19J 3jc01-2 NMR confirmed
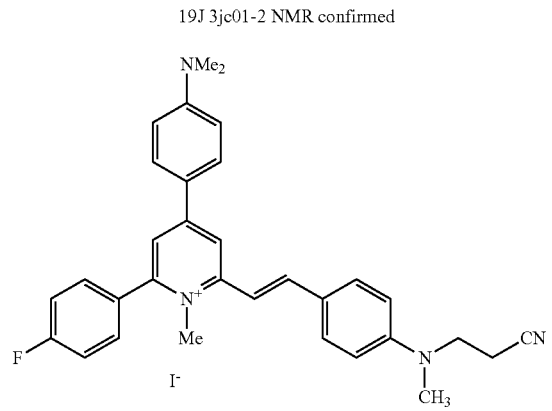
Formula Weight: 618.5261532
M6a 2jc44-2 NMR not done
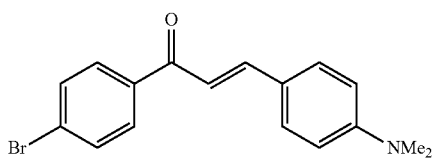
Formula Weight: 330.21904
TABLE 19-continued
Additional Compound Structures.
M6b 2jc45-2 NMR not done
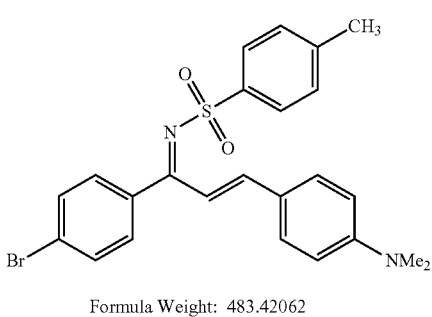
Formula Weight: 483.42062
M6c 2jc46-2 NMR not done
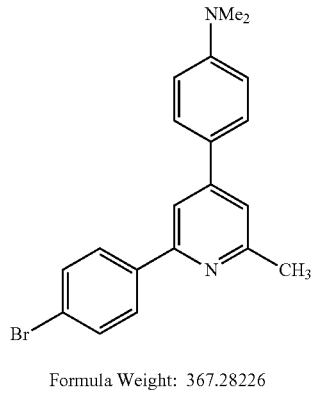
Formula Weight: 367.28226
M6d 2jc48-2 NMR confirmed
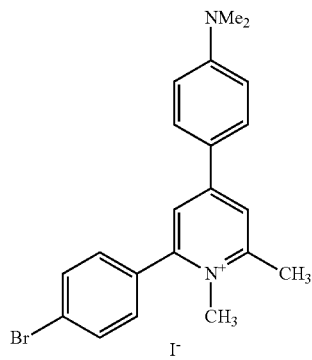
Formula Weight: 509.22125

TABLE 19-continued
Additional Compound Structures.
19K 3jc01-3 NMR confirmed
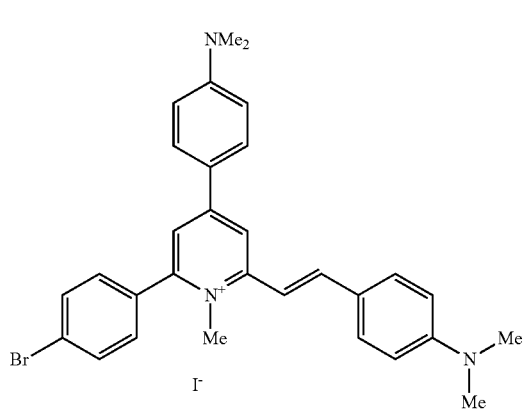
Formula Weight: 640.39571
19L 3jc01-4 NMR confirmed
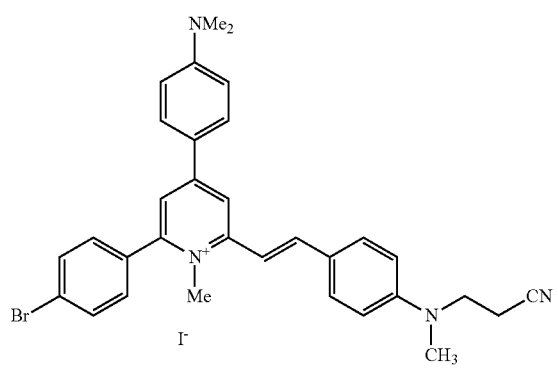
M7a 2jc44-3 NMR not done
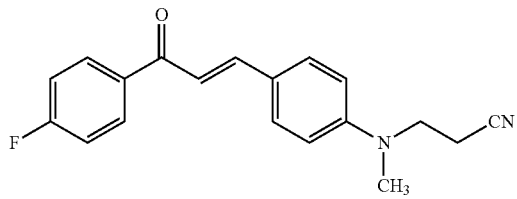
Formula Weight: 308.3494832
TABLE 19-continued
Additional Compound Structures.
M7b 2jc45-3 NMR not done
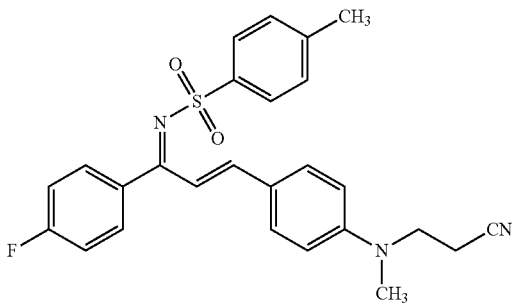
Formula Weight: 461.5510632
M7c 2jc47-1 NMR not done
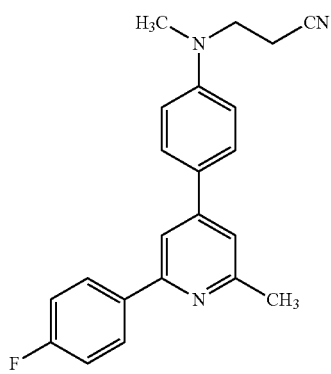
Formula Weight: 345.4127032
M7d 2jc48-3 NMR confirmed
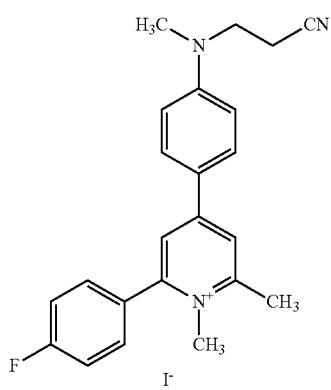
Formula Weight: 487.3516932

TABLE 19-continued
Additional Compound Structures.
19M 3jc01-5 NMR confirmed
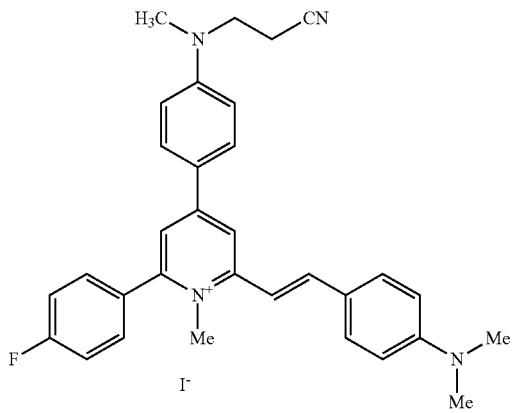
Formula Weight: 618.5261532
19N 3jc01-6 NMR confirmed
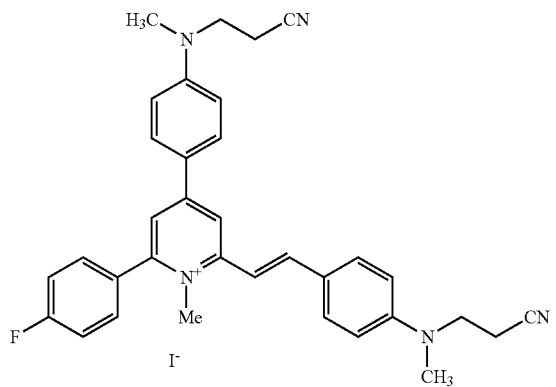
Formula Weight: 657.5621932
M8a 2jc44-4 NMR not done
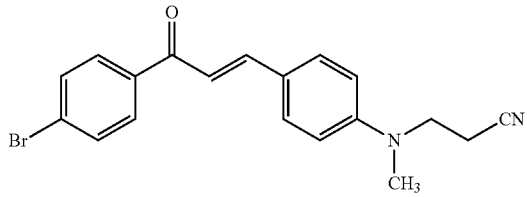
Formula Weight: 369.25508
TABLE 19-continued
Additional Compound Structures.
M8b 2jc45-4 NMR not done
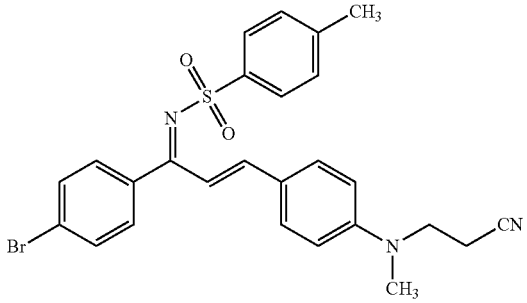
Formula Weight: 522.45666
M8c 2jc47-2 NMR not done
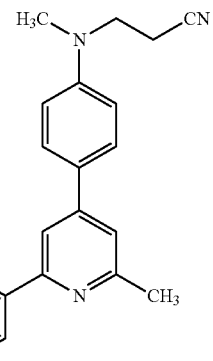
Formula Weight: 406.3183
M8d 2jc48-4 NMR confirmed
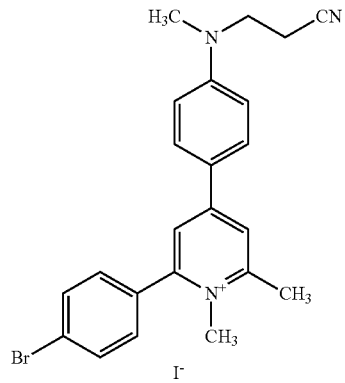
Formula Weight: 548.25729

TABLE 19-continued
Additional Compound Structures.
3jc01-7 NMR confirmed
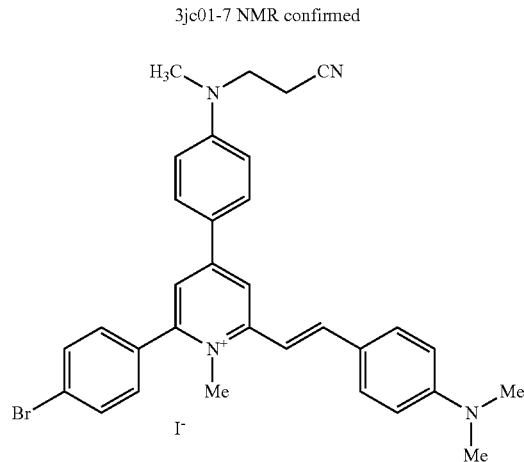
Formula Weight: 679.43175
3jc01-8 NMR confirmed
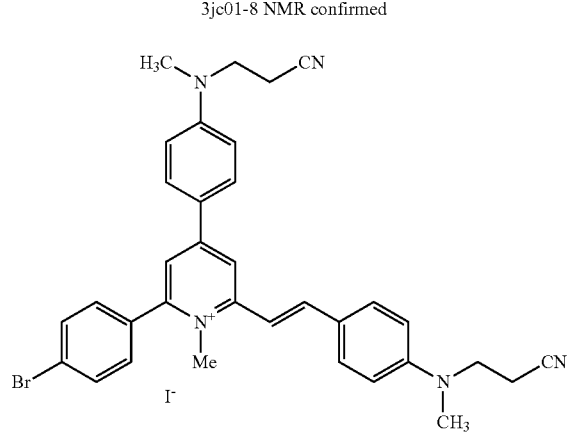
Formula Weight: 718.46779
M9a 2jc31-6 NMR not done
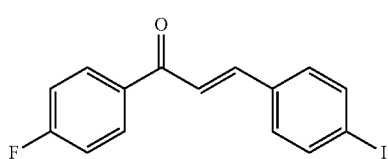
Formula Weight: 352.1421732
TABLE 19-continued
Additional Compound Structures.
M9b 3jc03-5 NMR not done
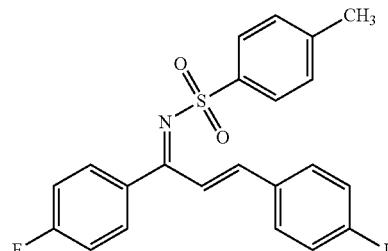
Formula Weight: 505.3437532
M9c 3jc04-5 NMR not done
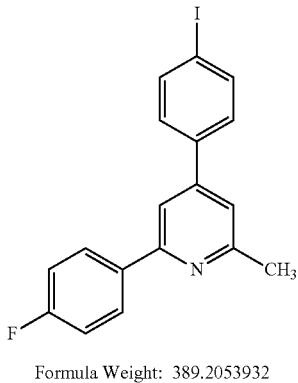
Formula Weight: 389.2053932
M9d 3jc05-5 NMR not done
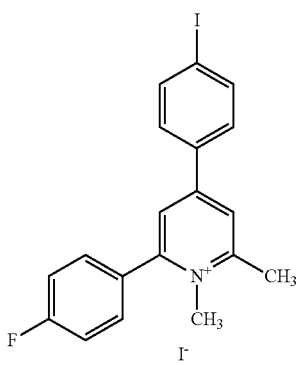
Formula Weight: 531.1443832

TABLE 19-continued
Additional Compound Structures.
19V 3jc07-9 NMR not done
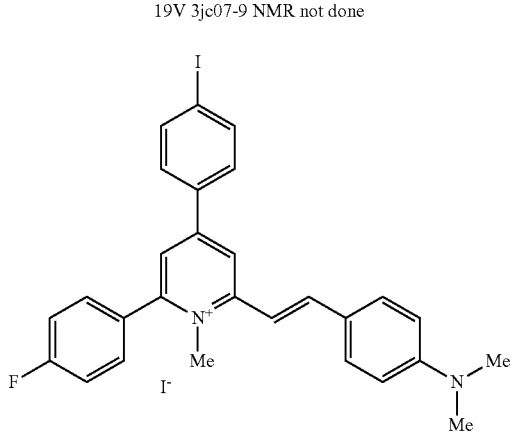
Formula Weight: 662.3188432
19W 3jc07-10 NMR not done
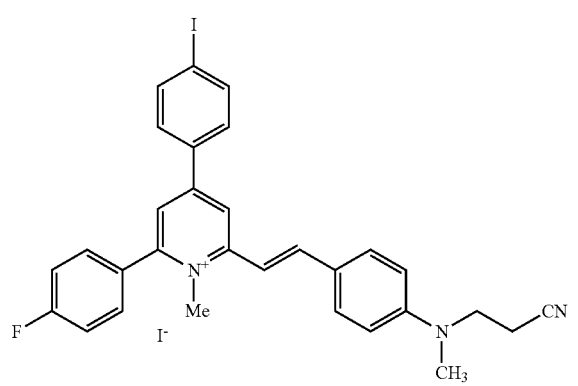
Formula Weight: 701.3548832
M10a 2jc31-5 NMR not done
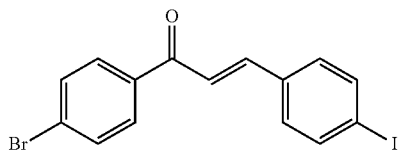
Formula Weight: 413.04777
TABLE 19-continued
Additional Compound Structures.
M10b 3jc03-6 NMR not done
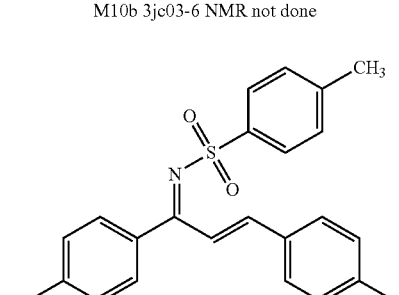
Formula Weight: 566.24935
M10c 3jc04-6 NMR not done
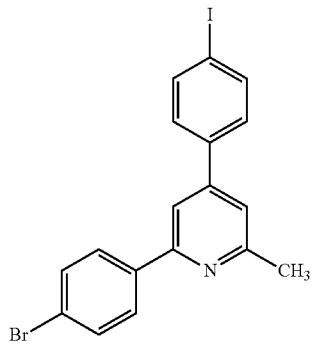
Formula Weight: 450.11099
M10d 3jc05-6 NMR not done
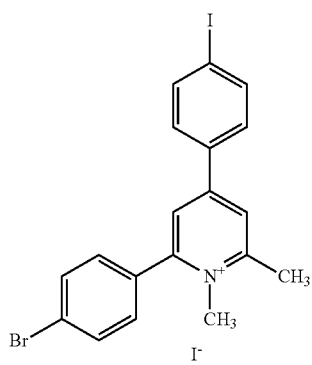
Formula Weight: 592.04998

TABLE 19-continued
Additional Compound Structures.
19X 3jc07-11 NMR not done
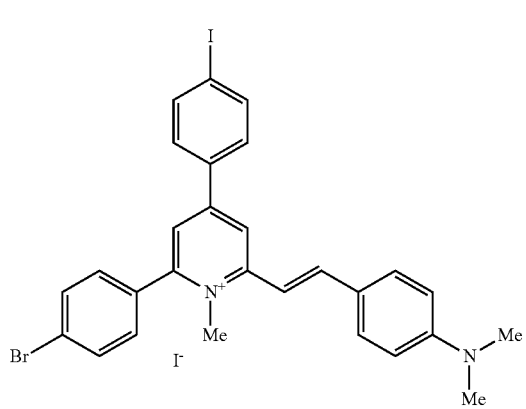
Formula Weight: 723.22444
19Y 3jc07-12 NMR not done
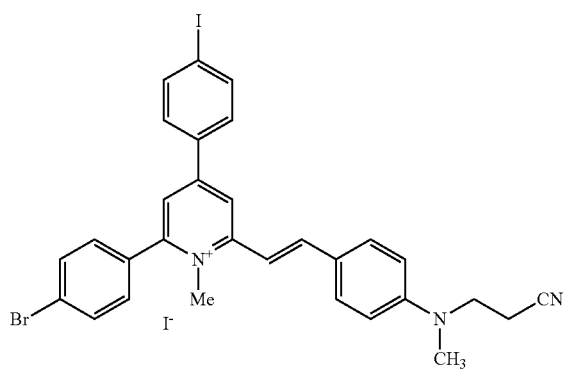
Formula Weight: 762.26048
M11a 3jc02-1 NMR not done
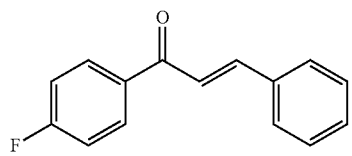
Formula Weight: 226.2456432
TABLE 19-continued
Additional Compound Structures.
M11b 3jc03-1 NMR not done
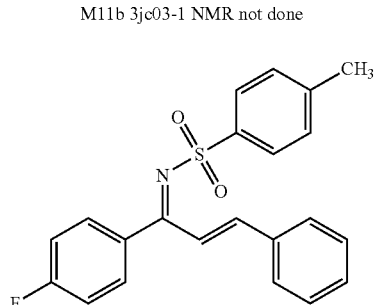
Formula Weight: 379.4472232
M11c 3jc04-1 NMR not done
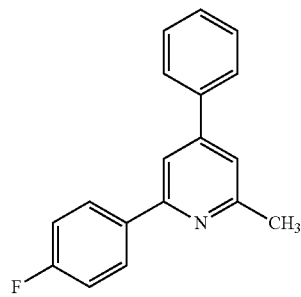
Formula Weight: 263.3088632
M11d 3jc05-1 NMR not done
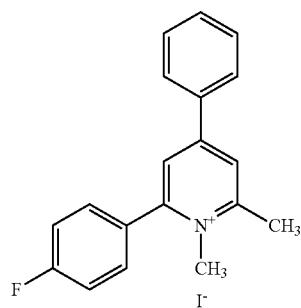
Formula Weight: 405.2478532

TABLE 19-continued
Additional Compound Structures.
19O 3jc07-1 NMR not done
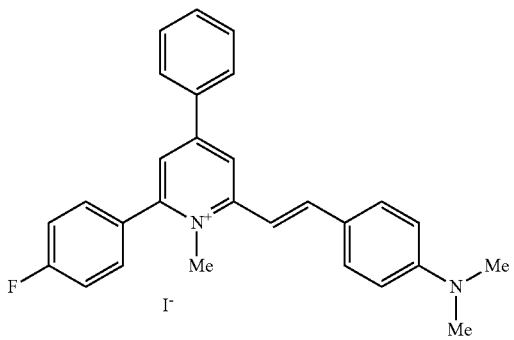
Formula Weight: 536.4223132
19P 3jc07-2 NMR not done
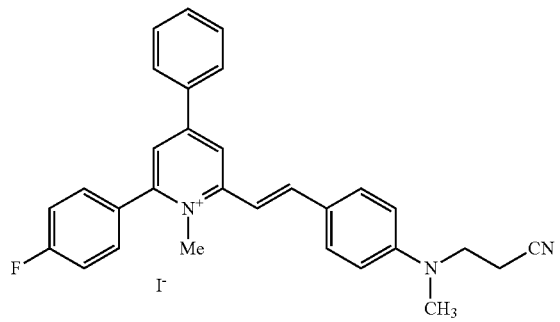
Formula Weight: 575.4583532
M12a 3jc02-2 NMR not done
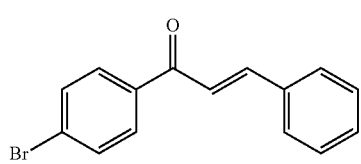
Formula Weight: 287.15124
M12b 3jc03-2 NMR not done
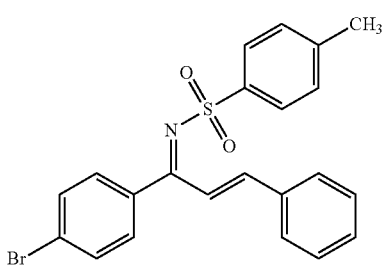
Formula Weight: 440.35282
TABLE 19-continued
Additional Compound Structures.
M12c 3jc04-2 NMR not done
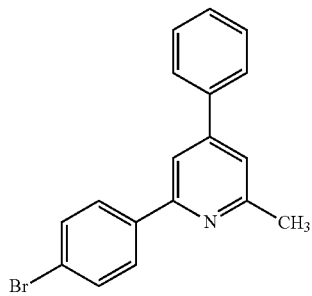
Formula Weight: 324.21446
M12d 3jc04-2 NMR not done
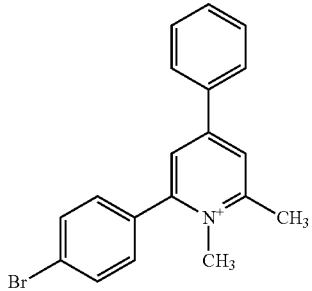
Formula Weight: 466.15345
19Q 3jc07-3 NMR not done
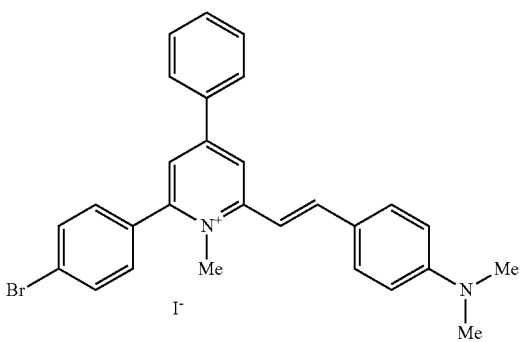
Formula Weight: 597.32791

TABLE 19-continued
Additional Compound Structures.
19R 3jc07-4 NMR not done
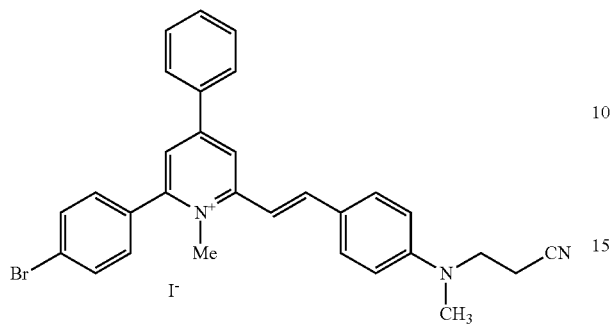
Formula Weight: 636.36395
M13a 3jc02-3 NMR not done
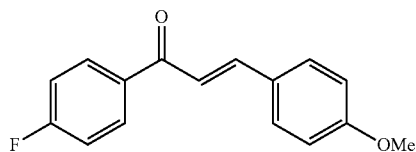
Formula Weight: 256.2716232
M13b 3jc03-3 NMR not done
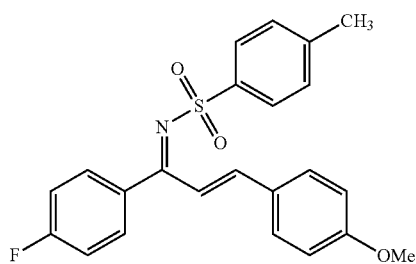
Formula Weight: 409.4732032
M13c 3jc04-3 NMR not done
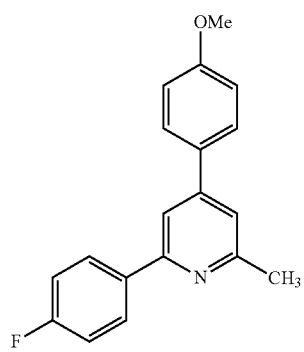
Formula Weight: 293.3348432
TABLE 19-continued
Additional Compound Structures.
M13d 3jc03-3 NMR not done
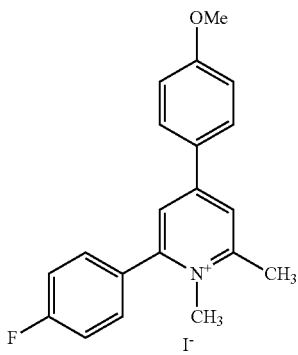
Formula Weight: 435.2738332
19S 3jc07-5 NMR not done
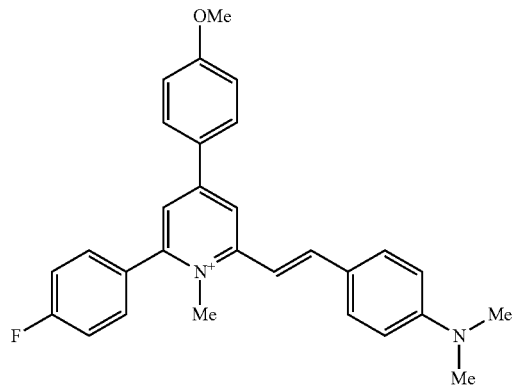
Formula Weight: 566.4482932
19T 3jc07-6 NMR not done
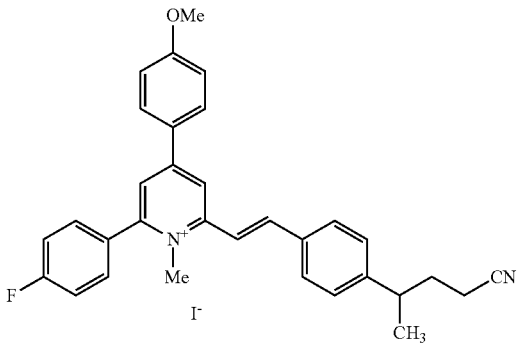
Formula Weight: 605.4843332

TABLE 19-continued

Additional Compound Structures.

M14a 3jc02-4 NMR not done

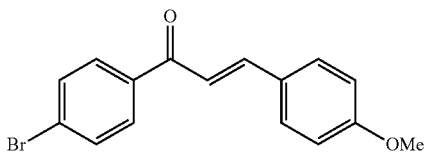

Formula Weight: 317.17722

M14b 3jc03-4 NMR not done

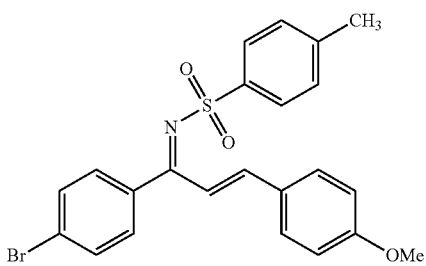

Formula Weight: 470.3788

M14c 3jc04-4 NMR not done

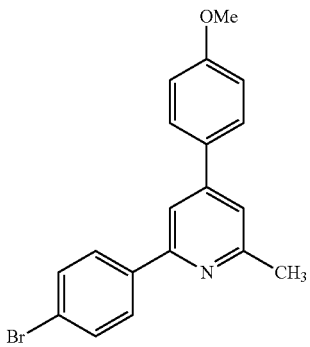

Formula Weight: 354.24044

M14d 3jc05-4 NMR not done

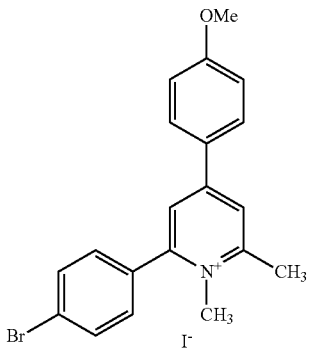

Formula Weight: 496.17943

TABLE 19-continued

Additional Compound Structures.

19U 3jc07-7 NMR not done

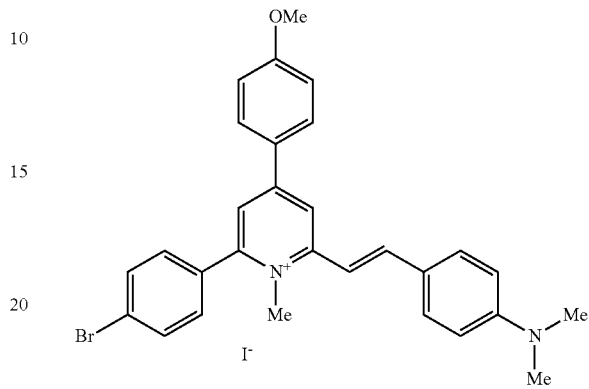

Formula Weight: 627.35389

3jc07-8 NMR not done

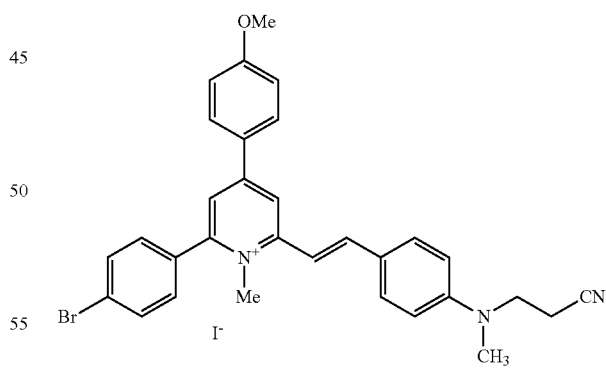

Formula Weight: 666.38993

Additional compounds were tested by NMR as described above, and for killing of bacteria as indicated in the table below. See Table 19, which provides MIC data for the indicated bacteria. The lower the number, the better the killing activity.

TABLE 21

Compound Structures and bacterial killing results.

| Structural Formula and Compound Name | NMR | *Staphylococcus aureus* MIC (μg/mL) | *Escherichia feacalis* MIC (μg/mL) |
|---|---|---|---|
| [Structure of compound 2jc23-1 with two 4-bromophenyl groups on pyrylium, styryl linker to 4-(N-methyl-N-(2-cyanoethyl)amino)phenyl, BF4⁻ counterion]<br>Formula Weight: 662.1183328<br>2jc23-1 | Yes | >64 | >64 |
| [Structure of compound 2jc23-2 with two 4-fluorophenyl groups on pyrylium, styryl linker to 4-(N-methyl-N-(2-cyanoethyl)amino)phenyl, BF4⁻ counterion]<br>Formula Weight: 540.3071392<br>2jc23-2 | Yes | >64 | >64 |

TABLE 21-continued
Compound Structures and bacterial killing results.
| Structural Formula and Compound Name | NMR | Staphylococcus aureus MIC (µg/mL) | Escherichia feacalis MIC (µg/mL) |
|---|---|---|---|
| 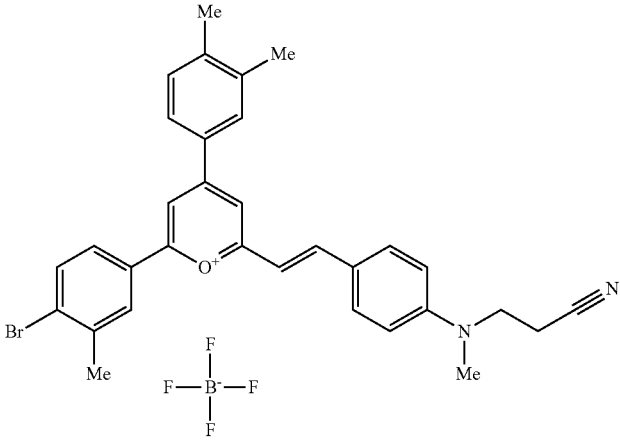<br>Formula Weight: 560.4325328<br>2jc24-1 | No | ND | ND |
| 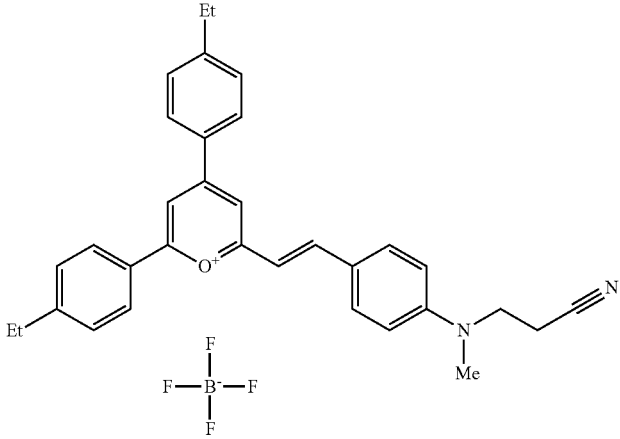<br>Formula Weight: 560.4325328<br>2jc24-2 | No | ND | ND |
| 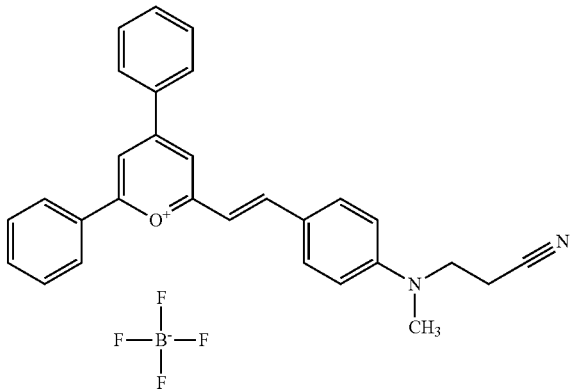<br>Formula Weight: 504.3262128<br>2jc25-1 | Yes | >64 | >64 |

TABLE 21-continued
Compound Structures and bacterial killing results.
| Structural Formula and Compound Name | NMR | Staphylococcus aureus MIC (µg/mL) | Escherichia feacalis MIC (µg/mL) |
|---|---|---|---|
| 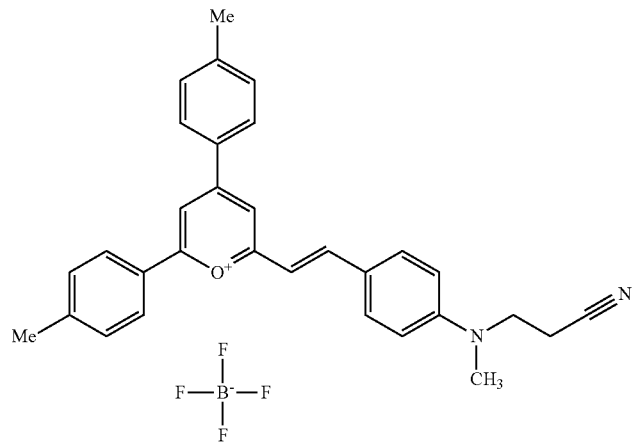<br>Formula Weight: 532.3793728<br>2jc25-2 | Yes | >64 | >64 |
| 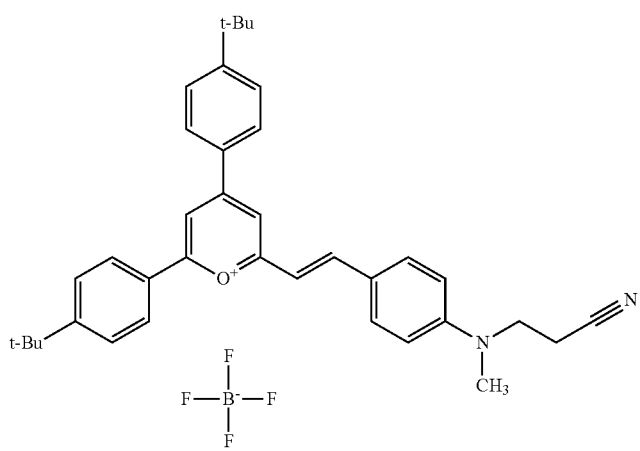<br>Formula Weight: 616.5388528<br>2jc25-3 | Yes | >64 | >64 |

TABLE 21-continued
Compound Structures and bacterial killing results.
| Structural Formula and Compound Name | NMR | *Staphylococcus aureus* MIC (μg/mL) | *Escherichia feacalis* MIC (μg/mL) |
|---|---|---|---|
| 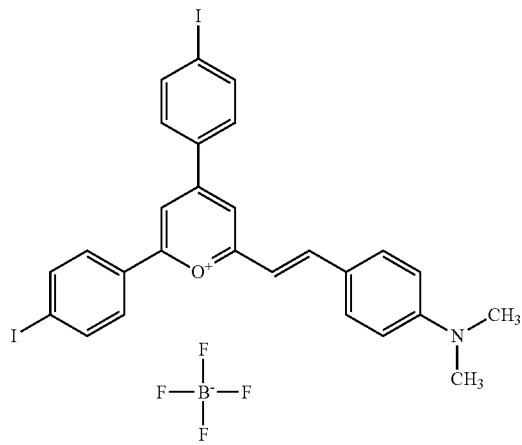<br>Formula Weight: 717.0832328<br>2jc27-1 | Yes | >64 | >64 |
| 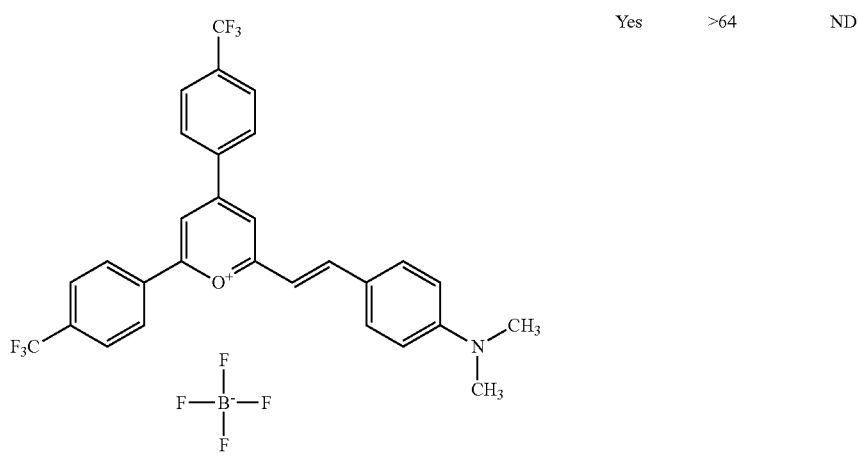<br>Formula Weight: 601.286112<br>2jc27-2 | Yes | >64 | ND |

TABLE 21-continued

Compound Structures and bacterial killing results.

| Structural Formula and Compound Name | NMR | *Staphylococcus aureus* MIC (µg/mL) | *Escherichia feacalis* MIC (µg/mL) |
|---|---|---|---|
| Formula Weight: 537.2520256<br>2jc27-3 | Yes | >64 | >64 |
| Formula Weight: 756.1192728<br>2jc28-1 | Yes | >64 | >64 |

TABLE 21-continued
Compound Structures and bacterial killing results.
| Structural Formula and Compound Name | NMR | *Staphylococcus aureus* MIC (μg/mL) | *Escherichia feacalis* MIC (μg/mL) |
|---|---|---|---|
| 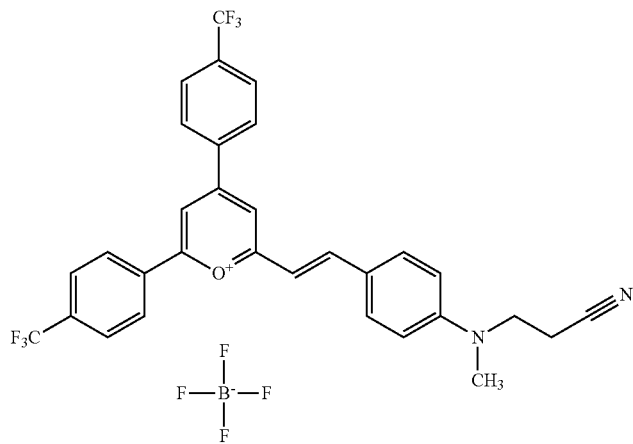<br>Formula Weight: 640.322152<br>2jc28-2 | Yes | >64 | >64 |
| 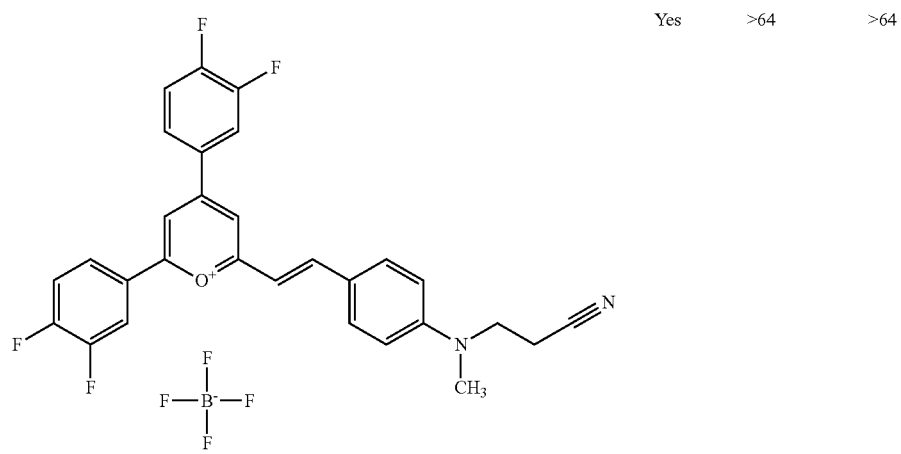<br>Formula Weight: 576.2880656<br>2jc28-3 | Yes | >64 | >64 |

TABLE 21-continued
Compound Structures and bacterial killing results.
| Structural Formula and Compound Name | NMR | Staphylococcus aureus MIC (µg/mL) | Escherichia feacalis MIC (µg/mL) |
|---|---|---|---|
| 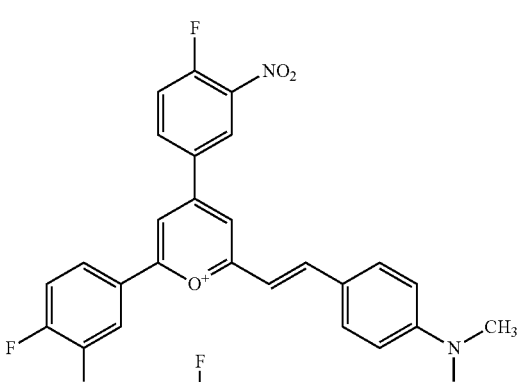
Formula Weight: 591.2662192
2jc30-1 | No | ND | ND |
| 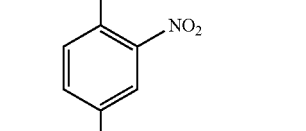
Formula Weight: 630.3022592
2jc30-2 | No | ND | ND |

TABLE 21-continued
Compound Structures and bacterial killing results.
| Structural Formula and Compound Name | NMR | *Staphylococcus aureus* MIC (µg/mL) | *Escherichia feacalis* MIC (µg/mL) |
|---|---|---|---|
| 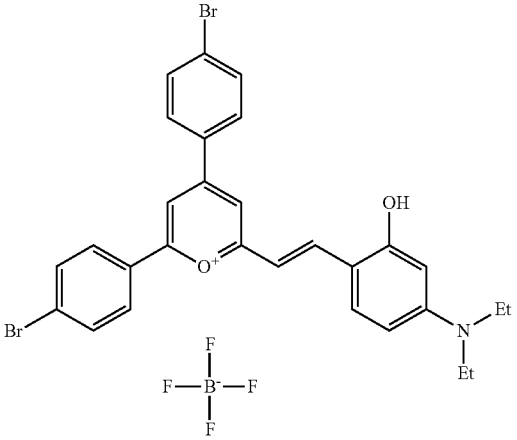<br>Formula Weight: 667.1348528<br>2jc34-1 | No | ND | ND |
| 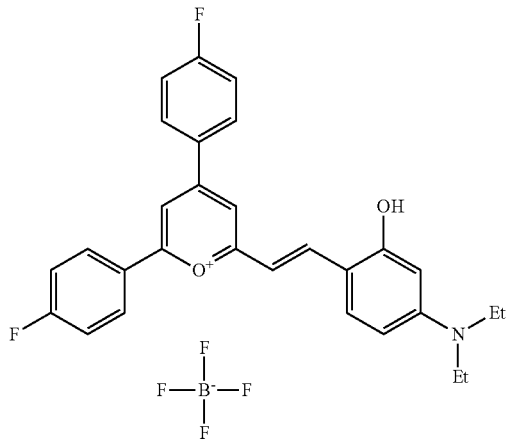<br>Formula Weight: 545.3236592<br>2jc34-2 | Yes | 64 | >64 |

TABLE 21-continued
Compound Structures and bacterial killing results.
| Structural Formula and Compound Name | NMR | *Staphylococcus aureus* MIC (µg/mL) | *Escherichia feacalis* MIC (µg/mL) |
|---|---|---|---|
| 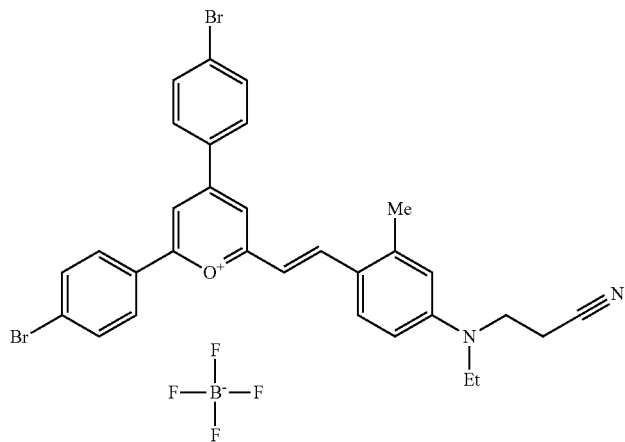<br>Formula Weight: 690.1714928<br>2jc34-3 | Yes | >64 | >64 |
| 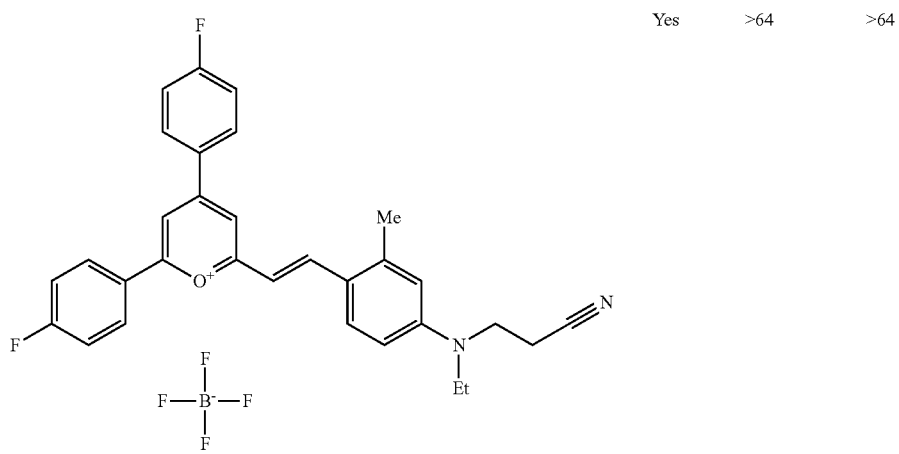<br>Formula Weight: 568.3602992<br>2jc34-4 | Yes | >64 | >64 |

TABLE 21-continued
Compound Structures and bacterial killing results.
| Structural Formula and Compound Name | NMR | *Staphylococcus aureus* MIC (μg/mL) | *Escherichia feacalis* MIC (μg/mL) |
|---|---|---|---|
| 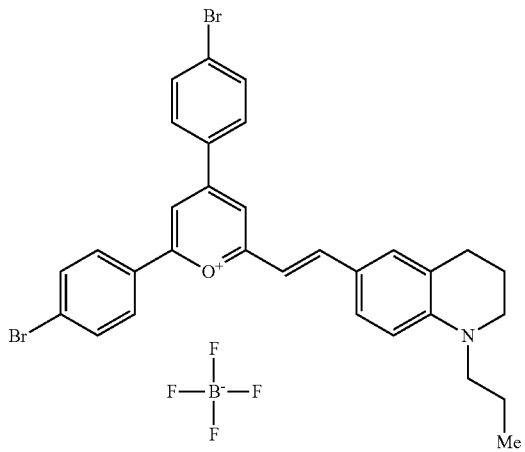<br>Formula Weight: 677.1727328<br>2jc34-5 | Yes | >64 | >64 |
| 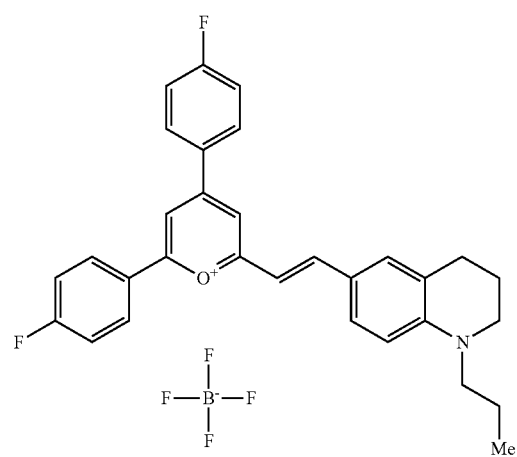<br>Formula Weight: 555.3615392<br>2jc34-6 | Yes | >64 | >64 |

Example 21: Additional Compounds and Synthetic Pathways
A.
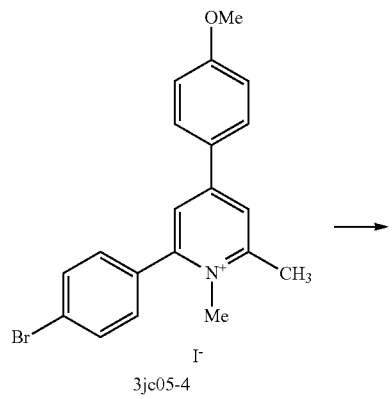
B.
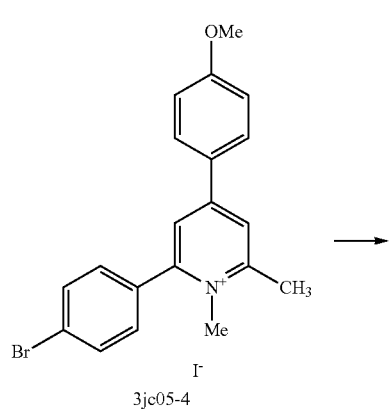
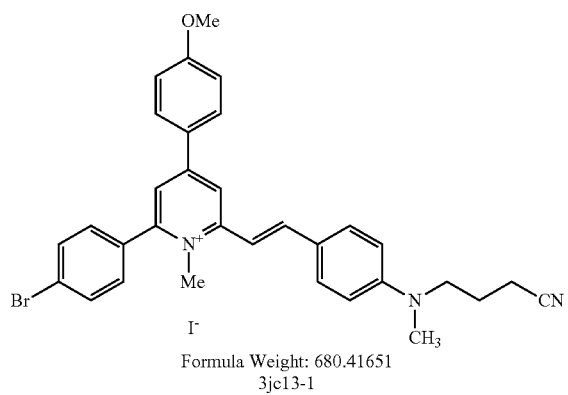
C.
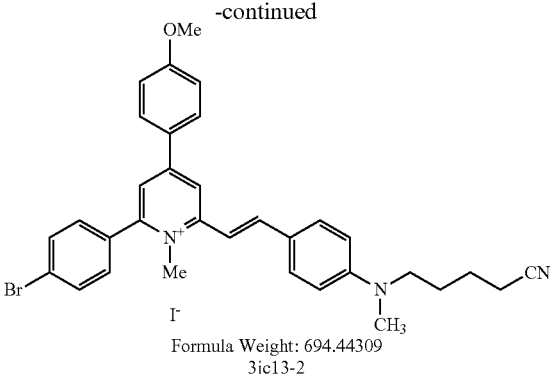

D.
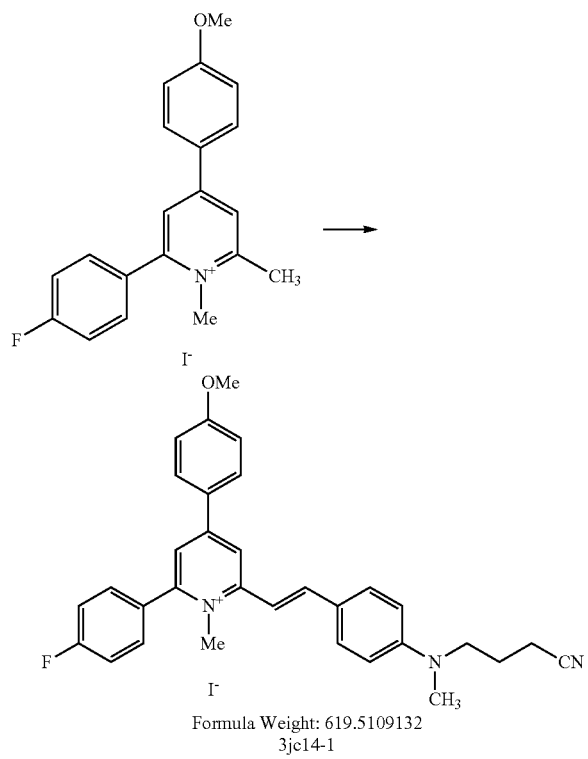
E.
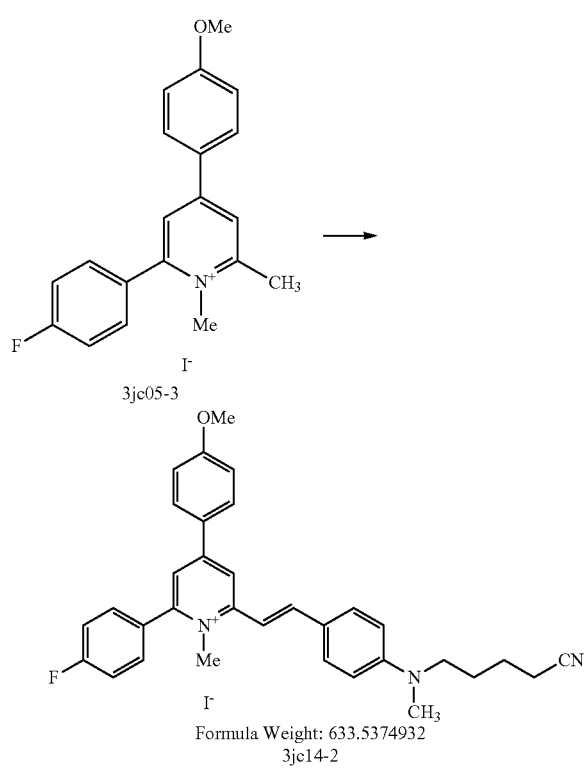
F.
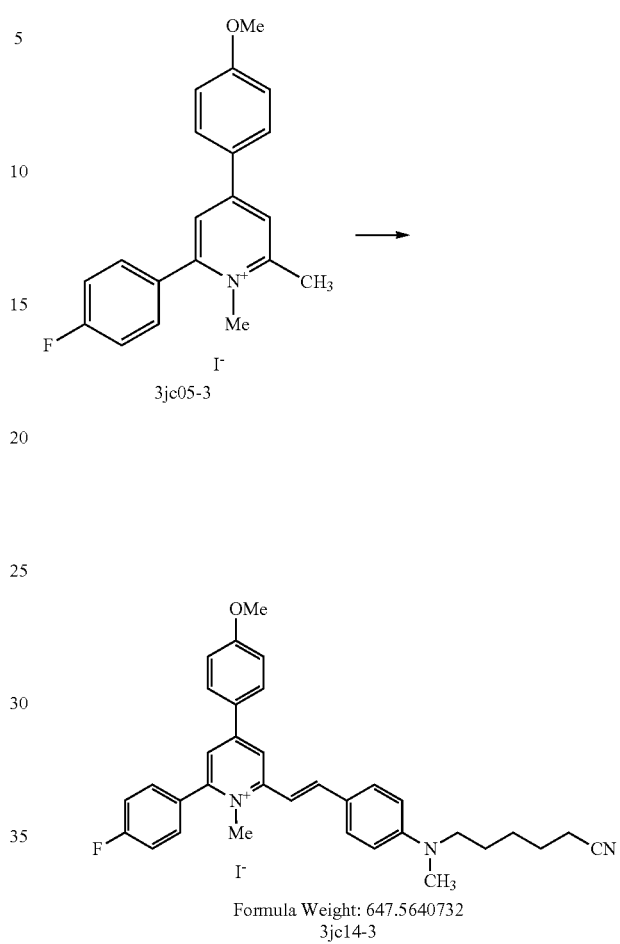
G.
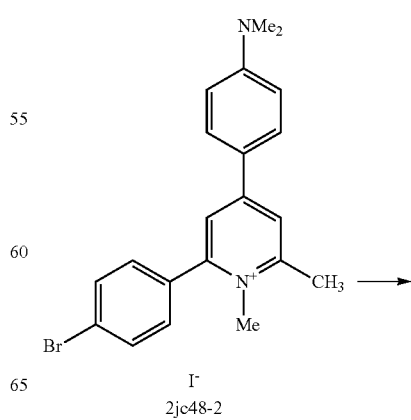

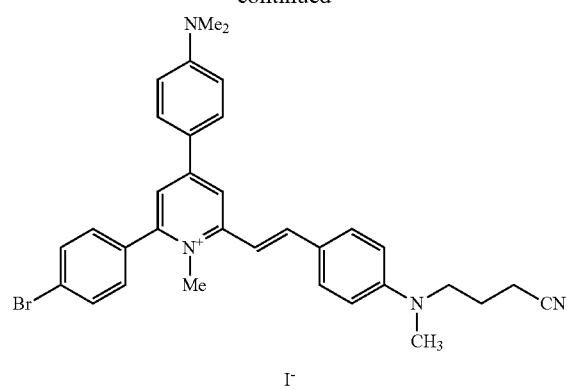
Formula Weight: 693.45833
3jc15-1
H.
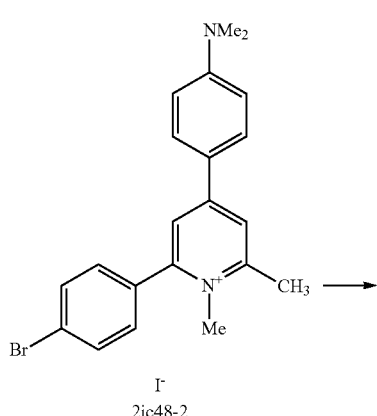
2jc48-2
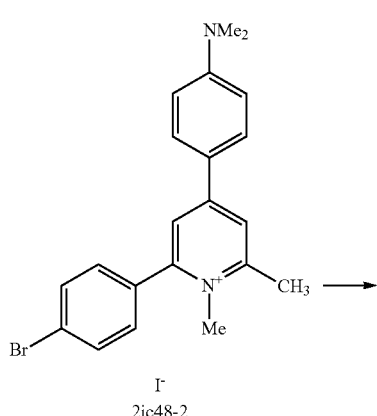
Formula Weight: 707.48491
3jc15-2
I.
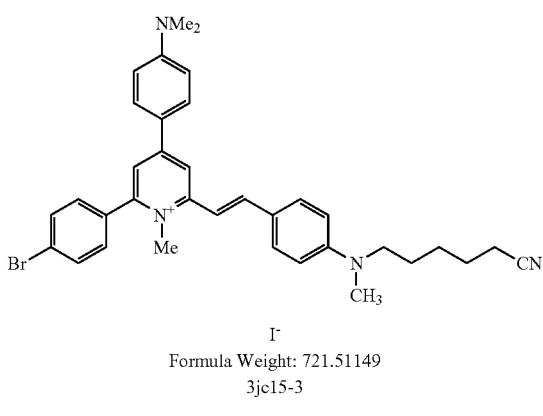
2jc48-2
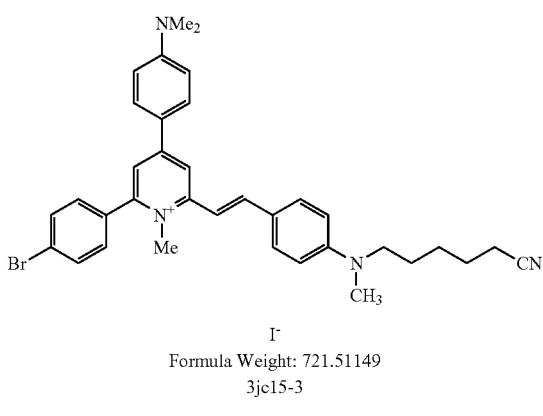
Formula Weight: 721.51149
3jc15-3
J.
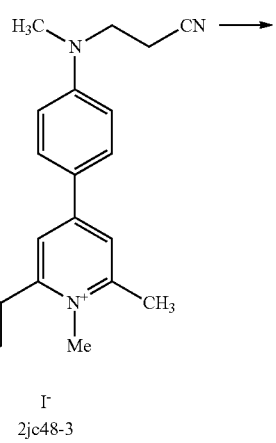
2jc48-3

275
-continued
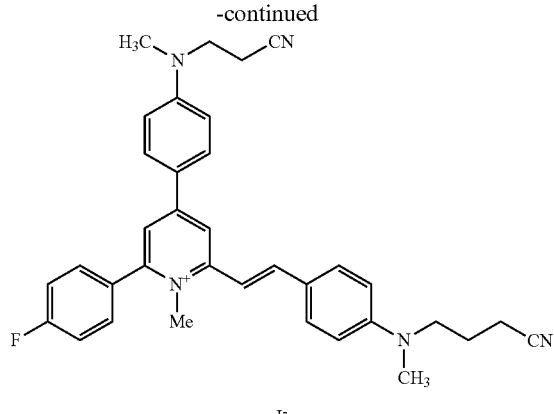
I⁻
Formula Weight: 671.5887732
3jc16-1
K.
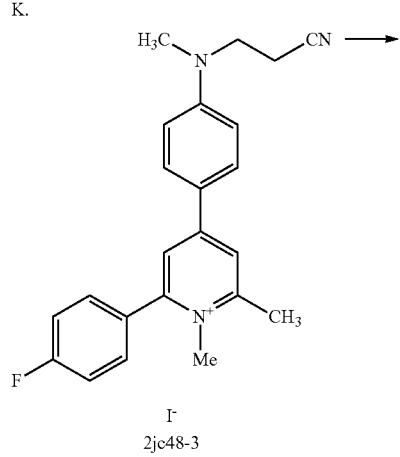
I⁻
2jc48-3
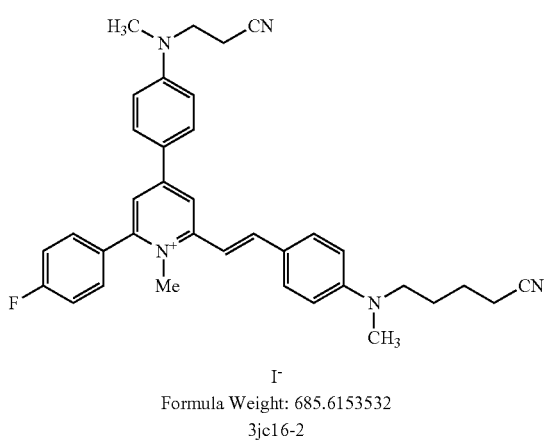
I⁻
Formula Weight: 685.6153532
3jc16-2
276
L.
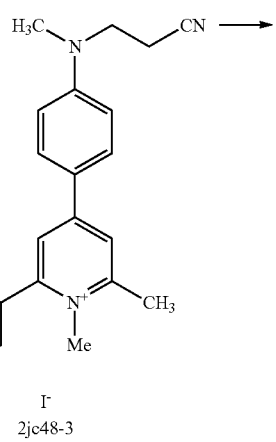
I⁻
2jc48-3
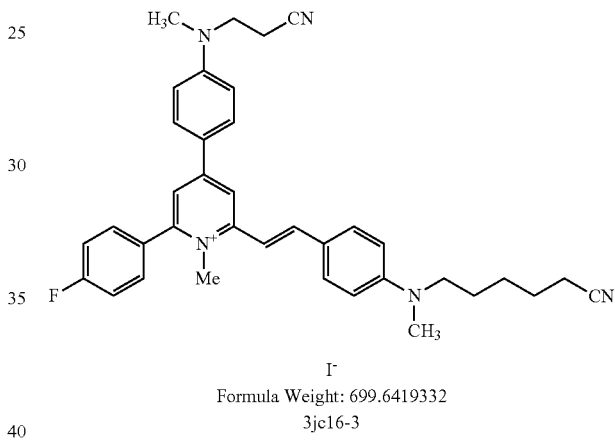
I⁻
Formula Weight: 699.6419332
3jc16-3
M.
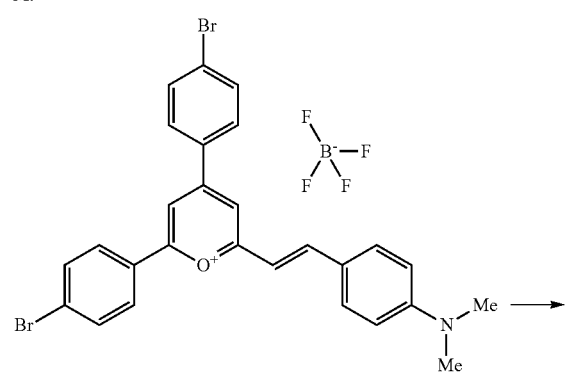

-continued
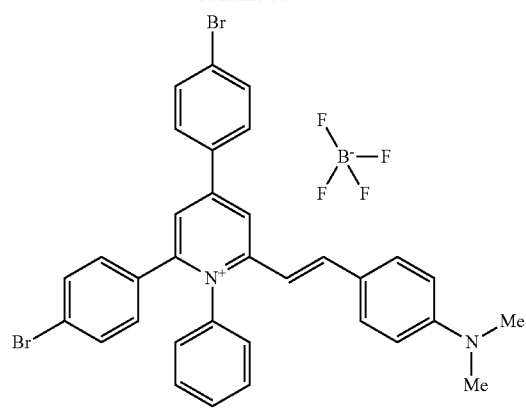
Formula Weight: 698.1934928
3jc12
O.
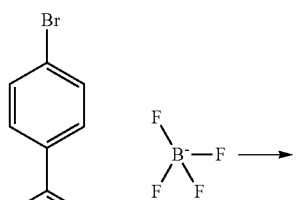
6jc47
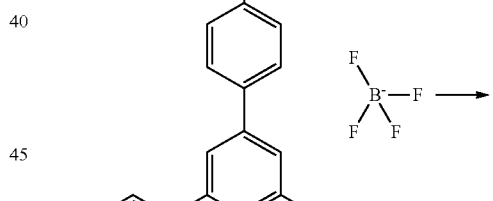
Formula Weight: 676.1449128
3jc20-2
N.
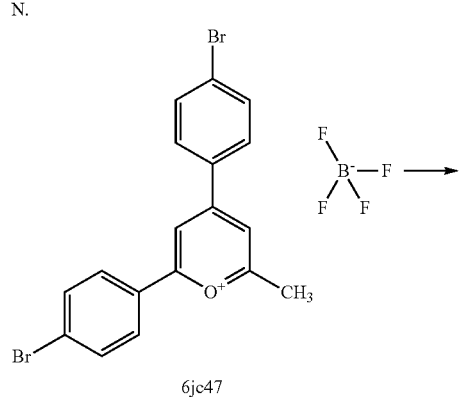
6jc47
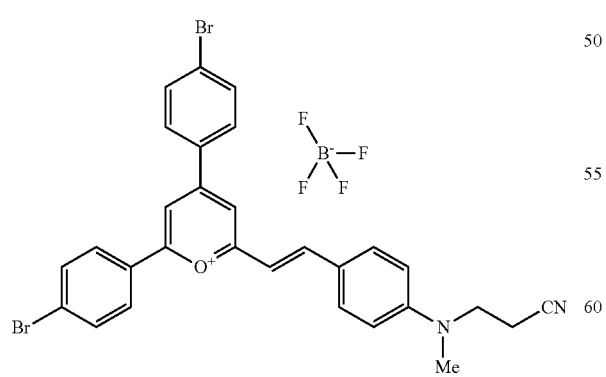
Formula Weight: 662.1183328
3jc20-1
P.
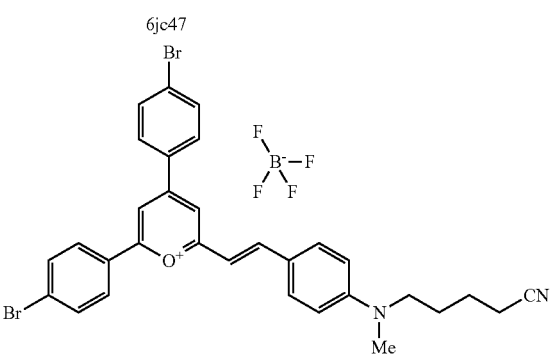
6jc47
Formula Weight: 690.1714928
3jc20-3

Q.
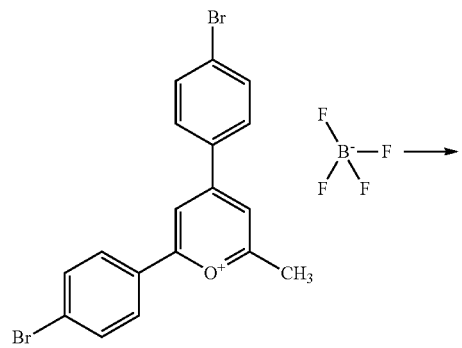
6jc47
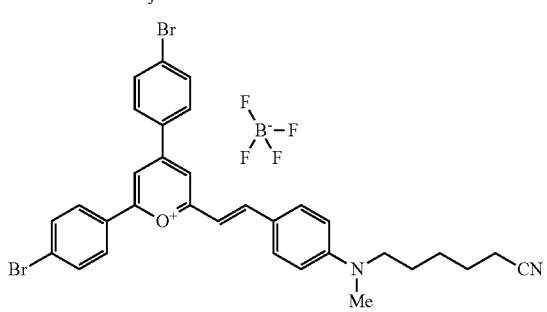
Formula Weight: 704.1980728
3jc20-4
R.
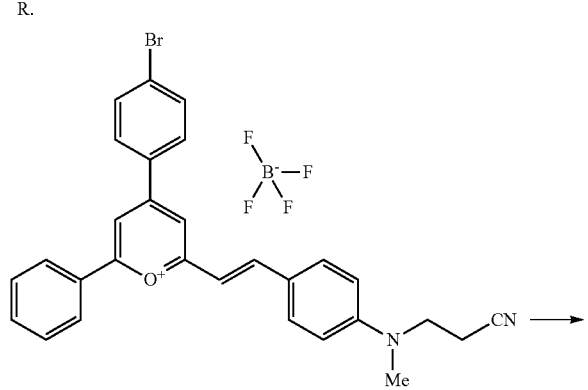
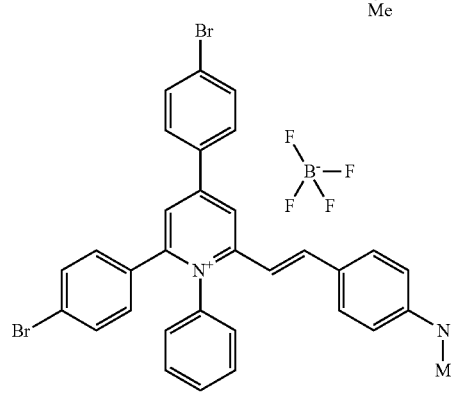
Formula Weight: 737.2295328
3jc21
S.
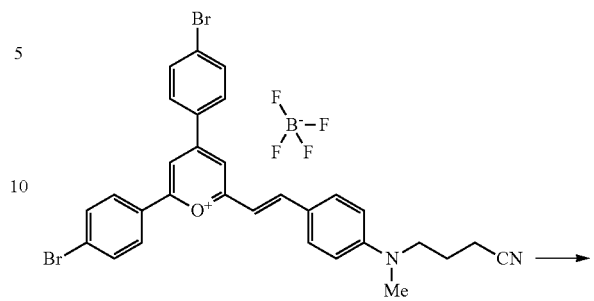
Formula Weight: 751.2561128
3jc24-1
T.
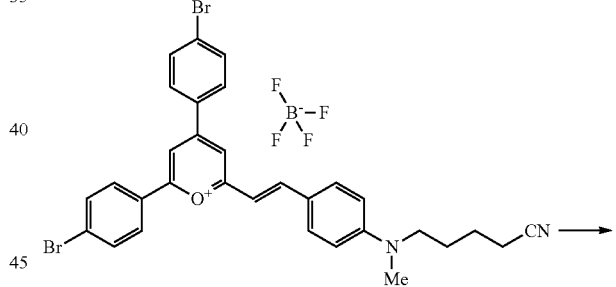
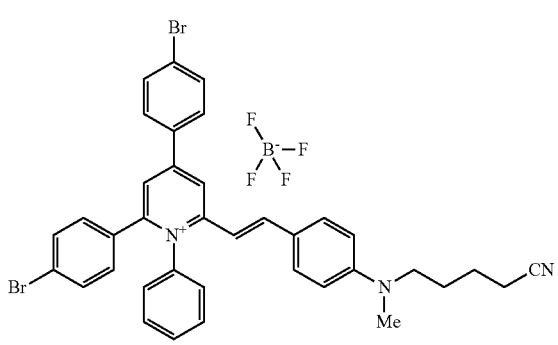
Formula Weight: 765.2826928
3jc24-2

U. 3jc12: (E)-2,4-bis(4-bromophenyl)-6-(4-(dimethylamino)styryl)-1-phenylpyridin-1-ium boron tetrafluoride salt X. 3jc13-3: (E)-2-(4-bromophenyl)-6-(4-((5-cyanopentyl)(methyl)amino)styryl)-4-(4-methoxyphenyl)-1-methylpyridin-1-ium iodide salt

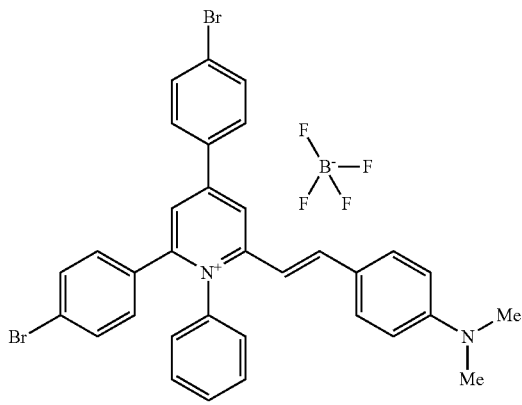 [SMILES: CN(C)c1ccc(/C=C/c2cc(-c3ccc(Br)cc3)cc(-c3ccc(Br)cc3)[n+]2-c2ccccc2)cc1 ; F[B-](F)(F)F]

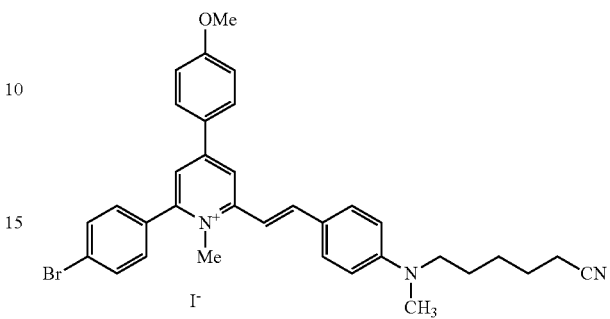

V. 3jc13-1: (E)-2-(4-bromophenyl)-6-(4-((3-cyanopropyl)(methyl)amino)styryl)-4-(4-methoxyphenyl)-1-methylpyridin-1-ium iodide salt Y. 3jc14-1: (E)-2-(4-(3-cyanopropyl)(methyl)amino)styryl)-6-(4-fluorophenyl)-4-(4-methoxyphenyl)-1-methylpyridin-1-ium iodide salt

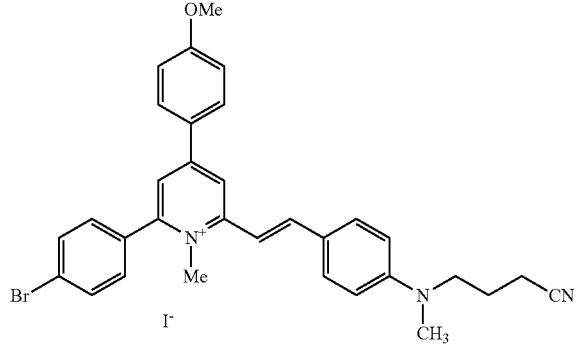 [SMILES: COc1ccc(-c2cc(/C=C/c3ccc(N(C)CCCC#N)cc3)[n+](C)c(-c3ccc(Br)cc3)c2)cc1 ; [I-]]

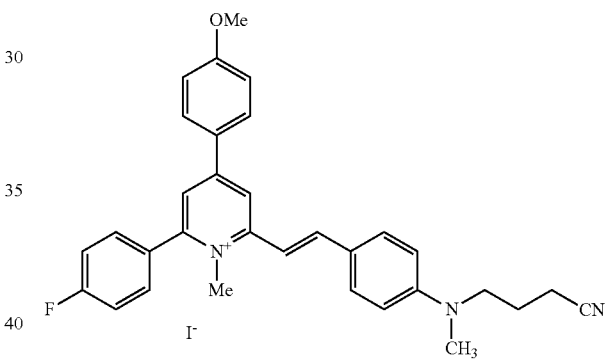

W. 3jc13-2: (E)-2-(4-bromophenyl)-6-(4-((4-cyanobutyl)(methyl)amino)styryl)-4-(4-methoxyphenyl)-1-methylpyridin-1-ium iodide salt Z. 3jc14-2: (E)-2-(4-((4-cyanobutyl)(methyl)amino)styryl)-6-(4-fluorophenyl)-4-(4-methoxyphenyl)-1-methylpyridin-1-ium iodide salt

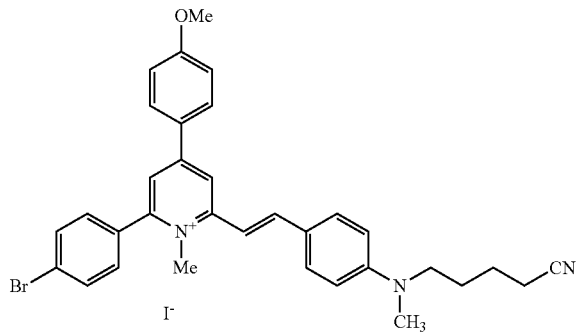 [SMILES: COc1ccc(-c2cc(/C=C/c3ccc(N(C)CCCCC#N)cc3)[n+](C)c(-c3ccc(Br)cc3)c2)cc1 ; [I-]]

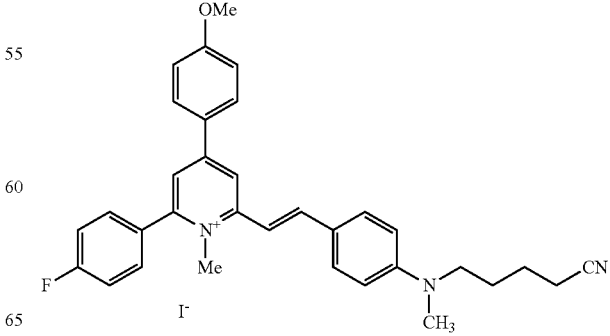

AA. 3jc14-3: (E)-2-(4-((5-cyanopentyl)(methyl)amino)styryl)-6-(4-fluorophenyl)-4-(4-methoxyphenyl)-1-methylpyridin-1-ium iodide salt

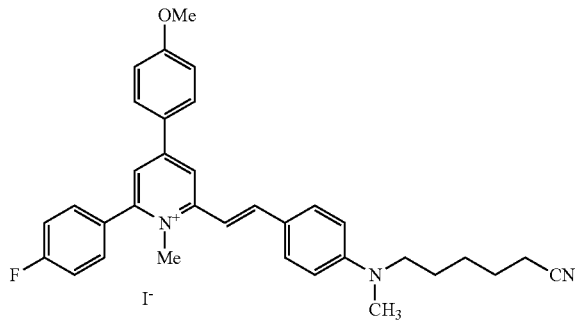 [SMILES: COc1ccc(-c2cc(/C=C/c3ccc(N(C)CCCCCC#N)cc3)[n+](C)c(-c3ccc(F)cc3)c2)cc1 ; [I-]]

BB. 3jc15-1: (E)-2-(4-bromophenyl)-6-(4-((3-cyanopropyl)(methyl)amino)styryl)-4-(4-(dimethylamino)phenyl)-1-methylpyridin-1-ium iodide salt

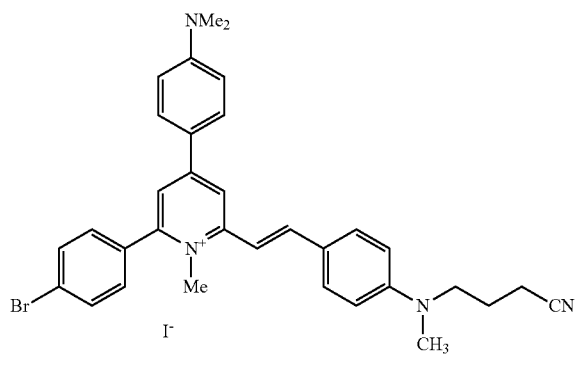 [SMILES: CN(C)c1ccc(-c2cc(/C=C/c3ccc(N(C)CCCC#N)cc3)[n+](C)c(-c3ccc(Br)cc3)c2)cc1 ; [I-]]

CC. 3jc15-2: (E)-2-(4-bromophenyl)-6-(4-((4-cyanobutyl)(methyl)amino)styryl)-4-(4-(dimethylamino)phenyl)-1-methylpyridin-1-ium iodide salt

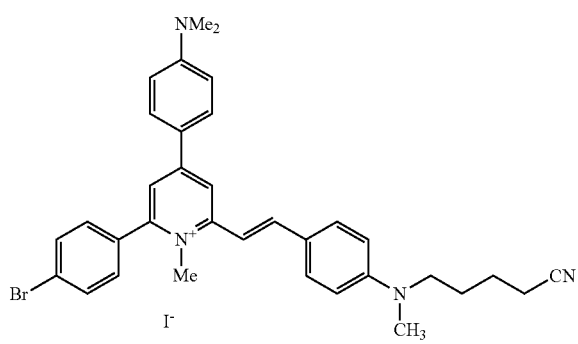 [SMILES: CN(C)c1ccc(-c2cc(/C=C/c3ccc(N(C)CCCCC#N)cc3)[n+](C)c(-c3ccc(Br)cc3)c2)cc1 ; [I-]]

DD. 3jc15-3: (E)-2-(4-bromophenyl)-6-(4-((5-cyanopentyl)(methyl)amino)styryl)-4-(4-(dimethylamino)phenyl)-1-methylpyridin-1-ium iodide salt

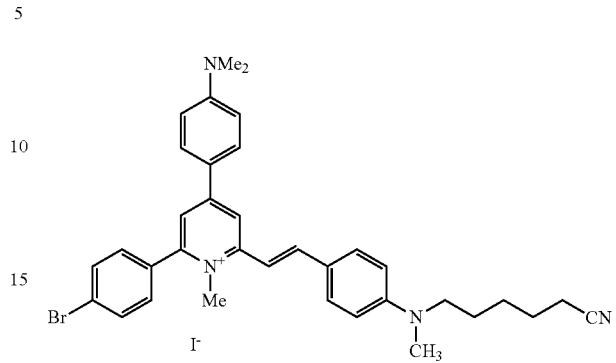

EE. 3jc16-1: (E)-4-(4-((2-cyanoethyl)(methyl)amino)phenyl)-2-(4-((3-cyanopropyl)(methyl)amino)styryl)-6-(4-fluorophenyl)-1-methylpyridin-1-ium iodide salt

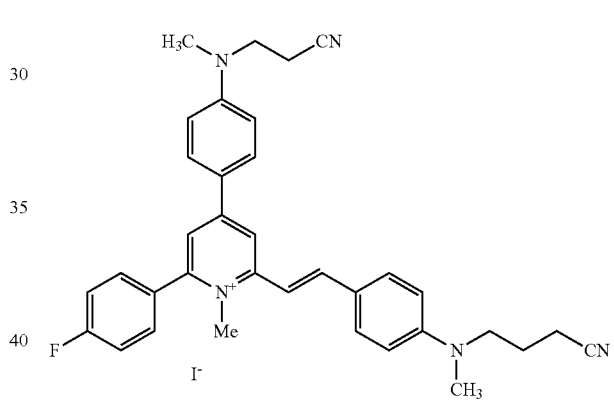

FF. 3jc16-2: (E)-2-(4-((4-cyanobutyl)(methyl)amino)styryl)-4-(4-((2-cyanoethyl)(methyl)amino)phenyl)-6-(4-fluorophenyl)-1-methylpyridin-1-ium iodide salt

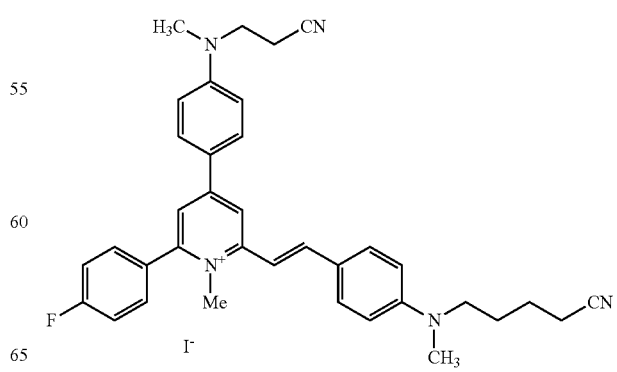

GG. 3jc16-3: (E)-4-(4-((2-cyanoethyl)(methyl)amino)phenyl)-2-(4-((5-cyanopentyl)(methyl)amino)styryl)-6-(4-fluorophenyl)-1-methylpyridin-1-ium iodide salt

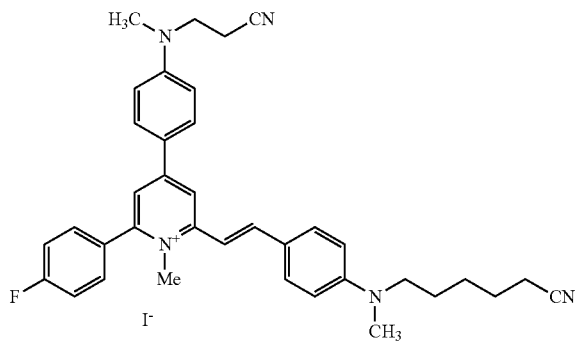 [SMILES: CN(CCC#N)c1ccc(-c2cc(/C=C/c3ccc(N(C)CCCCCC#N)cc3)[n+](C)c(-c3ccc(F)cc3)c2)cc1 ; [I-]]

Example 22: Effects of Changes to Scaffold

Figures 21A, 21B:
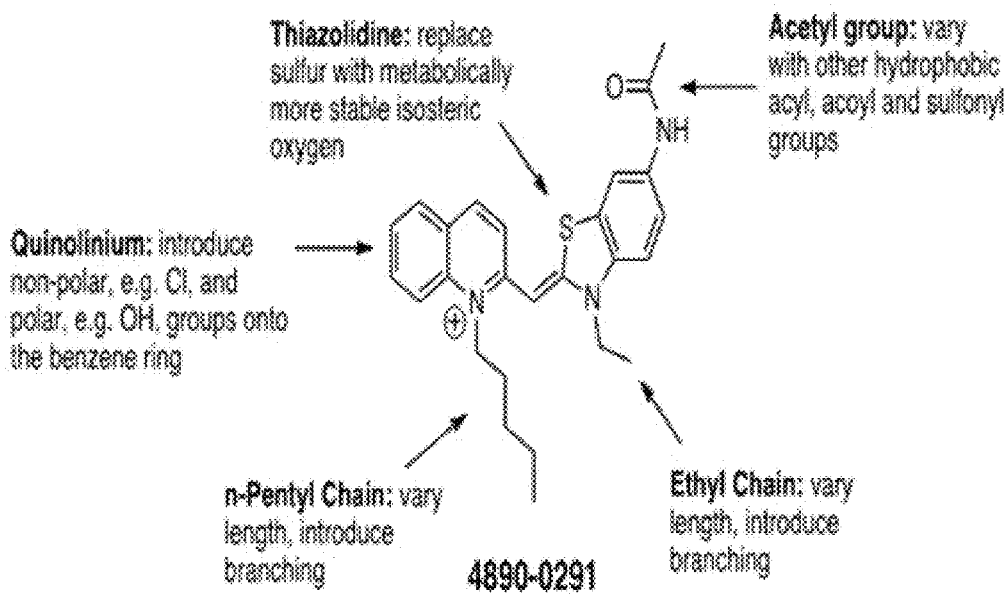
FIG. 21A is a table showing MIC, cytotoxicity and Lipid II binding of compound 4890-0291.
FIG. 21B presents the chemical structure and suggested optimization of the 4890-0291 scaffold.

Other lead compounds can be studied, such as 4890-0291. See FIG. 21B. MOA studies show that 4890-0291 inhibits cell wall, DNA and protein synthesis at $IC_{50}$ of 1.29, 1.45 and 1.86 µg/ml (see FIG. 21B) and lipid synthesis at $IC_{50}$ of 11.5 µg/ml, markedly different from 6jc48-1 (data not shown). In order to optimize 4890-0291, substituted quinolines can first be N-alkylated with alkyl halides to generate quinolinium salts. Subsequent treatment with thiazolium iodide salts and triethylamine (Et3N) then can furnish the target molecules.

Example 23: Summary of MIC and CC50 Data

Figure 22A:
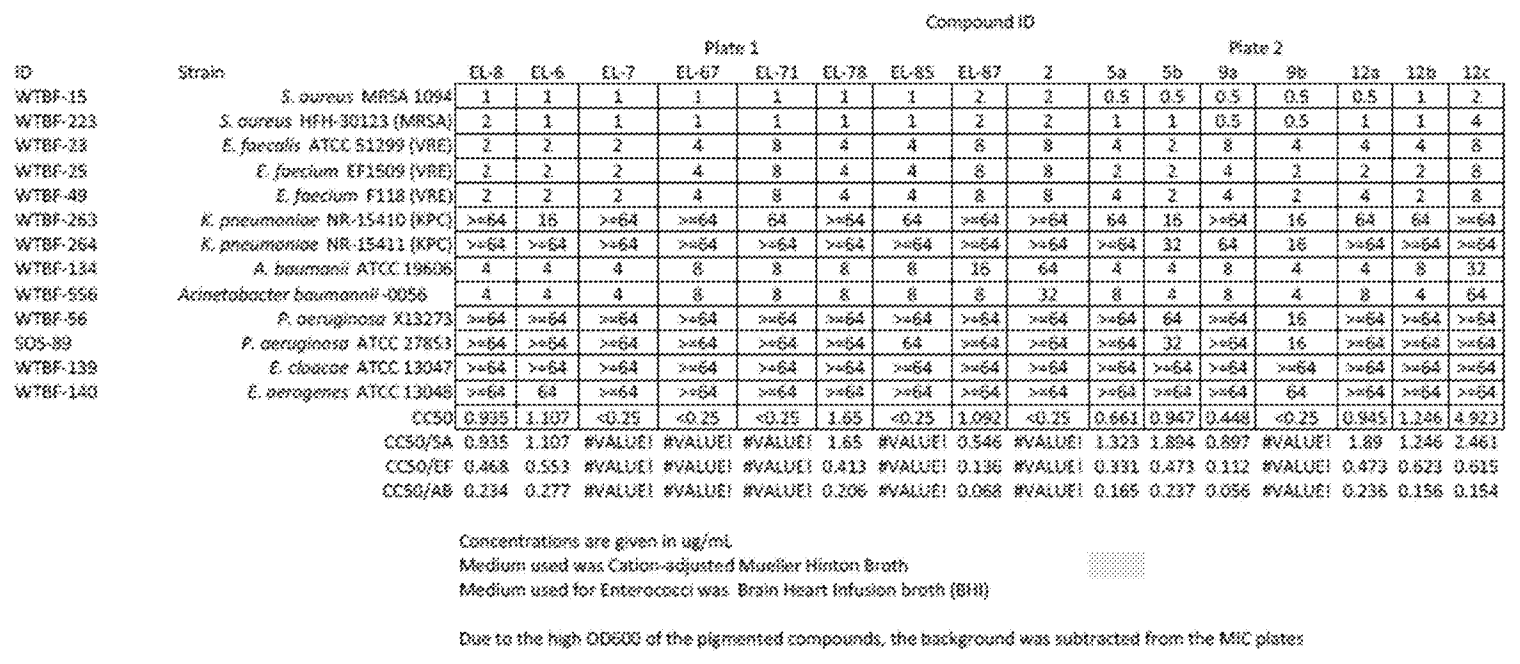

See FIG. 22A, FIG. 22B, and FIG. 22C for a summary of MIC and CC50 Data for the indicated compounds.

REFERENCES

All references listed below and throughout the specification are hereby incorporated by reference in their entirety.
1. Allen et al., *Inhibition of peptidoglycan biosynthesis in vancomycin-susceptible and-resistant bacteria by a semi-synthetic glycopeptide antibiotic.* Antimicrob. Agents Chemother. 40(10):2356-2362, 1996.
2. Anders and Huber, *Differential expression analysis for sequence count data.* Genome Biol. 11(10):R106, 2010.
3. Anders et al., *HTSeq—a Python framework to work with high-throughput sequencing data.* Bioinformatics 31(2): 166-169, 2015.
4. Arias and Murray, *The rise of the Enterococcus: beyond vancomycin resistance.* Nat. Rev. Microbiol. 10(4): p. 266-278, 2012.
5. Åqvist et al., *A new method for predicting binding affinity in computer-aided drug design.* Protein Eng. 7:385-391, 1994.
6. Belley et al., *Ultrastructural effects of oritavancin on methicillin-resistant Staphylococcus aureus and vancomycin-resistant Enterococcus.* Antimicrob. Agents Chemother. 53(2):800-804, 2009.
7. Best et al., *Optimization of the additive CHARMM all-atom protein force field targeting improved sampling of the backbone φ, ψ and side-chain χ1 and χ2 dihedral angles.* J. Chem. Theory and Comp. 8:3257-3273, 2012.
8. Breukink et al., *Use of the cell wall precursor lipid II by a pore-forming peptide antibiotic.* Science 286(5448): 2361-2364, 1999.
9. Breukink et al., *Lipid II is an intrinsic component of the pore induced by nisin in bacterial membranes.* J. Biol. Chem. 278(22):19898-19903, 2003.
10. Breukink and de Kruijff, *Lipid II as a target for antibiotics.* Nat. Rev. Drug Discov. 5(4):321-332, 2006.
11. Brooks, et al., *CHARMM: the biomolecular simulation program.* J. Comput. Chem. 30(10):1545-1614, 2009.
12. Bush and Bradford, *Beta-Lactams and beta-Lactamase Inhibitors: An Overview.* Cold Spring Harbor Perspect. Med. 2016:6:a025247.
13. Butler et al., *Antibacterial activity and mechanism of action of a novel anilinouracil-fluoroquinolone hybrid compound.* Antimicrob. Agents Chemother. 51(1):119-127, 2007.
14. Cardona and Wilson, *Skin and soft-tissue infections: a critical review and the role of telavancin in their treatment.* Clin. Infect. Dis. 61 Suppl 2:S69-78, 2015.
15. CLSI, *Methods for Dilution Antimicrobial Susceptibility Tests for Bacteria That Grow Aerobically; Approved Standard—Tenth Edition.* CLSI document M07-A10. Wayne, Pa.: Clinical and Laboratory Standards Institute, 2015.
16. Cotsonas and Wu, *Macromolecular synthesis and membrane perturbation assays for mechanisms of action studies of antimicrobial agents.* Curr. Protocols Pharmacol. Chapter 13, Unit 13A 7, 2009.
17. de Leeuw, *Efficacy of the small molecule inhibitor of Lipid II BAS00127538 against Acinetobacter baumannii.* Drug Des. Dev. Ther. 8:1061-1064, 2014.
18. de Leeuw et al., *Functional interaction of human neutrophil peptide-I with the cell wall precursor lipid II.* FEBS Lett. 584(8):1543-1548, 2010.
19. den Blaauwen et al., *Bacterial cell division proteins as antibiotic targets.* Bioorg. Chem. 55:27-38, 2014.
20. Dengler et al., *Induction kinetics of the Staphylococcus aureus cell wall stress stimulon in response to different cell wall active antibiotics.* BMC Microbiol. 11:16, 2011.
21. Essig et al., *Copsin, a novel peptide-based fungal antibiotic interfering with the peptidoglycan synthesis.* J. Biol. Chem. 289(50):34953-34964, 2014.
22. Fletcher et al., *Structure-activity exploration of a small-molecule Lipid II inhibitor.* Drug Des. Devel. Ther. 9:2383-2394, 2015.
23. Ganz, *Defensins: antimicrobial peptides of innate immunity.* Nat. Rev. Immunol. 3(9):710-720, 2003.
24. Guvench et al., *CHARMM additive all-atom force field for carbohydrate derivatives and its utility in polysaccharide and carbohydrate-protein modeling.* J. Chem. Theory Comput. 7(10):3162-3180, 2011.
25. Guvench et al., *CHARMM Additive All-Atom Force Field for Glycosidic Linkages between Hexopyranoses.* J. Chem. Theory Comput. 5(9):2353-2370, 2009.
26. Hanaki et al., *Increase in glutamine-non-amidated muropeptides in the peptidoglycan of vancomycin-resistant Staphylococcus aureus strain Mu50.* J. Antimicrob. Chemother. 42(3):315-320, 1998.
27. Holland et al., *Clinical management of Staphylococcus aureus bacteremia: a review.* JAMA, 312(13):1330-1341, 2014.
28. Howden et al., *Reduced vancomycin susceptibility in Staphylococcus aureus, including vancomycin-intermediate and heterogeneous vancomycin-intermediate strains: resistance mechanisms, laboratory detection, and clinical implications.* Clin. Microbiol. Rev. 23(1):99-139, 2010.

29. Jorgensen, *Transferable Intermolecular Potential Functions for Waters, Alcohols, and Ethers. Application to Liquid Water.* J. Am. Chem. Soc., 103:335, 1981.
30. Klauda et al., *Update of the CHARMM all-atom additive force field for lipids: validation on six lipid types.* J. Phys. Chem. B, 114(23):7830-7843, 2010.
31. Kuroda et al., *Identification of the up- and down-regulated genes in vancomycin-resistant Staphylococcus aureus strains Mui and Mu50 by cDNA differential hybridization method.* Biochem. Biophys. Res. Commun. 269(2):485-490, 2000.
32. Kuroda et al., *Two-component system VraSR positively modulates the regulation of cell-wall biosynthesis pathway in Staphylococcus aureus.* Mol. Microbiol. 49(3): 807-21, 2003.
33. Langmead et al., *Ultrafast and memory-efficient alignment of short DNA sequences to the human genome.* Genome Biol. 10(3):R25, 2009.
34. McCallum et al., *Mutational analyses of open reading frames within the vraSR operon and their roles in the cell wall stress response of Staphylococcus aureus.* Antimicrob. Agents Chemother. 55(4):1391-1402, 2011.
35. MacKerell et al., *All-atom empirical potential for molecular modeling and dynamics studies of proteins.* J. Phys. Chem. B, 102:3586-3616, 1998.
36. Munch et al., *Identification and in vitro analysis of the GatD/MurT enzyme-complex catalyzing lipid II amidation in Staphylococcus aureus.* PLoS Pathog, 8(1): e1002509, 2012.
37. Munita et al., *Daptomycin for the treatment of bacteraemia due to vancomycin-resistant enterococci.* Int. J. Antimicrob. Agents, 44(5):387-395, 2014.
38. Munita et al, *Evolving resistance among Gram-positive pathogens.* Clin. Infect. Dis. 1(suppl 2)):S48-S57, 2015.
39. O'Driscoll and Crank, *Vancomycin-resistant enterococcal infections: epidemiology, clinical manifestations, and optimal management.* Infect. Drug Resist. 8:217-230, 2015.
40. Oeemig et al., *Eurocin, a new fungal defensin: structure, lipid binding, and its mode of action.* J. Biol. Chem. 287(50):42361-42372, 2012.
41. Oppedijk et al., *Hit 'em where it hurts: The growing and structurally diverse family of peptides that target lipid-II.* Biochim. Biophys. Acta (5):947-957, 2015.
42. Overton et al., *Global network analysis of drug tolerance, mode of action and virulence in methicillin-resistant S. aureus.* BMC Syst. Biol. 5:68, 2011.
43. Paradise et al., *Cytochrome P450 inhibition assays using traditional and fluorescent substrates.* Curr. Protoc. Pharmacol., 2007. Chapter 7: p. Unit7 11.
44. Pietiainen et al., *Transcriptome analysis of the responses of Staphylococcus aureus to antimicrobial peptides and characterization of the roles of vraDE and vraSR in antimicrobial resistance.* BMC Genomics. 10:429, 2009.
45. Roberts et al., *Dalbavancin and Oritavancin: An Innovative Approach to the Treatment of Gram-Positive Infections.* Pharmacotherapy, 35(10):935-948, 2015.
46. Sass et al., *Human beta-defensin 3 inhibits cell wall biosynthesis in Staphylococci.* Infect. Immun. 78(6): 2793-2800, 2010.
47. Scherl et al., *Exploring glycopeptide-resistance in Staphylococcus aureus: a combined proteomics and transcriptomics approach for the identification of resistance-related markers.* BMC Genomics, 7:296, 2006.
48. Schmitt et al., *Insight into invertebrate defensin mechanism of action: oyster defensins inhibit peptidoglycan biosynthesis by binding to lipid II.* J. Biol. Chem. 285 (38):29208-29216, 2010.
49. Schneider and Sahl, *Lipid II and other bactoprenol-bound cell wall precursors as drug targets.* Curr. Opin. Investig. Drugs 11(2):157-164, 2010.
50. Schneider et al., *Plectasin, a fungal defensin, targets the bacterial cell wall precursor Lipid II.* Science 328(5982): 1168-1172, 2010.
51. Tran et al., *Mechanisms of drug resistance: daptomycin resistance.* Ann. N. Y. Acad. Sci. 1354(1):32-53, 2015.
52. van Heijenoort, *Lipid intermediates in the biosynthesis of bacterial peptidoglycan.* Microbiol. Mol. Biol. Rev. 71(4):620-635, 2007.
53. Vanommeslaeghe et al., *CHARMM general force field: A force field for drug-like molecules compatible with the CHARMM all-atom additive biological force fields.* J. Comp. Chem., 31(4):671-690, 2010.
54. Vanommeslaeghe and Mackerell, *Automation of the CHARMM General Force Field (CGenFF) I: Bond Perception and Atom Typing.* J. Chem. Inf. Model. 52(12): 3144-3154, 2012.
55. Vanommeslaeghe et al., *Automation of the CHARMM General Force Field (CGenFF) Assignment of Bonded Parameters and Partial Atomic Charges.* J. Chem. Inf. Model. 52(12):3155-3168, 2012.
56. Varney et al., *Turning defense into offense: defensin mimetics as novel antibiotics targeting lipid II.* PLoS Pathog. 9(11):e1003732, 2013.
57. Vollmer et al., *Peptidoglycan structure and architecture.* FEMS Microbiol. Rev. 32(2):149-167, 2008.

The invention claimed is:
1. A compound which is selected from the group consisting of:

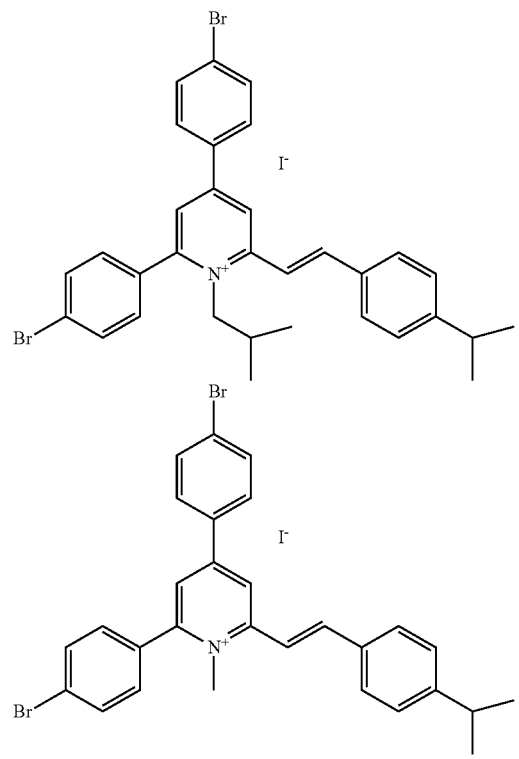

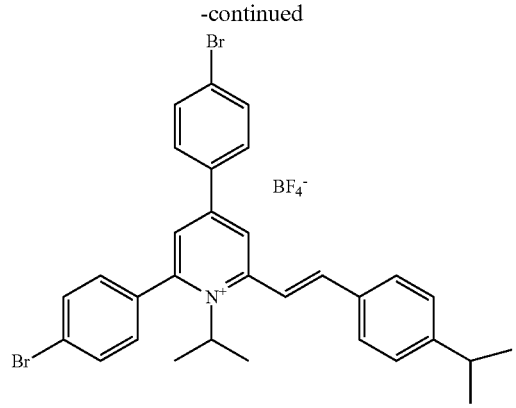
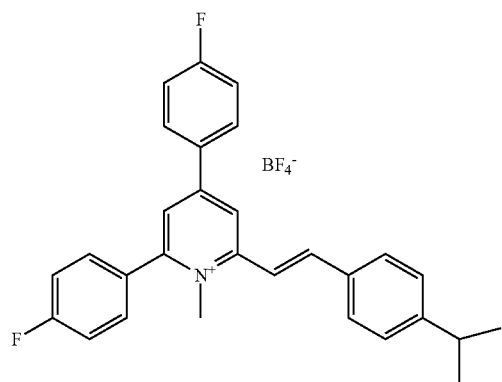
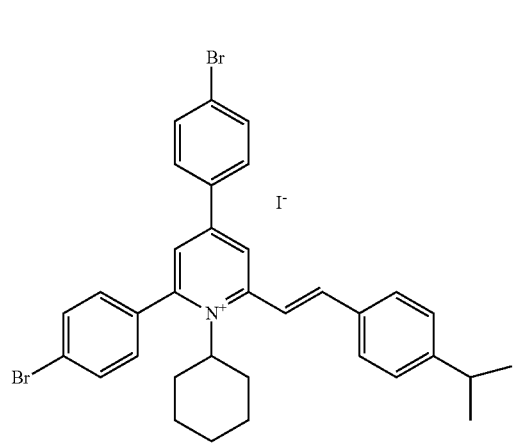
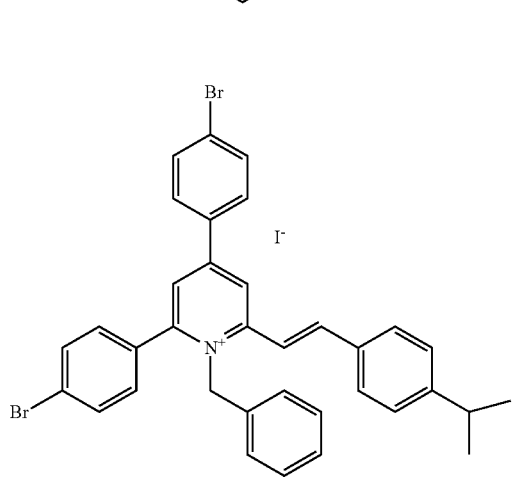
and
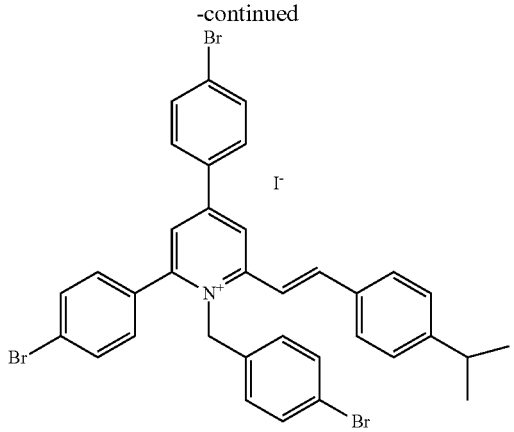
2. The compound of claim 1 which is selected from the group consisting of:
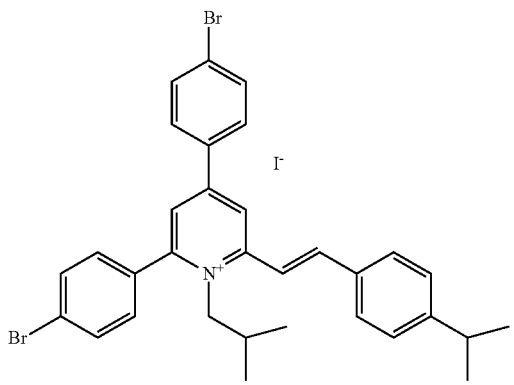
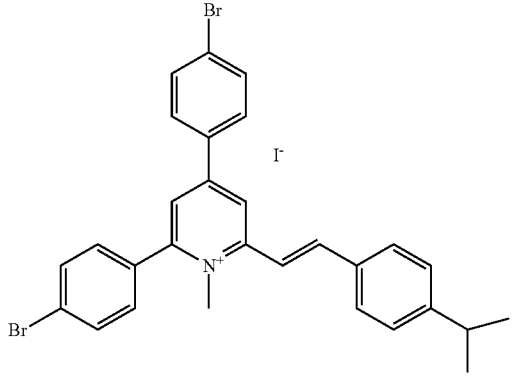
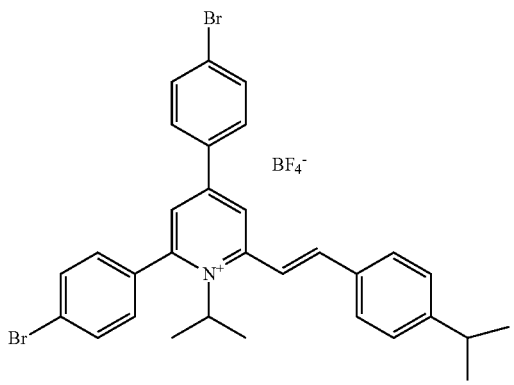

291

-continued

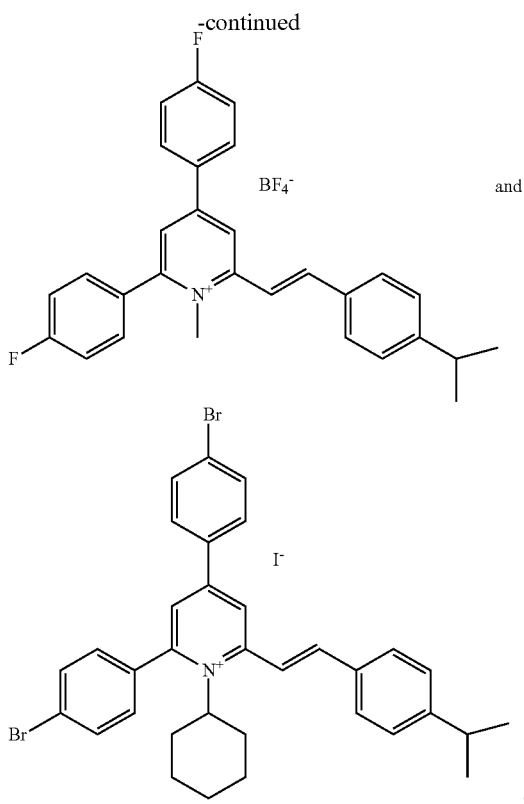

3. The compound

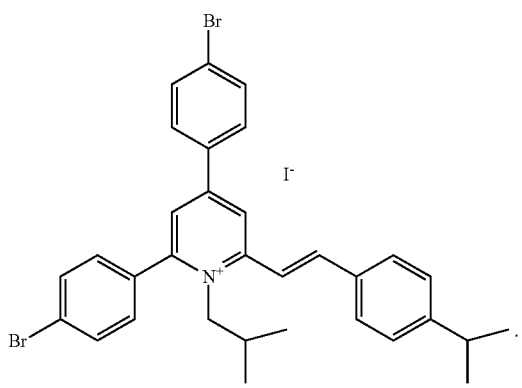 [SMILES: CC(C)C[n+]1c(/C=C/c2ccc(C(C)C)cc2)cc(-c2ccc(Br)cc2)cc1-c1ccc(Br)cc1 ; [I-]]

4. The compound

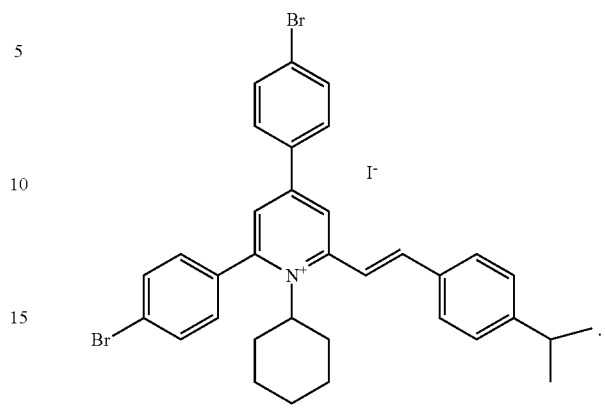

and

5. A pharmaceutical composition comprising a pharmaceutically acceptable vehicle and a compound of claim 1.

6. A pharmaceutical composition comprising a pharmaceutically acceptable vehicle and a compound of claim 2.

7. A pharmaceutical composition comprising a pharmaceutically acceptable vehicle and a compound of claim 3.

8. A pharmaceutical composition comprising a pharmaceutically acceptable vehicle and a compound of claim 4.

9. A method of treating a subject in need for bacterial infection, comprising administering to the subject a compound of claim 1.

10. A method of treating a subject in need for bacterial infection, comprising administering to the subject a compound of claim 2.

11. The method of claim 9 wherein the subject suffers from infection with bacteria selected from the group consisting of *E. faecalis, E. faecium, Staphylococcus aureus, Bacillus anthracis*, and *Acinetobacter baumanii*.

12. The method of claim 10 wherein the subject suffers from infection with bacteria selected from the group consisting of *E. faecalis, E. faecium, Staphylococcus aureus, Bacillus anthracis*, and *Acinetobacter baumanii*.

13. A method of killing or reducing bacteria comprising contacting the bacteria with a compound of claim 1.

14. A method of killing or reducing bacteria on an object comprising contacting the object with a compound of claim 1.

15. A method of protecting an object from colonization by bacteria comprising contacting the object with a compound of claim 1.

\* \* \* \* \*